US006015669A

United States Patent [19]
Holden

[11] Patent Number: 6,015,669
[45] Date of Patent: *Jan. 18, 2000

[54] IDENTIFICATION OF GENES

[75] Inventor: David William Holden, London, United Kingdom

[73] Assignee: Imperial College Innovations Limited, London, United Kingdom

[*] Notice: This patent is subject to a terminal disclaimer.

[21] Appl. No.: 08/871,355

[22] Filed: Jun. 9, 1997

Related U.S. Application Data

[63] Continuation of application No. PCT/GB95/02875, Dec. 11, 1995.

[30] Foreign Application Priority Data

Dec. 9, 1994 [GB] United Kingdom ................... 9424921
Jan. 31, 1995 [GB] United Kingdom ................... 9501881
May 5, 1995 [GB] United Kingdom ................... 9509239
Dec. 11, 1995 [GB] United Kingdom .... PCT/GB95/02875

[51] Int. Cl.[7] ............................. C12Q 1/68; G01N 33/53; C07H 21/02; C12N 15/00

[52] U.S. Cl. ................................ 435/6; 435/7.2; 435/440; 435/471; 536/23.1; 536/24.3; 935/76; 935/77; 935/78

[58] Field of Search ................................ 435/6, 7.2, 440, 435/471, 252, 31; 935/76, 77, 78; 536/23.1, 24.3

[56] References Cited

U.S. PATENT DOCUMENTS

| | | | |
|---|---|---|---|
| 5,397,697 | 3/1995 | Lam et al. | 435/6 |
| 5,527,674 | 6/1996 | Guerra et al. | 435/6 |
| 5,700,683 | 12/1997 | Stover et al. | 435/252.31 |
| 5,700,928 | 12/1997 | Hodgson et al. | 536/23.7 |
| 5,876,931 | 3/1999 | Holden | 436/6 |

FOREIGN PATENT DOCUMENTS

| | | |
|---|---|---|
| WO 92/01056 | 1/1992 | WIPO . |
| WO 93/04202 | 3/1993 | WIPO . |
| WO 94/26933 | 11/1994 | WIPO . |

OTHER PUBLICATIONS

Adachi et al. "Isolation of Dictyostelium discoideum cytokinesis mutants by restriction enzyme–mediaed integration of the blasticidin S resistance marker," *Biochem. Biophys. Res. Comm.* 205, 1808–1814 (1994). (Abstract only).

Albus et al. (1991) "Virulence of Staphylococcus aureus mutants altered in type 5 capsule production," *Infect. Immun.* 59, 1008–1014.

Anthony et al. (1991) "Transformation and allelic replacement in Francisella spp," *J. Gen. Microbiol.* 137, 2697–2703. (Abstract only).

Artiguenave et al. (1997) "High–efficiency transposon mutagenesis by electroporation of a Pseudomonas fluorescens strain," *FEMS Microbiol. Lett.* 153, 363–369.

Black et al. (1995) "Restriction enzyme–mediated integration elevates transformation frequency and enables co–transfection of Toxoplasma gondii," *Mol. Biochem. Parasitol.* 74, 55–63.

Bolker et al. (1995) "Tagging pathogenicity genes in Ustilago maydis by restriction enzyme–mediated integration (REMI)," *Mol. Gen. Genet.* 248, 547–552.

Brown et al. (1997) 19th Fungal Genetics Conference, Mar. 18–23, 1997 (Asilomar Conference Centre, Pacific Grove, CA).

Camilli et al. (1990) "Insertional mutagenesis of Listeria monocytogenes with a novel Tn917 derivative that allows direct cloning of DNA flanking transposon insertions," *J. Bacteriol.* 172, 3738–3744.

Cheung et al. (1992) "Regulation of exoprotein expression in Staphylococcus aureus by a locus (sar) distinct from agr," *Proc. Natl. Acad. Sci. USA* 89, 6462–6466.

Chiang & Mekalanos (1998) "Use of signature–tagged transposon mutagenesis to identify Vibrio cholerae genes critical for colonization," *Mol. Microbiol.* 27, 797–805.

Correia et al. (1995) "Insertional inactivation of binding determinants of Streptococcus crista CC5A using Tn916," *Oral Microbiol. Immunol.* 10, 220–226. (Abstract only).

Dolganov & Grossman (1993) "Insertional inactivation of genes to isolate mutants of Synechococcus sp. strain PCC 7942:isolation of filamentous strains," *J. Bacteriol.* 175, 7644–7651. (Abstract only).

Gaillard et al. (1986) "Transposon mutagenesis as a tool to study the role of hemolysin in the virulence of Listeria monocytogenes," *Infect. Immun.* 52, 50–55. (Abstract only).

(List continued on next page.)

*Primary Examiner*—Ardin H. Marschel
*Assistant Examiner*—Ethan Whisenant
*Attorney, Agent, or Firm*—Arnall Golden & Gregory, LLP

[57] ABSTRACT

A method for identifying a microorganism having a reduced adaptation to a particular environment comprising the steps of:

(1) providing a plurality of microorganisms each of which is independently mutated by the insertional inactivation of a gene with a nucleic acid comprising a unique marker sequence so that each mutant contains a different marker sequence, or clones of the said microorganism;

(2) providing individually a stored sample of each mutant produced by step (1) and providing individually stored nucleic acid comprising the unique marker sequence from each individual mutant;

(3) introducing a plurality of mutants produced by step (1) into the said particular environment and allowing those microorganisms which are able to do so to grow in the said environment;

(4) retrieving microorganisms from the said environment or a selected part thereof and isolating the nucleic acid from the retrieved microorganisms;

(5) comparing any marker sequences in the nucleic acid isolated in step (4) to the unique marker sequence of each individual mutant stored as in step (2); and (6) selecting an individual mutant which does not contain any of the marker sequences as isolated in step (4).

26 Claims, 112 Drawing Sheets

OTHER PUBLICATIONS

Han et al. (1997) "Tn5 tagging of the phenol–degrading gene on the chromosome of Pseudomonas putida," *Mol. Cells* 7, 40–44. (Abstract only).

Kahrs et al. (1994) "Generalized transposon shuttle mutagenesis in Neisseria gonorrhoeae: a method for isolating epithelial cell invasion–defective mutants," *Mol. Microbiol.* 12, 819–831. (Abstract only).

Kim et al. (1997) "The hrpA and hrpC operons of Erwinia amylovora encode components of a type III pathway that secretes harpin," *J. Bacteriol.* 179(5), 1690–1697. (Abstract only).

Leahy et al. (1993) "Transposon mutagenesis in Acinetobacter calcoaceticus RAG–1," *J. Bacteriol.* 175, 1838–1840.

Mei et al. (1997) "Identification of Staphylococcus aureus virulence genes in a murine model of bacteraemia using signature–tagged mutagenesis," *Mol. Microbiol.* 26, 399–407.

Mejia–Ruiz et al. (1997) "Isolation and characterization of an Azotobacter vinelandii algK mutant.," *FEMS Microbiol. Lett.* 156, 101–106.

Morrison et al. (1984) "Isolation of transformation–deficient Steptococcus pneumoniae mutants defective in control of competence, using insertion–duplication mutagenesis with the erythromycin resistance determinant of pAM beta 1," *J. Bacteriol.* 159, 870–876.

Myers & Myers (1997) "Isolation and characterization of a transposon mutant of Shewanella putrefaciens MR–1 deficient in fumarate reductase," *Lett. Appl. Microbiol.* 25, 162–168 (Abstract only).

Norgren et al. (1989) "A method for allelic replacement that uses the conjugative transposon Tn916: deletion of the emm6.1 allele in Steptococcus pyogenes JRS4," *Infect. Immun.* 57, 3846–3850. (Abstract only).

Pang et al. (1998) "Typhoid fever—important issues still remain," *Trends Microbiol.* 6, 131–133.

Pelicic et al. (1998) "Genetic advances for studying Mycobacterium tuberculosis pathogenicity," *Molecular Microbiology* 28, 413–420.

Polissi et al. (1997) *Fourth European Meeting on the Molecular Biology of the Pneumococcus*, Abstract A.18. (Abstract only).

Ramakrishnan et al. (1997) "Mycobacterium marinum causes both long–term subclinical infection and acute disease in the leopard frog (Rana pipiens)," *Infect. Immun.* 65, 767–773.

Regue et al. (1991) "A generalized transducing bacteriophage for Serratia marcescens," *Res. Microbiol.* 142, 23–27. (Abstract only).

Rella et al. (1985) "Transposon insertion mutagenesis of Pseudomonas aeruginosa with a Tn5 derivative: application to physical mapping of the arc gene cluster," *Gene* 33, 293–303.

Roberts et al. (1988) "Cloning of the egl gene of Pseudomonas solanacearum and analysis of its role in phytopathogenicity," *J. Bacteriol.* 170, 1445–1451. (Abstract only).

Roos et al. (1997) "Tagging genes and trapping promoters in Toxoplasma gondii by insertional mutagenesis,"*Methods* 13, 112–122. (Abstract only).

Rott et al. (1996) "At least two separate gene clusters are involved in albicidin production by Xanthomonas albilineans," *J. Bacteriol.* 178, 4590–4596. (Abstract only).

Roudier et al. (1992) "Characterization of translation termination mutations in the spv operon of the Salmonella virulence plasmid pSDL2," *J. Bacteriology* 174, 6418–6423. (Abstract only).

Schiestl & Petes (1991) "Integration of DNA fragments by illegitimate recombination in Saccharomyces cerevisiae," *Proc. Natl. Acad. Sci. USA* 88, 7585–7589.

Sharetzsky et al. (1991) "A novel approach to insertional mutagenesis of Haemophilus influenzae," *J. Bacteriol.* 173, 1561–1564. (Abstract only).

Subramanian et al. (1992) "Rapid mapping of Escherichia coli::Tn5 insertion mutations by REP–Tn5 PCR" *PCR Methods* 1, 187–192. (Abstract only).

Tam & Lefebvre (1993) "Cloning of flagellar genes in Chlamydomonas reinhardtii by DNA insertional mutagenesis" *Genetics* 135, 375–384. (Abstract only).

Trieu–Cuot et al. (1991) "An integrative vector exploiting the transposition properties of Tn1545 for insertional mutagenesis and cloning of genes from gram–positive bacteria," *Gene* 106, 21–27.

Wooley et al. (1989) "Transfer of Tn1545 and Tn916 to Clostridium acetobutylicum," *Plasmid* 22, 169–174. (Abstract only).

Hensel et al., Science 269: 400–403 (Jul. 21, 1995).

Chuang et al., J. of Bacteriology 175: 2026–2036 (1993).

Aldhous, "Fast Track to Disease Genes", *Science* 265:2008–2010 (1994).

Camilli, et al., "Insertional Mutagenesis Of Listeria Monocytogenes With A Novel Tn917 Derivative That Allows Direct Cloning of DNA Flanking Transposon Insertions", *J. Bacteriol.*, 172:3738–3744 (1990).

Carter & Collins, "The Route Of Enteric Infection In Normal Mice", J. Exp. Med., 139:1189–1203 (1974).

Fields, et al., "A Salmonella Locus That Controls Resistance To Microbicidal Proteins From Phagocytic Cells", *Science*, 243:1059–1062 (1989).

Finlay, et al., "Identification And Characterization Of TnphoA Mutants Of Salmonella That Are Unable To Pass Through A Polarized MDCK Epithelial Cell Monolayer", *Mol. Microbiol.*, 2:757–766 (1988).

Galan, et al., "Molecular And Functional Characterization Of The Salmonella Invasion Gene InvA: Homology Of InvA To Memebers Of A New Protein Family", (1992).

Groleman & Ochman, "How To Become A Pathogen", *Trends Microbiol.*, 2:289–293 (1994).

Grolsman, et al., "Molecular Functional And Evolutionary Analysis Of Sequences Specific To Salmonella", *Proc. Natl. Acad. Sci. USA*, 90:1033–1037 (1993).

Grolsman, et al., "Salmonella Typhimurium phoP Virulence Gene Is A Transcriptional Regulator", *Proc. Natl. Acad. Sci. USA*, 86:7077–7081 (1989).

Grolsman & Saie, "Salmonella Virulence: New Clues To Intramacrophage Survival", *Trends In Biochem. Sci.*, 15:30–33 (1990).

Hensel, et al., "Simultaneous Indentification Of Bacterial Virulence Genes By Negative Selection", *Science*, 269:400–403 (1995).

Holland, et al., "Tn916 Insertion Mutagenesis In Escherichia Coli And Haemophilus Influenzae Type b Following Conjugative Transfer", *J. Gen. Microbiol.*, 138:509–515 (1992).

Lee & Falkow, "Isolation Of Hyperinvasive Mutants Of Salmonella", *Methods Enzymol.*, 265:531–545 (1994).

Lisitsyn, et al., "Cloning The Difference Between Two Complex Genomes", *Science*, 259:946–951 (1993).

Lisitsyn, et al., "Direct Isolation Of Polymorphic Markers Linked To A Trait By Genetically Directed Representational Difference Analysis", *Nature Genetics*, 6:57–63 (1994).

Lu, et al., "Tagged Mutations At The Tox1 Locus Of Cochliobolus Heterostrophus By Restriction Enzyme–Mediated Integration", *Proc. Natl. Acad. Sci. USA*, 91:12649–12653 (1994).

Mahan, et al., "Selection Of Bacterial Virulence Genes That Are Specifically Induced In Host Tissues", Science, 259:686–688 (1993).

Miller, et al., "Isolation Of Orally Attenuated Salmonella Typhimurium Following TnphoA Mutagenesis", Infection Immun., 57:2758–2763 (1989).

Miller, et al., "A Two–Component Regulatory System (phoPphoQ) Controls Salmonella Typhimurium Virulence", *Proc. Natl. Acad. Sci. USA*, 86:5054–5058 (1989).

Nelson, et al., "Genomic Mismatch Scanning: A New Approach To Genetic Linkage Mapping", *Nature Genetics*, 4:11–17 (1993).

Pascopella, et al., "Use Of In Vivo Coplementation In Mycobacterium Tuberculosis To Identify A Genomic Fragment Associated With Virulence", *Infection Immun.*, 62:1313–1319 (1994).

Slauch, et al., "In Vivo Expression Technology For Selection Of Bacterial Genes Specifically Induced In Host Tissues", *Methods Enzymol*, 235:481–492 (1994).

Smith, et al., "Virulence Of Aspergillus Fumigatus Double Mutants Lacking Restriction And An Alkaline Protease In A Low–Dose Model Of Invasive Pulmonary Aspergillosis", *Infection Immun.*, (1994).

Smith, et al., "Genetic Footprinting: A Genomic Strategy For Determining A Gene's Function Given Its Sequence", *Proc. Natl. Acad. Sci. USA*, 92:6479–6483 (1995).

Walsh & Cepko, "Wildespread Dispersion Of Neuronal Clones Across Functional Gegions Of The Cerebral Cortex", Science, 255:434–440 (1992).

Maurizi, et al., "Sequence and Structure of Clp P, the Proteolytic Component of the ATP–Dependent Clp Protease of Escherichia coli", *J. Biol. Chem.*, 265(21): 12536–45 (1990) (Abstract Only).

Stojilijkovik, et al., "Ethanolamine utilization in Salmonella typhurium: nucleotide sequence, protein expression, and mutational analysis of the cchA cchB eutE eutJ eutH gene cluster", *J. Bacteriol.*, 177(5)1357–66 (1995). (Abstract Only).

1 2 3 4 5 6 7 8 9 10 11 12

Inoculum pattern

Spleen pattern

Name: mpcc2 1
J05534 Escherichia coli ATP-dependent clp
protease proteolytic component (clpP) gene
complete cds. Length = 1236
Minus Strand HSPs:

Score = 453 (125.2 bits), Expect = 4.3e-28, P = 4.3e-28
Identities = 113/141 (80%), Positives = 113/141 (80%),
Strand = Minus

```
                  Query is our Salmonella sequence
Query:359 CCACCAGCCGCTGGGGTACCAGGGCCAGGCCGACGGATATTGA 318
          ||| | ||  ||||||||  || |||||||||||| ||||||||| |||||
Sbjct:785 CCAACCGTTGGGCGGCTACCAGGGCCAGGGACCGATATCGA 826
                                          c/pP gene
Query:317 AATTCACGCCCCGCGAAATTTTGAAAGTAAAAGGGCGCATGAA 276
          |||||| |||  ||| |||| |||||||||| || |||||||||||
Sbjct:827 AATTCATGCCCCGTGAAATTCTGAAAGTTAAAGGGCGCATGAA 867

Query:275 TGAACTTATGRMKYKMMATACGGGTCANTCTCTTGA 240
          |||||||||   ||    ||     ||||| ||  || ||
Sbjct:868 TGAACTTATGGCGCTTCATACGGGTCAATCATTAGA 904

Query:239 GCAGATTGAASGTGATACTGA 219
          ||||||||||| ||||| ||||| ||
Sbjct:905 ACAGATTGAACGTGATACCGA 925
```

```
Score = 231 (63.8 bits), Expect = 4.0e-24,
Poisson P(2) = 4.03-24
Identities = 55/66 (83%), Positives = 55/66 (83%),
Strand = Minus Query:194 TGAAGCGGTAGAGTACGGTTTGGTTTGACTCAATTTTGACCCA 154
          |||||||||  ||  ||||||  ||||  ||  ||  |||||||
Sbjct:950 TGAAGCGGTGGAATACGGTCTGGTCGATTCGATTCTGACCCA 990

Query:153 TCGTAATTGATGCCCCTGG 135
          |||||||||||||||||| |
Sbjct:991 TCGTAATTGATGCCAGAG 1009

Query:134 ACGCAA 129
          |||||
Sbjct:1010 GCGCAA 1015
```

FIG. 5C

>ECCLPXGNA Z23278 E.coli Clpx gene, complete CDS
     Length = 1945

Minus Strand HSPs:

Score = 364 (100.6 bits), Expect =1.6e-20, P =1.6e-20
  Identities = 88/107 (82%), Positives = 88/107 (82%),
  Strand = Minus

```
Query:325 GATATTGAAATTCACGCCCCGGCGAAATTTTGAAAGTAAAAGGG 285
          ||||  |||||||||| |||| ||| ||||| ||||||| |||||
Sbjct:  1 GATATCGAAATTCATGCCCGTGAAATTCTGAAAGTTAAAGGG 41

Query:284 CGCATGAATGAACTTATG 266
          ||||||||||||||||||
Sbjct: 42 CGCATGAATGAACTTATG 60

Query:265 RMKYKMMATACGGGTCANTCTCTTGAGCAGATTGAASGTGATACTGA 219
          |||||| ||||||||| || ||| |||||||||||  |||||||| |
Sbjct: 61 GCGCTTCATACGGGTCAATCATTAGAACAGATTGAACGTGATACCGA 107
```

FIG. 5D

```
Score = 231 (63.8 bits), Expect = 6.8e-24,
Poisson P(2) = 6.8e-24
Identities = 55/66 (83%), Positives = 55/66 (83%),
Strand = Minus Query:194 TGAAGCGGGTAGAGTACGGGTTTGGTTTGACTCAATTTTGACCCA 154
          ||||||||| || |||| |||| |||| ||| ||| ||||||| |||||
Sbjct:132 TGAAGCGGGTGGAATACGGTCTGGTCGATTCGATTCTGACCCA 172

Query:153 TCGTAATTGATGCCCCTGG 135
          ||||||||||||||||| |
Sbjct:173 TCGTAATTGATGCCAGAG 191

Query:134 ACGCAA 129
          |||||
Sbjct:192 GCGCAA 197

Fetch ──→ Gb_ba:Ecoc1ppa
                        - OK then type J Biol Chem 265, 12536
                          (1990)
```

A) new virulence factors with similarity to sequenced genes:
1. p1F10
similarity to *clpP* (*E. coli*)
(Figure 5)

2. p2D6
similarity to *lcrD* (*Yersinia spp.*)
sequence p2D6_1_I

GGTCTTAATGTACGGGCATGGTCTGCATCGATAACTCCGGCACGCAAATCG
CCATCGATACTCATTTGTTTGGCTGGCATCCCATCAAGCGAGAAACGTGCG
CTAACTTCCGCCACCCTCTCGATACCTTTTGTAATGACAATAAATTGCACG
ATAGTAATGATGGTAAATACGACCAACCCAACGGTGAGATTTCCTCCTACG
ACAAACTTACCGAAAGCATCCACAAATATTACCGGCATTATGTTGTAACAG
TACCCAGCCGTGATGTGCTGATTGGGGAGTTAACAACCGATTTAT 3. s4C3
probably same gene as p2D6, but different region
similarity to *S. typhimurium invA* and *Yersinia spp.lcrD*
sequence s4C3_1_U GCGCGGACGCTAGTGTGGTGGGTGACAGCCAGACGTTACCGAACGGGATGG
GGCAGATCTGTTGGCTTACAAAGACATGGCCCATAAGGCGCAAGGTTTTG
GGACTGGACGTTTTCGCGGGCAGACAACGTATCTCTGTCTTATTAAAATGT
GTCCTGCTTCGGCATATGTATCGAACCCTCGGAGCAAAGTCGTTTGGGCGC
AGAATTAGTACGTTTGGGTCGGTTGCTGTTATTCCTTGGGCTCGGAAAAAG
AGTGCCAGCGTGAAGGAGTGGGATTTGGCAGACTGGCCGCCTAAT sequence s4C3_1_R CACTATAGGGAAAGCTTGCATGCCTGCAGGTCGACTCTAGAGGATCTACTA
GTCATATGGATTGCACTTGTGTATAAGAGTCAGGATTAGAGGACATGCGCC
GGGAACCATACTATCTTTTCCGGTGCTTCGACGCCATTTGCGGAAACCAC
AGACTTTTTGCGGCGAATGAGGATAATTGGCAATGCTAACAACGCTGAAAA
GAAAGCGAGAGTGATAAAAGGAAAGCCAGGAATTAAAGCGAGGAGCATTAA
AACCACAGCGGCTAATATGAGCGACTGAGGTTGTCTGGCAATTTG

Figure 6A 4. p3F4
similarity to invG (S. typhimurium)
sequence p3F4_1_U

TGCAGGCCGACTCTAGAGGATCCCCGGGTACCGGTAATTTCTTTAACCTCG
CATCCCGGTGGATGAAAGGATATTCTGGCTGCGTAAGTAATGAATGAACCG
CCCAGTAGATAAATATTGAAAGTGATAACCTGATGTTTTAATAACGATGC
AGGATATACATATAACATGCTGGCATCAAACCAGGTAAGCAAATCATATTG
TGCTGCCAGGTTATTCAAACTATCGACCGGTGGTCCAGGCGGGAATTTTTC
CACTAAATGTAGGTGGGATCAATGGGCTAATTGGTATAGGCGGAT 5. p7G2
similarity to yscC (Yersinia spp.)
sequence p7G2_1_U CCTGTGATTCCGGATGAAATAGCTTTTACGAAAGCTGTCAGACNTGCTGAA
GAATACGCTGCAAATGGTAAGCTTGTAACTTTTGGGTATTGTTCCAACGCA
TGCTGAAACGGGTTATGGATATATTCGTCGCGGTGAGTTGATAGGAAATGA
CGCTTATGCAGTGGCTGAATTTGTGGAGAAACCGGATATCGATACCGCCCG
TGACTATTTCAAATCAGGGGAAATATTACTGGCCTAGCGGCGATGTTTTTA
TTTCGCGCAAAGCCCTTATTTAAACGAATTAAACGTATCTATCACCCCCAA
ATTCATACAGCTTGTGAA sequence p7G2_3_O TTACTAAACAGGGCCCCGGACCATGTAAACACCACGCTTGCCAACACTAAA
AAACGATGCTTGCCGTAAAAAAATTGAACGTTATTTACTTAATACGCCTAT
TTTATTTACATTATGCACGGACAGAGGGTGAGGATTAAATGGATAATATTG
ATAATAAGTATACTCCACAGCTATGTAAAATTTTGGGGGCTATATCGGATT
TGGTTGTTTTTAATTTAGCCTTATGGCTTTCACTAGGATGTGTCTATTTTT
TTTGTGGTCAAGCACAGAGATTTATTCCCCAACCACC sequence p7G2_1_I TTTCCTTGCCGTGACAGTCCGGGATGCGAGGTTAACGAAATTACCGGCACC
AAAGCTGTGGAGGTGAGCGGTGTCCCCAGCTGCCTGACTCGTATTAGTCAA
TTAGCTTCAGTGCTGGATAATGCGTTAATCAAACGAAAGACAGTGCGGTG
AGTGTAAGTATATACACGCTTAAGTATGCCACTGCGATGGATACCCAGTAC
CATTATCGCGATCAGTCCGTCGTGGTTCCAGGGGTCGCCTAGTGTATTGCG
TGAGATGAGTAACACCAGCGTCCCGACGTCATCGACGAACAATGG

Figure 6B 6. p9B7
similarity to *fliQ, invX (E. coli)*
sequence p9B7_1_I

CATGAGTAACCTACCCAACTGTAATCTTTACCAATATGCATCATAATCTTC
TGCTGGTAAATGATTGGTAATATCGGAAAGGTAAGTGACATAAGCACGCCA
TTACGTAAAAGTGCGGCCCCTAAACTGCCACTTTTTAATAAGGGAAGTAAT
AAAGAAAGGCTCAATGGTCGAATAAAAGCCACAGCCAATGCAATAAGCCAC
TCATTTACCTGTTGTGCCATTCAACCATGCTCTCCAATTCGTAACATTATC
TGCCGGGTATAATTCAACAGGATACCGCTAAGCCATGGGTAG sequence p9B7_3_O ATTCCAGCCCCCGGGCCATCTAACCACTATGAACAATCATCTTCTGGGTGG
ACAATCATTGGTACCATCGGCCAGGCTTGTGCAATATGTATGTCATCACGT
AAAAGCGCGGCCCCTTAATCTCCCCATTCTTCCTTAAGGGCAGTTATCACG
GCTGGCTCAATGGCCGGCTTAACAGCCACAG 7. s6F5
similarity to *yscU (Y. enterocolitica)*
sequence s6F5_1_O GAGGCGCGTCTTCGGTTGAGGGTCGCCCTCCAGATCTTTATGCTCCTGTTT
TACGTCATCTTTACTCATTTTAAGATCTTTTCTAATCTTATAATATTGAAA
AGAATAGTCCAGTATGCCAACGACGAAATAAAGAAACATCACCCCAACCCA
TAACCATTTTTTCAATGATGAAAGCACAAGCACGCCACAGGCTACACCACA
GCCCGGAGGGGCCGGAAAGTGCTGGATCTTGATTAATGAAAAGGCAAA
GGGAAGAGATAGGATGATGCATGCTGGTTGGAGGCAGATTATTCATCTTCG

Figure 6C

B) new sequences without similarity to entries in DNA or protein database:
1. s4D10
sequence s4D10_1_U AGTTGCCGTATTTATTAAATATTCACCTCAGGTCAATATGGAGGTCTTCCC
GGCTAAAAATCATTGCTTTACTAGAGATATCACTCCCTGGGTTGCAATACA
GTACGATTAGTTATCTTGATGCAGCCTGCTGATTTCAGAATGGCAGCTGAC
GTACCCGCGAGACAAACATTCTGGATTATGGACGTTATCAACGCCAATATA
GGGAAGGTGGTGAAGTGGTTGATGAAATACCCCTATCCCTTGCATGTTATC
GCTGACAGGACTGTTATCAGGAGCGGGCATCCTCGATCGGCT sequence s4D10_1_R CAAGAGACAGATCCAACTCGGGCCGATCGCCATAACGCCAGCAGTTTGAAA
GATGAAAGCCCAGCTTATCCAGCCATTCCGGTACAGCGTAACGAGCAGGTT
GCCAGAAATAACGATAAAGTTGCAACACCTCGGGATCAGGTCGGCTCAAAA
ACGGGTCTCAGGCAAAAATAGCCGATCAGGATGCCCACTCCTAATAACAG
TCCTGTCAACGATAACATCAACGGATAAGGGTATTTCATCAACCACTTCAC
CACCTTCCCTTTATTGGCGTTGGATAACGTCCATAATCCAGA 2. s4H10
sequence s4H10_1_U AGGGCTTTATTGATTCCATTTTTACACTGATGAATGTTCCGTTGCGCTGCC
CGGATTACAGCCGGATCCTCTAGAGTCGACCTGCAGAACCGAGCCAGGAGC
AAATTAATTTTTTGGGCAATTGCTGAAAGATGAAGCATCCACCAGTAACG
CCAGTGCTTTATTACCGCAGGTTATGTTGACCAGACAAATAGATTATATGC
AGTTAACGGTAGGCGTCGATTATCTTGTCAGAATATCAGGCGCAGCATCGC
AAGCGCTTAATAAGCTGGGTAACATGGCATGAAGGGGCAACCC sequence s4H10_1_R CACTATAGGGAAAGCTTGCATGCCTGCAGGTCGACTCTAGAGGATCTACTA
GTCATATGGATTCCTAGGCGGCCAGATCTGATCAAGAGACAGATCCAACTC
GGGCCGATCGCCATAACGCCAGCAGTTTGAAAGATGAAAGCCCAGCTTATC
CAGCCATTCCGGTACAGCGTAACGAGCAGGTTGCCAGAAATAACGATAAAG
TTGCAACACCTCGGGATCAGGTCGGCTCAAAAACGGGTCTCAGGCAAAAA
TAGCCGATCAGGATGCCCACTCCTAATAACAGTCCTGTCAACG

Figure 6D 3. p4G5
sequence p4G5_1_O

CCCCCCCCCTTCTCCTGGCTTACACAGCCCCAGACCGGCGCTGGAAAAGGC
CATTCCCGCCATACAGGAGGCCAGCAACATATTTTCACGCGCCGCCAGATC
GTGGCCGTAACCCACGGCTTTCGGCAGCGATTTGCCAATCATCGCTATCGC
GCCAATCGCCAGGCTGTCGGTAAACGGCGTGGCGTTGAGCGCGCTGTAGGC
CTCAATCGCATGCGTCAACGCATCGATACCGGTCATCGCCGTCACGTTTGG
CGGAACGCCTTCGGTCACGGAAGCATCAAGAATCGCCACGTCCGGC sequence p4G5_1_U CGCGAACGTGCGCCGCAACTGCTTGTGGACGGTGAATTGCAGTTTGACGCC
GCTTTCGTGCCGGAGGTCGCCGCGCAAAAGCGCCTGACAGCCCGCTGCAA
GGCCGCGCCAACGTGATGATTTTCCCGTCGCTGGAGGCGGGCAATATTGGC
TACAAAATCACTCAGCGTCTGGGAGGCTATCGCGCTGTTGGGCCGCTAATT
CAGGGGCTTGGCGCGCCGCTTCACGACCTCTCCCGAGGCTGTAGCGTGCAG
GAAATTATCGAACTGCGGTTGGTGAGAAAACCAA 4. p7A3
sequence p7A3_1_U CGCCCTAGCATGCCTGGCGTTGTCCGGTTATTGCTCGTCAAGCGAACAGAT
GCAAAAGGTGAGAGCGACTCTCGAATCATGGGGGGTCATGTATCGGGATGG
TGTAATCTGTGATGACTTATTGGTACGAGAAGTGCAGGATGTTTTGGATAA
AAATGGGTTACCCGCATGCTGAAGTATCCAGCGAAGGGCCGGGGAGCGTGT
TAATTCATGATGATATACAAATGGATCAGCAATGGCGCAAGGTTCAACCAT
TACTTGCAGATATTCCCGGGTTATTGCACTGGCAGATTAGTCACTCTC sequence p7A3_1_I CCCTTCCCAGGCTCGACAGGTACACAGCCAGCCACTGGTGCAGGCAGTTAC
TTGCTTTCATCATGGGAAGGAGCAATATCCTGATATATTAAAGAAAGAGCG
GGATCCCCTTTCTTTACTGCTGCTAACGTTTCTTGCAAAATGCGTTGATGA
GATTCATCCAGCACACCACTGATAACAAAAGAGCGCCGCATTGGCGTAACA
TTGACAAGCCCCACTAAACCGCTCTCTATTATCGCAGAAATAATATCATCC
CCCTGAGACTGATGAGAGTGACTATTCTGCCAGCGCAAATAACCC 5. p10E11
sequence p10E11_1

ATACCGAGTATTAAGCGGCTGTGTAACATCGTCATCCAACAACATACGCAG
CGAGCCGCCACGCCGGAAAAACCGCATCGTGTCATGTGCCTGTTGTAGGGT
CGGGTCTTTTTTCATGAGTACGTTTCTGCGCTATCATACTGGAAATTTCC
CCCCACTTACTGATAAGCCCTGTCAGTTGGGTAAGGACAGAGTTAAGCTCC
TGAGACATTTTTTGGAATGGTTATCTTTCCCCGACTCATAAAATCGGTATT
CCCGCTGGGGGCAATATCCAAGACGCTTTGGTCGCCCGTAGGGCACC

Figure 6E sequence p10E11_U

GCCGTATGCCTGCAGTTGCCCGGTTATTGCTCGTCAAGCGAACCGATGCCA
AAGGTGAGAGCGACTCTCGAATCATGGGGGGTCATGTATCGGGATGGTGTA
ATCTGTGATGACTTATTGGTACGAGAAGTGCAGGATGTTTTGGTAAAAATG
GGTTACCCCCATGCTGAAGTATCCAGCGAAGGGGCGGGGAGCGTGTTAATT
CACGATGATATTCAAATGGGTCAGCAATGGGGCAAGGTTCAACCCCCACTT
GCAGATATTCCCCCCCCTATTGGACTGGCAGATTAGTCACTCTCA 6. s4B9
sequence s4B9_1_O GGGCGACCTGCCCGCGGCGCAACTTTCCCCGAAGCGTTTTCCATTTCCTTG
TTCTTAAATGACCTGGAAAGCTTACCTAAGCCTTGTCTTGCCTATGTGACA
ATACTGCTTGGAGAACACCCGGACGTCCATGATTATGCTATACAGATCACA
GCGGATGGGGATGGTGAATCGGTTATTATACCACAAGTCGCAGCTCTGAG
CTTATTGCTATTGAGATAGAAAAACACCCCGCTTCAACTTGGATTTTGAAT
AATGTAATACGCAATCACCATACACTATATTCGGGTGGCGTATAA sequence s4B9_1_R TTCGAGCTGGGGCACCGCTAATATCTTTAACCTCGCATCCCGGTGATGAAA
GGATATTCTGGCTGCGTAAGTAATGAATGAACCGCCCAGCAGATAAAATAT
TGACAGTGATAACCCGATGTTTTTTAACGATGCAGGCTATACATATAACA
TAGCTGGCCACCAACACAGCTGAAGTAAATCATATTGTTGCTGCCAGGCTA
CTTCACACTATTGTCCGGCGGGCCAGCGGGGATTTTCCCCCTAAATCTCGC
TGGTTCTCAAA 7. p4F8
sequence p4F8_1_I AGTCTACGATTTCGCTATATCTTCTCTTAATCATGGCCGCCATTTGTGGAT
GCGATTTTAAAATATCCGGGCGATCTTTCATTAAAAAATAAAGATTCCCCA
TGACTTCACAGATAAAGGTATCGGTATTTGAGTGATACGTAACAATTCGT
TCTCTTCGTGTGGGTCCATGATGCGAAGAATAATGGTGGCATCATTTTCAT
GAGGATTATGAACCCGAAATCTTTCTCTTTGCGATGCGCAGGCTAACTCTT
TCAACTCAAAAAAAATCTCTGTAAGCCGCTCTCGTGTGGGGCGC 8. p7B8
sequence p7B8_1_O GCGCCCCTTTAATTGGTTGAGGCGGCTGGTATTCTTGTAAGGGTAATACTA
GCGAGACCCAGGTTCCACCCCCGGGGACACTTTTTAGTGTCAGATTACCGC
CCATCATTTTAGCCAGGCTTGACGCAATAGTCAGTCCAATTCCTGTACCTT
GCGAATTTGTGTCTGCTTGATAAAAGCAGAAAAGATTTGAGACTGCTGCT
GTTTTTCAATCCCCCCACCGCTATCGCTAACCAGAAATATTAATTGTTCCT
CACCAAGATTGAGCGCCAGACGTATCCCTCCCCCCTCGGGAAAT

Figure 6F 9. p8G12
sequence p8G12_1_I

GGATAAGATCCCGGATAAGTATGTCAGGCTCGTATGCACAACAGGCATTAT
AAACCTCTAGACCATTTTTAACATGCTCTACTATTTTAAAATGAGGCCAGG
GTAATAAGGCATTCATAATGCCGTTAATGATGATTTCATGATCGTCTACTA
ATAAGATCTTATATTCTTTCATTTGGCTGCCCTCGCGAAAATTAAGATAAT
ATTAAGTAATGGTGTAGGTTGTGGAGATCATACGTATTTTCTGGCGTAAGT
CGGTTAGTTCCTCCAGCGCGATGATTTTCCCCATTTTTACGCGAT 10. p9G4
sequence p9G4_1_O TTCCATATTGCTCGTCCGGGGAGCGTGTTAATTCTTGATGATATACCAATG
GATCTGCAATGGCGCAAGGTTCAACCATTACTTGGAGATATTCCCGGGTTA
TTGTACTGGGAGATTAGTCACTCTCATCAGTCTCAGGGGGGTGATGTTATT
TCTGGGATAATAGAGCAACGGCGTTAGCAGGGGTCGGTCAGTAGTCACGGC
CAACTTCGGTGCACTTTTGCGTATCACTGGGGTATCATAACTGAATCTCAT
CCCCCCCACTTTGGTAATCACAC sequence p9G4_1_U AATTCTTTTACCTCCATAAGCTGCGTGGCATAGCGATACAGAGTATTAAGC
GGGTGTGTTACATCGTCATCCAACAACATACGCAGCGAGCCGCCACGCCGG
AAAAACCGCATCGTGTCATGTGCCTGTTGTAGGGTCGGGTCTTTTTTTCAT
GAGTACGTGTTCTGCGCTATCATACTGGAAATTTCCCCCACTTACTGATA
AGCCCTGTCAGTTGGGTAAGGACAGCGTTAAGCTCCTGAGACATTTTTGA
GTTGTTATCTGCCCCCCGACTCATAAGATCGGGTATTCCGCGGTGG 11. p9B6
sequence p9B6_1

ATATCCCTAATGCTTTTCCTTAAAATAAATACCACGGAAGGATACTGGCCA
CCTAGCCAAATTTAGAAAGCAATGAACATCCGGTTTATTCCTGAAAACGAT
TACTCCGGCGCACGTTGTTCTGGCGTTACCTGAGCCAGCAAACGATATAAT
GGGGTGGTGACCCGCATACCGGTCATTGGCATCCATCCACACCGGAGGGA
GTAAAACTCATTAGGCCATAGGTAATATCATTAAGACGCTCTAATAAATGA
GGGTGGGGGGCCCAAACTACCACTCCAGTATGTATTGAGTCA

Figure 6G 12. p6G5
sequence p6G5_2_I

```
CCCATGGGCGCAATTTGTTGCGCAGCGTTTACCCGACCATCGCGTTTATGA
GCTGTAATTCATGGGGGGTAAAAACGGGCGTGACGACCCCAACGGAAGATA
AGGCCGGGCTTAAACAGGAGATTATTGCTAATGCGCAGCGCAAAGTGTTGC
TGGCGGACAGCAGTAAGTATGGCGCGCATTCGCTCTTTAATGTGGTGCCGC
TTGAGCGCTTTAATGACGTGATTACCGACGTCAATCTGCCGCCGTCAGCGC
AGGTTGAACTGAAAGGGCGCGCTTTTTGCGCTAACG
```

Figure 6H

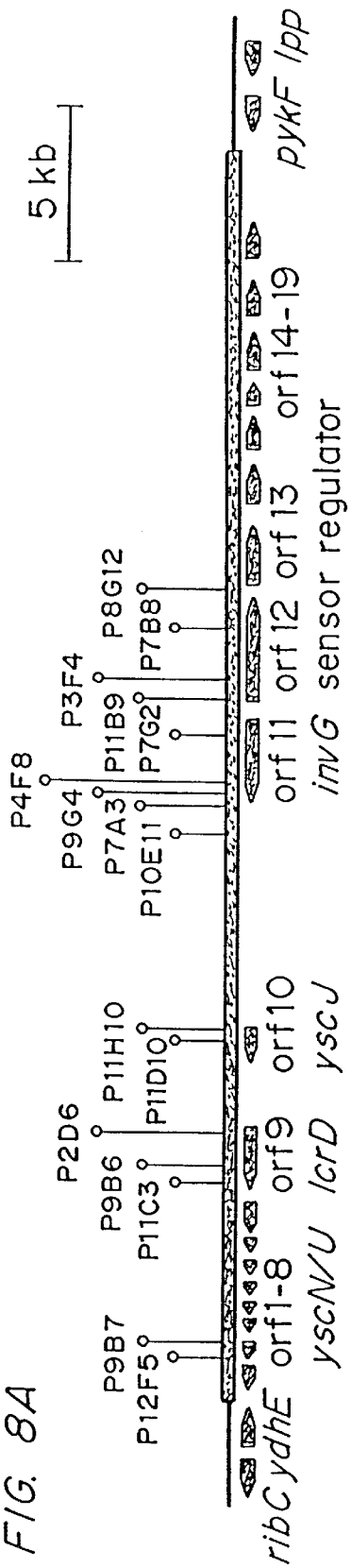
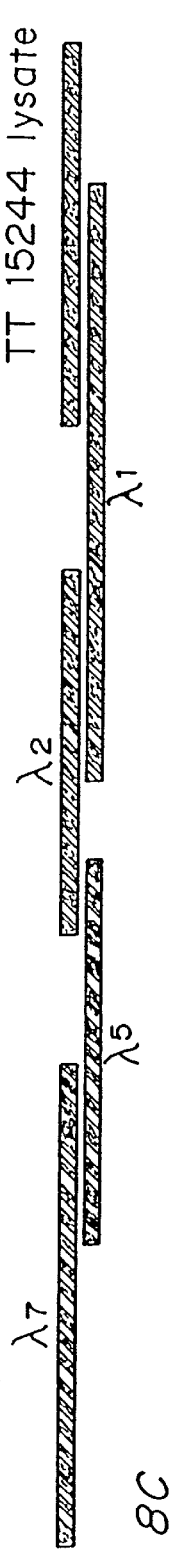
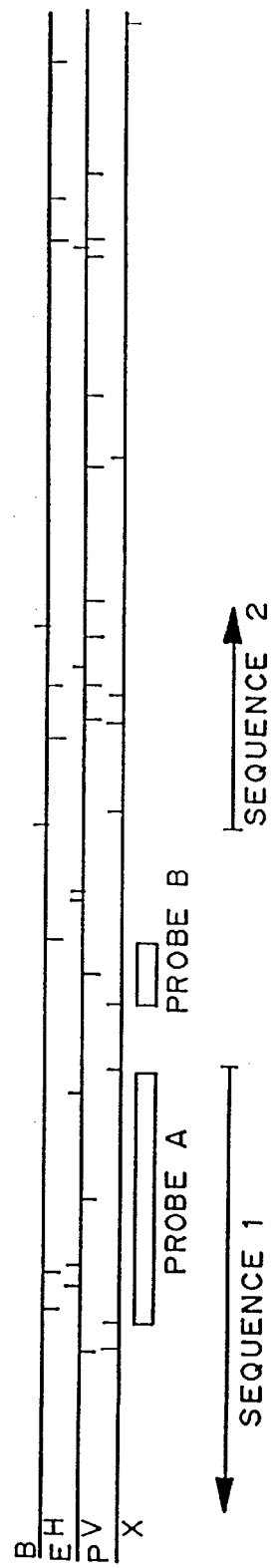
FIG. 8A
FIG. 8B
FIG. 8C

DNA sequence of VGC II from centre to left hand end

```
    CTGCAGAACCGAGCCAGGAGCCAGGAGCAAATTAATTTTTTGAACAATTGCTGAAAGATGAAGCAT      60
1   ---------+---------+---------+---------+---------+---------+
    GACGTCTTGGCTCGGTCCTCGGTCCTCGTTTAATTAAAAAACTTGTTAACGACTTTCTACTTCGTA
a     L  Q  N  R  A  R  S  K  L  I  F  L  N  C  -  K  M  K  H
b   C  R  T  E  P  G  A  N  -  F  F  -  T  I  A  E  R  -  S  I
c     A  E  P  S  Q  E  Q  I  N  F  F  E  Q  L  L  K  D  E  A  S

CCACCAGTAACGCCAGTGCTTTATTACCGCAGGTTATGTTGACCAGACAAATGGATTATA          120
61  ---------+---------+---------+---------+---------+---------+
    GGTGGTCATTGCGGTCACGAAATAATGGCGTCCAATACAACTGGTCTGTTTACCTAATAT
a     P  P  V  T  P  V  L  Y  Y  R  R  L  C  -  P  D  K  W  I  I
b   H  Q  -  R  Q  C  F  I  T  A  G  Y  V  M  L  T  R  Q  M  D  Y  M
c     T  S  N  A  S  A  L  L  P  Q  V  M  L  T  R  Q  M  D  Y  M

TGCAGTTAACGGTAGGCGTCGATTATCTTGCCAGAATATCACGGCCAGCATGCCAAGCG         180
121 ---------+---------+---------+---------+---------+---------+
    ACGTCAATTGCCATCCGCAGCTAATAGAACGGTCTTATAGTGCCGGTCGTACGGTTCGC
a     C  S  -  R  -  A  S  I  I  L  P  E  Y  H  G  A  A  C  Q  A
b   A  V  N  G  R  R  R  L  S  C  Q  N  I  T  A  Q  H  A  K  R
c     Q  L  T  V  G  V  D  Y  L  A  R  I  S  R  R  S  M  P  S  A
```

Figure 11A

```
181  CTTAATAAGCTGGATAACATGGCATGAAGGTTCATCGTATAGTATTTCTTACTGTCCTTA
     ------------+------------+------------+------------+------------+------------+  240
     GAATTATTCGACCTATTGTACCGTACTTCCAAGTAGCATATCATAAAGAATGACAGGAAT a       L  N  K  L  D  N  M  A  -  R  F  I  V  -  Y  F  L  L  S  L
b       L  I  S  W  I  T  W  H  E  G  S  S  Y  S  I  S  Y  C  P  Y
c       -  -  A  G  -  H  G  M  K  V  H  R  I  V  F  L  T  V  L  T

241  CGTTCTTTTCTTACGGCATGTGATGTGGATCTTTATCGCTCATTGCCAGAAGATGAAGCGA
     ------------+------------+------------+------------+------------+------------+  300
     GCAAGAAAGAATGCCGTACACTACACCTAGAAATAGCGAGTAACGGTCTTCTACTTCGCT
                              start yscJ*?
a       R  S  F  L  R  H  V  M  W  I  F  I  A  H  C  Q  K  M  K  R
b       V  L  S  Y  G  M  -  C  G  S  L  S  L  I  A  R  R  -  S  E
c       F  F  L  T  A  C  D  V  D  L  Y  R  S  L  P  E  D  E  A  N 301  ATCAAATGCTGGCATTACTTATGCAGCATCATATTGATGCGAAAAAAACAGGAAGAGGA
     ------------+------------+------------+------------+------------+------------+  360
     TAGTTTACGACCGTAATGAATACGTCGTAGTATAACTACGCTTTTTTTTGTCCTTCTCCT
                                              start yscJ*?
a       I  K  C  W  H  Y  L  C  S  I  I  L  M  R  K  K  T  G  R  G
b       S  N  A  G  I  T  Y  A  A  S  Y  -  C  E  K  K  Q  E  E  D
c       Q  M  L  A  L  L  M  Q  H  H  I  D  A  K  K  N  R  K  R  M
```

Figure 11B

```
361  TGGTGTAACCTTACGTGTGAGCAGTCGGCAGTTTATTAATGCGGTTGAGGCTACTTAGA  420
     ----+----|----+----|----+----|----+----|----+----|----+----|
     ACCACATTGGAATGCACAGCTCGTCAGCCGTCAAATAATTACGCCAACTCCGATGAATCT a     W  C  N  L  T  C  R  A  V  G  S  L  L  M  R  L  R  L  L  R
b     G  V  T  L  R  V  E  Q  S  S  R  Q  F  I  N  A  V  E  A  T  -
c     V  -  P  Y  V  S                               C  G  -  G  Y  L  D   T

421  CTTAACGGTTATCCGCATAGGGCAGTTTACAACGGGGATAAGATGTTTCCGGCTAATCA  480
     ----+----|----+----|----+----|----+----|----+----|----+----|
     GAATTGCCAATAGGCGTATCCCGTCAAATGTTGCCCTATTCTACAAAGGCCGATTAGT a     L  N  G  Y  P  H  R  A  V  Y  N  G  G  -  D  V  S  G  -  S
b     L  T  V  I  R  I  G  Q  F  T  T  A  D  K  M  F  P  A  N  Q
c     -  R  L  S  A  -  G  S  L  Q  R  R  I  R  C  F  R  L  I  S

481  GTTAGTGGTATCACCCCAGGAAGAACAGGGAAGATTAATTTTTAAAAGAACAAAGAA  540
     ----+----|----+----|----+----|----+----|----+----|----+----|
     CAATCACCATAGTGGGGTCCTTCTTGTCCGTCTTCTAATTAAAAATTTTCTTGTTTCTT a     V  S  G  I  T  P  G  R  T  G  R  R  L  I  F  -  K  N  K  E
b     L  V  V  S  P  Q  E  E  Q  A  E  D  -  F  F  K  R  T  K  N
c     -  W  Y  H  P  R  K  N  R  Q  K  I  N  F  L  K  E  Q  R  I
```

Figure 11C

```
541  TTGAAGGAATGCTGAGTCAGATGGAGGGCGTGATTAATGGCAAAAGTGACCATTGCGCT
     ----------+---------+---------+---------+---------+---------+  600
     AACTTCCTTACGACTCAGTCTACCTCCCCGCACTAATTACCGTTTTCACTGGTAACGCGA a      L  K  E  C  -  V  R  W  R  G  V  I  N  G  K  S  D  H  C  A
b    -  R  N  A  E  S  D  G  G  A  -  L  M  A  K  V  T  I  A  L
c      E  G  M  L  S  Q  M  E  G  R  D  -  W  Q  K  -  P  L  R  Y

601  ACCGACTTATGATGAGGGAAGTAACGCTTCTCCGAGCTCAGTTGCCGTATTTATAAAATA
     ----------+---------+---------+---------+---------+---------+  660
     TGGCTGAATACTACTCCCTTCATTGCGAAGAGGCTCGAGTCAACGGCATAAATATTTTAT a      T  D  L  -  G  K  -  R  F  S  E  L  S  C  R  I  Y  K  I
b      P  T  Y  D  E  G  S  N  A  S  P  S  S  V  A  V  F  I  K  Y
c      R  L  M  M  R  E  V  T  L  L  R  A  Q  L  P  Y  L  -  N  I

661  TTCACCTCAGGTCAATATGGAGGCCTTTCGGGTAAAAATTAAAGATTTAATAGAGATGTC
     ----------+---------+---------+---------+---------+---------+  720
     AAGTGGAGTCCAGTTATACCTCCGGAAAGCCCATTTTTAATTTCTAAATTATCTCTACAG a      F  T  S  G  Q  Y  G  G  L  S  G  K  N  -  R  F  N  R  D  V
b    S  P  Q  V  N  M  E  A  F  R  V  K  I  K  D  L  I  E  M  S
c      H  L  R  S  I  W  R  P  F  G  -  K  L  K  I  -  -  R  C  Q
```

Figure 11D

```
721  AATCCCTGGGTTGCAATACAGTAAGATTAGTATCTTGATGCAGCCTGCTGAATTCAGAAT     780
     ----+----+----+----+----+----+----+----+----+----+----+----+
     TTAGGGACCCAACGTTATGTCATTCTAATCATAGAACTACGTCGGACGACTTAAGTCTTA a     N  P  W  V  A  I  Q  -  D  -  Y  L  D  A  A  C  -  I  Q  N
b     I  P  G  L  Q  Y  S  K  I  S  I  L  M  Q  P  A  E  F  R  M
c     S  L  G  C  N  T  V  R  L  V  S  -  C  S  L  L  N  S  E  W

781  GGTAGCTGACGTACCCGCGAGACAAACATTCTGGATTATGGACGTTATCAACGCCAATAA     840
     ----+----+----+----+----+----+----+----+----+----+----+----+
     CCATCGACTGCATGGGCGCTCTGTTTGTAAGACCTAATACCTGCAATAGTTGCGGTTATT a     G  S  -  R  T  R  E  T  N  I  L  D  Y  G  R  Y  Q  R  Q  -
b     V  A  D  V  P  A  R  Q  T  F  W  I  M  D  V  I  N  A  N  K
c     -  L  T  Y  P  R  D  K  H  S  G  L  W  T  L  S  T  P  I  K

841  AGGGAAGGTGGTGAAGTGGTTGATGAAATACCCTTATCCGTTGATGTTATCGTTGACAGG     900
     ----+----+----+----+----+----+----+----+----+----+----+----+
     TCCCTTCCACCACTTCACCAACTACTTTATGGGAATAGGCAACTACAATAGCAACTGTCC a     R  E  G  G  E  V  V  D  E  I  P  L  S  V  D  V  I  V  D  R
b     G  K  V  V  K  W  L  M  K  Y  P  Y  P  L  M  L  S  L  T  G
c     G  R  W  -  S  G  -  N  T  L  I  R  -  C  Y  R  -  Q  D
```

Figure 11E

```
                    Tn insertion P11H11
                         ⇩
      ACTGTTATTAGGAGTGGGCATCCTGATCGGCTATTTTTGCCTGAGACGCCGTTTTGAGC
      ------------+---------+---------+---------+---------+---------+   960
      TGACAATAATCCTCACCCGTAGGACTAGCCGATAAAAACGGACTCTGCGGCAAAAACTCG

901 a      T V I R S G H P D R L F F L P E T P F L S
b        L L G V G I L I G Y F C L R R R F - A
c          C Y - E W A S - S A I F A - D A V F E P

CGACCTGATCCCGAGGTGTTGCAACTTTATCGTTATTTCTGGCAACCTGCTCGTTACGCT
      ------------+---------+---------+---------+---------+---------+   1020
      GCTGGACTAGGGCTCCACAACGTTGAAATAGCAATAAAGACCGTTGGACGAGCAATGCGA

961 a      R P D P E V L Q L Y R Y F W Q P A R Y A
b        D L I P R C C N F I V I S G N L L V T L
c          T - S R G V A T L S L F L A T C S L R C

Tn insertion P11D10
                                                    ⇩
      GTACCGGAATGGCTGGATAAGCTGGGCTTTCATCTTCAAACTGCTGGCCGTTATGGCGATC
      ------------+---------+---------+---------+---------+---------+   1080
      CATGGCCTTACCGACCTATTCGACCCGAAAGTAGAAGTTTGACGACCGGCAATACCGCTAG

```
1081 GGCCCGAGTTGGATCGTCTCTTGACAGAGCCGTTAAATAGACTAAGAGGAAGCTCTGTTA 1140
     ----+----+----+----+----+----+----+----+----+----+----+----+
     CCGGGCTCAACCTAGCAGAGAACTGTCTCGCAATTTATCTGATTCTCCTTCGAGACAAT a   G  P  S  W  I  V  F  L  T  E  R  -  I  D  -  E  E  A  L  L
   b   A  R  V  G  S  S  -  Q  S  V  K  -  T  K  R  K  L  C
   c   P  E  L  D  R  L  L  D  R  A  L  N  R  L  R  G  S  S  V  I

1141 TTCCAGCCTGTTAAATGACAGGCAAAAACGGCAGGTTCGTCTTGCGCCGCGTATATCGG 1200
     ----+----+----+----+----+----+----+----+----+----+----+----+
     AAGGTCGGACAATTTACTGTCCGTTTTTGCCGTCCAAGCAGAACGCGGCGCATATAGCC a   F  Q  P  V  -  M  T  G  K  N  G  R  F  V  L  R  R  V  Y  R
   b   S  S  L  F  K  -  Q  A  K  T  A  G  S  S  C  A  A  Y  I  G
   c   P  A  C  L  N  D  R  Q  K  R  Q  V  R  L  A  P  R  I  S  A

1201 CATTTGCCTTTGGGCTGGGATTATTCAAACTCAGGTGTAGTGACTATTTTATGCTACCAG 1260
     ----+----+----+----+----+----+----+----+----+----+----+----+
     GTAAACGGAAACCCGACCCTAATAAGTTTGAGTCCACATCACTGATAAAATACGATGGTC a   H  L  P  L  G  W  D  Y  S  N  S  G  V  V  -  L  F  Y  A  T  R
   b   I  C  L  W  A  G  I  I  Q  T  Q  V  -  L  F  Y  A  T  R
   c   F  A  F  G  L  G  L  F  K  L  R  C  S  D  Y  F  M  L  P  E
``` start lcrE*?

Figure 11G

```
1261   AGTATCGGCAATTGCTTCTACAGTGGTTTAGCGAGGATGAGATCTGGCAGCTATATGGTT
       ----+----+----+----+----+----+----+----+----+----+----+----+  1320
       TCATAGCCGTTAACGAAGATGTCACCAAATCGCTCCTACTCTAGACCGTCGATATACCAA a        S  I  G  N  C  F  Y  S  G  L  A  R  M  R  S  G  S  Y  M  V
b        V  S  A  I  A  S  T  V  V  -  R  G  -  D  L  A  A  I  W  L
c        Y  R  Q  L  L  Q  W  F  S  E  D  E  I  W  Q  L  Y  G  W

1321   GGTTGGGGCAAAGAGAGATGGCAAATTACTTCCTCCGCAAGTGATGCAACAAACTGCATTGC
       ----+----+----+----+----+----+----+----+----+----+----+----+  1380
       CCAACCCCGTTTCTCTCTACCGTTTAATGAAGGAGGCGTTCACTACGTTGTTTGACGTAACG a        G  W  G  K  E  M  A  N  Y  F  L  R  K  -  C  N  K  L  H  C
b        V  G  A  K  R  D  G  K  L  L  P  P  Q  V  M  Q  Q  T  A  L  Q
c        L  G  Q  R  D  G  K  L  L  P  P  Q  V  M  Q  Q  T  A  L  Q

1381   AGATCGGTACCGCCATTCTTAATCGGGAAGCGCATGACGATGCGGGTTTTACATGCGCTA
       ----+----+----+----+----+----+----+----+----+----+----+----+  1440
       TCTAGCCATGGCGGTAAGAATTAGCCCTTCGCGTACTGCTACGCCCAAAATGTACGCGAT a        R  S  V  P  P  F  L  I  G  K  R  M  T  M  R  V  L  H  A  L
b        D  R  Y  R  H  S  -  S  G  S  A  -  R  C  G  F  Y  M  R  Y
c        I  G  T  A  I  L  N  R  E  A  H  D  D  A  G  F  T  C  A  I
```

Figure 11H

```
1441  TTAGTATTATTACCCCCTCCGCAGCCGTATACTTTGGCCGAAGACTTCTCTTACCGAGATT
      ------+---------+---------+---------+---------+---------+  1500
      AATCATAATAATGGGGGAGGCGTCGCATATGAAACCGGCTTCTGAAGAGAATGCTCTAA a       L  V  L  L  P  P  P  Q  R  I  L  W  P  K  T  S  L  T  E  I
b       -  Y  Y  Y  P  L  R  S  V  Y  F  G  R  R  L  L  P  R  L
c       S  I  I  T  P  S  A  A  Y  T  L  A  E  D  F  S  Y  R  D  Y

1501  ATCTTCATGGAGCATTTGCTATGAGTTTTACTTCCACTTCCTCTGACGGAAATTAACCATA
      ------+---------+---------+---------+---------+---------+  1560
      TAGAAGTACCTCGTAAACGATACTCAAAATGAAGGTGAAGGAGACTGCCTTTAATTGGTAT a       I  F  M  E  H  L  L  -  V  L  L  H  F  L  -  R  K  L  T  I
b       S  W  S  I  C  Y  E  F  Y  F  T  S  S  D  G  N  -  P  -
c       L  H  G  A  F  A  M  S  F  T  S  L  P  L  T  E  I  N  H  K

1561  AGCTACCCGCTCGAAATATTATTGAGTCACAGTGGATAACATTACAATTAACTTTATTTG
      ------+---------+---------+---------+---------+---------+  1620
      TCGATGGGCGAGCTTTATAATAACTCAGTGTCACCTATTGTAATGTTAATTGAAATAAAC a       S  Y  P  L  E  I  L  L  S  H  S  G  -  H  Y  N  -  L  Y  L
b       A  T  R  S  K  Y  Y  -  V  T  V  D  N  I  T  I  N  F  I  C
c       L  P  A  R  N  I  E  S  Q  W  I  T  L  Q  L  T  L  F  A
```

Figure 11I

```
1621  CGCAAGAGCAACAAGCTAAGAGAGTTTCACATGCTATTGTGAGCTCCGCTTACCGTAAGG  1680
      ----------+---------+---------+---------+---------+---------+
      GCGTTCTCGTTGTTCGATTCTCTCAAAGTGTACGATAACACTCGAGGCGAATGGCATTCC a       R  K  S  N  K  L  R  E  F  H  M  L  L  -  A  P  L  T  V  R
b       A  R  A  T  S  -  E  S  F  T  C  Y  C  E  L  R  L  P  -  G
c       Q  E  Q  Q  A  K  R  V  S  H  A  I  V  S  S  A  Y  R  K  A

1681  CTGAAAAATCATCCGAGACGCCTATCGTTATCAGCGTGAACAGAAAGTTGAGCAGCAAC  1740
      ----------+---------+---------+---------+---------+---------+
      GACTTTTTAGTAGGCTCTGCGGATAGCAATAGTCGCACTTGTCTTTCAACTCGTCGTTG a       L  K  K  S  S  E  T  P  I  V  I  S  V  N  R  K  L  S  S  N
b       -  K  N  H  P  R  R  L  S  L  S  A  -  T  E  S  -  A  A  T
c       E  K  I  R  D  A  Y  R  Y  Q  R  E  Q  K  V  E  Q  Q  Q

1740  AAGAACTAGCCGTGCTTGCCGTAAAAAATACGCTGGAAAAAATGGAAGTGGAATGGCTGGAAC  1800
      ----------+---------+---------+---------+---------+---------+
      TTCTTGATCGCACGAACGCATTTTTATGCGACCTTTTTTACCTTCACCTTACCGACCTTG a       K  N  -  R  A  C  V  K  I  R  W  K  K  W  K  W  N  G  W  N
b       R  T  S  V  L  A  -  K  Y  A  G  K  K  N  G  S  G  M  A  G  T
c       E  L  A  C  L  R  K  N  T  L  E  K  M  E  V  E  W  L  E  Q
```

Figure 11J

```
1801 AGCATGTAAAACATTTACAAGACGATGAAAATCAATTTCGTTCATTGGTCGATCACGCAG 1860
     ----+----+----+----+----+----+----+----+----+----+----+----+
     TCGTACATTTTGTAAATGTTCTGCTACTTTTAGTTAAAGCAAGTAACCAGTAGTGCGTC a    S  M  -  N  I  Y  K  T  M  K  I  N  F  V  H  W  S  I  T  Q
  b    A  C  K  T  F  T  R  R  -  K  S  I  S  F  I  G  R  S  R  S
  c    H  V  K  H  L  Q  D  D  E  N  Q  F  R  S  L  V  D  H  A  A

1861 CGCATCATATTAAAAATAGTATAGAACAGGTTCTGTTGGCCTGTTCGACCAACAGTCGG 1920
     ----+----+----+----+----+----+----+----+----+----+----+----+
     GCGTAGTATAATTTTTATCATATCTTGTCCAAGACAACCGGACCAAGCTGGTTGTCAGCC a    R  I  I  L  K  I  V  -  N  R  F  C  W  P  G  S  T  N  S  R
  b    A  S  Y  -  K  -  Y  R  T  G  S  V  G  L  V  R  P  T  V  G
  c    H  H  I  K  N  S  I  E  Q  V  L  L  A  W  F  D  Q  Q  S  V

1921 TAGACAGTGTTATGTGCCATCGTCTGGCACCAGGCCACGGCCTATGGCGAAGAGGGAG 1980
     ----+----+----+----+----+----+----+----+----+----+----+----+
     ATCTGTCACAATACACGGTAGCAGACCGTGCGGTCCGGTGCCGATACCGCCTTCTCCCTC a    -  T  V  L  C  A  I  V  W  H  A  R  P  R  L  W  R  K  R  E
  b    R  Q  C  Y  V  P  S  S  G  T  P  G  H  G  Y  G  G  R  G  S
  c    D  S  V  M  C  H  R  L  A  R  Q  A  T  A  M  A  E  E  G  A
```

```
1981  CGCTTTATTTGCGTATTCATCCTGAAAAAGAGGCATTGATGCGAGAAACTTTTGGCAAGC
      ----------+---------+---------+---------+---------+---------+ 2040
      GCGAAATAAACGCATAAGTAGGACTTTTTCTCCGTAACTACGCTCTTTGAAAACCGTTCG a      R  F  I  C  V  F  I  L  K  K  R  H  -  C  E  K  L  L  A  S
b      A  L  F  A  Y  S  S  -  K  R  G  I  D  A  R  N  F  W  Q  A
c      L  Y  L  R  I  H  P  E  K  E  A  L  M  R  E  T  F  G  K  R

2040  GGTTTACGTTGATTATCGAGCCTGGTTTCTCCCGATCAGGCTGAACTTTCCTCAACAC
      ----------+---------+---------+---------+---------+---------+ 2100
      CCAAATGCAACTAATAGCTCGGACCAAAGAGAGGGCTAGTCCGACTTGAAAGGAGTTGTG a      G  L  R  -  L  S  S  L  V  S  L  P  I  R  L  N  F  P  Q  H
b      V  Y  V  D  Y  R  A  W  F  L  S  R  S  G  -  T  F  L  N  T
c      F  T  L  I  E  P  G  F  S  P  D  Q  A  E  L  S  S  T  R

2101  GATATGCCGTTGAATTTTCACTTTCTCGTCATTTCAACGCGTTACTGAAATGGTTACGTA
      ----------+---------+---------+---------+---------+---------+ 2160
      CTATACGGCAACTTAAAAGTGAAAGAGCAGTAAAGTTGCGCAATGACTTTACCAATGCAT a      D  M  P  L  N  F  H  F  L  V  I  S  T  R  Y  -  N  G  Y  V  -
b      I  C  R  -  I  F  T  F  S  S  F  Q  R  V  T  E  M  V  T  -
c      Y  A  V  E  F  S  L  S  R  H  F  N  A  L  L  K  W  L  R  N
```

Figure 11M

```
      ATAGGAATGGCGCTGAGTGGTAAACTGCGCGAAAATTATAAATTCACTGATGCTGAGAAA
2341  ------+---------+---------+---------+---------+---------+ 2400
      TATCCTTACCGCGACTCACCATTTGACGCGCTTTTAATATTTAAGTGACTACGACTCTT a      I  G  M  A  L  S  G  K  L  R  E  N  Y  K  F  T  D  A  E  K
b         E  W  R  -  V  V  N  C  A  K  I  I  N  S  L  M  L  R  N
c         R  N  G  A  E  W  -  T  A  R  K  L  -  I  H  -  C  -  E  T

CTGGAGCGCAGACAGCAGGCTTTGCTGCGTTTGATAAACAAATACAGGAGGATAATGGG
2401  ------+---------+---------+---------+---------+---------+ 2460
      GACCCTCGCGTCTGTCGTCCGAAACGACGCAAACTATTTGTTTATGTCCTCCTATTACCC a      L  E  R  R  Q  Q  A  L  L  R  L  I  K  Q  I  Q  E  D  N  G
b         W  S  A  D  S  R  L  C  C  V  -  -  N  K  Y  R  R  I  M  G
c         G  A  Q  T  A  G  F  A  A  F  D  K  T  N  T  G  G  -  W  G

GCAACGTTGCGTCCGCTTACCGAAGAGAATAGTGATCCTGATTTACAGAATGCGTATCAA
2461  ------+---------+---------+---------+---------+---------+ 2520
      CGTTGCAACGCAGGCGAATGGCTTCTCTTATCACTAGGACTAAATGTCTTACGCATAGTT a      A  T  L  R  P  L  T  E  E  N  S  D  P  D  L  Q  N  A  Y  Q
b         Q  R  C  V  R  L  P  K  R  R  E  -  S  -  F  T  E  C  V  S  N
c         N  V  A  S  A  Y  R  R  E  -  -  S  -  F  T  E  C  V  S  N
```

Figure 11N

```
        ATTATCGCTCTTGCAATGGCGCTTACTGCCGGGGTTGTCAAAAAGAAAAAACGCGAT
2521    ------+---------+---------+---------+---------+---------+  2580
        TAATAGCGAGAACGTTACCGCGAATGACGGCCCCAACAGTTTTTCTTTTTGCGCTA a        I  I  A  L  A  M  A  L  T  A  G  G  L  S  K  K  K  R  D
b        L  S  L  L  Q  W  R  L  L  P  A  G  C  Q  K  R  K  N  A  I
c           Y  R  S  C  N  G  A  Y  C  R  R  V  V  K  K  E  K  T  R  F

TTGCAATCGCAACTGGATACGTTACAGCGGAGGAGGGATGGGAACTTGCCGTTTTAGTT
2581    ------+---------+---------+---------+---------+---------+  2640
        AACGTTAGCGTTGACCTATGCAATGTCGCCTCCTCCCTACCCTTGAACGGCAAAAATCAA a        L  Q  S  Q  L  D  T  L  Q  R  R  R  D  G  N  L  P  F  L  V
b          C  N  R  N  W  I  R  Y  S  G  G  M  G  T  C  R  F  -  F
c        A  I  A  T  G  Y  V  T  A  E  E  G  W  E  L  A  V  F  S  L

TACTGGAACTTGGCGAAGTGGATACCGTTCACCTATGGCATGCGACAGGAGACTTCGCAACA
2641    ------+---------+---------+---------+---------+---------+  2700
        ATGACCTTGAACCGCTTCACCTATGGCAAGTGGATACCGTCTCTCTGAAGCGTTGTTATGCAACA a        Y  W  N  L  A  K  W  I  P  Y  A  V  L  S  E  A  F  Y  A  T
b        T  G  T  W  R  S  G  Y  R  T  L  S  S  L  K  R  F  M  Q  Q
c        L  E  L  G  E  V  D  T  V  R  C  P  L  -  S  V  L  C  N  R
```

Figure 110

```
         GGCGATAGACAACGATGAAATGCCCTTATCGCAGTGGTTCAGACGCCGTGGCAGACTGGCC
2701     ------+---------+---------+---------+---------+---------+   2760
         CCGCTATCTGTTGCTACTTTACGGGAATAGCGTCACCAAGTCTGCGCACCGTCTGACCGG a             G  D  R  Q  R  -  N  A  L  I  A  V  V  Q  T  R  G  R  L  A
b             A  I  D  N  D  E  M  P  L  S  Q  W  F  R  R  V  A  D  W  P
c             R  -  T  T  M  K  C  P  Y  R  S  G  S  D  A  W  Q  T  G  R

GGATCGCTGTGAACGGGTCCGTATTTGCTAAGAGCAGTAGCCTTTGAACTTAGCATATG
2761     ------+---------+---------+---------+---------+---------+   2820
         CCTAGCGACACTTGCCCAGGCATAAACGATTCTCGTCATCGGAAACTTGAATCGTATAC a             G  S  L  -  T  G  P  Y  F  A  K  S  S  L  -  T  -  H  M
b             D  R  C  E  R  V  R  I  L  L  R  A  V  A  F  E  L  S  I  C
c             I  A  V  N  G  S  V  F  C  -  E  Q  -  P  L  N  L  A  Y  A

CATCGAACCCTCGGAGCAAAGTCGTTTGGCCGCAGCATTAGTACGTTTGCGTCGTTTGCT
2821     ------+---------+---------+---------+---------+---------+   2880
         GTAGCTTGGGAGCCTCGTTTCAGCAAACCGGCGTCGTAATCATGCAAACGCAGCAAACGA a             H  R  T  L  G  A  K  S  F  G  R  S  I  S  T  F  A  S  F  L  A
b             I  E  P  S  E  Q  S  R  L  A  A  A  L  V  R  L  R  R  L  L
c             S  N  P  R  S  K  V  V  W  P  Q  H  -  Y  V  C  V  V  C  C
```

Figure 11P

```
2881  GTTATTCCTTGGCCTTGAAAAAGAGTGCCAGCGTGAGGAGTGGATTTGCCAGTTGCCGCC
      ------+---------+---------+---------+---------+---------+  2940
      CAATAAGGAACCGGAACTTTTTCTCACGGTCGCACTCCTCACCTAAACGGTCAACGGCGG a    V  I  P  W  P  -  K  R  E  C  Q  R  E  E  W  I  C  Q  L  P
   b       L  F  L  G  L  E  K  E  C  Q  R  E  E  W  I  C  Q  L  P  P
   c         Y  S  L  A  L  K  K  S  A  S  V  R  S  G  F  A  S  C  R  L

2941  TAATACATTACTGCCGCTACTACTCGATATTATTTGTGAGCGCTGGCTTTTCAGTGATTG
      ------+---------+---------+---------+---------+---------+  3000
      ATTATGTAATGACGGCGATGATGAGCTATAATAAACACTCGCGACCGAAAAGTCACTAAC a    -  Y  I  T  A  A  T  T  R  Y  Y  L  -  A  L  A  F  Q  -  L
   b       N  T  L  L  P  L  L  L  D  I  C  E  R  W  L  F  S  D  W
   c         I  H  Y  C  R  Y  Y  S  I  L  F  V  S  A  G  F  S  V  I  G

3001  GTTGCTTGATAGACTTACCGCTATAGTTTCTTCATCGAAGATGTTCAATCGGTTACTCCA
      ------+---------+---------+---------+---------+---------+  3060
      CAACGAACTATCTGAATGGCGATATCAAAGAAGTAGCTTCTACAAGTTAGCCAATGAGGT a    V  A  -  -  T  Y  R  Y  S  F  F  I  E  D  V  Q  S  V  T  P
   b       L  L  D  R  L  T  A  I  V  S  S  K  M  F  N  R  L  L  Q
   c         C  L  I  D  L  P  L  -  F  L  H  R  R  C  S  I  G  Y  S  N
```

Figure 11Q

```
3061  ACAACTTGATGCGCCAGTTTATGCTGATACCCGATAACTGTTTTAACGACGAAGATCAACG
      ----------+---------+---------+---------+---------+---------+  3120
      TGTTGAACTACGCCGTCAAATACGACTATGGGCTATTGACAAAATTGCTGCTTCTAGTTGC a          T   T   -   C   A   V   Y   A   D   T   R   -   L   F   -   R   R   R   S   T
b          Q   L   D   A   Q   F   M   L   I   P   D   N   C   F   N   D   E   D   Q   R
c              N   L   M   R   S   L   C   -   Y   P   I   T   V   L   T   T   K   I   N   V

TGAACAAATTCTCGAAACGCTTCGTGAAGTAAAGATAAATCAGGTTTTATTCTGATACCT
      ----------+---------+---------+---------+---------+---------+  3180
      ACTTGTTTAAGAGCTTTGCGAAGCACTTCATTTCTATTTAGTCCAAAATAAGACTATGGA a          -   T   N   S   R   N   A   S   -   S   K   D   K   S   G   F   I   L   I   P
b          E   Q   I   L   E   T   L   R   E   V   K   I   N   Q   V   L   F   -   Y   L
c              N   K   F   S   K   R   F   V   K   -   I   R   F   Y   S   D   T   W

GGCTTTCAATATTTAGGTAAAATTGGCTTTCTGGCTCATCATGAGGCGTCAGGATGGATTG
      ----------+---------+---------+---------+---------+---------+  3240
      CCGAAAGTTATAAATCCATTTTAACCGAAAGACCGAGTAGTACTCCGCAGTCCTACCTAAC a          G   F   Q   Y   L   G   K   L   A   F   W   L   I   M   R   R   Q   D   G   L
b          A   F   N   I   -   V   N   W   L   S   G   S   S   -   G   V   R   M   D   W
c              L   S   I   F   R   -   I   G   F   L   A   H   H   E   A   S   G   W   I   G
```

Figure 11R

```
3241    GGATCTCATTACTGAACGTAATATTCAGCTTTTTATTCAATTAGCAGGATTAGCTGAACG   3300
        ------+---------+---------+---------+---------+---------+
        CCTAGAGTAATGACTTGCATTATAAGTCGAAAAATAAGTTAATCGTCCTAATCGACTTGC a         G  S  H  Y  -  T  -  Y  S  A  F  Y  S  I  S  R  I  S  -  T
b         D  L  I  T  E  R  N  I  Q  L  F  I  Q  L  A  G  L  A  E  R
c         I  S  L  L  N  V  I  F  S  F  L  F  N  -  Q  D  -  L  N  G

3301    GCCTTTAGCAACCAATATGTTCTGGCGGCAAGGACAATATGAAACTATCATAACGGTCGT   3360
        ------+---------+---------+---------+---------+---------+
        CGGAAATCGTTGGTTATACAAGACCGCCGTTCCTGTTATACTTTGATAGTATTGCCAGCA a         A  F  S  N  Q  Y  V  L  A  A  R  T  I  -  N  Y  H  N  G  R
b         P  L  A  T  N  M  F  W  R  Q  G  Q  Y  E  T  I  I  T  V  V
c         L  -  Q  P  I  C  S  G  G  K  D  N  M  K  L  S  -  R  S  Y

3361    ATTCTCTTATGTCAGATACTCAAGCAAACCTTCGTTGAGTTGCTTGGAAGAATCTGCTTC   3420
        ------+---------+---------+---------+---------+---------+
        TAAGAGAATACAGTCTATGAGTTCGTTTGGAAGCAACTCAACGAACCTTCTTAGACGAAG a         I  L  L  C  Q  I  L  K  Q  T  F  L  D  E  E  L  L  F  K  A
b         F  S  Y  V  R  Y  S  S  K  P  S  -  T  K  N  C  F  L  K  R
c         S  L  M  S  D  T  Q  A  N  L  L  R  R  R  T  A  F  -  S  V
```

Figure 11S

```
     TTGGCTAACTGGAAACCCGCAGCGTTCCAGGGTATTCCTCAACGATTATTTTGTTGCGC
3421 ---------+---------+---------+---------+---------+---------+ 3480
     AACCGATTGACCTTTGGGCGTCGCAAGGTCCCATAAGGAGTTGCTAATAAAACAACGCG a     L  A  N  W  K  P  A  A  F  Q  G  I  P  Q  R  L  F  L  L  R
b     W  L  T  G  N  P  Q  R  S  V  P  G  Y  S  S  T  I  F  V  A  R
c     G  -  L  E  T  R  S  V  P  G  Y  S  S  T  I  F  V  A  R

GATGGGCTTGCAATGAGTTGTTCTCCACCTCTTTCCAGCTCCGCCGAGCTCTGGTTACGA
3481 ---------+---------+---------+---------+---------+---------+ 3540
     CTACCCGAACGTTACTCAACAAGAGGTGGAGAAAGGTCGAGGCGGCTCGAGACCAATGCT a     D  G  L  A  M  S  C  S  P  P  L  S  S  S  A  E  L  W  L  R
b     M  G  L  Q  -  V  V  L  H  L  F  P  A  P  P  S  S  G  Y  D
c     W  A  C  N  E  L  F  S  T  S  F  Q  L  R  R  A  L  V  T  I

TTACATCATCGACAAATAAAATTCNTGGAGTCGCAATGCGTTCATGTTAGGTGAGGGA
3541 ---------+---------+---------+---------+---------+---------+ 3600
     AATGTAGTAGCTGTTTATTTTAAAGNACCTCAGCGTTACGCAAGTACCAATCCACTCCCT a     L  H  H  R  Q  I  K  F  X  G  V  A  M  R  S  W  L  G  E  G
b     Y  I  I  D  K  -  N  F  X  E  S  Q  C  V  H  G  -  V  R  E
c     T  S  S  T  N  K  I  X  W  S  R  N  A  F  M  V  R  -  G  S
```

Figure 11T

```
                                                                          start lcrD*
3601 GTCAGGGGCGCAACAGTGGCTCAGTGTATGCGCGGGTCGGCAGGATATGGTTCTGGCGACG 3660
     ----------+---------+---------+---------+---------+---------+
     CAGTCCCGCGTTGTCACCGAGTCACATACGCGCCCAGCCGTCCTATACCAAGACCGCTGC a      V  R  A  Q  Q  W  L  S  V  C  A  G  R  Q  D  M  V  L  A  T
b    S  G  R  N  S  G  S  V  Y  A  R  V  G  R  I  W  F  W  R  R
c      Q  G  A  T  V  A  Q  C  M  R  G  S  A  G  Y  G  S  G  D  G 3661 GTGTTATTAATCGCTATTGTGATGATGCTGTTACCCTTGCCGACCTGGATGGTTGATATC 3720
     ----------+---------+---------+---------+---------+---------+
     CACAATAATTAGCGATAACACTACTACGACAATGGGAACGGCTGGACCTACCAACTATAG a      V  L  L  I  A  I  V  M  M  L  L  P  P  T  W  M  V  D  I
b    C  Y  -  S  L  L  -  C  C  Y  P  C  R  P  G  W  L  I  S
c      V  I  N  R  Y  C  D  D  A  V  T  L  A  D  L  D  G  -  Y  P 3721 CTGATTACTATCAACCTTATGTTTTCAGTGATCCTGCTCTTAATTGCTATTATCTTAGT 3780
     ----------+---------+---------+---------+---------+---------+
     GACTAATGATAGTTGGAATACAAAAGTCACTAGGACGAGAATTAACGATAAATAGAATCA a      L  I  T  I  N  L  M  F  S  V  I  L  L  L  I  A  I  Y  L  S
b    -  L  L  S  T  L  C  F  Q  -  S  C  S  -  L  L  F  I  L  V
c      D  Y  Y  Q  P  Y  V  F  S  D  P  A  L  N  C  Y  L  S  -
```

Figure 11U

```
3781  GACCCTCTCGATTTATCGGTATTTCCGTCTCTTATTACTTATTACTACATTATATCGTTTG
      ---------+---------+---------+---------+---------+---------+ 3840
      CTGGGAGAGCTAAATAGCCATAAAGGCAGAGAATAATGAATATGATGTAATATAGCAAAC a      D  P  L  D  L  S  V  F  F  P  S  L  L  L  I  T  T  L  Y  R  L
b       T  L  S  I  Y  R  V  F  F  R  L  Y  Y  L  L  L  H  Y  I  V  C
c        P  S  R  F  I  G  I  S  V  F  I  T  Y  Y  Y  I  I  S  F  V

3841  TCACTCACAATCAGCACATCACGGCTGGTACTGTTACAACATAATGCCGGTAATATTGTG
      ---------+---------+---------+---------+---------+---------+ 3900
      AGTGAGTGTTAGTCGTGTAGTGCCGACCATGACAATGTTGTATTACGGCCATTATAACAC a      S  L  T  I  S  T  S  R  L  V  L  L  Q  H  N  A  G  N  I  V
b       H  S  Q  S  A  H  H  G  W  Y  C  Y  N  I  M  P  V  I  L  W
c        T  H  N  Q  H  I  T  A  G  T  V  T  T  -  C  R  -  Y  C  G

3901  GATGCTTTCGGTAAGTTTGTCGTAGGAGGAAATCTCACCGTTGGGTTGGTCGTATTTACC
      ---------+---------+---------+---------+---------+---------+ 3960
      CTACGAAAGCCATTCAAACAGCATCCTCCTTTAGAGTGGCAACCCAACCAGCATAAATGG a      D  A  F  G  K  F  V  V  G  G  N  L  T  V  G  L  V  V  F  T
b       M  L  S  V  S  L  S  -  E  E  I  S  P  L  G  W  S  Y  L  P
c        C  F  R  -  V  C  R  R  R  K  S  H  R  W  V  G  R  I  Y  H
```

Figure 11V

```
3961  ATCATTACTATCGTGCAATTTATTGTCATTACAAAAGGTATCGAGAGGGTGGCCGAAGTT
      ----------+---------+---------+---------+---------+---------+  4020
      TAGTAATGATAGCACGTTAAATAACAGTAATGTTTTCCATAGCTCTCCCACGCCTTCAA a      I  I  T  I  V  Q  F  I  V  I  T  K  G  I  E  R  V  A  E  V
b      S  L  L  S  C  N  L  L  S  L  Q  K  V  S  R  G  W  R  K  L
c            H  Y  Y  R  A  I  Y  C  H  Y  K  R  Y  R  E  G  G  G  S  -

4021  AGCGCACGTTTCTCGCTTGATGGGATGCCAGGCAAACAAATGAGTATCGATGGCGATTTG
      ----------+---------+---------+---------+---------+---------+  4080
      TCGCGTGCAAAGAGCGAACTACCCTACGGTCCGTTTGTTTACTCATAGCTACCGCTAAAC a      S  A  R  F  S  L  D  G  M  P  G  K  Q  M  S  I  D  G  D  L
b      A  H  V  F  L  A  -  W  D  A  R  Q  T  N  E  Y  R  W  R  F  A
c         R  T  F  L  A  -                                             Tn insertion P2D6
                                                                       ⇓

4081  CGTGCCGGAGTTATCGATGCAGACCATGCCCGTACATTAAGACACAGTGTCCAGCAGGAA
      ----------+---------+---------+---------+---------+---------+  4140
      GCACGGCCTCAATAGCTACGTCTGGTACGGGCATGTAATTCTGTGTCACAGGTCGTCCTT a      R  A  G  V  I  D  A  D  H  A  R  T  L  R  Q  H  V  Q  Q  E
b      V  P  E  L  S  M  Q  T  M  P  V  H  -  D  S  M  S  S  R  K
c         C  R  S  Y  R  C  R  P  C  P  Y  I  K  T  A  C  P  A  G  K
```

Figure 11W

```
4141  AGCCGCTTTCTCGGTGCCGATGGACGGTGCCGATGAAATTTGTTAAAGGCGATACGATTGCC
      ----------+---------+---------+---------+---------+---------+ 4200
      TCGGCGAAAGAGCCACGGCTACCTGCCACGCTACTTTAAACAATTTCCGCTATGCTAACGG a    S  R  F  L  G  A  M  D  G  A  M  K  F  V  K  G  D  T  I  A
   b    A  A  F  S  V  R  W  T  V  R  -  N  L  L  K  A  I  R  L  P
   c    P  L  S  R  C  D  G  R  C  D  E  I  C  -  R  R  Y  D  C  R

4201  GGTATTATTGTTGTTCTGGTGAACATTATCGGGTATCATTATCGCTATCGTACAATAT
      ----------+---------+---------+---------+---------+---------+ 4260
      CCATAATAACAACAAGACCACTTGTAATAGCCGCCATAGTAATAGCGATAGCATGTTATA a    G  I  I  V  V  L  V  N  I  I  G  G  I  I  I  A  I  V  Q  Y
   b    V  L  L  F  W  -  T  L  S  A  V  S  L  S  L  S  Y  N  M  -
   c    Y  Y  C  C  S  G  E  H  Y  R  R  Y  H  Y  R  Y  R  T  I  -

4261  GATATGTCGATGAGTGAGGCTGTTCACACTTATAGCGTACTGTCAATCGGAGATGGTTTA
      ----------+---------+---------+---------+---------+---------+ 4320
      CTATACAGCTACTCACTCCGACAAGTGTGAATATCGCATGACAGTTAGCCTCTACCAAAT a    D  M  S  M  S  E  A  V  H  T  Y  S  V  L  S  I  G  D  G  L
   b    I  C  R  -  V  R  L  F  T  L  I  A  Y  C  Q  S  E  M  V  Y
   c    Y  V  D  E  -  G  C  S  H  L  -  R  T  V  N  R  R  W  F  M
```

Figure 11X

```
4321  TGTGGGCAAATTCCATCGCTGCTGATTTCCCTTAGCGCGGGAATTATTGTCACCCGTGTC
      ----------+---------+---------+---------+---------+---------+  4380
      ACACCCGTTTAAGGTAGCGACGACTAAAGGGAATCGCGCCCTTAATAACAGTGGGCACAG a      C  G  Q  I  P  S  L  L  I  S  L  S  A  G  I  I  V  T  R  V
b      V  G  K  F  H  R  C  -  F  P  L  A  R  E  L  L  S  P  V  S
c      W  A  N  S  I  A  A  D  F  P  -  R  G  N  Y  C  H  P  C  P

4381  CCGGGTGAGAAACGCCAGAACCTGGCGACAGAGTTGAGTTCTCAAATTGCCAGACAACCT
      ----------+---------+---------+---------+---------+---------+  4440
      GGCCCACTCTTTGCGGTCTTGGACCGCTGTCTCAACTCAAGAGTTTAACGGTCTGTTGGA a      P  G  E  K  R  Q  N  L  A  T  E  L  S  S  Q  I  A  R  Q  P
b      R  V  R  N  A  R  T  W  R  Q  S  -  V  L  K  L  P  D  N  L
c      G  -  E  T  P  E  P  G  D  R  V  E  F  S  N  C  Q  T  T  S

4441  CAGTCGCTCATATTAACCGCTGTGGTTTTAATGCTCCTCGCTTTAATTCCTGGCTTTCCT
      ----------+---------+---------+---------+---------+---------+  4500
      GTCAGCGAGTATAATTGGCGACACCAAAATTACGAGGAGCGAAATTAAGGACCGAAAGGA a      Q  S  L  I  L  T  A  V  V  L  M  L  L  A  L  I  P  G  F  P
b      S  R  S  Y  -  P  L  W  F  -  C  S  S  L  -  F  L  A  F  L
c      V  A  H  I  N  R  C  G  F  N  A  P  R  F  N  S  W  L  S  F
```

Figure 11Y

```
4501  TTTATCACTCTCGCTTTCTTTTCAGCGTTGTTAGCATTGCCAATTATCCTCATTCGCCGC
      ----+----+----+----+----+----+----+----+----+----+----+----+ 4560
      AAATAGTGAGAGCGAAAGAAAAGTCGCAACAATCGTAACGGTTAATAGGAGTAAGCGGCG a      F  I  T  L  A  F  F  S  A  L  L  A  L  P  I  I  L  I  R  R
b      L  S  L  S  L  S  F  Q  R  C  -  H  C  Q  L  S  S  F  A  A
c      Y  H  S  R  F  L  F  S  V  V  S  I  A  N  Y  P  H  S  P  Q

Tn insertion P11C3
                                    ⇓
4561  AAAAAGTCTGTGGTTCCGCAAATGGCGTCGAAGCACCGGAAAAAGATAGTATGGTTCCC
      ----+----+----+----+----+----+----+----+----+----+----+----+ 4620
      TTTTTCAGACACCAAGGCGTTTACCGCAGCTTCGTGGCCTTTTTCTATCATACCAAGGG a      K  K  S  V  V  S  A  N  G  V  E  A  P  E  K  K  D  S  M  V  F  P
b      K  S  L  W  F  P  Q  M  A  S  K  H  R  K  K  I  V  W  F  P
c      K  V  C  G  F  R  K  W  R  R  S  T  G  K  R  -  Y  G  S  R 4621  GGCGCATGTCCTCTAATCTTACGTCTTAGCCCGACGTTACATTCTGCCGACCTGATTCGT
      ----+----+----+----+----+----+----+----+----+----+----+----+ 4680
      CCGCGTACAGGAGATTAGAATGCAGAATCGGGCTGCAATGTAAGACGGCTGGACTAAGCA a      G  A  C  P  L  I  R  L  S  P  T  L  H  S  A  D  L  I  R
b      A  H  V  L  -  S  Y  V  L  A  R  R  Y  I  L  P  T  -  F  V
c      R  M  S  S  N  L  T  S  -  P  D  V  T  F  C  R  P  D  S  -
```

Figure 11Z

```
4681  GATATTGACGCCATGAGATGGTTTTTATTTGAGGATACCGGGGCGTCCCCTCCCTGAGGTG
      ------+---------+---------+---------+---------+---------+ 4740
      CTATAACTGCGGTACTCTACCAAAAATAAACTCCTATGGCCGCAGGGAGAGGACTCCAC a    D   I   D   A   M   R   W   F   L   F   E   D   T   G   V   P   L   P   E   V
  b    I   L   T   P   -   D   G   F   Y   L   R   I   P   A   S   L   S   L   R   -
  c    Y   -   R   H   E   M   V   F   I   I   -   G   Y   R   R   P   S   P   -   G   E

4741  AATATTGAGGTTTTGCCTGAACCCCACCGAAAAATTGACGGTACTGCTATATCAGGAACCC
      ------+---------+---------+---------+---------+---------+ 4800
      TTATAACTCCAAAACGGACTTGGGGTGGCTTTTTAACTGCCATGACGATATAGTCCTTGGG a    N   I   E   V   L   P   E   P   T   E   K   L   T   V   L   L   Y   Q   E   P
  b    I   L   R   F   C   L   N   P   P   K   N   -   R   Y   C   Y   I   R   N   P
  c    Y   -   G   F   A   -   T   H   R   K   I   D   G   T   A   I   S   G   T   R

4801  GTATTTAGTTTATCTATTCCCGCTCAGGCGGATTATTATTGATAGGCCGGACGCTAGT
      ------+---------+---------+---------+---------+---------+ 4860
      CATAAATCAAATAGATAAGGGCGAGTCCGCCTAATAATAACTATCCGCCTGCGATCA a    V   F   S   L   S   I   P   A   Q   A   D   Y   L   L   I   G   A   D   A   S
  b    Y   L   V   Y   L   F   P   L   R   R   I   I   Y   -   A   R   T   L   V
  c    I   -   F   I   Y   S   R   S   G   G   L   F   I   D   R   R   G   R   -   C
```

Figure 11AA

```
4861  GTGGTGGGTGACAGCCAGACGTTACCGAACGGGATGGGCAGATCTGTTGGCTTACAAAA  4920
      CACCACCCACTGTCGGTCTGCAATGGCTTGCCCTACCCGTCTAGACAACCGAATGTTT a      V  V  G  D  S  Q  T  L  P  N  G  M  G  Q  I  C  W  L  T  K
b      W  W  V  T  A  R  R  Y  R  T  G  W  G  R  S  V  G  L  Q  K
c      G  G  -  Q  P  D  V  T  E  R  D  G  A  D  L  L  A  Y  K  R

4921  GACATGGCCCATAAGGCGCAAGGTTTTGGACTGGACGTTTTCGCGGCAGCCAACGTATC  4980
      CTGTACCGGGTATTCCGCGTTCCAAAACCTGACCTGCAAAAGCGCCGTCGGTTGCATAG a      D  M  A  H  K  A  Q  G  F  G  L  D  V  F  A  G  S  Q  R  I
b      T  W  P  I  R  R  K  V  L  D  W  T  F  S  R  A  A  N  V  S
c      H  G  P  -  G  A  R  F  W  T  G  R  F  R  G  Q  P  T  Y  L

4981  TCTGCCTTATTAAAATGTGTCCTGCTTCCGGCATATGGGAGAGTTTATTGGTGTTCAGGAA  5040
      AGACGGAATAATTTTACACAGGACGAAGCCGTATACCCTCTCAAATAACCACAAGTCCTT a      S  A  L  L  K  C  V  L  L  R  H  M  G  E  F  I  G  V  Q  E
b      L  P  Y  -  N  V  S  C  F  G  I  W  E  S  L  L  V  F  R  K
c      C  L  I  K  M  C  P  A  S  A  Y  G  R  V  Y  W  C  S  G  N
```

Figure 11AB

```
5041  ACGCGTTATCTAATGAATGCGATGGAAAAAACTACTCTGAGCTGGTGAAAGAGCTTCAG
      ---------+---------+---------+---------+---------+---------+ 5100
      TGCGCAATAGATTACTTACGCTACCTTTTTTGATGAGACTCGACCACTTTCTCGAAGTC a       T  R  Y  L  M  N  A  M  E  K  N  Y  S  E  L  V  K  E  L  Q
b       R  V  I  -  M  R  W  -  K  K  T  T  L  S  W  -  K  S  F  S
c       A  L  S  N  E  C  D  D  G  K  K  L  L  -  A  G  E  R  A  S  A

5101  CGCCAGTTACCCATTAATAAAATCGCTGAAACTTTGCAACGGCTTGTATCAGAGCGGGTT
      ---------+---------+---------+---------+---------+---------+ 5160
      GCGGTCAATGGGTAATTATTTTAGCGACTTTGAAACGTTGCCGAACATAGTCTCGCCCAA a       R  Q  L  P  I  N  K  I  A  E  T  L  Q  R  L  V  S  E  R  V
b       A  S  Y  P  L  I  K  S  L  K  L  C  N  G  L  Y  Q  S  G  F
c       P  V  T  H  -  -  N  R  -  N  F  A  T  A  C  I  R  A  G  F

5161  TCTATTAGAGATTTACGTCTTATTTTCGGCACCTTAATTGACTGGGCGCCACGTGAAAAA
      ---------+---------+---------+---------+---------+---------+ 5220
      AGATAATCTCTAAATGCAGAATAAAAGCCGTGGAATTAACTGACCCGCGGTGCACTTTTT a       S  I  R  D  L  R  L  I  F  G  T  L  I  D  W  A  P  R  E  K
b       L  L  E  I  Y  V  L  F  S  A  P  -  L  T  G  R  H  V  K  K
c       Y  -  R  F  T  S  Y  F  R  H  L  N  -  L  G  A  T  -  K  R
```

Figure 11AC

```
5221 GATGTCCTGATGTTGACAGAATATGTCCGTATCGCGCTTCGTCGTCATATTCTGCGTCGT 5280
     ---------+---------+---------+---------+---------+---------+
     CTACAGGACTACAACTGTCTTATACAGGCATAGCGCGAAGCAGCAGTATAAGACGCAGCA a      D  V  L  M  L  T  E  Y  V  R  I  A  L  R  R  H  I  L  R  R
b      M  S  -  C  -  Q  N  M  S  V  S  R  F  V  V  I  F  C  V  V
c         C  P  D  V  D  R  I  C  P  Y  R  A  S  S  S  Y  S  A  S  S

5281 CTTAATCCGGAAGGAAAAACCGCTGCCGATTTTGCGGATCGGCGAAGGTATTGAAAACCTC 5340
     ---------+---------+---------+---------+---------+---------+
     GAATTAGGCCTTCCTTTTTGGCGACGGCTAAAACGCCTAGCCGCTTCCATAACTTTTGGAG a      L  N  P  E  G  K  P  L  P  I  L  R  I  G  E  G  I  E  N  L
b      L  I  R  K  E  N  R  C  R  F  C  G  S  A  K  V  L  K  T  S
c      -  S  G  R  K  T  A  A  D  F  A  D  R  R  R  Y  -  K  P  R

5341 GTGCGTGAATCCATTCGCCAGACGGCAATGGGGACCTATACTGCGCTGTCGTCTCGTCAT 5400
     ---------+---------+---------+---------+---------+---------+
     CACGCACTTAGGTAAGCGGTCTGCCGTTACCCCTGGATATGACGCGACAGCAGAGCAGTA a      V  R  E  S  I  R  Q  T  A  M  G  T  Y  T  A  L  S  S  R  H
b      C  V  N  P  F  A  R  R  Q  W  G  P  I  L  R  C  R  L  V  I
c      A  -  I  H  S  P  D  G  N  G  D  L  Y  C  A  V  V  S  S  -
```

Figure 11AD

```
5401  AAGACGCAGATCCTGCAACTTATCGAGCAGGCGCTGAAGCAGTCAGCCAAATTATTCATT  5460
      ------+---------+---------+---------+---------+---------+
      TTCTGCGTCTAGGACGTTGAATAGCTCGTCCGCGACTTCGTCAGTCGGTTTAATAAGTAA a    K  T  Q  I  L  Q  L  I  E  Q  A  L  K  Q  S  A  K  L  F  I
   b    R  R  R  S  C  N  L  S  S  R  R  -  S  S  Q  P  N  Y  S  L
   c    D  A  D  P  A  T  Y  R  A  G  A  E  A  V  S  Q  I  H  C

5461  GTCACTTCTGTCGACACCCGACGTTTCTTGCGAAAAATTACAGAAGCCACCTTGTTCGAC  5520
      ------+---------+---------+---------+---------+---------+
      CAGTGAAGACAGCTGTGGGCTGCAAAGAACGCTTTTTAATGTCTTCGGTGGAACAAGCTG a    V  T  S  V  D  T  R  R  F  L  R  K  I  T  E  A  T  L  F  D
   b    S  L  L  S  T  P  D  V  S  C  E  K  L  Q  K  P  P  C  S  T
   c    H  F  C  R  H  P  T  F  L  A  K  N  Y  R  S  H  L  V  R  R

5521  GTACCGATTTTGTCATGGCAGGAATTAGGAGAGGAGCCTTATACAAGTGGTAGAAAGT  5580
      ------+---------+---------+---------+---------+---------+
      CATGGCTAAAACAGTACCGTCCTTAATCCTCTCCTCGGAATATGTTCACCATCTTTCA a    V  P  I  L  S  W  Q  E  L  G  E  E  S  L  I  Q  V  V  E  S
   b    Y  R  F  C  H  G  R  N  -  E  R  R  A  L  Y  K  W  -  K  V
   c    T  D  F  V  M  A  G  I  R  R  G  E  P  Y  T  S  G  R  K  Y
```

Figure 11AE

```
                                                              end lcrD*                   start yscN*?
5581  ATTGACCTTAGCGGAAGAGGAGTTGGGCGGACAATGAAGAATGAATTGATGCAACGTCTGAG
      ----+----+----+----+----+----+----+----+----+----+----+----+  5640
      TAACTGGAATCGCCTTCTCCTCAACCGCCTGTTACTTCTTACTTAACTACGTTGCAGACTC
a       I  D  L  S  E  E  E  L  A  D  N  E  E  -  I  D  A  T  S  E
b       L  T  L  A  K  R  S  W  R  T  M  K  N  E  L  M  Q  R  L  R
c       -  P  -  R  R  G  V  G  G  Q  -  R  M  N  -  C  N  V  -  G 5641  GCTGAAATATCCGCCCCCCGATGGTTATTGTCGATGGGGCCGAATTCAGGATGTCAGCGC
      ----+----+----+----+----+----+----+----+----+----+----+----+  5700
      CGACTTTATAGGCGGGGGGCTACCAATAACAGCTACCCCGGCTTAAGTCCTACAGTCGCG
a       A  E  I  S  A  P  P  R  W  L  L  S  M  G  P  N  S  G  C  Q  R
b       L  K  Y  P  P  P  D  G  Y  C  R  W  G  R  I  Q  D  V  S  A
c       -  N  I  R  P  P  M  V  I  V  D  G  A  E  F  R  M  S  A  Q 5701  AACGTTGTTAAATGCGTGGTTGCCTGGGGTATTTATGGGCGAGTTGTGCTGTATAAAGCC
      ----+----+----+----+----+----+----+----+----+----+----+----+  5760
      TTGCAACAATTTACGCACCAACGGACCCCATAAATACCCGCTCAACACGACATATTTCGG
a       N  V  V  K  C  V  V  A  W  G  I  Y  G  R  V  V  L  Y  K  A
b       T  L  L  N  A  W  L  P  G  V  F  M  G  E  L  C  C  I  K  P
c       R  C  -  M  R  G  C  L  G  Y  L  W  A  S  C  A  V  -  S  L
```

Figure 11AF

```
                                                                    yscN*
                                                       W  Q  Q  S  F  A  I  S  P  F
      W  R  R  T  C  -  S  R  G  D  -  W  Q  Q  S  F  A  I  S  P  F
      G  E  E  L  A  E  V  V  G  I  N  G  S  K  A  L  L  S  P  F
        E  K  N  L  L  K  S  W  G  L  M  A  A  K  L  C  Y  L  L  L
5761 TGGAGAAGAACTTGCTGAAGTCGTGGGATTAATGGCAGCAAAGCTTTGCTATCTCCTTT 5820
     ----+----+----+----+----+----+----+----+----+----+----+----+
     ACCTCTTCTTGAACGACTTCAGCACCCTAATTACCGTCGTTTCGAAACGATAGAGGAAA Y  E  Y  N  R  A  S  L  R  A  A  S  D  G  L  K  R  R  H  Q
      T  S  T  I  G  L  H  C  G  Q  Q  V  M  A  L  S  D  A  I  R
        R  V  Q  S  G  F  T  A  G  S  K  -  W  P  -  A  T  P  S  G
5821 TACGAGTACAATCGGGCTTCACTGCGGGCAGCAAGTGATGGCCTTAAGCGACGCCATCAG 5880
     ----+----+----+----+----+----+----+----+----+----+----+----+
     ATGCTCATGTTAGCCCGAAGTGACGCCCGTCGTTCACTACCGGAATTCGCTGCGGTAGTC V  P  V  G  E  A  L  L  G  R  V  I  D  G  F  G  R  P  L  D
      F  P  W  A  K  R  Y  -  G  E  L  L  M  A  L  V  V  P  L  M
        S  R  G  R  S  V  I  R  A  S  Y  -  W  L  W  S  S  P  -  W
5881 GTTCCCGTGGGCGAAGCGTTATTAGGGCGAGTTATTGATGGCTTTGGTCGTCCCCTTGAT 5940
     ----+----+----+----+----+----+----+----+----+----+----+----+
     CAAGGGCACCCGCTTCGCAATAATCCCGCTCAATAACTACCGAAACCAGCAGGGGAACTA
```

Figure 11AG

```
5941  GGCCGCGAACTGCCCGACGTCTGCTGGAAAGACTATGATGCAATGCCTCCTCCCGCAATG
      ----+----+----+----+----+----+----+----+----+----+----+----+  6000
      CCGGCGCTTGACGGGCTGCAGACGACCTTTCTGATACTACGTTACGGAGGAGGGCGTTAC a         G  R  E  L  P  D  V  C  W  K  D  Y  D  A  M  P  P  P  A  M
b        A  A  N  C  P  T  S  A  G  K  T  M  M  Q  C  L  L  P  Q  W
c         P  R  T  A  R  R  L  E  R  L  -  C  N  A  S  S  R  N  G

6001  GTTCGACAGCCTATCACTCAACCATTAATGACGGGGATTCGGCTATTGATAGCCGTTGCG
      ----+----+----+----+----+----+----+----+----+----+----+----+  6060
      CAAGCTGTCGGATAGTGAGTTGGTAATTACTGCCCCTAAGCCGATAACTATCGCAACGC a         V  R  Q  P  I  T  Q  P  L  M  T  G  I  R  A  L  I  D  S  V  A
b        F  D  S  L  S  L  N  H  -  R  G  F  A  L  L  I  A  L  R
c         S  T  A  Y  H  S  T  I  N  D  G  D  S  R  Y  -  R  C  D

6061  ACCTGTGGCGAAGGGCAACGAGTGGGTATTTTTTCTGCTCCTGGCCGTTGGGAAAAGCACG
      ----+----+----+----+----+----+----+----+----+----+----+----+  6120
      TGGACACCGCTTCCCGTTGCTCACCCATAAAAAAGACGAGGACCGCACCCCTTTTCGTGC a         T  C  G  E  G  Q  R  E  V  G  I  F  S  A  P  G  V  G  K  S  T
b        P  V  A  K  G  N  E  W  V  F  F  L  L  L  A  W  G  K  A  R
c         L  W  R  R  A  T  S  G  Y  F  F  C  S  W  R  G  E  K  H  A
```

Figure 11AH

```
6121 CTTCTGGCGATGCTGTGTAATGCGCCAGACGCAGACAGCAATGTTCTGGTGTTAATTGGT 6180
     ---------+---------+---------+---------+---------+---------+
     GAAGACCGCTACGACACATTACGCGGTCTGCGTCTGTCGTTACAAGACCACAATTAACCA a  L  L  A  M  L  C  N  A  P  D  A  D  S  N  V  L  V  L  I  G
   b        F  W  R  C  C  V  M  R  Q  T  Q  T  A  M  F  W  C  -  L  V
   c           S  G  D  A  V  -  C  A  R  R  R  Q  Q  C  S  G  V  N  W  -

6181 GAACGTGGACGAGAAGTCCGCGAATTCATCGATTTTACACTGTCTGAAGAGACCCGAAAA 6240
     ---------+---------+---------+---------+---------+---------+
     CTTGCACCTGCTCTTCAGGCGCTTAAGTAGCTAAAATGTGACAGACTTCTCTGGGCTTTT a  E  R  G  R  E  V  R  E  F  I  D  F  T  L  S  E  E  T  R  K
   b     N  V  D  E  K  S  A  N  S  S  I  L  H  C  L  K  R  P  E  N
   c        T  W  T  R  S  P  R  I  H  R  F  Y  T  V  -  R  D  P  K  T

6241 CGTTGTGTCATTGTTGTCGCAACCTCTGACAGACCCGCCTTAGAGCGCGTGAGGGCGCTG 6300
     ---------+---------+---------+---------+---------+---------+
     GCAACACAGTAACAACAGCGTTGGAGACTGTCTGGGCGGAATCTCGCGCACTCCCGCGAC a  R  C  V  I  V  V  A  T  S  D  R  P  A  L  E  R  V  R  A  L
   b     V  V  S  L  L  S  Q  P  L  T  D  P  P  -  S  A  -  G  R  C
   c        L  C  H  C  C  R  N  L  -  Q  T  R  L  R  A  R  E  G  A  V
```

Figure 11AI

```
6301 TTTGTGGCCACCACGATAGCAGAATTTTTTCGCGATAATGGAAAGCGAGTCGTCTTGCTT 6360
     ---------+---------+---------+---------+---------+---------+
     AAACACCGGTGGTGCTATCGTCTTAAAAAAGCGCTATTACCTTTCGCTCAGCAGAACGAA a     F  V  A  T  T  I  A  E  F  F  R  D  N  G  K  R  V  V  L  L
b     L  W  P  P  R  -  Q  N  F  F  A  I  M  E  S  E  S  S  C  L
c     C  G  H  H  D  S  R  I  F  S  R  -  W  K  A  S  R  L  A  C

6361 GCCGACTCACTGACGCGTTATGCCAGGGCCGCACGGAAATCGCTCTGGCGCCGGAGAGAC 6420
     ---------+---------+---------+---------+---------+---------+
     CGGCTGAGTGACTGCGCAATACGGTCCCGGCGTGCCTTTAGCGAGACCGCGGCCTCTCTG a     A  D  S  L  T  R  Y  A  R  A  A  R  K  S  L  W  R  R  R  D
b     P  T  H  -  R  V  M  P  G  P  H  G  N  R  S  G  A  P  E  T
c     R  L  T  D  A  L  C  Q  G  R  T  E  I  A  L  A  P  E  R  P

6421 CGCGGTTTCTGGAGAATATCGCCAGGCGTATTTAGTGCATTGCCACGACTTTAGAACGT 6480
     ---------+---------+---------+---------+---------+---------+
     GCGCCAAAGACCTCTTATAGCGGTCCGCATAAATCACGTAACGGTGCTGAAAATCTTGCA a     R  G  F  W  R  I  S  P  G  V  F  S  A  L  P  R  L  L  E  R
b     A  V  S  G  E  Y  R  Q  A  Y  L  V  H  C  H  D  F  -  N  V
c     R  F  L  E  N  I  A  R  R  I  -  C  I  A  T  T  F  R  T  Y
```

Figure 11AJ

```
6481  ACGGGAATGGGAGAAAAAGGCAGTATTACCGCATTTTATACGGTACTGGTGTGGAAGGCGAT
      ---------+---------+---------+---------+---------+---------+ 6540
      TGCCCTTACCCTCTTTTTCCGTCATAATGGCGTAAAATATGCCATGACCACCACCTTCCGCTA a      T  G  M  G  E  K  G  S  I  T  A  F  Y  T  V  L  V  E  G  D
b      R  E  W  E  K  K  A  V  L  P  H  F  I  R  Y  W  W  K  A  M
c      G  N  G  R  K  R  Q  Y  Y  R  I  L  Y  G  T  G  G  R  R  -

6541  GATATGAATGAAGCCGTTGGCGGATGAAGTCCGTTCACTGCTTGATGGACATATTGTACT
      ---------+---------+---------+---------+---------+---------+ 6600
      CTATACTTACTTCGGCAACCGCCTACTTCAGGCAAGTGACGAACTACCTGTATAACATGA yscN*
a      D  M  N  E  A  V  G  G  -  S  P  F  T  A  -  W  T  Y  C  T
b      I  -  M  K  P  L  A  D  E  V  R  S  L  L  D  G  H  I  V  L
c      Y  E  -  S  R  W  R  M  K  S  V  H  C  L  M  D  I  L  Y  Y 6601  ATCCCGACGGCTTGCAGAGAGGGGGCATTATCCTGCCATTGACGTGTTGGCAACGCTCAG
      ---------+---------+---------+---------+---------+---------+ 6660
      TAGGGCTGCCGAACGTCTCTCCCCCGTAATAGGACGGTAACTGCACAACCGTTGCGAGTC a      I  P  T  A  C  R  E  G  A  L  S  C  H  -  R  V  G  N  A  Q
b      S  R  R  L  A  E  R  G  H  Y  P  A  I  D  V  L  A  T  L  S
c      P  D  G  L  Q  R  G  G  I  I  L  P  L  T  C  W  Q  R  S  A
```

Figure 11AK

```
6661  CCGCGTTTTCCAGTCGTTACCAGCCATGAGCATCGTCAACTGGCGGGCGATATTGCGACG  6720
      GGCGCAAAAGGTCAGCAATGGTCGGTACTCGTAGCAGTTGACCGCCCGCTATAACGCTGC
a        P  R  F  S  S  R  Y  Q  P  -  A  S  S  T  G  G  D  I  A  T
b        R  V  F  P  V  V  T  S  H  E  H  R  Q  L  A  A  I  L  R  R
c        A  F  F  Q  S  L  P  A  M  S  I  V  N  W  R  R  Y  C  D  G

6721  GTGCCTGGGCGCTTTACCAGGAGGTTGAACTGTTAATACGCATTGGGAATACCAGCGAGG  6780
      CACGGACCCGCGAAATGGTCCTCCAACTTGACAATTATGCGTAACCCCTTATGGTCGCTCC
a        V  P  G  A  L  P  G  G  -  T  V  N  T  H  W  G  I  P  A  R
b        C  L  A  L  Y  Q  E  V  E  L  L  I  R  I  G  E  Y  Q  R  G
c        A  W  R  F  T  R  R  L  N  C  -  Y  A  L  G  N  T  S  E  E

6781  AGTTGATACAGATACTGACAAAGCCATTGATACCTATCCGGATATTTGCACATTTTTGCG  6840
      TCAACTATGTCTATGACTGTTTCGGTAACTATGGATAGGCCTATAAACGTGTAAAAACGC
a        S  -  Y  R  Y  -  Q  S  H  -  Y  L  S  G  Y  L  H  I  F  A
b        V  D  T  D  T  D  K  A  I  D  T  Y  P  D  I  C  T  F  L  R
c        L  I  Q  I  L  T  K  P  L  I  P  I  R  I  F  A  H  F  C  D
```

Figure 11AL

```
6841  ACAAAGTAAGGATGAAGTAGTATGCGGACCCGAGCTACTTATAGAAAAATTACACCAAATACT
      ---------+---------+---------+---------+---------+---------+ 6900
      TGTTTCATTCCTACTTCATACGCCTGGGCTCGATGAATATCTTTTTAATGTGGTTTATGA
                                                       end yscN*
a         T  K  -  G  -  S  M  R  T  R  A  T  Y  R  K  I  T  P  N  T
b         Q  S  K  D  E  V  C  G  P  E  L  L  I  E  K  L  H  Q  I  L
c            K  V  R  M  K  Y  A  D  P  S  Y  L  -  K  N  Y  T  K  Y  S 6901  CACCGAGTGATCATGGAAACTTTGCTGGAGATAAATCGCGGCTGAAAAGCAATTACGCG
      ---------+---------+---------+---------+---------+---------+ 6960
      GTGGCTCACTAGTACCTTTGAAACGACCTCTATTAGCGCCGACTTTTCGTTAATGCGC
              yscO*
a         H  R  V  I  M  E  T  L  L  E  I  I  A  R  L  K  S  N  Y  A
b         T  E  -  S  W  K  L  C  W  R  -  S  R  G  -  K  A  I  T  R
c         P  S  D  H  G  N  F  A  G  D  N  R  A  A  E  K  Q  L  R  G 6961  GCAAGCTTACCGTACTTGATCAGCAGCAACAGGCGATTATTACGGAACAGCAGATTTGCC
      ---------+---------+---------+---------+---------+---------+ 7020
      CGTTCGAATGGCATGAACTAGTCGTCGTTGTCCGCTAATAATGCCTTGTCGTCTAAACGG
a         A  S  L  P  Y  L  I  S  S  N  R  R  L  L  R  N  S  R  F  A
b         Q  A  Y  R  T  -  S  A  A  T  G  D  Y  Y  G  T  A  D  L  P
c         K  L  T  V  L  D  Q  Q  Q  Q  A  I  I  T  E  Q  Q  I  C  Q
```

Figure 11AM

```
       7021 AGACGCGCGCTTTAGCAGTGTCTACCAGACTGAAAGAATTAATGGGCTGGCAAGGTACGT 7080
            ----+----+----+----+----+----+----+----+----+----+----+----+
            TCTGCGCGCGAAATCGTCACAGATGGTCTGACTTTCTTAATTACCCGACCGTTCCATGCA a   R  R  A  L  -  Q  C  L  P  D  -  K  N  -  W  A  G  K  V  R
         b   D  A  R  F  S  S  V  Y  Q  T  E  R  I  N  G  L  A  R  Y  V
         c   T  R  A  L  A  V  S  T  R  L  K  E  L  M  G  W  Q  G  T  L

7081 TATCTTGTCATTTATTGTTGGATAAGAAACAACAAATGGCCGGGTTATTCACTCAGGCGC 7140
            ----+----+----+----+----+----+----+----+----+----+----+----+
            ATAGAACAGTAAATAACAACCTATTCTTTGTTGTTTACCGGCCCAATAAGTGAGTCCGCG a   Y  L  V  I  Y  C  W  I  R  N  N  K  W  P  G  Y  S  L  R  R
         b   I  L  S  F  I  V  G  -  E  T  T  N  G  R  V  I  H  S  G  A
         c   S  C  H  L  L  L  D  K  K  Q  Q  M  A  G  L  F  T  Q  A  Q

7141 AGAGCTTTTTGACGCAACGGCAAGCAGTTAGAGAATCAGTATCAGCAGCTTGTCTCCCGG 7200
            ----+----+----+----+----+----+----+----+----+----+----+----+
            TCTCGAAAAACTGCGTTGCCGTTCGTCAATCTCTTAGTCATAGTCGTCGAACAGAGGGCC a   R  A  F  -  R  N  G  K  Q  L  E  N  Q  Y  Q  Q  L  V  S  R
         b   E  L  F  D  T  A  S  S  -  R  I  S  I  S  S  L  P  G
         c   S  F  L  T  Q  R  Q  A  V  R  E  S  V  S  A  A  C  L  P  A
```

Figure 11AN

```
      CGAAGCGAATTACAGAAGAATTTAATGCGCTTATGAAAAAGAAAGAAAAATTACTATG
7201  ------+---------+---------+---------+---------+---------+  7260
      GCTTCGCTTAATGTCTTCTTAAATTACGCGAATACTTTTTCTTTCTTTTTAATGATAC end yscO*
a       R  S  E  L  Q  K  N  F  N  A  L  M  K  K  K  E  K  I  T  M
b       E  A  N  Y  R  R  E  I  L  M  R  L  -  K  R  K  K  K  L  W
c         K  R  I  T  E  E  F  -  C  A  Y  E  K  E  R  K  N  Y  Y  G GTATTAAGCGATGCGTATTACCAAAGTTGAGGGAAGTCTTGGGTTGCCATGCCAGTCTTA
7261  ------+---------+---------+---------+---------+---------+  7320
      CATAATTCGCTACGCATAATGGTTTCAACTCCCTTCAGAACCCAACGGTACGGTCAGAAT start yscP*
a       V  L  S  D  A  Y  Y  Q  S  -  G  K  S  W  V  A  M  P  V  L
b       Y  -  A  M  R  I  T  K  V  E  G  S  L  G  L  P  C  Q  S  Y
c         I  K  R  C  V  L  P  K  L  R  E  V  L  G  C  H  A  S  L  I TCAGGATGATAACGAGGCGGAGGCGGAACGTATGGACTTTGAACAACTCATGCACCAGGC
7321  ------+---------+---------+---------+---------+---------+  7380
      AGTCCTACTATTGCTCCGCCTCCGCCTTGCATACCTGAAACTTGTTGAGTACGTGGTCCG a       S  G  -  R  G  G  G  G  T  Y  G  L  -  T  T  H  A  P  G
b       Q  D  D  N  E  A  E  R  M  D  F  E  Q  L  M  H  Q  A
c         R  M  I  T  R  R  R  R  N  V  W  T  L  N  N  S  C  T  R  H Figure 11AO
```

```
7381    ATTACCCATTGGTGAGAATAATCCTCCTGCAGCATTGAATAAGAACGTGGTTTTCACGCA
        ------+---------+---------+---------+---------+---------+      7440
        TAATGGGTAACCACTCTTATTAGGAGGACGTCGTAACTTATTCTTGCACCAAAAGTGCGT a    I  T  H  W  -  E  -  S  S  C  S  I  E  -  E  R  G  F  H  A
    b    L  P  I  G  E  N  N  P  P  A  A  L  N  K  N  V  V  F  T  Q
    c    Y  P  L  V  R  I  I  L  L  Q  H  -  I  R  T  W  F  S  R  N

7441    ACGTTATCGTGTTAGTGGCGGTTATCTTGACGGTGTAGAGTGTGAAGTATGTGAATCAGG
        ------+---------+---------+---------+---------+---------+      7500
        TGCAATAGCACAATCACCGCCAATAGAACTGCCACATCTCACACTTCATACACTTAGTCC a    T  L  S  C  -  W  R  L  S  -  R  C  R  V  -  S  M  -  I  R
    b    R  Y  R  V  S  G  G  Y  L  D  G  V  E  C  E  V  C  E  S  G
    c    V  I  V  L  V  A  V  I  L  T  V  -  S  V  K  Y  V  N  Q  G

7501    GGGGCTAATCCAGTTAAGAATCAATGTCCCTCATCATGAAATTTACCGTTCGATGAAAGC
        ------+---------+---------+---------+---------+---------+      7560
        CCCCGATTAGGTCAATTCTTAGTTACAGGGAGTAGTACTTTAAATGGCAAGCTACTTTCG a    G  A  N  P  V  K  N  Q  C  P  S  S  -  N  L  P  F  D  E  S
    b    G  L  I  Q  L  R  I  N  V  P  H  H  E  I  Y  R  S  M  K  A
    c    G  -  S  S  -  E  S  M  S  L  I  M  K  F  T  V  R  -  K  R
```

Figure 11AP

```
7561  GCTAAAGCAGTGGCTGGAGTCTCAGTTGCTGCATATGGGGTATATAATTTCCCTGGAGAT  7620
      ----------+---------+---------+---------+---------+---------+
      CGATTTCGTCACCGACCTCAGAGTCAACGACGTATACCCCATATATTAAAGGACCTCTA a      A  K  A  V  A  G  V  S  V  A  A  Y  G  V  Y  N  F  P  G  D
b      L  K  Q  W  L  E  S  Q  L  H  M  G  Y  I  -  F  P  W  R  Y
c      -  S  S  G  W  S  L  S  C  C  I  W  G  I  -  F  P  W  R  Y

7621  ATTCTATGTTAAGAATAGCGAATGAAGAGCGTCCGTGGGTGGAGATACTTCCAACGCAAG  7680
      ----------+---------+---------+---------+---------+---------+
      TAAGATACAATTCTTATCGCTTACTTCTGCAGGCACCCACCTCTATGAAGGTTGCGTTC end yscP*   start yscQ*?
a      I  L  C  -  E  -  R  M  K  S  V  R  G  W  R  Y  F  Q  R  K
b      F  Y  V  K  N  S  E  -  R  A  S  V  G  G  D  T  S  N  A  R
c         S  M  L  R  I  A  N  E  E  R  P  W  V  E  I  L  P  T  Q  G 7681  GCGGCTACCATTGGTGAGCTGACATTGAGTATGCAACAATATCCAGTACAGCAAGGACAT  7740
      ----------+---------+---------+---------+---------+---------+
      CGCCGATGGTAACCACTCGACTGTAACTCATACGTTGTTATAGGTCATGTCGTTCCTGTA start yscQ*?
a      A  L  P  L  V  S  -  H  -  V  C  N  N  I  Q  Y  S  K  G  H
b      R  Y  H  W  -  A  D  I  E  Y  A  T  I  S  T  A  R  D  I
c      A  T  I  G  E  L  T  L  S  M  Q  Q  Y  P  V  Q  Q  G  T  L
```

```
7921  GTCAGAACGAGCCGCCAACATCCTGCAGTAATCTACCACATCAGCTAGCGTTGCATATTA
      ------+---------+---------+---------+---------+---------+  7980
      CAGTCTTGCTCGGCGGTTGTAGGACGTCATTAGATGGTGTAGTCGATCGCAACGTATAAT a         V  R  T  S  R  Q  H  P  A  V  I  Y  H  I  S  -  R  C  I  L
b       S  E  R  A  A  N  I  L  Q  -  S  T  T  S  A  S  V  A  Y  -
c         Q  N  E  P  P  T  S  C  S  N  L  P  H  Q  L  A  L  H  I  K

7981  AATGGACAGTTGAAGAGCATGAGTTCCATAGCATTATTTTTACATGGCCAACGGGTTTTT
      ------+---------+---------+---------+---------+---------+  8040
      TTACCTGTCAACTTCTCGTACTCAAGGTATCGTAATAAAAATGTACCGGTTGCCCAAAAA a         N  G  Q  L  K  S  M  S  S  I  A  L  F  L  H  G  Q  R  V  F  F
b       M  D  S  -  R  A  -  V  P  -  H  Y  F  Y  M  A  N  G  F  F
c         W  T  V  E  E  H  E  F  H  S  I  F  F  T  W  P  T  G  F  L

8041  TGCGCAATATAGTCGGAGAGCTTTCTGCTGAGCGACAACAGATTTATCCTGCCCCTCCTG
      ------+---------+---------+---------+---------+---------+  8100
      ACGCGTTATATCAGCCTCTCGAAAGACGACTCGCTGTTGTCTAAATAGGACGGGGAGGAC a         C  A  I  -  S  E  S  F  L  L  S  D  N  R  F  I  L  P  L  L
b       A  Q  Y  S  R  R  E  L  S  A  E  R  Q  Q  I  Y  P  A  P  P  V
c         R  N  I  V  G  E  L  S  A  E  R  Q  Q  I  Y  P  A  P  P  V
```

Figure 11AS

```
8101  TGGTAGTCCCTGTATATTCAGGCTGGTGCCAGCTTACATTAATCGAACTTGAGTCTATCG
      ------+---------+---------+---------+---------+---------+ 8160
      ACCATCAGGGACATATAAGTCCGACCACGGTCGAATGTAATTAGCTTGAACTCAGATAGC a   W  -  S  L  Y  I  Q  A  G  A  S  L  H  -  S  N  L  S  L  S
   b   G  S  P  C  I  F  R  L  V  P  A  Y  I  N  R  T  -  V  Y  R
   c   V  V  P  V  Y  S  G  W  C  Q  L  T  L  I  E  L  E  S  I  E

8161  AAATCGGCATGGGCGTTCGGATTCATTGCTTCGGCGACATCAGACTCGGTTTTTTGCTA
      ------+---------+---------+---------+---------+---------+ 8220
      TTTAGCCGTACCCGCAAGCCTAAGTAACGAAGCCGCTGTAGTCTGAGCCAAAAAACGAT a   K  S  A  W  A  F  G  F  I  A  S  A  T  S  D  S  V  F  L  L
   b   N  R  H  G  R  S  D  S  L  L  R  R  H  Q  T  R  F  F  C  Y
   c   I  G  M  G  V  R  I  H  C  F  G  D  I  R  L  G  F  F  A  I

8221  TTCAACTACCTGGGGAATCTACGCAAGGGTGTTGCTGACAGAGGATAACACGATGAAAT
      ------+---------+---------+---------+---------+---------+ 8280
      AAGTTGATGGACCCCTTAGATGCGTTCCCACAACGACTGTCTCCTATTGTGCTACTTTA a   F  N  Y  L  G  E  S  T  Q  G  C  C  -  Q  R  I  T  R  -  N
   b   S  T  T  W  G  N  L  R  K  G  V  A  D  R  G  -  H  D  E  I
   c   Q  L  P  G  G  I  Y  A  R  V  L  L  T  E  D  N  T  M  K  F
```

Figure 11AT

```
        TTGACGAATTAGTCCAGGATATCGAAACGCTACTTGCGTCAGGGAGCCCAATGTCAAAGA
8281    ------+---------+---------+---------+---------+---------+    8340
        AACTGCTTAATCAGGTCCTATAGCTTTGCGATGAACGCAGTCCCTCGGGTTACAGTTTCT a         L  T  N  -  S  R  I  S  K  R  Y  L  R  Q  G  A  Q  C  Q  R
b         -  R  I  S  P  G  Y  R  N  A  T  C  V  R  E  P  N  V  K  E
c         D  E  L  V  Q  D  I  E  T  L  L  A  S  G  S  P  M  S  K  S

GTGACGGAACGTCTTCAGTCGAACTTGAGCAGATACCACACAGGTGCTCTTTGAGGTCG
8341    ------+---------+---------+---------+---------+---------+    8400
        CACTGCCTTGCAGAAGTCAGCTTGAACTCGTCTATGGTGTGTCCACGAGAAACTCCAGC a         V  T  E  R  L  Q  S  N  L  S  R  Y  H  N  R  C  S  L  R  S
b         -  R  N  V  F  S  R  T  -  A  D  T  T  T  G  A  L  -  G  R
c         D  G  T  S  S  V  E  L  E  Q  I  P  Q  Q  V  L  F  E  V  G

GACGTGCGAGTCTGGAAATTGGACAATTACGACAACTTAAAACGGGGACGTTTGCCTG
8401    ------+---------+---------+---------+---------+---------+    8460
        CTGCACGCTCAGACCTTTAACCTGTTAATGCTGTTGAATTTGCCCCTGCAAAACGGAC a         D  V  R  V  W  K  L  D  N  Y  D  N  L  K  R  G  T  F  C  L
b         T  C  E  S  G  N  W  T  I  T  T  -  N  G  G  R  F  A  C
c         R  A  S  L  E  I  G  Q  L  R  Q  L  K  T  G  D  D  V  L  P  V
```

Figure 11AU

```
                     TAGGTGGATGTTTTGCGCCAGAGGTGACGAGATAAGAGTAAATGACCGTATTATTGGCAAG
8461      ---------+---------+---------+---------+---------+---------+ 8520
                     ATCCACCTACAAAACGCGGTCTCCACTGCTATTCTCATTTACTGGCATAATAACCCGTTC a    -  V  D  V  L  R  Q  R  -  R  -  E  -  M  T  V  L  L  G  K
       b       R  W  M  F  C  A  R  G  D  D  K  S  K  -  P  Y  Y  W  A  R
       c          G  G  C  F  A  P  E  V  T  I  R  V  N  D  R  I  I  G  Q  G

GTGAGTTGATTGCCTGTGGCAATGAATTTATGGTGCGTATTACACGTTGGTATCTTTGCA
8521      ---------+---------+---------+---------+---------+---------+ 8580
                     CACTCAACTAACGGACACCGTTACTTAAATACCACGCATAATGTGCAACCATAGAAACGT a    V  S  -  L  P  V  A  M  N  L  W  C  V  L  H  V  G  I  F  A
       b    -  V  D  C  L  W  Q  -  I  Y  G  A  Y  Y  T  L  V  S  L  Q
       c       E  L  I  A  C  G  N  E  F  M  V  R  I  T  R  W  Y  L  C  K

AAAATACAGCGTAAACCTGATAAGAAAAAATAATATGCGAACAATATAATAGCGTTCCAGG
8581      ---------+---------+---------+---------+---------+---------+ 8640
                     TTTTATGTCGCATTTGGACTATTCTTTTTTATTATACGCTTGTTATATTATCGCAAGGTCC end yscQ*
       a    K  I  Q  R  K  P  D  K  K  N  N  M  R  T  I  -  R  S  R
       b    K  Y  S  V  N  L  I  R  K  I  C  E  Q  Y  N  S  V  P  G
       c    N  T  A  -  T  -  -  E  K  -  Y  A  N  N  I  A  F  Q  V
```

Figure 11AV

```
8641  TCGTGTCATGAGAGATACAGTATGTCTTTACCCGATTCGCCTTTGCAACTGATTGGTATA
      ----------+---------+---------+---------+---------+---------+ 8700
      AGCACAGTACTCTCTATGTCATACAGAAATGGGCTAAGCGGAAACGTTGACTAACCATAT
                              start yscR*?
a                           M  S  L  P  D  S  P  L  Q  L  I  G  I
b     S  C  H  E  R  Y  S
c     R  V  M  R  D  T  V   C  L  Y  P  I  R  L  C  N  -  L  V  Y
                          V  S  -  E  I  Q  Y  V  F  T  R  F  A  F  A  T  D  W  Y  I 8701  TTGTTTCTGCTTTCAATACTGCCTCTCATTATCGTCATGGGAACTTCTTTCCTTAAACTG
      ----------+---------+---------+---------+---------+---------+ 8760
      AACAAAGACGAAAGTTATGACGGAGAGTAATAGCAGTACCCTTGAAGAAAGGAATTTGAC
a     L  F  L  L  S  I  L  P  L  I  I  V  M  G  T  S  F  L  K  L
b     C  F  F  Q  Y  C  L  S  L  S  S  W  E  L  L  S  L  N  W
c     V  S  A  F  N  T  A  S  H  Y  R  H  G  N  F  F  P  -  T  G 8761  GCGGGTGGTATTTTCGATTTTACGAAATGCTCTGGGTATTCAACAAGTCCCCCAAATATC
      ----------+---------+---------+---------+---------+---------+ 8820
      CGCCCACCATAAAAGCTAAAATGCTTTACGAGACCCATAAGTTGTTCAGGGGGTTTATAG
a     A  V  V  F  S  I  L  R  N  A  L  G  I  Q  Q  V  P  P  N  I
b     R  W  Y  F  R  F  Y  E  M  L  W  V  F  N  K  S  P  P  Q  I  S
c     G  G  I  F  D  F  T  K  C  S  G  Y  S  T  S  P  P  K  Y  R
```

Figure 11AW

```
8821  GCACTGTGTATGGCCTTGCGCTTGTACTTTCCTTATTCATTATGGGCCGACGCTATTAGCT
      ------------+---------+---------+---------+---------+---------+  8880
      CGTGACATACCGGAACGCGAACATGAAAGGAATAAGTAATACCCGGCTGCGATAATCGA
a       A  L  Y  G  L  A  L  R  L  Y  F  P  Y  S  L  F  I  M  G  P  T  L  L  A
b          H  C  M  A  L  R  L  Y  F  P  Y  S  L  W  G  R  R  Y  -  L
c            T  V  W  P  C  A  C  T  F  L  I  H  Y  G  A  D  A  I  S  C

8881  GTAAAAGAGCGCTGGCATCCGGTTCAGGTCGCTGGCGCTCCTTTCTGGACGTCTGAGTGG
      ------------+---------+---------+---------+---------+---------+  8940
      CATTTTCTCGCGACCGTAGGCCAAGTCCAGCGACCGCGAGGAAAGACCTGCAGACTCACC
a    V  K  E  R  W  H  P  V  Q  V  A  G  A  P  F  W  T  S  E  W
b    -  K  S  A  G  I  R  F  R  S  L  A  L  L  S  G  R  L  S  G
c       K  R  A  L  A  S  G  S  G  R  W  R  S  F  L  D  V  -  V  G

8941  GACAGTAAAGCATTAGCGCCCTTATCGACAGCCTTATCGACAGTTTTTGCAAAAAAACTCTGAAGAGAAGGAA
      ------------+---------+---------+---------+---------+---------+  9000
      CTGTCATTTCGTAATCGCGGGAATAGCTGTCGGAATAGCTGTCAAAAACGTTTTTTGAGACTTCTCTTCCTT
a    D  S  K  A  L  A  P  Y  R  Q  F  L  Q  K  N  S  E  E  K  E
b    T  V  K  H  -  R  L  I  D  S  F  C  K  K  T  L  K  R  R  K
c    Q  -  S  I  S  A  L  S  T  V  F  A  K  K  L  -  R  E  G  S
```

Figure 11AX

```
9001  GCCAATTATTTCGGAATTTGATAAAACGAACCTGGCCTGAAGACATAAAAGAAAGATA
      ----+----+----+----+----+----+----+----+----+----+----+----+ 9060
      CGGTTAATAAAGCCTTAAACTATTTTGCTTGGACCGGACTTCTGTATTTTCTTTCTAT a       A  N  Y  F  R  N  L  I  K  R  T  W  P  E  D  I  K  R  K  I
b       P  I  F  G  I  -  N  E  P  G  L  K  T  -  K  E  R  -
c       Q  L  F  S  E  F  D  K  T  N  L  A  -  R  H  K  K  D  K

9061  AAACCTGATTCTTTGCTCATATTAATTCCGGCATTTACGGTGAGTCAGTTAACGCAGGCA
      ----+----+----+----+----+----+----+----+----+----+----+----+ 9120
      TTTGGACTAAGAAACGAGTATAATTAAGGCCGTAAATGCCACTCAGTCAATTGCGTCCGT a       K  P  D  S  L  L  I  L  I  P  A  F  T  V  S  Q  L  T  Q  A
b       N  L  I  L  C  S  Y  -  F  R  H  L  R  -  V  S  -  R  R  H
c       T  -  F  F  A  H  I  N  S  G  I  Y  G  E  S  V  N  A  G  I

9121  TTTCGGATTGGATTACTTATTTATCTTCCCTTTCTGCTATTGACCTGCTTATTCAAAT
      ----+----+----+----+----+----+----+----+----+----+----+----+ 9180
      AAAGCCTAACCTAATGAATAAATAGAAGGGAAAGACGATAACTGGACGAATAAAGTTTA a       F  R  I  G  L  L  I  Y  L  P  F  L  A  I  D  L  L  I  S  N
b       F  G  L  D  Y  L  F  I  F  P  F  W  L  L  T  C  L  F  Q  I
c       S  D  W  I  T  Y  L  S  S  L  S  G  Y  -  P  A  Y  F  K  Y
```

Figure 11AY

```
         ATACTGCTGGCTATGGGGATGATGATGGTGTCGCCGATGACCATTTCATTACCGTTTAAG
         ------+---------+---------+---------+---------+---------+  9240
         TATGACGACCGATACCCCTACTACCACAGCGGCTACTGGTAAAGTAATGGCAAATTC

9181 a             I  L  L  A  M  G  M  M  V  S  P  M  T  I  S  L  P  F  K
b              Y  C  W  L  W  G  -  W  C  R  R  -  P  F  H  Y  R  L  S
c               T  A  G  Y  G  D  D  D  D  G  V  A  D  D  H  F  I  T  V  -  A

CTGCTAATATTTTACTGGCAGGCGGTTGGGATCTGACACTGGCGCAATTGGTACAGAGC
         ------+---------+---------+---------+---------+---------+  9300
         GACGATTATAAAATGACCGTCCGCCAACCCTAGACTGTGACCGCGTTAACCATGTCTCG 9241
                                                          end yscR*
a            L  L  I  F  L  L  A  G  G  W  D  L  T  L  A  Q  L  V  Q  S
b             C  -  Y  F  Y  W  Q  A  V  G  I  -  H  W  R  N  W  Y  R  A
c              A  N  I  F  T  G  R  R  L  G  S  D  T  G  A  I  G  T  E  L TTTTCATGAATGATTCTGAATTGACGCAACTTTTATGGATCGTCCTTT
         ------+---------+---------+---------+---------+---------+  9360
         AAAAGTACTTACTAAGACTTAACTGCGTTGAAAATACCTAGCAGGAAA 9301
         start yscS*
a        F  S  -  M  I  L  N  -  R  N  L  -  R  A  T  F  M  D  R  P  F
b         F  H  E  -  F  -  I  D  A  I  C  N  A  T  F  M  D  R  P  F
c          F  M  N  D  S  E  L  T  Q  F  V  T  Q  L  L  W  I  V  L  F Figure 11AZ
```

```
        TTACGTCTATGCCGGTAGTGTTGGTGGCATCGGTAGTTGGTGTCATCGTAAGCCTTGTTC
9361    ------+---------+---------+---------+---------+---------+   9420
        AATGCAGATACGGCCATCACAACCACCGTAGCCATCAACCACAGTAGCATTCGGAACAAG a         L  R  L  C  R  -  C  W  H  R  -  L  V  S  S  -  A  L  F
b         Y  V  Y  A  G  S  V  G  G  I  G  S  W  C  H  R  K  P  C  S
c       T  S  M  P  V  V  L  V  A  S  V  V  G  V  I  V  S  L  V  Q

AGGCCTTGACTCAAATACAGGACCAAACGCTACAGTTCATGATTAAATTATTGGCAATTG
9421    ------+---------+---------+---------+---------+---------+   9480
        TCCGGAACTGAGTTTATGTCCTGGTTTGCGATGTCAAGTACTAATTTAATAACCGTTAAC a         R  P  -  L  K  Y  R  T  K  R  Y  S  S  -  L  N  Y  W  Q  L
b         G  L  D  S  N  T  G  P  N  A  T  V  H  D  -  I  I  G  N  C
c       A  L  T  Q  I  Q  D  Q  T  L  Q  F  M  I  K  L  L  A  I  A

CAATAACCTTAATGGTCAGCTACCCATGGCTTAGCGGTATCCTGTTGAATTATACCCGGC
9481    ------+---------+---------+---------+---------+---------+   9540
        GTTATTGGAATTACCAGTCGATGGGTACCGAATCGCCATAGGACAACTTAATATGGGCCG a         Q  -  P  -  W  S  A  T  H  G  L  A  V  S  C  -  I  I  P  G
b         N  N  L  N  G  Q  L  P  M  A  -  R  Y  P  V  E  L  Y  P  A
c       I  T  L  M  V  S  Y  P  W  L  S  G  I  L  L  N  Y  T  R  Q
```

Figure 11BA

```
9541  AGATAATGTTACGAATTGGAGAGCATGGTTGAATGGCACAACAGGTAAATGAGTGGCTTA
      ----+----+----+----+----+----+----+----+----+----+----+----+  9600
      TCTATTACAATGCTTAACCTCTCGTACCAACTTACCGTGTTGTCCATTTACTCACCGAAT
                           end yscS*              start yscT*
a       R  -  C  Y  E  L  E  S  M  V  E  W  H  H  N  R  -  M  S  G  L
b       D  N  V  T  N  W  R  A  W  L  N  G  T  G  K  -  V  A  Y
c             I  M  L  R  I  G  E  H  G  -  M  A  Q  Q  V  N  E  W  L  I 9601  TTGCATTGGCTGTGTGGCTTTTATTCGACCATTGAGCCTTTCTTTATTACTTCCCTTATTAA
      ----+----+----+----+----+----+----+----+----+----+----+----+  9660
      AACGTAACCGACACACCGAAAATAAGCTGGTAACTCGGAAAGAAATAATGAAGGGAATAATT
a       L  H  W  L  W  L  L  F  D  H  -  A  F  L  Y  Y  F  P  Y  -
b        C  I  G  C  G  F  Y  S  T  I  E  P  F  F  I  T  S  L  I  K
c       A  L  A  V  A  F  I  R  P  L  S  L  L  L  P  L  L  K 9661  AAAGTGGCAGTTTAGGGGCCCGCACTTTTACGTAATGGCCGTGCTTATGTCACTTACCTTTC
      ----+----+----+----+----+----+----+----+----+----+----+----+  9720
      TTTCACCGTCAAATCCCCGGGCGTGAAAATGCATTACCGGCACGAATACAGTGAATGGAAAG
a       K  V  A  V  -  G  P  H  F  Y  V  M  A  C  L  C  H  L  P  F
b       K  W  Q  F  R  G  R  T  F  T  -  W  R  A  Y  V  V  T  Y  L  S
c         S  G  S  L  G  A  A  L  L  R  N  G  V  L  M  S  L  T  F  P
```

Figure 11BB

```
9721  CGATATTACCAATCATTTACCAGCAGAAGATTATGATGCATATATTGGTAAAGATTACAGTT  9780
      ------------+---------+---------+---------+---------+---------+
      GCTATAATGGTTAGTAAATGGTCGTCTTCTAATACTACGTATAACCATTTCTAATGTCAA a    R  Y  Y  Q  S  F  T  S  R  R  L  -  C  I  L  V  K  I  T  V
 b    D  I  T  N  H  L  P  A  E  D  Y  D  A  Y  W  -  R  L  Q  L
 c    I  L  P  I  I  Y  Q  Q  K  I  M  M  H  I  G  K  D  Y  S  W

Tn insertion P9B7
                                  ⇒
9781  GGTTAGGGTTAGTCACTGGAGAGGTGATTATTGGTTTTTCAATTGGGTTTTGTGCGGCGG  9840
      ------------+---------+---------+---------+---------+---------+
      CCAATCCCAATCAGTGACCTCTCCACTAATAACCAAAAAGTTAACCCAAAACACGCCGCC a    G  -  G  -  S  L  E  R  -  L  L  V  F  Q  L  G  F  V  R  R
 b    V  R  V  S  H  W  R  G  D  Y  W  F  F  N  W  V  L  C  G  G
 c    L  G  L  V  T  G  E  V  I  I  G  F  S  I  G  F  C  A  A  V 9841  TTCCCTTTTGGGCCGTTGATATGGCGGGGGTTTCTGCTTGATACTTTACGTGGCGACAA  9900
      ------------+---------+---------+---------+---------+---------+
      AAGGGAAAACCCGGCAACTATACCGCCCCCAAAGACGAACTATGAAATGCACCGCTGTT a    F  P  F  G  P  L  I  W  R  G  F  C  L  I  L  Y  V  A  R  Q
 b    S  L  L  G  R  -  Y  G  G  V  S  A  -  Y  F  T  W  R  D  N
 c    P  F  W  A  V  D  M  A  G  F  L  L  D  T  L  R  G  A  T  M
```

Figure 11BC

```
                  TGGGTACGATATATTCAATTCTACAATAGAAGCTGAAACCTCACTTTTTGGCTTGCTTTTCA
9901         ----+---------+---------+---------+---------+---------+---------+ 9960
                  ACCCATGCTATATAAGTTAAGATGTTATCTTCGACTTTGGAGTGAAAAACCGAACGAAAAGT a         W   V   R   Y   S   I   L   Q   -   K   L   K   P   H   F   L   A   C   F   S
    b           G   Y   D   I   Q   F   Y   N   R   S   -   N   L   T   F   W   L   A   F   Q
    c             G   T   I   F   N   S   T   I   E   A   E   T   S   L   F   G   L   L   F   S

GCCAGTTCTTGTGTGTTATTTTCTTTATAAGCGGCGGCATGGAGTTTATATTAAACATTC
9961         ----+---------+---------+---------+---------+---------+---------+ 10020
                  CGGTCAAGAACACACAATAAAAGAAATATTCGCCGCCGTACCTCAAATATAATTTGTAAG a         A   S   S   C   V   L   F   S   L   -   A   A   A   W   S   L   Y   -   T   F
    b           P   V   L   V   C   Y   F   L   Y   K   R   R   H   G   V   Y   I   K   H   S
    c             Q   F   L   C   V   I   F   F   I   S   G   G   M   E   F   I   L   N   I   L

TGTATGAGTCATATCAATATTTACCACCAGGGCGTACTTTATTATTGACCAGCAATTTT
10021        ----+---------+---------+---------+---------+---------+---------+ 10080
                  ACATACTCAGTATAGTTATAAATGGTGGTCCCGCATGAAATAATAAACTGGTCGTTAAAA a         C   M   S   H   I   N   I   Y   H   Q   G   V   L   Y   Y   L   T   S   N   F
    b           V   -   V   I   S   I   F   T   T   R   A   Y   F   I   I   -   P   A   I   F
    c             Y   E   S   Y   Q   Y   L   P   P   G   R   T   L   L   F   D   Q   Q   F   L

Figure 11BD
```

```
           TAAAATATATCCAGGCAGAGTGGAGAACGCTTTATCAATTATGTATCAGCTTCTCTTC
10081      ---------+---------+---------+---------+---------+---------+  10140
           ATTTTATATAGGTCCGTCTCACCCTCTTGCGAAATAGTTAATACATAGTCGAAGAGAAG a            -  N  I  S  R  Q  S  G  E  R  F  I  N  Y  V  S  A  S  L  F
b            K  I  Y  P  G  R  V  E  N  A  L  S  I  M  Y  Q  L  L  S  S
c            K  Y  I  Q  A  E  W  R  T  L  Y  Q  L  C  I  S  F  S  L  P

CTGCCATAATATGTATGGTATTAGCCGATCTGGCTTTAGGTCTTTTAAATCGGTCGGCAC
10141      ---------+---------+---------+---------+---------+---------+  10200
           GACGGTATTATACATACCATAATCGGCTAGACCGAAATCCAGAAAATTTAGCCAGCCGTG a            L  P  -  Y  V  W  Y  -  P  I  W  L  -  V  F  -  I  G  R  H
b            C  H  N  M  Y  G  I  S  R  S  G  F  R  S  F  K  S  V  G  T
c            A  I  I  C  M  V  L  A  D  L  A  L  G  L  L  N  R  S  A  Q

AACAATTGAATGTGTTTTCTTCTCAATGCCGCTCAAAAGTATATTGGTTCTACTGACGY
10201      ---------+---------+---------+---------+---------+---------+  10260
           TTGTTAACTTACACAAAAGAAGAGTTACGGCGAGTTTTCATATAACCAAGATGACTGCR a            N  N  -  M  C  F  S  S  Q  C  R  S  K  V  Y  W  F  Y  -  X
b            T  I  E  C  V  F  F  L  L  N  A  A  Q  K  Y  I  G  S  T  D  X
c            Q  L  N  V  F  F  F  S  M  P  L  K  S  I  L  V  L  L  T  X
```

Figure 11BE

```
                CCTGATCTCATTCCCTTATGCTCTTCATCACTATTTGGTTGAAAGCGATAAATTTATAT
10261           ------------+---------+---------+---------+---------+---------+  10320
                GGACTAGAGTAAGGGAATACGAGAAGTAGTGATAAACCAACTTTCGCTATTTAAATATA a                  P  D  L  I  P  L  C  S  S  L  F  G  -  K  R  -  I  L  Y
b                L  I  S  F  P  Y  A  L  H  H  Y  L  V  E  S  D  K  F  Y  I
c                -  S  H  S  L  M  L  F  I  T  I  W  L  K  A  I  N  F  I  F

TTATCTAAAAGACTGGTTTCCATCTGTATGAGCGAGAAAACAGAACAGCCTACAGAAAAG
10321           ------------+---------+---------+---------+---------+---------+  10380
                AATAGATTTTCTGACCAAAGGTAGACATACTCGCTCTTTTGTCTTGTCGGATGTCTTTTC
                                  end yscT*   start yscU*
a                  L  S  K  R  L  V  S  I  C  M  S  E  K  T  E  Q  P  T  E  K
b                Y  L  K  D  W  F  P  S  V  -  A  R  K  Q  N  S  L  Q  K  R
c                  I  -  K  T  G  F  H  L  Y  E  R  E  N  R  T  A  Y  R  K  E AAATTACGTGATGGCCGTAAGGAAGGGCAGGTTGTCAAAAGTATTGAAATAACATCATTA
10381           ------------+---------+---------+---------+---------+---------+  10440
                TTTAATGCACTACCGGCATTCCTTCCCGTCCAACAGTTTTCATAACTTTATTGTAGTAAT a                  K  L  R  D  G  R  K  E  G  Q  V  V  K  S  I  E  I  T  S  L
b                N  Y  V  M  A  V  R  K  G  R  L  S  K  V  L  K  -  N  N  I  I  Y
c                  I  T  -  W  P  -  G  R  A  G  C  Q  K  Y  -  N  N  I  I  I Figure 11BF
```

```
10441   TTTCAGCTGATTGCGCTTTATTTGTATTTCATTTCTTTACTGAAAAGATGATTTGATA
        -----------+---------+---------+---------+---------+----  10500
        AAAGTCGACTAACGCGAAATAAACATAAAGTAAGAAATGACTTTTCTACTAAACTAT a        F  Q  L  I  A  L  Y  L  Y  F  H  F  F  T  E  K  M  I  L  I
b        F  S  -  L  R  F  I  C  I  F  I  S  L  L  K  R  -  F  -  Y
c        S  A  D  C  A  L  F  V  F  S  F  L  Y  -  K  D  D  F  D  T

10501   CTGATTGAGTCAATAACTTTCACATTACAATTAGTAAATAAACCATTTCTTATGCATTA
        -----------+---------+---------+---------+---------+----  10560
        GACTAACTCAGTTATTGAAAGTGTAATGTTAATCATTTATTTGGTAAAGAATACGTAAT a        L  I  E  S  I  T  F  T  L  Q  L  V  N  K  P  F  S  Y  A  L
b        -  L  S  Q  -  L  S  H  Y  N  -  I  N  H  F  L  M  H  -
c        D  -  V  N  N  F  H  I  T  I  S  K  -  T  I  F  L  C  I  N

10561   ACGCAATTGAGTCATGCTTTAATAGAGTCACTCTGCACTTCTGACTGAAGACGTGACGA
        -----------+---------+---------+---------+---------+----  10620
        TGCGTTAACTCAGTACGAAATTATCTCAGTGAGTCGAAGACTGACTTCTGCACTGCTGCT a        T  Q  L  S  H  A  L  I  E  S  L  T  S  A  L  L  F  L  G  A
b        R  N  -  V  M  L  -  S  H  -  L  L  H  C  C  F  W  A  L
c        A  I  E  S  C  F  N  R  V  T  D  F  C  T  A  V  S  G  R  W
```

Figure 11BG

```
10621  GGGGTAATAGTTGCTACTGTGGGTAGCGTGTTTCTTCAGGTGGGGTGGTTATTGCCAGC
       -----+---------+---------+---------+---------+---------+ 10680
       CCCCATTATCAACGATGACACCCATCGCACAAAGAAGTCCACCCCCACCAATAACGGTCG a        G  V  I  A  T  V  G  S  V  F  L  Q  V  G  V  V  I  A  S
b        G  -  L  L  W  V  A  C  F  F  R  W  G  W  L  L  P  A
c        G  N  S  C  Y  C  G  -  R  V  S  G  G  G  G  Y  C  Q  Q

10681  AAGGCCATTGGTTTTAAAAGCGAGCATATAAATCCGGTAAGTAATTTTAAGCAGATATTC
       -----+---------+---------+---------+---------+---------+ 10740
       TTCCGGTAACCAAAATTTTCGCTCGTATATTTAGGCCATTCATTAAAATTCGTCTATAAG a        K  A  I  G  F  K  S  E  H  I  N  P  V  S  N  F  K  Q  I  F
b        R  P  L  V  L  K  A  S  I  -  I  R  -  V  I  L  S  R  Y  S
c        G  H  W  F  -  K  R  A  Y  K  S  G  K  -  F  -  A  D  I  L

10741  TCTTTACATAGCGTAGTAGAATTATGTAAAATCCAGCCTAAAAGTTATCATGCTATCTCTT
       -----+---------+---------+---------+---------+---------+ 10800
       AGAAATGTATCGCATCATCTTAATACATTTAGGTCGGATTTTCAATAGTACGATAGAGAA a        S  L  H  S  V  V  E  L  C  K  S  S  L  K  V  I  M  L  S  L  L
b        L  Y  I  A  -  N  Y  V  N  P  A  -  K  L  S  C  Y  L  L
c        F  T  -  R  S  R  I  M  -  I  Q  P  K  S  Y  H  A  I  S  Y
```

Figure 11BH

```
       ATCTTTGCCTTTTCTTTATTATTATGCCAGTACTTTTCGGGGCTACCGTGTGGG
10801  ----+----+----+----+----+----+----+----+----+----+----+----+  10860
       TAGAAACGGAAAAGAAAATAATAATACGGTCATGAAAAGCCCGCGATGGCATGACACCC a          I   F   A   F   F   F   Y   Y   Y   A   S   T   F   R   A   L   P   Y   C   G
b            S   L   P   F   F   I   I   M   P   V   L   F   G   R   Y   R   T   V   G
c              L   C   L   F   L   L   L   C   Q   Y   F   S   G   A   T   V   L   W   V

TTAGCCTGTGGCGTGCTTGTGGTTTCTTCTTTAATAAAATGGTTATGGGTAGGGGTGATG
10861  ----+----+----+----+----+----+----+----+----+----+----+----+  10920
       AATCGGACACCGCACGAACACCAAAGAAGAAATTATTTTACCAATACCCATCCCCACTAC a          L   A   C   G   V   L   V   V   S   S   L   I   K   W   L   W   V   G   V   M
b            -   P   V   A   C   L   W   F   L   L   -   N   G   Y   G   -   G   -   W
c              S   L   W   R   A   C   G   F   F   F   N   K   M   V   M   G   R   G   D   G

GTTTTTATATCGTCGTTGGCATACTGGACTATTCTTTTCAATATTATAAGATTAGAAAA
10921  ----+----+----+----+----+----+----+----+----+----+----+----+  10980
       CAAAAATATAGCAGCAACCGTATGACCTGATAAGAAAAGTTATAATATTCTAATCTTTT a          V   F   Y   I   V   V   G   I   L   D   Y   S   F   Q   Y   Y   K   I   R   K
b            F   F   I   S   S   L   A   Y   W   T   I   L   F   N   I   R   L   E   K
c              F   L   Y   R   R   W   H   T   G   L   F   F   S   I   L   -   D   -   K   S
```

Figure 11BI

```
10981   GCTATCTAAAAATGAGTAAAGATGACGTAAAACAGGAGCATAAAGATCTGGAGGGCGACC  11040
        ---------+---------+---------+---------+---------+---------+
        CGATAGATTTTACTCATTTCTACTGCATTTTGTCCTCGTATTTCTAGACCTCCCGCTGG a       A  I  -  K  -  V  K  M  T  -  N  R  S  I  K  I  W  R  A  T
b       L  S  K  N  E  -  R  -  R  K  T  G  A  -  R  S  G  G  R  P
c       Y  L  K  M  S  K  D  D  V  K  Q  E  H  K  D  L  E  G  D  P

Tn insertion P12F5
11041   CTCAAATGAAGACGCGGGCGTCGGAAATGCAGAGTGAAATACAAAGTGGGAGTTTAGCTCA  11100
        ---------+---------+---------+---------+---------+---------+
        GAGTTTACTTCTGCGCCCGCAGCCTTTACGTCTCACTTTATGTTTCACCCTCAAATCGAGT a       L  K  -  R  R  G  V  G  N  A  E  -  N  T  K  W  E  F  S  S
b       S  N  E  D  A  A  S  E  M  Q  S  E  I  Q  S  G  S  L  A  Q
c       Q  M  K  T  R  R  R  K  C  R  V  K  Y  K  V  G  V  -  L  N 11101   ATCTGTTAAACAATCTGTTGCCGTAGTGCGTAATCCAACGCATATTGCGGTTTGTCTTGG  11160
        ---------+---------+---------+---------+---------+---------+
        TAGACAATTTGTTAGACAACGCCATCACGCATTAGTTGCGTATAACGCCAAACAGAACC a       I  C  -  T  I  C  C  G  S  A  -  S  N  A  Y  C  G  L  S  W
b       S  V  K  Q  S  V  A  V  V  R  N  P  T  H  I  A  V  C  L  G
c       L  L  N  N  L  L  R  -  C  V  I  Q  R  I  L  R  F  V  L  A
```

Figure 11BJ

```
11161  CTATCATCCCACCGATATGCCAATACCACGCGTCCTGGAAAAAGGCAGTGATGCTCAAGC
       ------------+---------+---------+---------+---------+---------+  11220
       GATAGTAGGGTGGCTATACGGTTATGGTGCGCAGGACCTTTTTCCGTCACTACGAGTTCG a        L  S  S  H  R  Y  A  N  T  T  R  P  G  K  R  Q  -  C  S  S
b        Y  H  P  T  D  M  P  I  P  R  V  L  E  K  K  G  S  D  A  Q  A
c        I  I  P  P  I  C  Q  Y  H  A  S  W  K  K  K  A  V  M  L  K  L

11221  TAACTATATATTGTTAACATCGCTGAACGCAACTGCATCCCCGTTGTTGAAAATGTTGAGCT
       ------------+---------+---------+---------+---------+---------+  11280
       ATTGATATAACAATTGTAGCGACTTGCGTTGACGTAGGGCAACAACTTTTACAACTCGA a        -  L  Y  C  -  H  R  -  T  Q  L  H  P  R  C  -  K  C  -  A
b        N  Y  I  V  N  I  A  E  R  N  C  I  P  V  V  E  N  V  E  L
c        T  I  L  L  T  S  L  N  A  T  A  S  P  L  L  K  M  L  S  W

11281  GGCCCGCTCATTATTTTTTGAAGTGGAACGCGGAGATAAAATTCCTGAAACGTTATTGA
       ------------+---------+---------+---------+---------+---------+  11340
       CCGGGCGAGTAATAAAAAACTTCACCTTGCGCCTCTATTTTAAGGACTTTGCAATAAACT a        G  P  L  I  F  F  -  S  G  T  R  R  -  N  S  -  N  V  I  -
b        A  R  S  L  F  F  E  V  E  R  G  D  K  I  P  E  T  L  F  E
c        P  A  H  Y  F  L  K  W  N  A  E  I  K  F  L  K  R  Y  L  N
```

```
11521 CAAGCACCAGATAGCGTATTATAAAATTAAACAAGATAATGGATTGGTGCGTCTGAATGG 11580
       ------+---------+---------+---------+---------+---------+
       GTTCGTGGTCTATCGCATAATATTTTAATTTGTTCTATTACCTAACCACGCAGACTTACC a        Q  A  P  D  S  V  L  -  N  -  T  R  -  W  I  G  A  S  E  W
b        K  H  Q  I  A  Y  Y  K  I  K  Q  D  N  G  L  V  R  L  N  G
c        S  T  R  -  R  I  I  K  L  N  K  I  M  D  W  C  V  -  M  D

11581 ACTCGAACCACTCGACCCCCACCATGTCAAGGTGGTCTCTAACCAACTGAGCTATGAAC 11640
       ------+---------+---------+---------+---------+---------+
       TGAGCTTGGTGAGCTGGGGGTGGTACAGTTCCACCAGAGATTGGTTGACTCGATACTTG a        T  R  T  T  R  P  P  P  C  Q  G  G  A  L  T  N  -  A  M  N
b        L  E  P  L  D  P  H  H  V  K  V  V  L  -  P  T  E  L  -  T
c        S  N  H  S  T  P  T  M  S  R  W  C  S  N  Q  L  S  Y  E  R

11641 GGCAACGTTGTAGGTGACAACGGGGACGAATATTAGCGTCACAACCGCAATGAGGCAAGA 11700
       ------+---------+---------+---------+---------+---------+
       CCGTTGCAACATCCACTGTTGCCCCTGCTTATAATCGCAGTGTTGGCGTTACTCCGTTCT a        G  N  V  V  G  D  N  G  D  E  Y  -  R  H  N  R  N  E  A  R
b        A  T  L  -  V  T  T  G  T  N  I  S  V  T  T  A  M  R  Q  E
c        Q  R  C  R  -  Q  R  G  R  I  L  A  S  Q  P  Q  -  G  K  R
```

Figure 11BM

```
11701  GGGAAATCGCAATTTCTTCCTGAAATCACCTGATTGCGGTGAAATATGCAACATGTCG
       ------+---------+---------+---------+---------+---------+ 11760
       CCCTTTAGCGTTAAAAGAAGGACTTTAGTGGACTAACGCCACCTTTATACGTTGTACAGC a       G  K  S  Q  F  S  S  -  N  H  L  I  A  V  E  I  C  N  M  S
b       G  N  R  N  F  L  P  E  I  T  -  L  R  W  K  Y  A  T  C  R
c       E  I  A  I  F  F  L  K  S  P  D  C  G  G  N  M  Q  H  V  E

11761  AGAAAATAGCCGCCATGCGACGGCTATCGTCGTATTATCGGAGCGCTGCAAAATGATG
       ------+---------+---------+---------+---------+---------+ 11820
       TCTTTTATCGGCGGTACGCTGCCGATAGCAGCATAATAGCCTCGCCGACGTTTTACTAC a       R  K  -  P  P  C  D  G  Y  R  R  I  I  G  A  R  C  K  M  M
b       E  N  S  R  H  A  T  A  I  V  V  L  S  E  R  A  A  K  -  W
c       K  I  A  A  M  R  R  L  S  S  Y  Y  R  S  A  L  Q  N  D  G

11821  GCGGACGGCTGACGTTGTAGATAGCGCATCCGTAGCATCATTAACACCGCCGGAGGTC
       ------+---------+---------+---------+---------+---------+ 11880
       CGCCTGCCGACTGCAACATCTATCGCGTAGGCATCGTAGTAATTGTGGCGGCCTCCAG a       A  D  G  -  R  C  R  -  R  I  R  S  I  I  N  T  A  A  E  V
b       R  T  A  D  V  V  D  S  A  S  V  A  S  L  T  P  P  P  R  S
c       G  R  L  T  L  -  I  A  H  P  -  H  H  -  H  R  R  R  G  Q
```

Figure 11BN

```
11881   AGGCCGATGATGAACCCATCCAGAAGCCTGCCGGTCCCATACGATCCACCAAATCC
        ----+----|----+----|----+----|----+----|----+----|----+  11940
        TCCGGCTACTACTTGGGTAGGTCTTCGGACGGCCAGGGTATGCTAGGTGGTTTAGG a         R  P  M  M  N  P  I  Q  K  P  A  G  P  I  R  S  T  T  K  S
b         G  R  -  T  P  S  R  S  L  P  V  P  Y  D  P  P  P  N  P
c         A  D  D  E  P  H  P  E  A  C  R  S  H  T  I  H  H  Q  I  R

11941   GTTAAACGCCAGGATATAACCGCTGGGTAAACCTAACACCCAGTAGGCGGTAAAGGTGATA
        ----+----|----+----|----+----|----+----|----+----|----+  12000
        CAATTGCGGTCCTATATTGGCGACCCATTTGGATTGTGGGTCATCCGCCATTTCCACTAT a         V  N  A  R  I  -  P  L  G  K  P  N  T  Q  -  A  V  K  V  I
b         L  T  P  G  Y  N  R  W  V  N  L  T  P  S  R  R  -  R  -  -
c         -  R  Q  D  I  T  A  G  -  T  -  H  P  V  G  G  K  G  D  K

12001   AAAAAGATGGAACGCGTATCTTTATAACCGGCCAGAATACCGCCTGCCGATAACCTGTATA
        ----+----|----+----|----+----|----+----|----+----|----+  12060
        TTTTTCTACCTTGCGCATAGAAATATTGGCCGGTCTTATGGCGACGGCTATTGGACATAT a         K  K  M  E  R  V  S  L  -  P  R  R  I  P  L  P  I  T  C  I
b         K  R  W  N  A  Y  L  Y  N  R  A  E  Y  R  C  R  -  P  V  -
c         K  D  G  T  R  I  F  I  T  A  Q  N  T  A  A  D  N  L  Y  R
```

Figure 11BO

```
12061  GAGTCGGAAATCTGGTAAACCGCAGCAGCATTAATTGCGGCAAGCGCCACGACCTC
       ----+----+----+----+----+----+----+----+----+----+----+  12120
       CTCAGCCTTTAGACCATTTGGCGTCGTCGTAATTAACGCCGTTCGCGGTGCTGGAG a       E  S  E  I  W  -  T  A  A  S  S  I  N  C  G  K  R  H  D  L
b        S  R  K  S  G  K  P  Q  R  A  A  L  I  A  A  S  A  T  T  S
c         V  G  N  L  V  N  R  S  E  Q  H  -  L  R  Q  A  P  R  P  Q

12121  AGGGTTGTCATTGTAGAGCAAAGCAATATGCTTACGCAGAGTAACGGTAAAAATAGCGGT
       ----+----+----+----+----+----+----+----+----+----+----+  12180
       TCCCAACAGTAACATCTCGTTTCGTTATACGAATGCGTCTCATTGCCATTTTATCGCCA a       R  V  V  I  V  E  Q  S  N  M  L  T  Q  S  N  G  K  N  S  G
b        G  L  S  L  -  S  K  A  I  C  L  R  R  V  T  V  K  I  A  V
c         G  C  H  C  R  A  K  Q  Y  A  Y  A  E  -  R  -  K  -  R  -

12181  AACCACAGCCATACAAATGCCGACGCCTAAACGCTGCCGATTTGGCCATGCGGACGCAAACGCGTAGGTCG
       ----+----+----+----+----+----+----+----+----+----+----+  12240
       TTGGTGTCGGTATGTTTACGGCTGCGGATTTGCGACGGCTAAACCGGTACGCCTGCGTTTGCGCATCCAGC a       N  H  S  H  T  N  A  D  A  -  T  G  T  R  C  V  C  A  S  S
b        T  T  A  I  Q  M  P  T  P  K  P  V  R  A  A  F  A  H  P  A
c         P  Q  P  Y  K  C  R  R  L  N  R  Y  A  L  R  L  R  I  Q  R
```

Figure 11BP

```
12241      GTTGAGCCCTGGCCCCAGACCGATAACCCACTCGAATCGTTACCGCCCGCAGCCAGCGACAT     12300
           ----------+---------+---------+---------+---------+---------+
           CAACTCGGGACCGGGGTCTGGCTATTGGGTGAGCTTAGCAATGGCGGGCGTCGGTCGCTGTA
``` a     V  E  P  W  P  R  P  I  T  H  S  N  R  Y  R  R  S  Q  R  H
b     L  S  P  G  P  D  R  -  P  T  R  I  V  T  A  A  A  S  D  I
c     -  A  L  A  Q  T  D  N  P  L  E  S  L  P  P  Q  P  P  A  T  S

```
12301      CGGCAGTACGAACATCAGCGAGCTAAAGTTAAGCGCAATCTGATGACCGGACATCCAC     12360
           ----------+---------+---------+---------+---------+---------+
           GCCGTCATGCTTGTAGTCGCTCGATTTCAATTCGCGTTAGACTACTGGCCTGTAGGTG
``` a     R  Q  Y  E  H  Q  R  A  K  V  K  R  N  L  M  T  G  D  I  H
b     G  S  T  N  I  S  E  L  K  L  S  A  I  -  P  A  T  S  T
c     A  V  R  T  S  A  S  -  S  -  A  Q  S  D  D  R  R  H  P  Q

```
12361      AATACCTAATGGCGAAACCAGCAGCCAACGACCGCAAATAACGTCACTTCAAAGAACAG     12420
           ----------+---------+---------+---------+---------+---------+
           TTATGGATTACCGCTTTGGTCGTCGGTTGCTGGCGTTTATTGCAGTGAAGTTTCTTGTC
``` a     N  T  -  W  R  E  N  Q  Q  R  N  D  R  K  -  R  H  F  K  E  Q
b     I  P  N  G  E  T  S  S  A  T  T  A  N  N  V  T  S  K  N  S
c     Y  L  M  A  K  P  A  A  Q  R  P  Q  I  T  S  L  Q  R  T  A

Figure 11BQ

```
                CCAGGCGCAATCGGCCAACCCCAGTTGAATCAGGCGCTTCATGACGACGCTATCGGGTTTGC
12421           ----------+---------+---------+---------+---------+---------+ 12480
                GGTCGCGTTAGCCGGTTGGGGTCAACTTAGTCCGCGAAGTACTGCTGCGATAGCCCAAACG a       P  A  Q  S  A  T  P  V  E  S  G  A  S  -  R  R  Y  R  V  C
            b       Q  R  N  R  Q  P  Q  L  N  Q  A  L  H  D  D  A  I  G  F  A
            c    S  A  I  G  N  P  S  -  I  R  R  F  M  T  T  L  S  G  L  P

CAAAGCCTTTTTCATTACGAATATCACGCATTGAACGCGGTGTTTAATGTAAGAAAGCA
12481           ----------+---------+---------+---------+---------+---------+ 12540
                GTTTCGGAAAAAGTAATGCTTATAGTGCGTAACTTGCGCCACAAATTACATTCTTTCGT a    Q  S  L  F  H  Y  E  Y  H  A  L  N  A  R  V  -  C  K  K  A
            b       K  A  F  F  I  T  N  I  T  H  -  T  R  V  F  N  V  R  K  H
            c       K  P  F  S  L  R  I  S  R  I  E  R  A  C  L  M  -  E  S  M

TGGCGATAAACATCACCCAATAGACCCGCCAGTCGCAACGCCCGCAGCCGATACCGCCGA
12541           ----------+---------+---------+---------+---------+---------+ 12600
                ACCGCTATTTGTAGTGGGTTATCTGGGCGGTCAGCGTTGCGGGCGTCGGCTATGGCGGCT a    W  R  -  T  S  P  N  R  P  P  Q  S  Q  R  R  S  R  Y  R  R
            b       G  D  K  H  H  P  I  D  R  R  S  R  N  A  A  A  D  T  A  E
            c       A  I  N  I  T  Q  -  T  A  A  V  A  T  P  Q  P  I  P  P  S

Figure 11BR
```

```
12601 GTTCCGGCATACCAAAATGGCCATAGATAAAAATATAGTTCACCGGAATATTCACCAGCA 12660
      ------+---------+---------+---------+---------+---------+
      CAAGGCCGTATGGTTTTACCGGTATCTATTTTTATATCAAGTGGCCTTATAAGTGGTCGT a       V  P  A  Y  Q  N  G  H  R  -  K  Y  S  S  P  E  Y  S  P  A
b       F  R  H  T  K  M  A  I  D  K  N  I  V  H  R  N  I  H  Q  Q
c        S  G  I  P  K  W  P  -  I  K  I  -  F  T  G  I  F  T  S  R

12661 GGCCCAAAAATCCCATCACCATACCCGGTTTGGTTTTTGGCCAGACCTTCGCACTGGTTTC 12720
      ------+---------+---------+---------+---------+---------+
      CCGGGTTTTTAGGGTAGTGGTATGGGCCAAACCAAAACCGGTCTGGAAGCGTGACCAAAG a       G  P  K  I  P  S  P  Y  P  V  W  F  W  P  D  L  R  T  G  F
b       A  Q  K  S  H  H  H  T  R  F  G  F  G  Q  T  F  A  L  V  S
c        P  K  N  P  I  T  I  P  G  L  V  L  A  R  P  S  H  W  F  R

12721 GCGCTACCTGAAAGAAAAAGGTATCCTGCGCCCCACAGCAGCGCGAAGATAACCCACGG 12780
      ------+---------+---------+---------+---------+---------+
      CGCGATGGACTTTCTTTTTCCATAGGACGCGGGGTGTCGTCGCGCTTCTATTGGGTGCC a       A  L  P  E  R  K  G  I  L  R  P  T  A  A  R  E  D  N  P  R
b       R  Y  L  K  E  K  K  V  S  C  A  P  Q  Q  R  A  K  I  T  H  G
c        A  T  -  K  K  R  R  Y  P  A  P  H  S  S  A  R  R  -  P  T  A
```

Figure 11BS

```
      CTTTATGGCCAGCGCCCGGATCAATATTATGCATAGAGCGGATAATGTATCCGGCATTCC
12781 ------+---------+---------+---------+---------+---------+ 12840
      GAAATAGCCGGTCGCGGGCCTAGTTATAATACGTATCTCGCCTATTACATAGGCCGTAAGG a      L  Y  R  P  A  P  D  Q  Y  Y  A  -  S  G  -  C  I  R  H  S
b       F  I  G  Q  R  R  I  N  I  M  H  R  A  D  N  V  S  G  I  P
c        L  S  A  S  A  G  S  I  L  C  I  E  R  I  M  Y  P  A  F  H

ACAGGACGATCATCACCAGCACGGAGACAAAGCCCGCCAGCCAGAACCCTTGTCGAACCT
12841 ------+---------+---------+---------+---------+---------+ 12900
      TGTCCTGCTAGTAGTGGTCGTGCCTCTGTTTCGGGCGGTCGGTCTTGGGAACAGCTTGGA a      T  G  R  S  S  P  A  R  R  Q  S  P  P  A  R  T  L  V  E  P
b       Q  D  D  H  H  Q  H  G  D  K  A  R  Q  P  E  P  L  S  N  L
c        R  T  I  I  T  S  T  E  T  K  P  A  S  Q  N  P  C  R  T  -

GATGCGCGATACGCTCACGACGGCCATTGAGTTGCGCAATCACAGGCGTCAAGG
12901 ------+---------+---------+---------+---------+---------+ 12960
      CTACGCGCTATGCGAGTGCTGCCGGTAACTCAACGCGTTAGTGTCCGCAGTTCC a      D  A  R  Y  A  H  D  G  R  S  H  -  V  A  Q  S  Q  A  S  R
b       M  R  D  T  L  T  T  A  G  A  I  E  L  R  N  H  R  R  Q  G
c        C  A  I  R  S  R  R  P  E  P  L  S  C  A  I  T  G  V  K  A
```

Figure 11BT

```
12961 CCAGCAGTAAGCCGTGACCAAACAAAATGGCGGAAGCAGATAGAGGTGCCGATAGCGAC
      ----+----+----+----+----+----+----+----+----+----+----+----+ 13020
      GGTCGTCATTCGGCACTGGTTTGTTTTACCGCCCTTCGTCTATCTCCACGGCTATCGCTG
   a    P  A  V  S  R  D  Q  T  K  W  R  E  A  D  R  G  A  D  S  D
   b    Q  Q  -  A  V  T  K  Q  N  G  G  K  Q  I  E  V  P  I  A  T
   c    S  S  K  P  -  P  N  K  M  A  G  S  R  -  R  C  R  -  R  R

13021 GGCAGCCATGTCCGTAGCGCTATAGCCTCCCGCCATGACGGTATCGACGAATCCATTGCG
      ----+----+----+----+----+----+----+----+----+----+----+----+ 13080
      CCGTCGGTACAGGCATCGCGATATCGGAGGGCGGTACTGCCATAGCTGCTTAGGTAACGC
   a    G  S  H  V  R  S  A  I  A  S  R  H  D  G  I  D  E  S  I  A
   b    A  A  M  S  V  A  L  -  P  P  A  M  T  V  S  T  N  P  L  R
   c    Q  P  C  P  -  R  Y  S  L  P  P  -  R  Y  R  R  I  H  C  G

13081 GTCTATACCACTTGCGCAAGGATCACCGGTATCTGAACGCTAATAACTGACGCGCTTCAC
      ----+----+----+----+----+----+----+----+----+----+----+----+ 13140
      CAGATATGGTGAACGCGTTCCTAGTGGCCATAGACTTGCGATTATTGACTGCGCGAAGTG
   a    V  Y  T  T  C  A  R  I  T  G  I  -  T  L  I  T  D  A  L  H
   b    S  I  P  L  A  Q  G  S  P  V  S  E  R  -  L  T  R  F  T
   c    L  Y  H  L  R  K  D  H  R  Y  L  N  A  N  N  -  R  A  S  L
```

Figure 11BU

```
         TGGTATACTTCTGCACGTATTCACCTTTTATTTGTTGTTATATGAAAGACTAAAAAGCC
13141    ------------+------------+------------+------------+------------+------------+  13200
         ACCATATGAAGACGTGCATAAGTGGAAAATAACAATATACTTTCTGATTTTTCGG a      W  Y  T  S  A  R  I  H  H  L  F  C  C  Y  M  K  D  -  K  A
    b         G  I  L  L  H  V  F  T  F  Y  F  V  V  I  -  K  T  K  K  P
    c            V  Y  F  C  T  Y  S  P  F  I  L  L  Y  E  R  L  K  S  R

GCCGAAGTGGCAGCCAAAAGAAATAGCAGGGGAAATTTCAGTCTATTGTAGCGGGTATT
13201    ------------+------------+------------+------------+------------+------------+  13260
         CGGCTTCACCGTCGGTTTTCTTTATCGTCCCCTTTAAAGTCAGATAACATCGCCCATAA a      A  E  V  A  A  K  R  N  S  R  G  N  F  S  L  L  -  R  G  I
    b         P  K  W  Q  P  K  E  I  A  G  E  I  S  V  C  S  G  V  L
    c            R  S  G  S  Q  K  K  -  Q  G  K  F  Q  S  I  V  A  G  Y  Y

ACTATTTCTCCAGTGAAAAAAACAGTTGTTAACGGCGCATTGCTGGCAAGCTGTTTTCCA
13261    ------------+------------+------------+------------+------------+------------+  13320
         TGATAAAGAGGTCACTTTTTTGTCAACAATTGCCGCGTAACGACCGTTCGACAAAAAGGT a      T  I  S  P  V  K  K  Q  L  L  T  A  H  C  W  Q  A  V  F  P
    b         L  F  L  Q  -  K  N  S  C  -  R  R  I  A  G  K  L  F  F  H
    c            Y  F  S  S  E  K  T  V  V  N  G  A  L  L  A  S  C  F  S  T
```

Figure 11BV

```
13321  CCTGCTATTGTGCTGAACAGTTCTGCTTTTATTTATTCAGGAGTTGAAGATATGTTTAC
       ------+---------+---------+---------+---------+---------+  13380
       GGACGATAACACGACTTGTCAAGACGAAAATAAAGTCCTCAACTTCTATACAAATG a        P  A  I  V  L  N  S  S  A  F  I  Y  F  R  S  -  R  Y  V  Y
b        L  L  L  C  -  T  V  L  L  F  I  S  G  V  E  D  M  F  T
c        C  Y  C  A  E  Q  F  C  F  Y  L  F  Q  E  L  K  I  C  L  R

13381  GGGGATCGTACAGGGGTACCGCGAAACTGGTATCGATA
       ------+---------+---------+---------+  13417
       CCCCTAGCATGTCCCCATGGCGCTTTGACCATAGCTAT a        G  D  R  T  G  Y  R  E  T  G  I  D
b        G  I  V  Q  G  T  A  K  L  V  S  I
c        G  S  Y  R  V  P  R  N  W  Y  R
```

Figure 11BW

Figure 12A
DNA Sequence of VGC II cluster C

Tn insertion P9B4
⇩
1    GGATCCTTTTTCTTTAATGCTGCTAACGTTTCTTGCAAAATGCGTTGATGAGATTCATCC    60
     ------+---------+---------+---------+---------+---------+
     CCTAGGAAAAAGAAATTACGACGATTGCAAAGAACGTTTACGCAACTACTCTAAGTAGG 61   AGTACACCACTGATAACAAAAGAGAGCGNCGCATTGGCNWAMMWTKRNNMRNNSCNNNACTA   120
     ------+---------+---------+---------+---------+---------+
     TCATGTGGTGACTATTGTGTTTTCTCGCNGCGTAACCGNWTKKWAMYNNKYNNSGNNNTGAT Tn insertion P7A3
⇩
121  AACCGTTCTCTATTATCGCAGAAATAATATCATCCCCCTGAGACTGATGAGAGTGACTAA   180
     ------+---------+---------+---------+---------+---------+
     TTGGCAAGAGATAATAGCGTCTTTATTATAGTAGGGGACTCTGACTACTCTCACTGATT 181  TCTGCCAGTGCAATAACCCGGGAATATCTGCAAGTAATGGTTGAACCTTGCGCCATTGCT   240
     ------+---------+---------+---------+---------+---------+
     AGACGGTCACGTTATTGGGCCCTTATAGACGTTCATTACCAACTTGGAACGCGGTAACGA Tn insertion P964
⇩
241  GATCCATTGTATATCATCATGAATTAACACGCTCCCCGGCCCTTGCTGATACTTCAG   300
     ------+---------+---------+---------+---------+---------+
     CTAGGTAAACATATAGTAGTACTTAATTGTGCGAGGGGCCGGGAAGCGACCTATGAAGTC

Figure 12B

```
        CATNSSGGTAACCCATTTTTATCAAAACATCCTGCACTTCTCGTACCAATAAGTCATCAC
301     ---------+---------+---------+---------+---------+---------+   360
        GTANSSCCATTGGGTAAAAATAGTTTTGTAGGACGTGAAGAGCATGGTTATTCAGTAGTG

AGATTACACCATCCCGATACATGACCCCCATGATTCGAGAGTCGCTCTCACCTTTGCA
361     ---------+---------+---------+---------+---------+---------+   420
        TCTAATGTGGTAGGGCTATGTACTGGGGGTACTAAGCTCTCAGCGAGAGTGGAAAACGT

TCTGTTCGCTTGACGAGCAATAACCGGACAACTGCAGGCTGCCATCTTCTTTCCATTGCG
421     ---------+---------+---------+---------+---------+---------+   480
        AGACAAGCGAACTGCTCGTTATTGGCCTGTTGACGTCCGACGGTAGAAGAAGGTAACGC

CCCGCACATAATGAATATTGCTTTTGTCTAATAAAAACTTAACCCGCAAAGGTAAGTCAT
481     ---------+---------+---------+---------+---------+---------+   540
        GGGCGTGTATTACTTATAACGAAAAACAGATTATTTTGAATTGGGCGTTTCCATTCAGTA

TTACCGTTTCAGGCTGACCACTAATACTTAACAGGACACCCATTCCACCGATGAAAATCA
541     ---------+---------+---------+---------+---------+---------+   600
        AATGGCAAAGTCCGACTGGTGATTATGAATTGTCCTGTGGGTAAGGTGGCTACTTTTAGT

AGAATACGCCAGCCAACCACCAGTACCCTGATCTGGAAACGGGTATTTGATAATCAGCAA
601     ---------+---------+---------+---------+---------+---------+   660
        TCTTATGCGGTCGGTTGGTGGTCATGGGACTAGACCTTTGCCCATAAACTATTAGTCGTT
```

Figure 12C

```
      GTTCACAATCCTGTTTACCAAACGCGATASSCACTCCCGCAACCTGCAAAACCCCACTGG
661   ------+---------+---------+---------+---------+---------+   720
      CAAGTGTTAGGACAAATGGTTTGCGCTATSSGTGAGGGCGTTGGACGTTTGGGTGACC

ATGGTAGCGGCTTATTTGGATTAAATCTGCGGCCATTAACTCTAACTCTGGCTTTCCCGG
721   ------+---------+---------+---------+---------+---------+   780
      TACCATCGCCGAATAAACCTAATTTAGACGCCGGTAATTGAGATTGAGACCGAAAGGCC

CATCAACAAATAAACTATCTGCCCTGTTCTCTCAGAATAATTTTTCATTTATAGCCAGCG
781   ------+---------+---------+---------+---------+---------+   840
      GTAGTTGTTTATTTGATAGACGGACAAGAGAGTCTTATTAAAAAGTAAATATCGGTCGC

AATACAAATATCGCATCCCCTTCTCCCCCAGTGACAGGTTACCTTCATTCAGCCATACTTC
841   ------+---------+---------+---------+---------+---------+   900
      TTATGTTTATAGCGTAGGGAAGAGGGGGTCACTGTCCAATGGAAGTAAGTCGGTATGAAG

CCGGCCCTTGTAAAACGTGACCTAAAAAACGTATTTCCAGGAACTCTTTGGATTAACCAT
901   ------+---------+---------+---------+---------+---------+   960
      GGCCGGGAACATTTTGCACTGGATTTTTGCATAAAAGGTCCTTGAGAAACCTAATTGGTA

GAGATATGCCATTATTTACTACTGAGGCTTTAATCAAAAAAGCCTGATTACACTATGTA
961   ------+---------+---------+---------+---------+---------+   1020
      CTCTATACGGTAATAAATGATGACTCCGAAATTAGTTTTTTTCGGACTAATGTGATACAT
```

Figure 12D

```
1021 CTTGAGTCGTATCATTGCGAAACAAATGACCTACAACAGGAATATCGCCCAATAAAGGA
     ----+----+----+----+----+----+----+----+----+----+----+----+ 1080
     GAACTCAGCATAGTAACGCTTTGTTTACTGGATGTTGTCCTTATAGCGGGTTATTCCCT

1081 TTTGTTTGCGAGTGGATTTGTTTACCTTGTTTAAACCCTCCCAGCAATNAGACTTTGC
     ----+----+----+----+----+----+----+----+----+----+----+----+ 1140
     AAAACAAAACGCTCACCTAAACAAATGGAACAAATTGGGAGGGTCGTTANTCTGAAACG

1141 CCGGCCAATAATGTGGCTTGCGAANCRATTTCAGAATTTGCACTTCGGGCAGCGGGTCT
     ----+----+----+----+----+----+----+----+----+----+----+----+ 1200
     GGCCGGTTATTACACCGAACGCTTNGYTAAAGTCTTAAAACGTGAAGCCCGTCGCCCAGA

1201 GTNTYGCYTTKGNSTATCACTTTGTTGTCCATCCCTGAANTATTAAGATTAAGCATTATTT
     ----+----+----+----+----+----+----+----+----+----+----+----+ 1260
     CANARCGRAAMCNSATAGTGAAACAACAGGTAGGACTTNATAATTCTAATTCGTAATAAA

1261 TTTGCGTGCCATTGTCATTTAACAAGCGAGGTGTAACGCGWNAACAAAGAACCCGTAGTG
     ----+----+----+----+----+----+----+----+----+----+----+----+ 1320
     AAACGCACGGTAACAGTAAATTGTTCGCTCCACATTGCGCWNTTGTTTCTTGGCATCAC

1321 ATGGATTCAAGTTTAGCCACTTTTCTCCCCTGCAGTTTGGTATAGAAAGTAATATTTTA
     ----+----+----+----+----+----+----+----+----+----+----+----+ 1380
     TACCTAAGTTCAAATCGGTGAAAAAGAGGACGTCAAACCATATCTTTCATTATAAAAAT
```

Figure 12E

```
1381  TCCAGCACACAGCCTGGATATTATTTAAAGTCACCACAGATGGCTGGGAAAGTACATAAGCC  1440
      ----+----+----+----+----+----+----+----+----+----+----+----+
      AGGTCGTGTGTCGGACCTATAATAAATTTCAGTGGTGTCTACCGACCCTTTCATGTATTCGG

1441  TGAGAGCTTTTTCCAGGGCATTCAGACGCACCATAAAGTTTGAGGTATCGCTGATTACC    1500
      ----+----+----+----+----+----+----+----+----+----+----+----+
      ACTCTCGAAAAAGGTCCCGTAAGTCTGCGTGGTATTTCAAACTCCATAGCGACTAATGG

1501  GTTGANNAACCACTAGCACCACCGTCATTCAAACCTGTATTGAACGCAATTTTCTTGCCA   1560
      ----+----+----+----+----+----+----+----+----+----+----+----+
      CAACTNNTTGGTGATCGTGGTGGCAGTAAGTTTGGACATAACTTGCGTTAAAAGAACGGT

1561  CCCAGCGACACTGCCGTTCCCCAGTCGATGCCTAACTGGTTAATATCTCCAGCATTAACA  1620
      ----+----+----+----+----+----+----+----+----+----+----+----+
      GGGTCGCTGTGACGGCAAGGGGTCAGCTACGGATTGACCAATTATAGAGGTCGTAATTGT

1621  TCGATAATTTCACCGAAATCTCTATCATCTGCTGGCGTTGATCTAATTCTGTGATGAGT   1680
      ----+----+----+----+----+----+----+----+----+----+----+----+
      AGCTATTAAAAGTGGCTTTAGAGATAGTAGACGACCGCAACTAGATTAAGACACTACTCA

1681  TTCCGATACNNNGCCATATTGGNNNCATAATCACGAACGATCACTGCATTCTGGCGTNGG   1740
      ----+----+----+----+----+----+----+----+----+----+----+----+
      AAGGCTATGNNNCGGTATAACCNNNGTATTAGTGCTTGCTAGTGACGTAAGACCGCANCC
```

Figure 12G

```
2101  AACCGTCCAGTAGATAAAATATTGAAAGTGATAACCTGATGTTTAATAACGATGCAGGA
      ----+----|----+----|----+----|----+----|----+----|----+----|  2160
      TTGGCAGGTCATCTATTTTATAACTTTCACTATTGGACTACAAAATTATTGCTACGTCCT

2161  TATACATATAACATGCTGCCATCAAACCAGGTAAGCAAATCATATTGTGCTGCCAGGTTA
      ----+----|----+----|----+----|----+----|----+----|----+----|  2220
      ATATGTATATTGTACGACGGTAGTTTGGTCCATTCGTTTAGTATAACACGACGGTCCAAT

2221  TTCAAAATATCGACCGGTGGTCCAGGCGGAATTTTCCACTAAATGTAGCTGTTATCAAT
      ----+----|----+----|----+----|----+----|----+----|----+----|  2280
      AAGTTTTATAGCTGGCCACCAGGTCCGCCTTAAAAAGGTGATTACATCGACAATAGTTA

2281  GGGCTAATAGTAATAGCCGTATCATAGTTCTCTGAGAGCAGATGTNAAAACCTCTGCTAA
      ----+----|----+----|----+----|----+----|----+----|----+----|  2340
      CCCGATTATCATTATCGGCATAGTATCAAGAGACTCTCGTCTACANTTTTGGAGACGATT

2341  TGGCATTTGTCTGGCATAAAGGGTGAAGTCATTACCTTTCCATGATAACTCATCACTCTT
      ----+----|----+----|----+----|----+----|----+----|----+----|  2400
      ACCGTAAACAGACCGTATTTCCCACTTCAGTAATGGAAAGGTACTATTGAGTAGTGAGAA

2401  TGCTGTATTGAGTATAAATAGTAAAATTAAGATTAAACGTTTATTTACTACCATTTTATA
      ----+----|----+----|----+----|----+----|----+----|----+----|  2460
      ACGACATAACTCATATTTATCATTTAATTCTAATTTGCAAATAAATGATGGTAAAATAT
```

Figure 12H

```
2461 CCCCACCCGAATAAAGTTTATGGTGATTGCCGTATTACATTTTTTNAAAATGCAAGTTAAA 2520
     GGGGTGGGCTTATTTCAAATACCACTAACGCCATAATGTAAAAAANTTTACGTTCAATTT

2521 GCCAGGTGTTTTCTATCTCAATAGCAATAAGCTCAGAGCTACTACTTGTGGTATAATAA 2580
     CGGTCCACAAAAGATAGAGTTATCGTTATTCGAGTCTCGATGATGAACACCATATTATT

2581 CCGTTTAACCATCCCCCCATCCGCTGTGAGCTGTATAGCATAATCATGGACGTCCGGGTGT 2640
     GGCAAATTGGTAGGGGGTAGGCGACACTCGATATCGTATTAGTACCTGCAGGCCCACA

2641 GCGCAARCRGTAGTGTCAMMTAGGCAAGACAAGGCTTAGGTAAGCTTTCCAGGTCATTTA 2700
     CGCGTTYGYCATCACAGTKKATCCGTTCTGTTCCGAATCCATTCGAAAGGTCCAGTAAAT
                                             ⇑
                                     Tn insertion P11B9

2701 AGAACAAAGAAATAGAAAATGCTTCTGAGAAAATTTCTYCYBHNNNNNNNNNNNNNNNN 2760
     TCTTGTTTCTTTATCTTTTACGAAGACTCTTTAAAGAGARGRVDNNNNNNNNNNNNNN

2761 NNNNNNNCATCAATAGTCATTATCCAGGATSSKMTWWYMNYYKSSSCYSWKATMYYSWR 2820
     NNNNNNNGTAGTTATCAGTAATAGGTCCTASSMKAWWRKNRRMSSSGRSWMTAKRRSWY
```

Figure 12I

```
                WWTTAAATGGAATGCCTTTTAAAAACTGCCAGCATGAATCCCTCCTCAGACATAAATGGGAG
                ------+---------+---------+---------+---------+---------+         2880
                WWAATTACCTTACGGAAAATTTGACGGTCGTACTTAGGGAGGAGTCTGTATTTACCCTC

TTTCTATCAAATTCGCTCACAACCACATCCGTAAAAAGCCTGATTCACATTTATTTCGAC
                ------+---------+---------+---------+---------+---------+         2940
                AAAGATAGTTTAAGCGAGTGTTGGTGTAGGCATTTTCGGACTAAGTGTAAATAAAGCTG

TATACTCTTCTTGTACAATATCAGGATGCTGTCTACATATACCTTGTCACAGGCGATTCT
                ------+---------+---------+---------+---------+---------+         3000
                ATATGAGAAGAACATGTTATAGTCCTACGACAGATGTATATGGAACAGTGTCCGCTAAGA

ATCATTCGGATTTTCCGATAAATTNMCAATTACATTTTCAGCATTGACATAAAAACTTA
                ------+---------+---------+---------+---------+---------+         3060
                TAGTAAGCCTAAAAGGCTATTTAANKKGTTAAATGTAAAAGTCGTAACTGTATTTTGAAT

CAATTTGNAAAATTATTTATTAAATAAACTGTTACGATGTTTTACATCGCCATCTTATT
                ------+---------+---------+---------+---------+---------+         3120
                GTTAAACNTTTTAATAAATAATTTATTTGACAATGCTACAAAAATGTAGCGGTAGAATAA

AAAAAGTAATTGTGTAGTCATCGACTNGGTTATATATGAAGAAATTTATCTTCCTAATGATA
                ------+---------+---------+---------+---------+---------+         3180
                TTTTTCATTAACATCAGTAGCTGANCCAATATACTTCTTTAAATAGAAGGATTACTAT
```

```
      ACACCATCGATTAATCWMCTGATGAAACTATATGTACTGCGATAGTGATCAAGTGCCAAA
3181  ------+---------+---------+---------+---------+---------+    3240
      TGTGGTAGCTAATTAGWMGACTACTTTGATATACATGACGCTATCACTAGTTCACGGTTT

GATTTGCAACAGGCAACTGGAGGGAAGCATTATGAATTSSTCAATCTCAAGAATACSS
3241  ------+---------+---------+---------+---------+---------+    3300
      CTAAAACGTTGTCCGTTGACCTCCCTTCGTAATACTTAAASSAGTTAGAGTTCTTATGSS

YSYRNNNNNTCTTTAGTAATCAGGCTAACTTTTTTATTTTATTAACAACAATAATTWT
3301  ------+---------+---------+---------+---------+---------+    3360
      RSRYNNNNNAGAAATCATTAGTCCGATTGAAAAAATAAAAATAATTGTTGTTATTAAWA

TTGGCTGCTATCTGTGCTTACCGCAGCTTATATATATCAATGGTTCRGAAACGGCAGCATAT
3361  ------+---------+---------+---------+---------+---------+    3420
      AACCGACGATAGACACGAATGGCGTCGAATATAGTTACCAAGYCTTTGCCGTCGTATA

AATAGAGGATTTATCCGTTCTATCCGAGATGAATATTGTACTAAGCAATCAACGGTTTGA
3421  ------+---------+---------+---------+---------+---------+    3480
      TTATCTCCTAAATAGGCAAGATAGGCTCTACTTATAACATGATTCGTTAGTTGCCAAACT

AGAAGCTGAACGTGACGCTAAAAATTTAATGTATCAATGCTCATTAGCGACTGAGATTCA
3481  ------+---------+---------+---------+---------+---------+    3540
      TCTTCGACTTGCACTGCGATTTTTAAATTACATAGTTACGAGTAATCGCTGACTCTAAGT
```

```
3901  TCCCGATCTCATTACTAAGAGCCACCTGCCATTAGATGATAGTATTCGAGTATGGCTGGA  3960
      ---------+---------+---------+---------+---------+---------+
      AGGGCTAGAGTAATGATTCTCGGTGGACGGTAATCTACTATCATAAGCTCATACCGACCT

3961  TCAAAAACAACCACTTATTGCCGTTTTCATACATCCCGGCAAAAATACGTACACAGTTAG  4020
      ---------+---------+---------+---------+---------+---------+
      AGTTTTGTTGGTGAATAACGGCAAAAGTATGTAGGGCCGTTTTTATGCATGTGTCAATC

4021  AAAATGTAACGCTGCATGATGGATGGCAGCAAATTCCCGGATTTCTGATATTACGCACAA  4080
      ---------+---------+---------+---------+---------+---------+
      TTTTACATTGCGACGTACTACCTACCGTCGTTTAAGGGCCTAAAGACTATAATGCGTGTT

4081  CCTTGCATGGCCCCGGATGGAGTCTGGTTACGCTGTACCCATACGGTAATCTACATAATC  4140
      ---------+---------+---------+---------+---------+---------+
      GGAACGTACCGGGGCCTACCTCAGACCAATGCGACATGGGTATGCCATTAGATGTATTA

4141  GCATCTTAAAAATTATCCTTCAACAAATCCCCTTTACATTAACAGCATTGGTGTTGATGA  4200
      ---------+---------+---------+---------+---------+---------+
      CGTAGAATTTTTAATAGGAAGTTGTTTAGGGAAATGTAATTGTCGTAACCACAACTACT

4201  CGTCGGCTTTTTGCTGGTTACTACATCGCTCACTGCCAAACCGTTATGGCGTTTGTCG  4260
      ---------+---------+---------+---------+---------+---------+
      GCAGCCCGAAAAACGACCAATGATGTAGCGAGTGACCGGTTTGCAATACCGCAAACAGC
```

Figure 12M

```
      ATGTCATTAATAAAACCGCAACTGCACCGCTGAGCACACGTTTACCAGCACAACGACTGG
4261  ------+---------+---------+---------+---------+---------+  4320
      TACAGTAATTATTTTGGCGTTGACGTGGCGACTCGTGTGCAAATGGTCGTGTTGCTGACC

ATGAATTAGATAGTATTGCCGGTTGCCTTTTAACCAACTGCTTGATACTCTACAAGTCCAAT
4321  ------+---------+---------+---------+---------+---------+  4380
      TACTTAATCTATCATAACGGCCACGAAAATTGGTTGACGAACTATGAGATGTTCAGTTA

ACGACAATCTGGAAAACAAAGTCGCAGACGCACCCAGGCGCTAAATGAAGCAAAAAACG
4381  ------+---------+---------+---------+---------+---------+  4440
      TGCTGTTAGACCTTTTGTTTCAGCGTCTGCGTGGGTCCGCGATTTACTTCGTTTTTTGC

CGCTGAGCNAGCTAACAAACGTAAAAGCATTCATCTTACGGTAATAAGTCATGAGTTACG
4441  ------+---------+---------+---------+---------+---------+  4500
      GCGACTCGNTCGATTGTTTGCATTTTCGTAAGTAGAATGCCATTATTCAGTACTCAATGC

TACTCCGATGAATGGCGTACTCGGTGCAATTGAATTATTACAAACCACCCTTTAAACAT
4501  ------+---------+---------+---------+---------+---------+  4560
      ATGAGGCTACTTACCGCATGAGCCACGTTAACTTAATAATGTTTGGTGGGAAATTGTA

AGAGCAACAAGGATTAGCTGATACCGCCAGAAATTGTACACTGTCTTTGTTAGCTATTAT
4561  ------+---------+---------+---------+---------+---------+  4620
      TCTCGTTGTTCCTAATCGACTATGGCGGTCTTTAACATGTGACAGAAACAATGATAATA
```

Figure 12N

```
4621 TAATAATCTGCTGGATTTTCACGCATCGAGTCTGGTCATTTCACATTACATATGGAAGA
     ----+----+----+----+----+----+----+----+----+----+----+----+  4680
     ATTATTAGACGACCTAAAAAGTGCGTAGCTCAGACCAGTAAAGTGTAATGTATACCTTCT

4681 AACAGCGTTACTGCCGTTACTGGACCAGGCAATGCAAACCATCCAGGGCCAGCGCNAAA
     ----+----+----+----+----+----+----+----+----+----+----+----+  4740
     TTGTCGCAATGACGGCAATGACCTGGTCCGTTACGTTTGGTAGGTCCCGGTCGCGNTTT

4741 GCAAAAAACTGTCATTACGTACTTTTGTCGGTCAACATGTCCCTCTATTTCATACCG
     ----+----+----+----+----+----+----+----+----+----+----+----+  4800
     CGTTTTTTGACAGTAATGCATGAAAACAGCCAGTTGTACAGGAGAGATAAAAGTATGGC

4801 ACAGTATCCGTTTACNNCAAATTTGGTTAATTTACTCGGGAACGCGGTAAAATTTACCG
     ----+----+----+----+----+----+----+----+----+----+----+----+  4860
     TGTCATAGGCAAATGNNGTTTAAACCAATTAAATGAGCCCTTGCGCCATTTTAAATGGC

4861 AAACCGGAGGATACGTCTGACGGTCAAGCGTCATGAGGAACAATTAATATTTCTGGTTAG
     ----+----+----+----+----+----+----+----+----+----+----+----+  4920
     TTTGGCCTCCTATGCAGACTGCCAGTTCGCCAGTACTCCTTGTTAATTATAAAGACCAATC

4921 CGATAGCGGTAAAGGGATTGAAATACAGCAGTCTCAAATCTTTACTGCTTTTATCA
     ----+----+----+----+----+----+----+----+----+----+----+----+  4980
     GCTATCGCCATTTCCCTAACTTTATGTCGTCGTCAGAGTTTAGAAATGACGAAAATAGT
```

Figure 120

```
4981  AGCAGACACAAATTCGCAAGGTACACAGGAATTGGACTGACTATTGCGTCAAGCCTGGCTAA
      ---------+---------+---------+---------+---------+---------+ 5040
      TCGTCTGTGTTTAAGCGTTCCATGTGTCCTTAACCTGACTGATAACGCAGTTCGGACCGATT

5041  AATGATGGGCGGTAATCTGACACTAAAAAGTGTCCCCGGGTTGGAACCTGTGTCTCGCT
      ---------+---------+---------+---------+---------+---------+ 5100
      TTACTACCCGCCATTAGACTGTGATTTTTCACAGGGCCCCAACCTTGGACACAGAGCGA
                                                    Tn insertion
                                                         ⇩
5101  AGTATTACCCTTACAAGAATACCAGCCGCCCTCAACCAATTAAAGGGACGCTGTCAGNNNC
      ---------+---------+---------+---------+---------+---------+ 5160
      TCATAATGGGAATGTTCTTATGGTCGGCGGGAGTTGGTTAATTTCCCTGCGACAGTCNNNG 5161  CGTTCTGCCTGCATCGGCAACTGGCTTGCTGGGGAATACGCGGTGAACCACCCCACCAGC
      ---------+---------+---------+---------+---------+---------+ 5220
      GCAAGACGGAGCGTAGCCGTTGACCGAACGACCCCTTATGCGCCACTTGGTGGGGGTGGTCG 5221  AAAATGCGCTTCTCAANNCNAGAGCTTTTGTATTCTCCGAAAACTCTACGACCTGGCG
      ---------+---------+---------+---------+---------+---------+ 5280
      TTTTACGCGAAGAGTTNNGNTCTCGAAAACATAAAGAGGCCTTTTGAGATGCTGGACCGC 5281  CAACAGTTAATATTGTGTACACCAAATATGCCAGTAATAAATAATTTGTTACCACCCTGG
      ---------+---------+---------+---------+---------+---------+ 5340
      GTTGTCAATTATAACACATGTGGTTTATACGGTCATTATTTATTAAACAATGGTGGGACC
```

Figure 12P

```
5341  CAGTTGCAGATTCTTTTGGTTGATGATGCCGATATTAATCGGATATCATCGGCAAAATG
      ------+---------+---------+---------+---------+---------+  5400
      GTCAACGTCTAAGAAAACCAACTACTACGGCTATAATTAGCCCTATAGTAGCCGTTTTAC

5401  CTTGTCAGCCTGGGCCAACACGTCACTATTGCCGCCAGTAGTAACGAGGCTCTGACTTTA
      ------+---------+---------+---------+---------+---------+  5460
      GAACAGTCGGACCCGGTTGTGCAGTGATAACGGCGGTCATCATTGCTCCGAGACTGAAAT

5461  TCACAACAGCAGCGATTCGATTAGTACTGATTGACATTAGAATGCCAGAAATAGATGGT
      ------+---------+---------+---------+---------+---------+  5520
      AGTGTTGTCGTCGCTAAGCTAAATCATGACTAACTGTAATCTTACGGTCTTTATCTACCA

5521  ATTGAATGTGTACGATTATGCATGATGAGCCGAATAATTTAGATCCTGACTGCATGTTT
      ------+---------+---------+---------+---------+---------+  5580
      TAACTTACACATGCTAATACCGTACTACTCGGCTTATTAAATCTAGGACTGACGTACAAA

5581  GTGGCACTATCCGCTAGCGTASCVNMAGAWRWTMWTCRTYGTDDAAAAAWRDGRKDHWT
      ------+---------+---------+---------+---------+---------+  5640
      CACCGTGATAGGCGATCGCATSGBNKTCTWYWAKWAGYARCAHHTTTTTWYHCYMHDWA

5641  CATHAYANNTTACAAAACCAGTGACATTGGCTCGCTACCTTAGCTCGCTACATCAGTATTGCCG
      ------+---------+---------+---------+---------+---------+  5700
      GTADTRTNNAATGTTTTGGTCACTGTAACCGATGAATCGAGCGATGTAGTCATAACGGC

5701  CAGAATACCAACTTTTACGAAATATAGAGCTACAGGAGCAGGATCC
      ------+---------+---------+---------+-------  5746
      GTCTTATGGTTGAAAATGCTTTATATCTCGATGTCCTCGTCCTAGG
```

IDENTIFICATION OF GENES

This application is a continuation of International Application No. PCT/GB95/02875 with an international filing date Dec. 11, 1995.

The present invention relates to methods for the identification of genes involved in the adaptation of a microorganism to its environment, particularly the identification of genes responsible for the virulence of a pathogenic microorganism.

BACKGROUND OF THE INVENTION

Antibiotic resistance in bacterial and other pathogens is becoming increasingly important. It is therefore important to find new therapeutic approaches to attack pathogenic microorganisms.

Pathogenic microorganisms have to evade the host's defence mechanisms and be able to grow in a poor nutritional environment to establish an infection. To do so a number of "virulence" genes of the microorganism are required.

Virulence genes have been detected using classical genetics and a variety of approaches have been used to exploit transposon mutagenesis for the identification of bacterial virulence genes. For example, mutants have been screened for defined physiological defects, such as the loss of iron regulated proteins (Holland et al, 1992), or in assays to study the penetration of epithelial cells (Finlay et al, 1988) and survival within macrophages (Fields et al, 1989; Miller et al, 1989a; Groisman et al, 1989). Transposon mutants have also been tested for altered virulence in live animal models of infection (Miller et al, 1989b). This approach has the advantage that genes can be identified which are important during different stages of infection, but is severely limited by the need to test a wide range of mutants individually for alterations to virulence Miller et al (1989b) used groups of 8 to 10 mice and infected orally 95 separate groups with a different mutant thereby using between 760 and 950 mice. Because of the extremely large numbers of animals required, comprehensive screening of a bacterial genome for virulence genes has not been feasible.

Recently a genetic system (in vivo expression technology [IVET]) was described which positively selects for Salmonella genes that are specifically induced during infection (Mahan et al, 1993). The technique will identify genes that are expressed at a particular stage in the infection process. However, it will not identify virulence genes that are regulated posttranscriptionally, and more importantly, will not provide information on whether the gene(s) which have been identified are actually required for, or contribute to, the infection process.

Lee & Falkow (1994) *Methods Enzymol.* 236, 531–545 describe a method of identifying factors influencing the invasion of Salmonella into mammalian cells in vitro by isolating hyperinvasive mutants.

Walsh and Cepko (1992) *Science* 255, 434–440 describe a method of tracking the spatial location of cerebral cortical progenitor cells during the development of the cerebral cortex in the rat. The Walsh and Cepko method uses a tag that contains a unique nucleic acid sequence and the lacZ gene but there is no indication that useful mutants or genes could be detected by their method.

WO 94/26933 and Smith et al (1995) *Proc. Natl. Acad. Sci. USA* 92, 6479–6483 describe methods aimed at the identification of the functional regions of a known gene, or at least of a DNA molecule for which some sequence information is available.

Groisman et al (1993) *Proc. Natl. Acad. Sci. USA* 90, 1033–1037 describes the molecular, functional and evolutionary analysis of sequences specific to Salmonella.

Some virulence genes are already known for pathogenic microorganisms such as *Escherichia coli, Salmonella typhimurium, Salmonella typhi, Vibrio cholerae, Clostridium botulinum, Yersinia pestis, Shigella flexneri* and *Listeria monocytogenes* but in all cases only a relatively small number of the total have been identified.

The disease which *Salmonella typhimurium* causes in mice provides a good experimental model of typhoid fever (Carter & Collins, 1974). Approximately forty two genes affecting Salmonella virulence have been identified to date (Groisman & Ochman, 1994). These represent approximately one third of the total number of predicted virulence genes (Groisman and Saier, 1990).

The object of the present invention is to identify genes involved in the adaptation of a microorganism to its environment, particularly to identify further virulence genes in pathogenic microorganisms, with increased efficiency. A further object is to reduce the number of experimental animals used in identifying virulence genes. Still further objects of the invention provide vaccines, and methods for screening for drugs which reduce virulence.

SUMMARY OF THE INVENTION

A first aspect of the invention provides a method for identifying a microorganism having a reduced adaptation to a particular environment comprising the steps of:

(1) providing a plurality of microorganisms each of which is independently mutated by the insertional inactivation of a gene with a nucleic acid comprising a unique marker sequence so that each mutant contains a different marker sequence, or clones of the said microorganism;

(2) providing individually a stored sample of each mutant produced by step (1) and providing individually stored nucleic acid comprising the unique marker sequence from each individual mutant;

(3) introducing a plurality of mutants produced by step (1) into the said particular environment and allowing those microorganisms which are able to do so to grow in the said environment;

(4) retrieving microorganisms from the said environment or a selected part thereof and isolating the nucleic acid from the retrieved microorganisms;

(5) comparing any marker sequences in the nucleic acid isolated in step (4) to the unique marker sequence of each individual mutant stored as in step (2); and (6) selecting an individual mutant which does not contain any of the marker sequences as isolated in step (4).

Thus, the method uses negative selection to identify microorganisms with reduced capacity to proliferate in the environment.

A microorganism can live in a number of different environments and it is known that particular genes and their products allow the microorganism to adapt to a particular environment. For example, in order for a pathogenic microorganism, such as a pathogenic bacterium or pathogenic fungus, to survive in its host the product of one or more virulence genes is required. Thus, in a preferred embodiment of the invention a gene of a microorganism which allows the microorganism to adapt to a particular environment is a virulence gene.

Conveniently, the particular environment is a differentiated multicellular organism such as a plant or animal. Many bacteria and fungi are known to infect plants and they are able to survive within the plant and cause disease because of the presence of and expression from virulence genes. Suitable microorganisms when the particular environment is a plant include the bacteria *Agrobacterium tumefaciens* which forms tumours (galls) particularly in grape; *Erwinia amylovara*; *Pseudomonas solanacearum* which causes wilt in a wide range of plants; *Rizobium leguminosarum* which causes disease in beans; *Xanthomonas campestris* p.v. citri which causes canker in citrus fruits; and include the fungi *Magnaporthe grisea* which causes rice blast disease; Fusarium spp. which cause a variety of plant diseases; Erisyphe spp.; *Colletotrichum gloeosporiodes*; *Gaeumannomyces graminis* which causes root and crown diseases in cereals and grasses; Glomus spp., Laccaria spp.; *Leptosphaeria maculans*; *Phoma tracheiphila*; Phytophthora spp., *Pyrenophora teres*; *Verticillium alboatrum* and *V. dahliae*; and *Mycosphaerella musicola* and *M. fijiensis*. As described in more detail below, when the microorganism is a fungus a haploid phase to its life cycle is required.

Similarly, many microorganisms including bacteria, fungi, protozoa and trypanosomes are known to infect animals, particularly mammals including humans. Survival of the microorganism within the animal and the ability of the microorganism to cause disease is due in large part to the presence of and expression from virulence genes. Suitable bacteria include Bordetella spp. particularly *B. pertussis*, Campylobacter spp. particularly *C. jejuni*, Clostridium spp. particularly *C. botulinum*, Enterococcus spp. particularly *E. faecalis*, Escherichia spp. particularly *E. coli*, Haemophilus spp. particularly *H. ducreyi* and *H. influenzae*, Helicobacter spp. particularly *H. pylori*, Klebsiella spp. particularly *K. pneumoniae*, Legionella spp. particularly *L. pneumophila*, Listeria spp. particularly *L. monocytogenes*, Mycobacterium spp. particularly *M. smegmatis* and *M. tuberculosis*, Neisseria spp. particularly *N. gonorrhoeae* and *N. meningitidis*, Pseudomonas spp., particularly *Ps. aeruginosa*, Salmonella spp., Shigella spp., Staphylococcus spp. particularly *S. aureus*, Streptococcus spp. particularly S. pyogenes and pneumoniae, Vibrio spp. and Yersinia spp. particularly *Y. pestis*. All these bacteria cause disease in man and also there are animal models of the disease. Thus, when these bacteria are used in the method of the invention, the particular environment is an animal which they can infect and in which they cause disease. For example, when *Salmonella typhimurium* is used to infect a mouse the mouse develops a disease which serves as a model for typhoid fever in man. *Staphylococcus aureus* causes bacteraemia and renal abscess formation in mice (Albus et al (1991) *Infect. Immun.* 59, 1008–1014) and endocarditis in rabbits (Perlman & Freedman (1971) *Yale J. Biol. Med.* 44, 206–213).

It is required that a fungus or higher eukaryotic parasite is haploid for the relevant parts of its life (such as growth in the environment). Preferably, a DNA-mediated integrative transformation system is available and, when the microorganism is a human pathogen, conveniently an animal model of the human disease is available. Suitable fungi pathogenic to humans include certain Aspergillus spp. (for example *A. fumigatus*), *Cryptococcus neoformans* and *Histoplasma capsulatum*. Clearly the above-mentioned fungi have a haploid phase and a DNA-mediated integrative transformation systems are available for them. Toxoplasma may also be used, being a parasite with a haploid phase during infection. Bacteria have a haploid genome.

Animal models of human disease are often available in which the animal is a mouse, rat, rabbit, dog or monkey. It is preferred if the animal is a mouse. Virulence genes detected by the method of the invention using an animal model of a human disease are clearly very likely to be genes which determine the virulence of the microorganism in man.

Particularly preferred microorganisms for use in the methods of the invention are *Salmonella typhimurium, Staphylococcus aureus, Streptococcus pneumoniae, Enterococcus faecalis, Pseudomonas aeruginosa* and *Aspergillus fumigatus*.

A preferred embodiment of the invention is now described.

A nucleic acid comprising a unique marker sequence is made as follows. A complex pool of double stranded DNA sequence "tags" is generated using oligonucleotide synthesis and a polymerase chain reaction (PCR). Each DNA "tag" has a unique sequence of between about 20 and 80 bp, preferably about 40 bp which is flanked by "arms" of about 15 to 30 bp, preferably about 20 bp, which are common to all "tags". The number of bp in the unique sequence is sufficient to allow large numbers (for example $>10^{10}$) of unique sequences to be generated by random oligonucleotide synthesis but not too large to allow the formation of secondary structures which may interfere with a PCR. Similarly, the length of the arms should be sufficient to allow efficient priming of oligonucleotides in a PCR.

It is well known that the sequence at the 5' end of the oligonucleotide need not match the target sequence to be amplified.

It is usual that the PCR primers do not contain any complementary structures with each other longer than 2 bases, especially at their 3' ends, as this feature may promote the formation of an artifactual product called "primer dimer". When the 3' ends of the two primers hybridize, they form a "primed template" complex, and primer extension results in a short duplex product called "primer dimer".

Internal secondary structure should be avoided in primers. For symmetric PCR, a 40–60% G+C content is often recommended for both primers, with no long stretches of any one base. The classical melting temperature calculations used in conjunction with DNA probe hybridization studies often predict that a given primer should anneal at a specific temperature or that the 72° C. extension temperature will dissociate the primer/template hybrid prematurely. In practice, the hybrids are more effective in the PCR process than generally predicted by simple $T_m$ calculations.

Optimum annealing temperatures may be determined empirically and may be higher than predicted. Taq DNA polymerase does have activity in the 37–55° C. region, so primer extension will occur during the annealing step and the hybrid will be stabilized. The concentrations of the primers are equal in conventional (symmetric) PCR and, typically, within 0.1- to 1- $\mu$M range.

The "tags" are ligated into a transposon or transposon-like element to form the nucleic acid comprising a unique marker sequence. Conveniently, the transposon is carried on a suicide vector which is maintained as a plasmid in a "helper" organism, but which is lost after transfer to the microorganism of the method of the invention. For example, the "helper" organism may be a strain of *Escherichia coli*, the microorganism of the method may be Salmonella and the transfer is a conjugal transfer. Although the transposon can be lost after transfer, in a proportion of cells it undergoes a transposition event through which it integrates at random, along with its unique tag, into the genome of the microorganism used in the method. It is most preferred if the transposon or transposon-like element can be selected. For example, in the case of Salmonella, a kanamycin resistance gene may be present in the transposon and exconjugants are selected on medium containing kanamycin. It is also possible to complement an auxotrophic marker in the recipient cell with a functional gene in the nucleic acid comprising the unique marker. This method is particularly convenient when fungi are used in the method.

Preferably the complementing functional gene is not derived from the same species as the recipient microorganism, otherwise non-random integration events may occur.

It is also particularly convenient if the transposon or transposon-like element is carried on a vector which is maintained episomally (ie not as part of the chromosome) in the microorganism used in the method of the first aspect of the invention when in a first given condition whereas, upon changing that condition to a second given condition, the episome cannot be maintained permitting the selection of a cell in which the transposon or transposon-like element has undergone a transposition event through which it integrates at random, along with its unique tag, into the genome of the microorganism used in the method. This particularly convenient embodiment is advantageous because, once a microorganism carrying the episomal vector is made, then each time the transposition event is selected for or induced by changing the condition of the microorganism (or a clone thereof) from a first given condition to a second given condition, the transposon can integrate at a different site in the genome of the microorganism. Thus, once a master collection of microorganisms are made, each member of which contains a unique tag sequence in the transposon or transposon-like element carried on the episomal vector (when in the first given condition), it can be used repeatedly to generate pools of random insertional mutants, each of which contains a different tag sequence (ie unique within the pool). This embodiment is particularly useful because (a) it reduces the number and complexity of manipulations required to generate the plurality ("pool") of independently mutated microorganisms in step (1) of the method; and (b) the number of different tags need only be the same as the number of microorganisms in the plurality of microorganisms in step (1) of the method. Point (a) makes the method easier to use in organisms for which transposon mutagenesis is more difficult to perform (for example, *Staphylococcus aureus*) and point (b) means that tag sequences with particularly good hybridisation characteristics can be selected therefore making quality control easier. As is described in more detail below, the "pool" size is conveniently about 100 or 200 independently-mutated microorganisms and, therefore the master collection of microorganisms is conveniently stored in one or two 96-well microtitre plates.

In a particularly preferred embodiment the first given condition is a first particular temperature or temperature range such as 25° C. to 32° C., most preferably about 30° C. and the second given condition is a second particular temperature or temperature range such as 35° C. to 45° C., most preferably 42° C. In further preferred embodiments the first given condition is the presence of an antibiotic, such as streptomycin, and the second given condition is the absence of the said antibiotic; or the first given condition is the absence of an antibiotic and the second given condition is the presence of the said antibiotic.

Transposons suitable for integration into the genome of Gram negative bacteria include Tn5, Tn10 and derivatives thereof. Transposons suitable for integration into the genome of Gram positive bacteria include Tn916 and derivatives or analogues thereof. Transposons particularly suited for use with *Staphylococcus aureus* include Tn917 (Cheung et al (1992) *Proc. Natl. Acad. Sci. USA* 89, 6462–6466) and Tn918 (Albus et al (1991) *Infect. Immun.* 59, 1008–1014).

It is particularly preferred if the transposons have the properties of the Tn917 derivatives described by Camilli et al (1990) *J. Bacteriol.* 172, 3738–3744, and are carried by a temperature-sensitive vector such as pE194Ts (Villafane et al (1987) *J. Bacteriol.* 169, 4822–4829).

It will be appreciated that although transposons are convenient for insertionally inactivating a gene, any other known method, or method developed in the future may be used. A further convenient method of insertionally inactivating a gene, particularly in certain bacteria such as Streptococcus, is using insertion-duplication mutagenesis such as that described in Morrison et al (1984) *J. Bacteriol* 159, 870 with respect to *S. pneumoniae*. The general method may also be applied to other microorganisms, especially bacteria.

For fungi, insertional mutations are created by transformation using DNA fragments or plasmids carrying the "tags" and, preferably, selectable markers encoding, for example, resistance to hygromycin B or phleomycin (see Smith et al (1994) *Infect. Immunol.* 62, 5247–5254). Random, single integration of DNA fragments encoding hygromycin B resistance into the genome of filamentous fungi, using restriction enzyme mediated integration (REMI; Schiestl & Petes (1991); Lu et al (1994) *Proc. Natl. Acad. Sci. USA* 91, 12649–12653) are known.

A simple insertional mutagenesis technique for a fungus is described in Schiestl & Petes (1994) incorporated herein by reference, and include, for example, the use of Ty elements and ribosomal DNA in yeast.

Random integration of the transposon or other DNA sequence allows isolation of a plurality of independently mutated microorganisms wherein a different gene is insertionally inactivated in each mutant and each mutant contains a different marker sequence.

A library of such insertion mutants is arrayed in welled microtitre dishes so that each well contains a different mutant microorganism. DNA comprising the unique marker sequence from each individual mutant microorganism (conveniently, the total DNA from the clone is used) is stored. Conveniently, this is done by removing a sample of the microorganism from the microtitre dish, spotting it onto a nucleic acid hybridisation membrane (such as nitrocellulose or nylon membranes), lysing the microorganism in alkali and fixing the nucleic acid to the membrane. Thus, a replica of the contents of the welled microtitre dishes is made.

Pools of the microorganisms from the welled microtitre dish are made and DNA is extracted. This DNA is used as a target for a PCR using primers that anneal to the common "arms" flanking the "tags" and the amplified DNA is labelled, for example with $^{32}P$. The product of the PCR is used to probe the DNA stored from each individual mutant to provide a reference hybridisation pattern for the replicas of the welled microtitre dishes. This is a check that each of the individual microorganisms does, in fact, contain a marker sequence and that the marker sequence can be amplified and labelled efficiently.

Pools of transposon mutants are made to introduce into the particular environment. Conveniently, 96-well microtitre dishes are used and the pool contains 96 transposon mutants. However, the lower limit for the pool is two mutants; there is no theoretical upper limit to the size of the pool but, as discussed below, the upper limit may be determined in relation to the environment into which the mutants are introduced.

Once the microorganisms are introduced into the said particular environment those microorganisms which are able to do so are allowed to grow in the environment. The length of time the microorganisms are left in the environment is determined by the nature of the microorganism and the environment. After a suitable length of time, the microorganisms are recovered from the environment, DNA is extracted and the DNA is used as a template for a PCR using primers that anneal to the "arms" flanking the "tags". The PCR product is labelled, for example with $^{32}P$, and is used to probe the DNA stored from each individual mutant replicated from the welled microtitre dish. Stored DNA are identified which hybridise weakly or not at all with the probe generated from the DNA isolated from the microorganisms recovered from environment. These non-hybridising DNAs correspond to mutants whose adaptation to the particular environment has been attenuated by insertion of the transposon or other DNA sequence.

In a particularly preferred embodiment the "arms" have no, or very little, label compared to the "tags". For example, the PCR primers are suitably designed to contain no, or a single, G residue, the $^{32}P$-labelled nucleotide is dCTP and, in this case, no or one radiolabelled C residue is incorporated in each "arm" but a greater number of radiolabelled C residues are incorporated in the "tag". It is preferred if the "tag" has at least ten-fold more label incorporated than the "arms"; preferably twenty-fold or more; more preferably fifty-fold or more. Conveniently the "arms" can be removed from the "tag" using a suitable restriction enzyme, a site for which may be incorporated in the primer design.

As discussed above, a particularly preferred embodiment of the invention is when the microorganism is a pathogenic microorganism and the particular environment is an animal. In this embodiment, the size of the pool of mutants introduced into the animal is determined by (a) the number of cells of each mutant that are likely to survive in the animal (assuming a virulence gene has not been inactivated) and (b) the total inoculum of the microorganism. If the number in (a) is too low then false positive results may arise and if the number in (b) is too high then the animal may die before enough mutants have had a chance to grow in the desired way. The number of cells in (a) can be determined for each microorganism used but it is preferably more than 50, more preferably more than 100.

The number of different mutants that can be introduced into a single animal is preferably between 50 and 500, conveniently about 100. It is preferred if the total inoculum does not exceed $10^6$ cells (and it is preferably $10^5$ cells) although the size of the inoculum may be varied above or below this amount depending on the microorganism and the animal.

In a particularly convenient method an inoculum of $10^5$ is used containing 1000 cells each of 100 different mutants for a single animal. It will be appreciated that in this method one animal can be used to screen 100 mutants compared to prior art methods which require at least 100 animals to screen 100 mutants.

However, it is convenient to inoculate three animals with the same pool of mutants so that at least two can be investigated (one as a replica to check the reliability of the method), whilst the third is kept as a back-up. Nevertheless, the method still provides a greater than 30-fold saving in the number of animals used.

The time between the pool of mutants being introduced into the animal and the microorganisms being recovered may vary with the microorganism and animal used. For example, when the animal is a mouse and the microorganism is *Salmonella typhimurium*, the time between inoculation and recovery is about three days.

In one embodiment of the invention microorganisms are retrieved from the environment in step (5) at a site remote from the site of introduction in step (4), so that the virulence genes being investigated include those involved in the spread of the microorganism between the two sites.

For example, in a plant the microorganism may be introduced in a lesion in the stem or at one site on a leaf and the microorganism retrieved from another site on the leaf where a disease state is indicated.

In the case of an animal, the microorganism may be introduced orally, intraperitoneally, intravenously or intranasally and is retrieved at a later time from an internal organ such as the spleen. It may be useful to compare the virulence genes identified by oral administration and those identified by intraperitoneal administration as some genes may be required to establish infection by one route but not by the other. It is preferred if Salmonella is introduced intraperitoneally.

Other preferred environments which may be used to identify virulence genes are animal cells in culture (particularly macrophages and epithelial cells) and plant cells in culture. Although using cells in culture will be useful in its own right, it will also complement the use of the whole animal or plant, as the case may be, as the environment.

It is also preferred if the environment is a part of the animal body. Within a given host-parasite interaction, a number of different environments are possible, including different organs and tissues, and parts thereof such as the Peyer's patch.

The number of individual microorganisms (ie cells) recovered from the environment should be at least twice, preferably at least ten times, more preferably 100-times the number of different mutants introduced into the environment. For example, when an animal is inoculated with 100 different mutants around 10,000 individual microorganisms should be retrieved and their marker DNA isolated.

A further preferred embodiment comprises the steps:
(1A) removing auxotrophs from the plurality of mutants produced in step (1); or
(6A) determining whether the mutant selected in step (6) is an auxotroph; or
both (1A) and (6A).

It is desirable to distinguish an auxotroph (that is a mutant microorganism which requires growth factors not needed by the wild type or by prototrophs) and a mutant microorganism wherein a gene allowing the microorganism to adapt to a particular environment is inactivated. Conveniently, this is done between steps (1) and (2) or after step (6).

Preferably auxotrophs are not removed when virulence genes are being identified

A second aspect of the invention provides a method of identifying a gene which allows a microorganism to adapt to a particular environment, the method comprising the method of the first aspect of the invention, followed by the additional step:
(7) isolating the insertionally-inactivated gene or part thereof from the individual mutant selected in step (6).

Methods for isolating a gene containing a unique marker are well known in the art of molecular biology.

A further preferred embodiment comprises the further additional step:
(8) isolating from a wild-type microorganism the corresponding wild-type gene using the insertionally-inactivated gene isolated in step (7) or part thereof as a probe.

Methods for gene probing are well known in the art of molecular biology.

Molecular biological methods suitable for use in the practice of the present invention are disclosed in Sambrook et al (1989) incorporated herein by reference.

When the microorganism is a microorganism pathogenic to an animal and the gene is a virulence gene and a transposon has been used to insertionally inactivate the gene, it is convenient for the virulence genes to be cloned by digesting genomic DNA from the individual mutant selected in step (6) with a restriction enzyme which cuts outside the transposon, ligating size-fractionated DNA containing the transposon into a plasmid, and selecting plasmid recombinants on the basis of antibiotic resistance conferred by the transposon and not by the plasmid. The microorganism genomic DNA adjacent to the transposon is sequenced using two primers which anneal to the terminal regions of the transposon, and two primers which anneal close to the polylinker sequences of the plasmid. The sequences may be subjected to DNA database searches to determine if the transposon has interrupted a known virulence gene. Thus, conveniently, sequence obtained by this method is compared against the sequences present in the publicly available databases such as EMBL and GenBank. Finally, if the interrupted sequence appears to be in a new virulence gene, the mutation is transferred to a new genetic background (for example by phage P22-mediated transduction in the case of Salmonella) and the $LD_{50}$ of the mutant strain is determined to confirm that the avirulent phenotype is due to the transposition event and not a secondary mutation.

The number of individual mutants screened in order to detect all of the virulence genes in a microorganism depends on the number of genes in the genome of the microorganism. For example, it is likely that 3000–5000 mutants of Salmonella typhimurium need to be screened in order to detect the majority of virulence genes whereas for Aspergillus spp., which has a larger genome than Salmonella, around 20 000 mutants are screened. Approximately 4% of non-essential S. typhimurium genes are thought to be required for virulence (Grossman & Saier, 1990) and, if so, the S. typhimurium genome contains approximately 150 virulence genes. However, the methods of the invention provide a faster, more convenient and much more practicable route to identifying virulence genes.

A third aspect of the invention provides a microorganism obtained using the method of the first aspect of the invention.

Such microorganisms are useful because they have the property of not being adapted to survive in a particular environment.

In a preferred embodiment, a pathogenic microorganism is not adapted to survive in a host organism (environment) and, in the case of microorganisms that are pathogenic to animals, particularly mammals, more particularly humans, the mutant obtained by the method of the invention may be used in a vaccine. The mutant is avirulent, and therefore expected to be suitable for administration to a patient, but it is expected to be antigenic and give rise to a protective immune response.

In a further preferred embodiment the pathogenic microorganism not adapted to survive in a host organism, obtained by the methods of the invention, is modified, preferably by the introduction of a suitable DNA sequence, to express an antigenic epitope from another pathogen. This modified microorganism can act as a vaccine for that other pathogen.

A fourth aspect of the invention provides a microorganism comprising a mutation in a gene identified using the method of the second aspect of the invention.

Thus, although the microorganism of the third aspect of the invention is useful, it is preferred if a mutation is specifically introduced into the identified gene. In a preferred embodiment, particularly when the microorganism is to be used in a vaccine, the mutation in the gene is a deletion or a frameshift mutation or any other mutation which is substantially incapable of reverting. Such gene-specific mutations can be made using standard procedures such as introducing into the microorganism a copy of the mutant gene on an autonomous replicon (such as a plasmid or viral genome) and relying on homologous recombination to introduce the mutation into the copy of the gene in the genome of the microorganism.

Fifth and sixth aspects of the invention provide a suitable microorganism for use in a vaccine and a vaccine comprising a suitable microorganism and a pharmaceutically-acceptable carrier.

The suitable microorganism is the aforementioned avirulent mutant.

Active immunisation of the patient is preferred. In this approach, one or more mutant microorganisms are prepared in an immunogenic formulation containing suitable adjuvants and carriers and administered to the patient in known ways. Suitable adjuvants include Freund's complete or incomplete adjuvant, muramyl dipeptide, the "Iscoms" of EP 109 942, EP 180 564 and EP 231 039, aluminium hydroxide, saponin, DEAE-dextran, neutral oils (such as miglyol), vegetable oils (such as arachis oil), liposomes, Pluronic polyols or the Ribi adjuvant system (see, for example GB-A-2 189 141). "Pluronic" is a Registered Trade Mark. The patient to be immunised is a patient requiring to be protected from the disease caused by the virulent form of the microorganism.

The aforementioned avirulent microorganisms of the invention or a formulation thereof may be administered by any conventional method including oral and parenteral (eg subcutaneous or intramuscular) injection. The treatment may consist of a single dose or a plurality of doses over a period of time.

Whilst it is possible for an avirulent microorganism of the invention to be administered alone, it is preferable to present it as a pharmaceutical formulation, together with one or more acceptable carriers. The carrier(s) must be "acceptable" in the sense of being compatible with the avirulent microorganism of the invention and not deleterious to the recipients thereof. Typically, the carriers will be water or saline which will be sterile and pyrogen free.

It will be appreciated that the vaccine of the invention, depending on its microorganism component, may be useful in the fields of human medicine and veterinary medicine.

Diseases caused by microorganisms are known in many animals, such as domestic animals. The vaccines of the invention, when containing an appropriate avirulent microorganism, particularly avirulent bacterium, are useful in man but also in, for example, cows, sheep, pigs, horses, dogs and cats, and in poultry such as chickens, turkeys, ducks and geese.

Seventh and eighth aspects of the invention provide a gene obtained by the method of the second aspect of the invention, and a polypeptide encoded thereby.

By "gene" we include not only the regions of DNA that code for a polypeptide but also regulatory regions of DNA such as regions of DNA that regulate transcription, translation and, for some microorganisms, splicing of RNA. Thus, the gene includes promoters, transcription terminators, ribosome-binding sequences and for some organisms introns and splice recognition sites.

Typically, sequence information of the inactivated gene obtained in step 7 is derived. Conveniently, sequences close to the ends of the transposon are used as the hybridisation site of a sequencing primer. The derived sequence or a DNA restriction fragment adjacent to the inactivated gene itself is used to make a hybridisation probe with which to identify, and isolate from a wild-type organism, the corresponding wild type gene.

It is preferred if the hybridisation probing is done under stringent conditions to ensure that the gene, and not a relative, is obtained. By "stringent" we mean that the gene hybridises to the probe when the gene is immobilised on a membrane and the probe (which, in this case is >200 nucleotides in length) is in solution and the immobilised gene/hybridised probe is washed in 0.1× SSC at 65° C. for 10 min. SSC is 0.15 M NaCl/0.015 M Na citrate.

Preferred probe sequences for cloning Salmonella virulence genes are shown in FIGS. 5 and 6 (SEQ ID Nos 39–44 and 8–36) and described in Example 2.

In a particularly preferred embodiment the Salmonella virulence genes comprise the sequence shown in FIGS. 5 and 6 and described in Example 2.

In further preference the genes are those contained within, or at least part of which is contained within, the sequences shown in FIGS. 11 and 12 (SEQ ID Nos 37 and 38) and which have been identified by the method of the second aspect of the invention. The sequences shown in FIGS. 11 and 12 are part of a gene cluster from *Salmonella typhimurium* which I have called virulence gene cluster 2 (VGC2). The position of transposon insertions are indicated within the sequence, and these transposon insertions inactivate a virulence determinant of the organism. As is discussed more fully below, and in particular in Example 4, when the method of the second aspect of the invention is used to identify virulence genes in *Salmonella typhimurium*, many of the nucleic acid insertions (and therefore genes identified) are clustered in a relatively small part of the genome. This region, VGC2, contains other virulence genes which, as described below, form part of the invention.

The gene isolated by the method of the invention can be expressed in a suitable host cell. Thus, the gene (DNA) may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued Apr. 3, 1984 to Rutter et al, U.S. Pat. No. 4,530,901 issued Jul. 23, 1985 to Weissman, U.S. Pat. No. 4,582,800 issued Apr. 15, 1986 to Crowl, U.S. Pat. No. 4,677,063 issued Jun. 30, 1987 to Mark et al, U.S. Pat. No. 4,678,751 issued Jul. 7, 1987 to Goeddel, U.S. Pat. No. 4,704,362 issued Nov. 3, 1987 to Itakura et al, U.S. Pat. No. 4,710,463 issued Dec. 1, 1987 to Murray, U.S. Pat. No. 4,757,006 issued Jul. 12, 1988 to Toole, Jr. et al, U.S. Pat. No. 4,766,075 issued Aug. 23, 1988 to Goeddel et al and U.S. Pat. No. 4,810,648 issued Mar. 7, 1989 to Stalker, all of which are incorporated herein by reference.

The DNA encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal cells and insect cells.

The vectors include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., U.S.A.) and pTrc99A and pKK223-3 available from Pharmacia, Piscataway, N.J., U.S.A.

A typical mammalian cell vector plasmid is pSVL available from Pharmacia, Piscataway, N.J., U.S.A. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403–406 and pRS413–416 and are generally available from Stratagene Cloning Systems, La Jolla, Calif. 92037, U.S.A. Plasmids pRS403, pRS404, pRS405 and pRS406 are Yeast Integrating plasmids (YIps) and incorporate the yeast selectable markers HIS3, TRP1, LEU2 and URA3. Plasmids pRS413–416 are Yeast Centromere plasmids (YCps)

A variety of methods have been developed to operably link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., U.S.A.

A desirable way to modify the DNA encoding the polypeptide of the invention is to use the polymerase chain reaction as disclosed by Saiki et al (1988) *Science* 239, 487–491.

In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

Variants of the genes also form part of the invention. It is preferred if the variant has at least 70% sequence identity, more preferably at least 85% sequence identity, most preferably at least 95% sequence identity with the genes isolated by the method of the invention. Of course, replacements, deletions and insertions may be tolerated. The degree of similarity between one nucleic acid sequence and another can be determined using the GAP program of the University of Wisconsin Computer Group.

Similarly, variants of proteins encoded by the genes are included.

By "variant" we include insertions, deletions and substitutions, either conservative or non-conservative, where such changes do not substantially alter the normal function of the protein.

By "conservative substitutions" is intended combinations such as Gly, Ala; Val, Ile, Leu; Asp, Glu; Asn, Gln; Ser, Thr; Lys, Arg; and Phe, Tyr.

Such variants may be made using the well known methods of protein engineering and site-directed mutagenesis.

A ninth aspect of the invention provides a method of identifying a compound which reduces the ability of a microorganism to adapt to a particular environment comprising the steps of selecting a compound which interferes with the function of (1) a gene obtained by the method of the second aspect of the invention or of (2) a polypeptide encoded by such a gene.

Pairwise screens for compounds which affect the wild type cell but not a cell overproducing a gene isolated by the methods of the invention form part of this aspect of the invention.

For example, in one embodiment one cell is a wild type cell and a second cell is the Salmonella which is made to overexpress the gene isolated by the method of the invention. The viability and/or growth of each cell in the particular environment is determined in the presence of a compound to be tested to identify which compound reduces the viability or growth of the wild type cell but not the cell overexpressing the said gene.

It is preferred if the gene is a virulence gene.

For example, in one embodiment the microorganism (such as *S. typhimurium*) is made to over-express the virulence gene identified by the method of the first aspect of the invention. Each of (a) the "over-expressing" microorganism and (b) an equivalent microorganism (which does not over-express the virulence gene) are used to infect cells in culture. Whether a particular test compound will selectively inhibit the virulence gene function is determined by assessing the amount of the test compound which is required to prevent infection of the host cells by (a) the over-expressing microorganism and (b) the equivalent microorganism (at least for some virulence gene products it is envisaged that the test compound will inactivate them, and itself be inactivated, by binding to the virulence gene product). If more of the compound is required to prevent infection by the (a) than (b) then this suggests that the compound is selective. It is preferred if the microorganisms (such as Salmonella) are destroyed extracellularly by a mild antibiotic such as gentamicin (which does not penetrate host cells) and that the effect of the test compound in preventing infection of the cell by the microorganism is by lysing the said cell and determining how many microorganisms are present (for example by plating on agar).

Pairwise screens and other screens for compounds are generally disclosed in Kirsch & Di Domenico (1993) in "The Discovery of Natural Products with a Therapeutic Potential" (Ed, V. P. Gallo), Chapter 6, pages 177–221, Butterworths, V. K. (incorporated herein by reference).

Pairwise screens can be designed in a number of related formats in which the relative sensitivity to a compound is compared using two genetically related strains. If the strains differ at a single locus, then a compound specific for that target can be identified by comparing each strain's sensitivity to the inhibitor. For example, inhibitors specific to the target will be more active against a super-sensitive test strain when compared to an otherwise isogenic sister strain. In an agar diffusion format, this is determined by measuring the size of the zone of inhibition surrounding the disc or well carrying the compound. Because of diffusion, a continuous concentration gradient of compound is set up, and the strain's sensitivity to inhibitors is proportional to the distance from the disc or well to the edge of the zone. General antimicrobials, or antimicrobials with modes of action other than the desired one are generally observed as having similar activities against the two strains.

Another type of molecular genetic screen, involving pairs of strains where a cloned gene product is overexpressed in one strain compared to a control strain. The rationale behind this type of assay is that the strain containing an elevated quantity of the target protein should be more resistant to inhibitors specific to the cloned gene product than an isogenic strain, containing normal amounts of the target protein. In an agar diffusion assay, the zone size surrounding a specific compound is expected to be smaller in the strain overexpressing the target protein compared to an otherwise isogenic strain.

Additionally or alternatively selection of a compound is achieved in the following steps:

1. A mutant microorganism obtained using the method of the first aspect of the invention is used as a control (it has a given phenotype, for example, avirulence).
2. A compound to be tested is mixed with the wild-type microorganism.

3. The wild-type microorganism is introduced into the environment (with or without the test compound).
4. If the wild-type microorganism is unable to adapt to the environment (following treatment by, or in the presence of, the compound), the compound is one which reduces the ability of the microorganism to adapt to, or survive in, the particular environment.

When the environment is an animal body and the microorganism is a pathogenic microorganism, the compound identified by this method can be used in a medicament to prevent or ameliorate infection with the microorganism.

A tenth aspect of the invention therefore provides a compound identifiable by the method of the ninth aspect.

It will be appreciated that uses of the compound of the tenth aspect are related to the method by which it can be identified, and in particular in relation to the host of a pathogenic microorganism. For example, if the compound is identifiable by a method which uses a virulence gene, or polypeptide encoded thereby, from a bacterium which infects a mammal, the compound may be useful in treating infection of a mammal by that bacterium.

Similarly, if the compound is identifiable by a method which uses a virulence gene, or polypeptide encoded thereby, from a fungus which infects a plant, the compound may be useful in treating infection of a plant by that fungus.

An eleventh aspect of the invention provides a molecule which selectively interacts with, and substantially inhibits the function of, a gene of the seventh aspect of the invention or a nucleic acid product thereof.

By "nucleic acid product thereof" we include any RNA, especially mRNA, transcribed from the gene.

Preferably a molecule which selectively interacts with, and substantially inhibits the function of, said gene or said nucleic acid product is an antisense nucleic acid or nucleic acid derivative.

More preferably, said molecule is an antisense oligonucleotide.

Antisense oligonucleotides are single-stranded nucleic acid, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise sequence-specific molecules which specifically bind double-stranded DNA via recognition of major groove hydrogen binding sites.

Clearly, the sequence of the antisense nucleic acid or oligonucleotide can readily be determined by reference to the nucleotide sequence of the gene in question. For example, antisense nucleic acid or oligonucleotides can be designed which are complementary to a part of the sequence shown in FIGS. 11 or 12, especially to sequences which form a part of a virulence gene.

Oligonucleotides are subject to being degraded or inactivated by cellular endogenous nucleases. To counter this problem, it is possible to use modified oligonucleotides, eg having altered internucleotide linkages, in which the naturally occurring phosphodiester linkages have been replaced with another linkage. For example, Agrawal et al (1988) *Proc. Natl. Acad. Sci. USA* 85, 7079–7083 showed increased inhibition in tissue culture of HIV-1 using oligonucleotide phosphoramidates and phosphorothioates. Sarin et al (1988) *Proc. Natl. Acad. Sci. USA* 85, 7448–7451 demonstrated increased inhibition of HIV-1 using oligonucleotide methylphosphonates. Agrawal et al (1989) *Proc. Natl. Acad. Sci. USA* 86, 7790–7794 showed inhibition of HIV-1 replication in both early-infected and chronically infected cell cultures, using nucleotide sequence-specific oligonucleotide phosphorothioates. Leither et al (1990) *Proc. Natl. Acad. Sci. USA* 87, 3430–3434 report inhibition in tissue culture of influenza virus replication by oligonucleotide phosphorothioates.

Oligonucleotides having artificial linkages have been shown to be resistant to degradation in vivo. For example, Shaw et al (1991) in *Nucleic Acids Res.* 19, 747–750, report that otherwise unmodified oligonucleotides become more resistant to nucleases in vivo when they are blocked at the 3' end by certain capping structures and that uncapped oligonucleotide phosphorothioates are not degraded in vivo.

A detailed description of the H-phosphonate approach to synthesizing oligonucleoside phosphorothioates is provided in Agrawal and Tang (1990) *Tetrahedron Letters* 31, 7541–7544, the teachings of which are hereby incorporated herein by reference. Syntheses of oligonucleoside methylphosphonates, phosphorodithioates, phosphoramidates, phosphate esters, bridged phosphoramidates and bridge phosphorothioates are known in the art. See, for example, Agrawal and Goodchild (1987) *Tetrahedron Letters* 28, 3539; Nielsen et al (1988) *Tetrahedron Letters* 29, 2911; Jager et al (1988) *Biochemistry* 27, 7237; Uznanski et al (1987) *Tetrahedron Letters* 28, 3401; Bannwarth (1988) *Helv. Chim. Acta.* 71, 1517; Crosstick and Vyle (1989) *Tetrahedron Letters* 30, 4693; Agrawal et al (1990) *Proc. Natl. Acad. Sci. USA* 87, 1401–1405, the teachings of which are incorporated herein by reference. Other methods for synthesis or production also are possible. In a preferred embodiment the oligonucleotide is a deoxyribonucleic acid (DNA), although ribonucleic acid (RNA) sequences may also be synthesized and applied.

The oligonucleotides useful in the invention preferably are designed to resist degradation by endogenous nucleolytic enzymes. In vivo degradation of oligonucleotides produces oligonucleotide breakdown products of reduced length. Such breakdown products are more likely to engage in non-specific hybridization and are less likely to be effective, relative to their full-length counterparts. Thus, it is desirable to use oligonucleotides that are resistant to degradation in the body and which are able to reach the targeted cells. The present oligonucleotides can be rendered more resistant to degradation in vivo by substituting one or more internal artificial internucleotide linkages for the native phosphodiester linkages, for example, by replacing phosphate with sulphur in the linkage. Examples of linkages that may be used include phosphorothioates, methylphosphonates, sulphone, sulphate, ketyl, phosphorodithioates, various phosphoramidates, phosphate esters, bridged phosphorothioates and bridged phosphoramidates. Such examples are illustrative, rather than limiting, since other internucleotide linkages are known in the art. See, for example, Cohen, (1990) *Trends in Biotechnology*. The synthesis of oligonucleotides having one or more of these linkages substituted for the phosphodiester internucleotide linkages is well known in the art, including synthetic pathways for producing oligonucleotides having mixed internucleotide linkages.

Oligonucleotides can be made resistant to extension by endogenous enzymes by "capping" or incorporating similar groups on the 5' or 3' terminal nucleotides. A reagent for capping is commercially available as Amino-Link II™ from Applied BioSystems Inc, Foster City, Calif. Methods for capping are described, for example, by Shaw et al (1991) *Nucleic Acids Res.* 19, 747–750 and Agrawal et al (1991) *Proc. Natl. Acad. Sci. USA* 88(17), 7595–7599, the teachings of which are hereby incorporated herein by reference.

A further method of making oligonucleotides resistant to nuclease attack is for them to be "self-stabilized" as described by Tang et al (1993) *Nucl. Acids Res.* 21, 2729–2735 incorporated herein by reference. Self-stabilized oligonucleotides have hairpin loop structures at their 3' ends, and show increased resistance to degradation by snake venom phosphodiesterase, DNA polymerase I and fetal bovine serum. The self-stabilized region of the oligonucleotide does not interfere in hybridization with complementary nucleic acids, and pharmacokinetic and stability studies in mice have shown increased in vivo persistence of self-stabilized oligonucleotides with respect to their linear counterparts.

In accordance with the invention, the inherent binding specificity of antisense oligonucleotides characteristic of base pairing is enhanced by limiting the availability of the antisense compound to its intend locus in vivo, permitting lower dosages to be used and minimizing systemic effects. Thus, oligonucleotides are applied locally to achieve the desired effect. The concentration of the oligonucleotides at the desired locus is much higher than if the oligonucleotides were administered systemically, and the therapeutic effect can be achieved using a significantly lower total amount. The local high concentration of oligonucleotides enhances penetration of the targeted cells and effectively blocks translation of the target nucleic acid sequences.

The oligonucleotides can be delivered to the locus by any means appropriate for localized administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus.

The oligonucleotides are most preferably administered via a hydrogel material. The hydrogel is noninflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10 to about 80% by weight ethylene oxide and from about 20 to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic$^R$.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warms, it solidifies to form a gel, out of oligonucleotides diffuse out of the gel into the surrounding cells over a period of time defined by the exact composition of the gel.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerized or solidified, using melt or solvent evaporation techniques, or mechanically mixed with the material. In one embodiment, the oligonucleotides are mixed into or applied onto coatings for implantable devices such as dextran coated silica beads, stents, or catheters.

The dose of oligonucleotides is dependent on the size of the oligonucleotides and the purpose for which is it administered. In general, the range is calculated based on the surface area of tissue to be treated. The effective dose of oligonucleotide is somewhat dependent on the length and chemical composition of the oligonucleotide but is generally in the range of about 30 to 3000 $\mu$g per square centimeter of tissue surface area.

The oligonucleotides may be administered to the patient systemically for both therapeutic and prophylactic purposes. The oligonucleotides may be administered by any effective method, for example, parenterally (eg intravenously, subcutaneously, intramuscularly) or by oral, nasal or other means which permit the oligonucleotides to access and circulate in the patient's bloodstream. Oligonucleotides administered systemically preferably are given in addition to locally administered oligonucleotides, but also have utility in the absence of local administration. A dosage in the range of from about 0.1 to about 10 grams per administration to an adult human generally will be effective for this purpose.

It will be appreciated that the molecules of this aspect of the invention are useful in treating or preventing any infection caused by the microorganism from which the said gene has been isolated, or a close relative of said microorganism. Thus, the said molecule is an antibiotic.

Thus, a twelfth aspect of the invention provides a molecule of the eleventh aspect of the invention for use in medicine.

A thirteenth aspect of the invention provides a method of treating a host which has, or is susceptible to, an infection with a microorganism, the method comprising administering an effective amount of a molecule according to the eleventh aspect of the invention wherein said gene is present in said microorganisms, or a close relative of said microorganism.

By "effective amount" we mean an amount which substantially prevents or ameliorates the infection. By "host" we include any animal or plant which may be infected by a microorganism.

It will be appreciated that pharmaceutical formulations of the molecule of the eleventh aspect of the invention form part of the invention. Such pharmaceutical formulations comprise the said molecule together with one or more acceptable carriers. The carrier(s) must be "acceptable" in the sense of being compatible with the said molecule of the invention and not deleterious to the recipients thereof. Typically, the carriers will be water or saline which will be sterile and pyrogen free.

As mentioned above, and as described in more detail in Example 4 below, I have found that certain virulence genes are clustered in *Salmonella typhimurium* in a region of the chromosome that I have called VGC2. DNA-DNA hybridisation experiments have determined that sequences homologous to at least part of VGC2 are found in many species and strains of Salmonella but are not present in the *E. coli* and Shigella stains tested (see Example 4). These sequences almost certainly correspond to conserved genes, at least in Salmonella, and at least some of which are virulence genes. It is believed that equivalent genes in other Salmonella species and, if present, equivalent genes in other enteric or other bacteria will also be virulence genes.

Whether a gene within the VGC2 region is a virulence gene is readily determined. For example, those genes within VGC2 which have been identified by the method of the second aspect of the invention (when applied to *Salmonella typhimurium* and wherein the environment is an animal such as a mouse) are virulence genes. Virulence genes are also identified by making a mutation in the gene (preferably a non-polar mutation) and determining whether the mutant strain is avirulent. Methods of making mutations in a selected gene are well known and are described below.

A fourteenth aspect of the invention provides the VGC2 DNA of *Salmonella typhimurium* or a part thereof, or a variant of said DNA or a variant of a part thereof.

The VGC2 DNA of *Salmonella typhimurium* is depicted diagrammatically in FIG. 8 and is readily obtainable from *Salmonella typhimurium* ATCC 14028 (available from the American Type Culture Collection, 12301 Parklawn Drive, Rockville, Md. 20852, U.S.A.; also deposited at the NCTC, Public Health Laboratory Service, Colindale, UK under accession no. NCTC 12021) using the information provided in Example 4. For example, probes derived from the sequences shown in FIGS. 11 and 12 may be used to identify λ clones from a *Salmonella typhimurium* genomic library. Standard genome walking methods can be employed to obtain all of the VGC2 DNA. The restriction map shown in FIG. 8 can be used to identify and locate DNA fragments from VGC2.

By "part of the VGC2 DNA of *Salmonella typhimurium*" we mean any DNA sequence which comprises at least 10 nucleotides, preferably at least 20 nucleotides, more preferably at least 50 nucleotides, still more preferably at least 100 nucleotides, and most preferably at least 500 nucleotides of VGC2. A particularly preferred part of the VGC2 DNA is the sequence shown in FIG. 11, or a part thereof. Another particularly preferred part of the VGC2 DNA is the sequence shown in FIG. 12, or a part thereof.

Advantageously, the part of the VGC2 DNA is a gene, or part thereof.

Genes can be identified within the VGC2 region by statistical analysis of the open reading frames using computer programs known in the art. If an open reading frame is greater than about 100 codons it is likely to be a gene (although genes smaller than this are known). Whether an open reading frame corresponds to the polypeptide coding region of a gene can be determined experimentally. For example, a part of the DNA corresponding to the open reading frame may be used as a probe in a northern (RNA) blot to determine whether mRNA is expressed which hybridises to the said DNA; alternatively or additionally a mutation may be introduced into the open reading frame and the effect of the mutation on the phenotype of the microorganism can be determined. If the phenotype is changed then the open reading frame corresponds to a gene. Methods of identifying genes within a DNA sequence are known in the art.

By "variant of said DNA or a variant of a part thereof" we include any variant as defined by the term "variant" in the seventh aspect of the invention.

Thus, variants of VGC2 DNA of *Salmonella typhimurium* include equivalent genes, or parts thereof, from other Salmonella species, such as *Salmonella typhi* and *Salmonella enterica*, as well as equivalent genes, or parts thereof, from other bacteria such as other enteric bacteria.

By "equivalent gene" we include genes which are functionally equivalent and those in which a mutation leads to a similar phenotype (such as avirulence). It will be appreciated that before the present invention VGC2 or the genes contained therein had not been identified and certainly not implicated in virulence determination.

Thus, further aspects of the invention provide a mutant bacterium wherein if the bacterium normally contains a gene that is the same as or equivalent to a gene in VGC2, said gene is mutated or absent in said mutant bacterium; methods of making a mutant bacterium wherein if the bacterium normally contains a gene that is the same as or equivalent to a gene in VGC2, said gene is mutated or absent in said mutant bacterium. The following is a preferred method to inactivate a VGC2 gene. One first subclones the gene on a DNA fragment from a Salmonella λ DNA library or other DNA library using a fragment of VGC2 as a probe in hybridisation experiments, and map the gene with respect to restriction enzyme sites and characterise the gene by DNA sequencing in *Escherichia coli*. Using restriction enzymes, one then introduces into the coding region of the gene a segment of DNA encoding resistance to an antibiotic (for example, kanamycin), possibly after deleting a portion of the coding region of the cloned gene by restriction enzymes. Methods and DNA constructs containing an antibiotic resistance marker are available to ensure that the inactivation of the gene of interest is preferably non-polar, that is to say, does not affect the expression of genes downstream from the gene of interest. The mutant version of the gene is then transferred from *E. coli* to *Salmonella typhimurium* using phage P22 transduction and transductants checked by Southern hybridisation for homologous recombination of the mutant gene into the chromosome.

This approach is commonly used in Salmonella (and can be used in *S. typhi*), and further details can be found in many papers, including Galan et al (1992) 174, 4338–4349.

Still further aspects provide a use of said mutant mutant bacterium in a vaccine; pharmaceutical compositions comprising said bacterium and a pharmaceutically acceptable carrier; a polypeptide encoded by VGC2 DNA of *Salmonella typhimurium* or a part thereof, or a variant of a part thereof; a method of identifying a compound which reduces the ability of a bacterium to infect or cause disease in a host; a compound identifiable by said method; a molecule which selectively interacts with, and substantially inhibits the function of, a gene in VGC2 or a nucleic product thereof; and medical uses and pharmaceutical compositions thereof.

The VGC2 DNA contains genes which have been identified by the methods of the first and second aspects of the invention as well as genes which have been identified by their location (although identifiable by the methods of the first and second aspects of the invention). These further aspects of the invention relate closely to the fourth, fifth, sixth, seventh, eighth, ninth, tenth, eleventh, twelfth and thirteenth aspects of the invention and, accordingly, the information given in relation to those aspects, and preferences expressed in relation to those aspects, applies to these further aspects.

It is preferred if the gene is from VGC2 or is an equivalent gene from another species of Salmonella such as *S. typhi*. It is preferred if the mutant bacterium is a *S. typhimurium* mutant or a mutant of another species of Salmonella such as *S. typhi*.

It is believed that at least some of the genes in VGC2 confer the ability for the bacterium, such as *S. typhimurium*, to enter cells.

BRIEF DESCRIPTION OF THE DRAWINGS

The invention will now be described with reference to the following Examples and Figures wherein:

FIGS. 5A through 5D show the sequence of a Salmonella gene isolated using the method of the invention and a comparison to the *Escherichia coli* clp protease genome (SEQ ID Nos. 39–44)

FIGS. 6A through 6H show partial sequences of further Salmonella gene isolated using the method of the invention (SEQ ID Nos. 8 to 36).

FIGS. 8A, 8B and 8C show a physical and genetic map of VGC2. (A) The positions of 16 transposon insertions are shown above the line. The extent of VGC2 is indicated by the thicker line. The position and direction of transcription of ORFs described in the text of Example 4 are shown by arrows below the line, together with the names of similar genes, with the exception of ORFs 12 and 13 whose products are similar to the sensor and regulatory components respectively, of a variety of two component regulatory systems. (B) The location of overlapping clones and an EcoRI/XbaI restriction fragment from Mud-P22 prophage strain TT15244 are shown as filled bars. Only the portions of the λ clones which have been mapped are shown and the clones may extend beyond these limits. (C) The positions of restriction sites are marked: B. BamHI; E, EcoRI; V, EcoRV; H, HindIII; P, PstI and X, XbaI. The positions of the 7.5 kb PstI fragment (probe A) used as a probe in FIG. 7 and that of the 2.2 kb PstI/HindIII fragment (probe B) used as a probe in FIG. 10 are shown below the restriction map. The positions of Sequence 1 (described in FIG. 11) and Sequence 2 (described in FIG. 12) are shown by the thin arrows (labelled Sequence 1 and Sequence 2).

FIG. 11 shows the DNA sequence of "Sequence 1" of VGC2 from the centre to the left-hand end (see the arrow labelled Sequence 1 in FIG. 2). The DNA is translated in all six reading frames and the start and stop positions of putative genes, and the transposon insertion positions for various mutants identified by STM are indicated (SEQ ID No 37). The amino acid sequences in the "a" reading frame are SEQ ID Nos. 45–187, the amino acid sequences in the "b" reading frame of are SEQ ID Nos. 188–356, and the amino acid sequences in the "c" reading frame are SEQ ID Nos. 357–501.

As is conventional a * indicates a stop codon and standard nucleotide ambiguity codes are used where necessary.

Figure 12F:
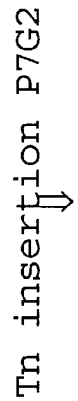

FIGS. 12A through 12P shows the DNA sequence of "Sequence 2" of VGC2 (cluster C) (see the arrow labelled Sequence 2 in FIG. 8). The DNA is translated in all six reading frames and the start and stop positions of putative genes, and the transposon insertion positions for various mutants identified by STM are indicated (SEQ ID No 38).

As is conventional a * indicates a stop codon and standard nucleotide ambiguity codes are used where necessary.

FIGS. 7 to 12 are most relevant to Example 4.

EXAMPLE 1

Identification of Virulence Genes in *Salamonella typhimurium*

Materials and Methods
Bacterial Strains and Plasmids

*Salmonella typhimurium* strain 12023 (equivalent to American Type Culture Collection (ATCC) strain 14028) was obtained from the National Collection of Type Cultures (NCTC), Public Health Laboratory Service, Colindale, London, UK. A spontaneous nalidixic acid resistant mutant of this strain (12023 Nal$^r$) was selected in our laboratory. Another derivative of strain 12023, CL1509 (aroA::Tn10) was a gift from Fred Heffron. *Escherichia coil* strains CC118λpir (Δ[ara-leu]), araD, 66 lacX74, galE, galK, phoA20, thi-1, rpsE, rpoB, argE(Am), recA1, λpir phage lysogen) and S17-1λpir (Tp$^r$, Sm$^r$, recA, thi, pro, hsd$^-$M$^+$, RP4:2-Tc:Mu:KmTn7, λpir ) were gifts from Kenneth Timmis. *E. coli* DH5α was used for propagating pUC18 (Gibco-BRL) and Bluescript (Stratagene) plasmids containing *S. typhimurium* DNA. Plasmid pUTmini-Tn5Km2 (de Lorenzo et al, 1990) was a gift from Kenneth Timmis.

Construction of Semi-Random Sequence Tags and Ligations

The oligonucleotide pool RT1(5'-CTAGGTACCTACAACCTCAAGCTT-[NK]$_{20}$-AAGCTTGGTTAGAATGGGTACCATG-3') (SEQ ID No 1), and primers P2 (5'-TACCTACAACCTCAAGCT-3') (SEQ ID No 2), P3 (5'-CATGGTACCCATTCTAAC-3') (SEQ ID No 3), P4-(5'-TACCCATTCTAACCAAGC-3') (SEQ ID No 4) and P5 (5'-CTAGGTACCTACAACCTC-3') (SEQ ID No 5) were synthesized on a oligonucleotide synthesizer (Applied Biosystems, model 380B). Double stranded DNA tags were prepared from RT1 in a 100 μl volume PCR containing 1.5 mM MgCl$_2$, 50 mM KCl, and 10 mM Tris-Cl (pH 8.0) with 200 pg of RT1 as target; 250 μM each dATP, dCTP, dGTP, dTTP; 100 pM of primers P3 and P5; and 2.5 U of Amplitaq (Perkin-Elmer Cetus). Thermal cycling conditions were 30 cycles of 95° C. for 30 s, 50° C. for 45 s, and 72° C. for 10 s. The PCR product was gel purified (Sambrook et al, 1989), passed through an elutipD column (available from Schleicher and Schull) and digested with KpnI prior to ligation into pUC18 or pUTmini-Tn5Km2. For ligations, plasmids were digested with KpnI and dephosphorylated with calf intestinal alkaline phosphatase (Gibco-BRL). Linearized plasmid molecules-were gel-purified (Sambrook et al, 1989) prior to ligation to remove any residual uncut plasmid DNA from the digestion. Ligation reactions contained approximately 50 ng each of plasmid and double stranded tag DNA in a 25 μl volume with 1 unit T4 DNA ligase (Gibco-BRL) in a buffer supplied with the enzyme.

Ligations were carried out for 2 h at 24° C. To determine the proportion of bacterial colonies arising from either self ligation of the plasmid DNA or uncut plasmid DNA, a control reaction was carried out in which the double stranded tag DNA was omitted from the ligation reaction. This yielded no ampicillin resistant bacterial colonies following transformation of *E. coli* CC118 (Sambrook et al, 1989), compared with 185 colonies arising from a ligation reaction containing the double stranded tag DNA.

Bacterial Transformation and Matings

The products of several ligations between pUT mini-Tn5Km2 and the double stranded tag DNA were used to transform *E. coli* CC118 (Sambrook et al, 1989). A total of approximately 10,300 transformants were pooled and plasmid DNA extracted from the pool was used to transform *E. coli* S-17λpir (de Lorenzo & Timmis, 1994). For mating experiments, a pool of approximately 40,000 ampicillin resistant *E. coli* S-17λpir transformants, and *S. typhimurium* 12023 Nal$^r$ were cultured separately to an optical density (OD)$_{580}$ of 1.0. Aliquots of each culture (0.4 ml) were mixed in 5 ml 10 mM MgSO$_4$, and filtered through a Millipore membrane (0.45 μm diameter). The filters were placed on the surface of agar containing M9 salts (de Lorenzo & Timmis, 1994) and incubated at 37° C. for 16 h. The bacteria were recovered by shaking the filters in liquid LB medium for 40 min at 37° C. and exconjugants were selected by plating the suspension onto LB medium containing 100 μg ml$^{-1}$ nalidixic acid (to select against the donor strain) and 50 μg ml$^{-1}$ kanamycin (to select for the recipient strain). Each exconjugant was checked by transferring nalidixic acid resistant (nal$^r$), kanamycin resistant (kan$^r$) colonies to MacConkey Lactose indicator medium (to distinguish between *E. coli* and *S. typhimurium*), and to LB medium containing ampicillin. Approximately 90% of the nal$^r$, kan$^r$ colonies were sensitive to ampicillin, indicating that these resulted from authentic transposition events (de Lorenzo & Timmis, 1994). Individual ampicillin-sensitive exconjugants were stored in 96 well microtitre dishes containing LB medium. For long term storage at −80° C., either 7% DMSO or 15% glycerol was included in the medium.

Phenotypic Characterisation of Mutants

Mutants were replica plated from microtitre dishes onto solid medium containing M9 salts and 0.4% glucose (Sambrook et al, 1989) to identify auxotrophs. Mutants with rough colony morphology were detected by low magnification microscopy of colonies on agar plates.

Colony Blots, DNA Extractions, PCRs, DNA Labelings and Hybridisations

For colony blot hybridizations, a 48-well metal replicator (Sigma) was used to transfer exconjugants from microtitre dishes to Hybond N nylon filters (Amersham, UK) that had been placed on the surface of LB agar containing 50 μg ml$^{-1}$ kanamycin. After overnight incubation at 37° C., the filters supporting the bacterial colonies were removed and dried at room temperature for 10 min. The bacteria were lysed with 0.4 N NaOH and the filters washed with 0.5 N Tris-Cl pH 7.0 according to the filter manufacturer's instructions. The bacterial DNA was fixed to the filters by exposure to UV light from a Stratalinker (Stratagene). Hybridisations to $^{32}$P-labelled probes were carried out under stringent conditions as previously described (Holden et al, 1989). For DNA extractions, *S. typhimurium* transposon mutant strains were grown in liquid LB medium in microtitre dishes or resuspended in LB medium following growth on solid media. Total DNA was prepared by the hexadecyltrimethylammoniumbromide (CTAB) method according to Ausubel et at (1987). Briefly, cells from 150 to 1000 μl volumes were precipitated by centrifugation and resuspended in 576 μl TE. To this was added 15 μl of 20% SDS and 3 μl of 20 mg ml$^{-1}$ proteinase K. After incubating at 37° C. for 1 hour, 166 μl of 3 M NaCl was added and mixed thoroughly, followed by 80 μl of 10% (w/v) CTAB and 0.7 M NaCl. After thorough mixing, the solution was incubated at 65° C. for 10 min. Following extraction with phenol and phenol-chloroform, the DNA was precipitated by addition of isopropanol, washed with 70% ethanol and resuspended in TE at a concentration of approximately 1 μg μl$^{-1}$.

The DNA samples were subjected to two rounds of PCR to generate labelled probes. The first PCR was performed in 100 μl reactions containing 20 mM Tris-Cl pH 8.3; 50 mM KCl; 2 mM MgCl$_2$; 0.01 % Tween 80; 200 μM each dATP, dCTP, dGTP, dTTP; 2.5 units of Amplitaq polymerase (Perkin-Elmer Cetus); 770 ng each primer P2 and P4; and 5 μg target DNA. After an initial denaturation of 4 min at 95° C., thermal cycling consisted of 20 cycles of 45 s at 50° C., 10 s at 72° C., and 30 s at 95° C. PCR products were extracted with chloroform/isoamyl alcohol (24/1) and precipitated with ethanol. DNA was resuspended in 10 μl TE and the PCR products were purified by electrophoresis through a 1.6% Seaplaque (FMC Bioproducts) gel in TAE buffer. Gel slices containing fragments of about 80 bp were excised and used for the second PCR. This reaction was carried out in a 20 μl total volume, and contained 20 mM Tris-Cl pH 8.3; 50 mM KCl; 2 mM MgCl$_2$; 0.01 % Tween 80; 50 μM each dATP, dTTP, dGTP; 10 μl $^{32}$P-dCTP (3000 Ci/mmol, Amersham); 150 ng each primer P2 and P4; approximately 10 ng of target DNA (1–2 μl of 1.6% Seaplaque agarose containing the first round PCR product); 0.5 units of Amplitaq polymerase. The reaction was overlayed with 20 μl mineral oil and thermal cycling was performed as described above. Incorporation of the radioactive label was quantitated by absorbance to Whatman DE81 paper (Sambrook et al, 1989).

Infection Studies

Individual Salmonella exconjugants containing tagged transposons were grown in 2% tryptone, 1% yeast extract, 0.92% v/v glycerol, 0.5% $Na_2PO_4$, 1% $KNO_3$ (TYGPN medium) (Ausubel et al, 1987) in microtitre plates overnight at 37° C. A metal replicator was used to transfer a small volume of the overnight cultures to a fresh microtitre plate and the cultures were incubated at 37° C. until the $OD_{580}$ (measured using a Titertek Multiscan microtitre plate reader) was approximately 0.2 in each well. Cultures from individual wells were then pooled and the $OD_{550}$ determined using a spectrophotometer. The culture was diluted in sterile saline to approximately $5\times10^5$ cfu $ml^{-1}$. Further dilutions were plated out onto TYGPN containing nalidixic acid (100 mg $ml^{-1}$) and kanamycin (50 mg $ml^{-1}$) to confirm the cfu present in the inoculum.

Groups of three female BALB/c mice (20–25 g) were injected intraperitoneally with 0.2 ml of bacterial suspension containing approximately $1\times10^5$ cfu $ml^{-1}$. Mice were sacrificed three days post-inoculation and their spleens were removed to recover bacteria. Half of each spleen was homogenized in 1 ml of sterile saline in a microfuge tube. Cellular debris was allowed to settle and 1 ml of saline containing cells still in suspension was removed to a fresh tube and centrifuged for two minutes in a microfuge. The supernatant was aspirated and the pellet resuspended in 1 ml of sterile distilled water. A dilution series was made in sterile distilled water and 100 ml of each dilution was plated onto TYGPN agar containing nalidixic acid (100 ug $ml^{-1}$) and kanamycin (50 ug $ml^{-1}$). Bacteria were recovered from plates containing between 1000 and 4000 colonies, and a total of over 10,000 colonies recovered from each spleen were pooled and used to prepare DNA for PCR generation of probes to screen colony blots.

Virulence Gene Cloning and DNA Sequencing

Total DNA was isolated from *S. typhimurium* exconjugants and digested separately with SstI, SalI, PstI and SphI. Digests were fractionated through agarose gels, transferred to Hybond $N^+$ membranes (Amersham) and subjected to Southern hybridisation analysis using the kanamycin resistance gene of pUT mini-Tn5Km2 as a probe. The probe was labelled with digoxygenin (Boehringer-Mannheim) and chemiluminescence detection was carried out according to the manufacturer's instructions. The hybridisation and washing conditions were as described above. Restriction enzymes which gave rise to hybridising fragments in the 3–5 kb range were used to digest DNA for a preparative agarose gel, and DNA fragments corresponding to the sizes of the hybridisation signals were excised from this, purified and ligated into pUC18. Ligation reactions were used to transform *E. coli* DH5a to kanamycin resistance. Plasmids from kanamycin-resistant transformants were purified by passage through an elutipD column and checked by restriction enzyme digestion. Plasmid inserts were partially sequenced by the di-deoxy method (Sanger et al, 1977) using the 40 primer and reverse sequencing primer (United States Biochemical Corporation) and the primers P6 (5'-CCTAGGCGGCCAGATCTGAT-3') (SEQ ID No 6) and P7 (5'GCACTTGTGTATAAGAGTCAG-3') (SEQ ID No 7) which anneal to the I and O termini of Tn5, respectively. Nucleotide sequences and deduced amino acid sequences were assembled using the Macvector 3.5 software package run on a Macintosh SE/30 computer. Sequences were compared with the EMBL and Genbank DNA databases using the UNIX/SUN computer system at the Human Genome Mapping Project Resource Centre, Harrow, UK.

Results

Tag Design

Figure 1A:
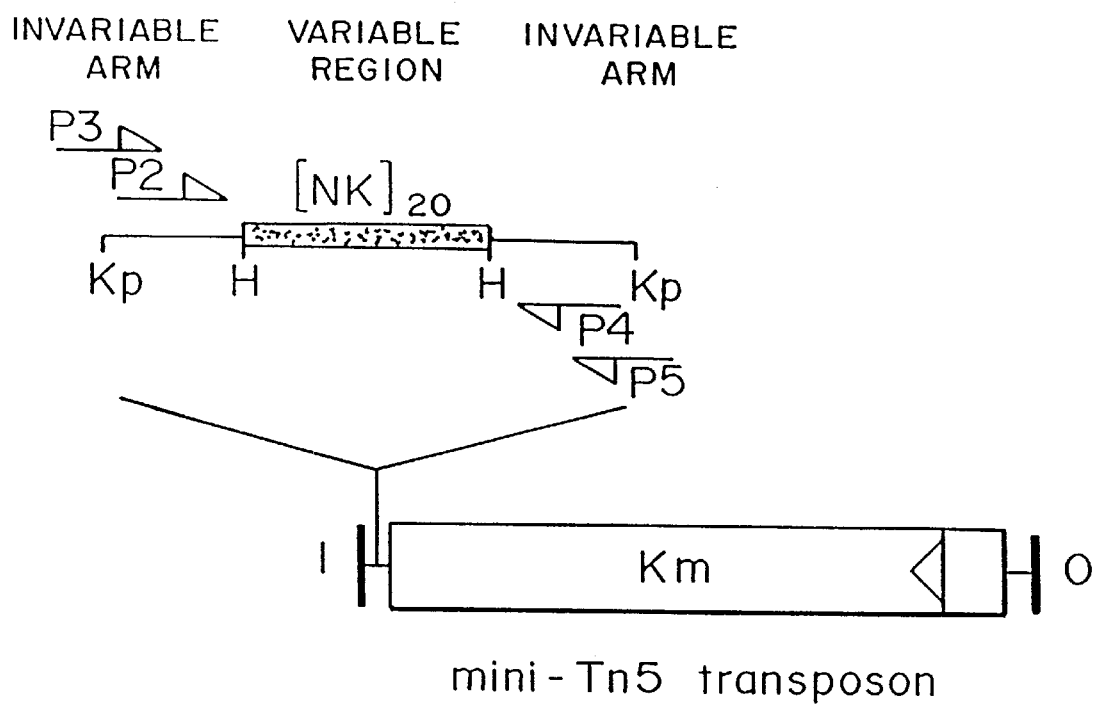
FIGS. 1A and 1B illustrate diagrammatically one particularly preferred method of the invention.
Figure 1B:
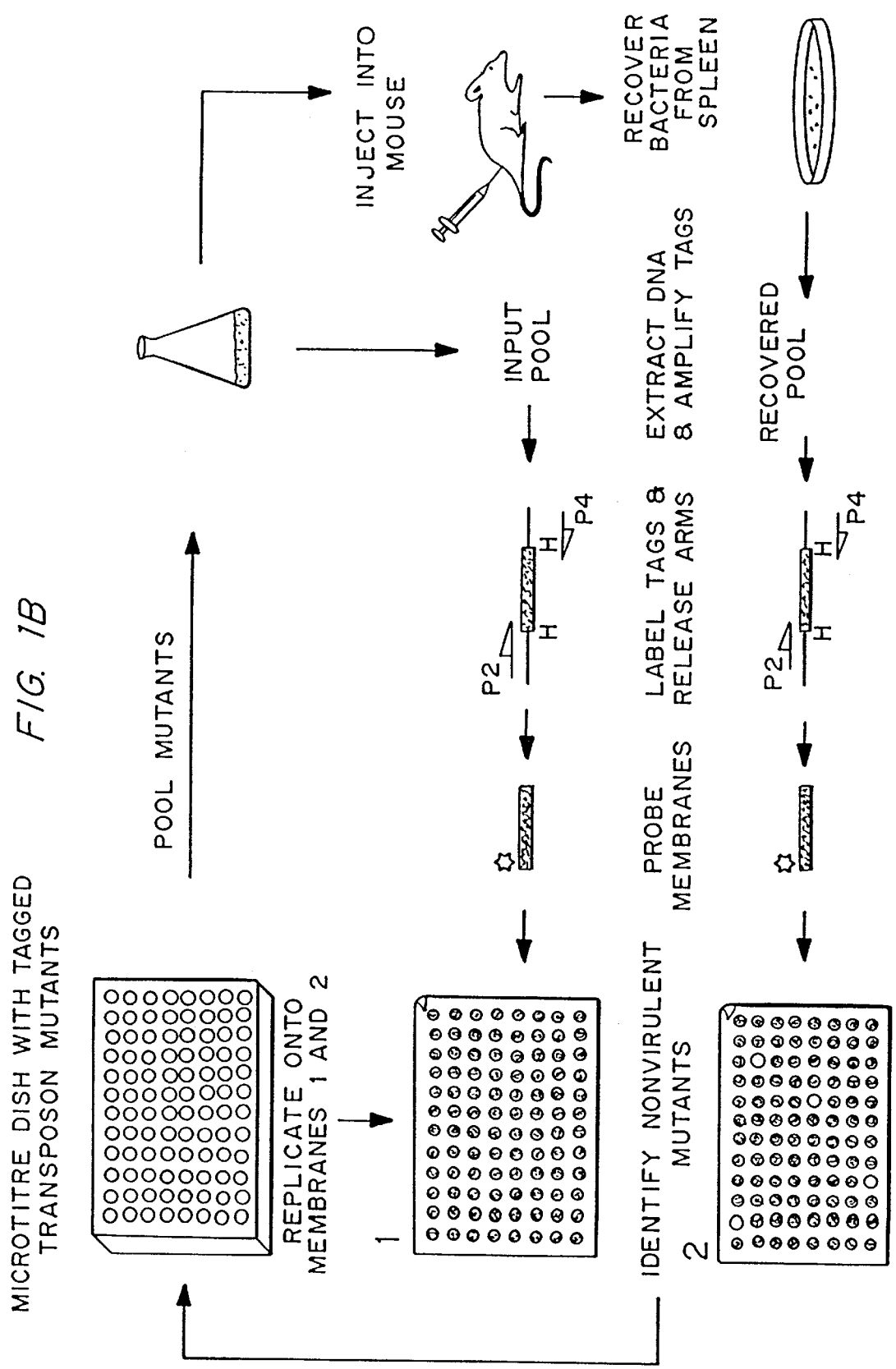
Figure 2:
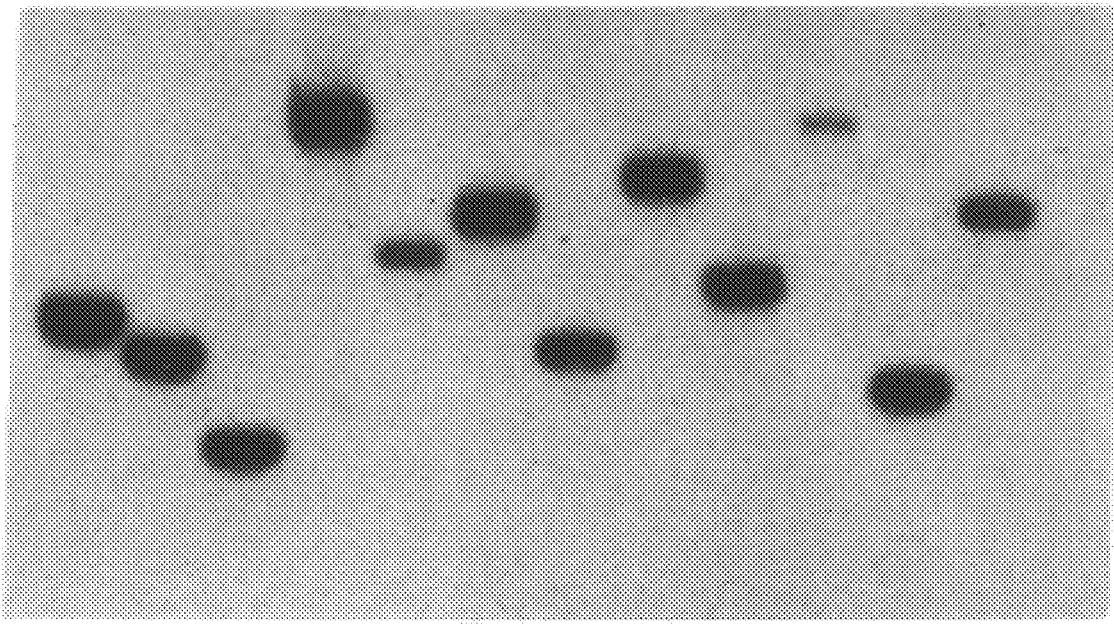
FIG. 2 shows a Southern hybridisation analysis of DNA from 12 *S. typhimurium* exconjugants following digestion with EcoRV. The filter was probed with the kanamycin resistance gene of the mini-Tn5 transposon.

The structure of the DNA tags is shown in FIG. 1a. Each tag consists of a variable central region flanked by "arms", of invariant sequence. The central region sequence ($[NK]_{20}$) was designed to prevent the occurrence of sites for the commonly used 6 bp-recognition restriction enzymes, but is sufficiently variable to ensure that statistically, the same sequence should only occur once in $2\times10^{11}$ molecules (DNA sequencing of 12 randomly selected tags showed that none shared more than 50% identity over the variable region). N means any base (A, G, C or T) and K means G or T.) The arms contain KpnI sites close to the ends to facilitate the initial cloning step, and the HindIII sites bordering the variable region were used to release radiolabelled variable regions from the arms prior to hybridisation analysis. The arms were also designed such that primers P2 and P4 each contain only one guanine residue. Therefore during a PCR using these primers, only one cytosine will be incorporated into each newly synthesised arm, compared to an average of ten in the unique sequence. When radiolabelled dCTP is included in the PCR, an average of ten-fold more label will be present in the unique sequence compared with each arm. This is intended to minimise background hybridisation signals from the arms, after they have been released from the unique sequences by digestion with HindIII. Double stranded tags were ligated into the KpnI site of the mini-Tn5 transposon Km2, carried on plasmid pUT (de Lorenzo & Timmis, 1994). Replication of this plasmid is dependent on the R6K-specified π product of the pir gene. It carries the oriT sequence of the RP4 plasmid, permitting transfer to a variety of bacterial species (Miller & Mekalanos, 1988), and the tnp gene needed for transposition of the mini-Tn5 element. The tagged mini-Tn5 transposons were transferred to *S. typhimurium* by conjugation, and 288 exconjugants resulting from transposition events were stored in the wells of microtitre dishes. Total DNA isolated from 12 of these was digested with EcoRV, and subjected to Southern hybridisation analysis using the kanamycin resistance gene of the mini-Tn5 transposon as a probe. In each case, the exconjugant had arisen as a result a single integration of the transposon into a different site of the bacterial genome (FIG. 2).

Specificity and Sensitivity Studies

We next determined the efficiency and uniformity of amplification of the DNA tags in PCRs involving pools of exconjugant DNAs as targets for the reactions. In an attempt to minimise unequal amplification of tags in the PCR, we determined the maximum quantity of DNA target that could be used in a 100 μl reaction, and the minimum number of PCR cycles, that resulted in products which could be visualised by ethidium bromide staining of an agarose gel (5 μg DNA and 20 cycles, respectively).

*S. typhimurium* exconjugants which had reached stationary growth phase in microtitre dishes were combined, and used to extract DNA. This was subjected to a PCR using primers P2 and P4. PCR products of 80 bp were gel-purified and used as targets for a second PCR, using the same primers but with $^{32}$P-labelled CTP. This resulted in over 60% of the radiolabelled dCTP being incorporated into the PCR products. The radiolabelled products were digested with HindIII and used to probe colony blotted DNA from their corresponding microtitre dishes. Of the 1510 mutants tested in this way, 358 failed to yield a clear signal on an autoradiogram following an overnight exposure of the colony blot. There are three potential explanations for this. Firstly, it is possible that a proportion of the transposons did not carry tags. However, by comparing the transformation frequencies resulting from ligation reactions involving the transposon in the presence or absence of tags, it seems unlikely that untagged transposons could account for more than approximately 0.5% of the total (see Materials and Methods). More probable causes are that the variable sequence was truncated in some of the tags, and/or that some of the sequences formed secondary structures, both of which might have prevented amplification. Mutants which failed to give clear signals were not included in further studies. The specificity of the efficiently amplifiable tags was demonstrated by generating a probe from 24 colonies of a microtitre dish, and using it to probe a colony blot of 48 colonies, which included the 24 used to generate the probe. The lack of any hybridisation signal from the 24 colonies not used to generate the probe (FIG. 3) shows that the hybridisation conditions employed were sufficiently stringent to prevent cross-hybridisation among labelled tags, and suggests that each exconjugant is not reiterated within a microtitre dish.

There are further considerations in determining the maximum pool size that can be used as an inoculum in animal experiments. As the quantity of labelled tag for each transposon is inversely proportional to the complexity of the tag pool, there is a limit to the pool size above which hybridisation signals become too weak to be detected after overnight exposure of an autoradiogram. More importantly, as the complexity of the pool increases, so must the likelihood of failure of a virulent representative of the pool to be present in sufficient numbers, in the spleen of an infected animal, to produce enough labelled probe. We have not determined the upper limit for pool size in the murine model of salmonellosis that we have employed, but it must be in excess of 96.

Virulence Tests of the Transposon Mutants

Figure 3:
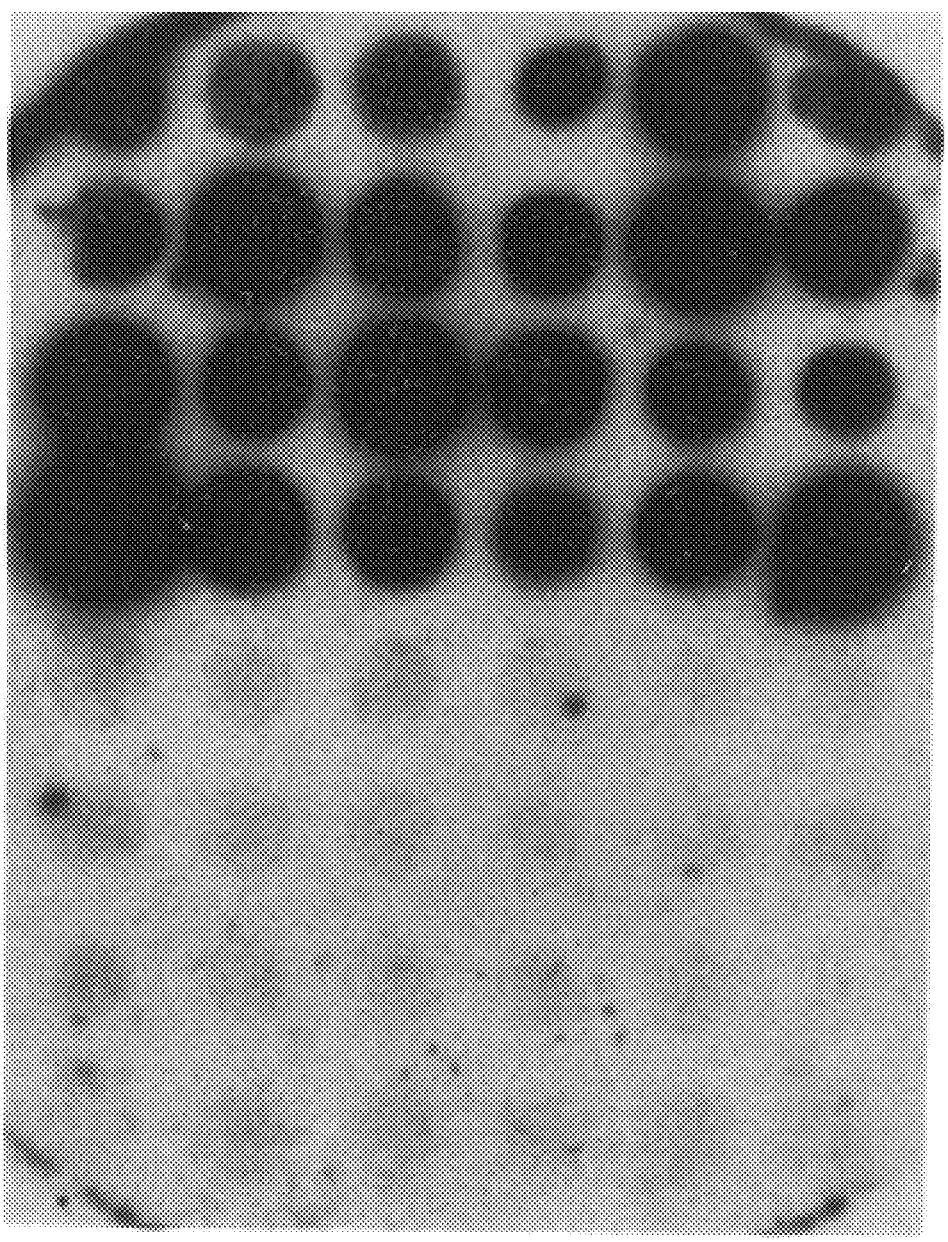
FIG. 3 shows a colony blot hybridisation analysis of DNA from 48 *S. typhimurium* exconjugants from a half of a microtitre dish (A1-H6). The filter was hybridised with a probe comprising labelled amplified tags from DNA isolated from a pool of the first 24 colonies (A1-D6).
Figure 4A:
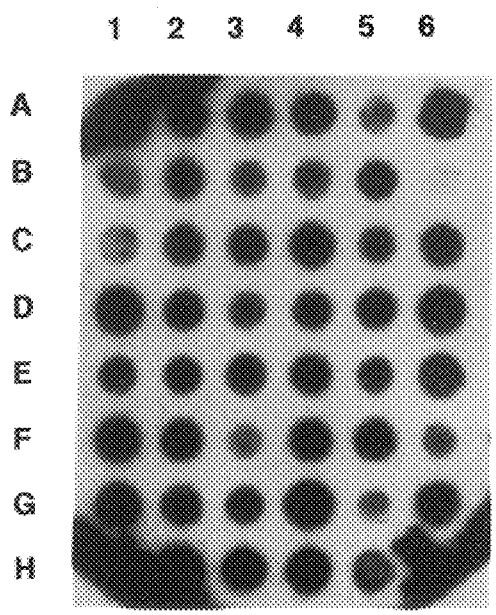
FIGS. 4A–4D show a DNA colony blot hybridisation analysis of 95 *S. typhimurium* exconjugants of a microtitre dish (A1-H11), which were injected into a mouse. Replicate filters were hybridised with labelled amplified tags from the pool (inoculum pattern), or with labelled amplified tags from DNA isolated from over 10,000 pooled colonies that were recovered from the spleen of the infected animal (spleen pattern). Colonies B6, A11 and C8 gave rise to weak hybridisation signals on both sets of filters. Hybridisation signals from colonies A3, C5, G3 (aroA), and F10 are present on the inoculum pattern but not on the spleen pattern.
Figure 4B:
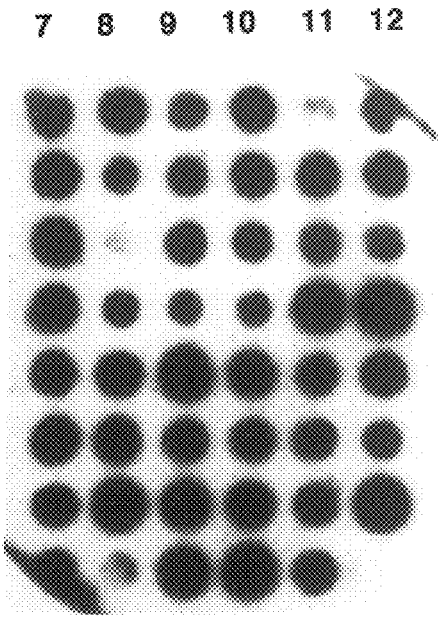
Figure 4C:
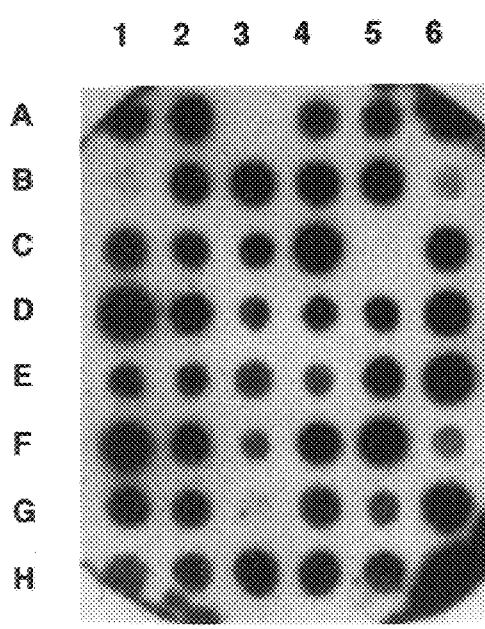
Figure 4D:
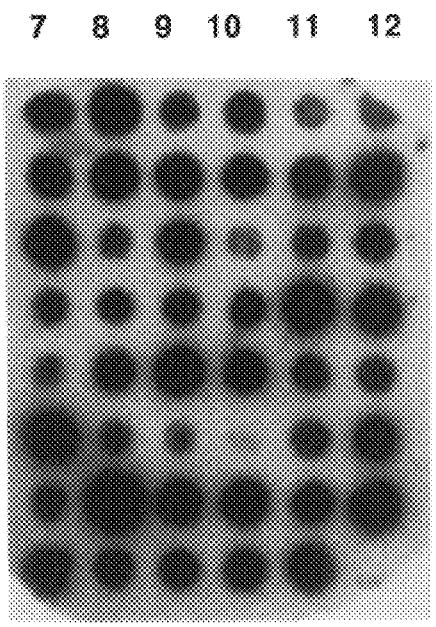
Figures 7A, 7B:
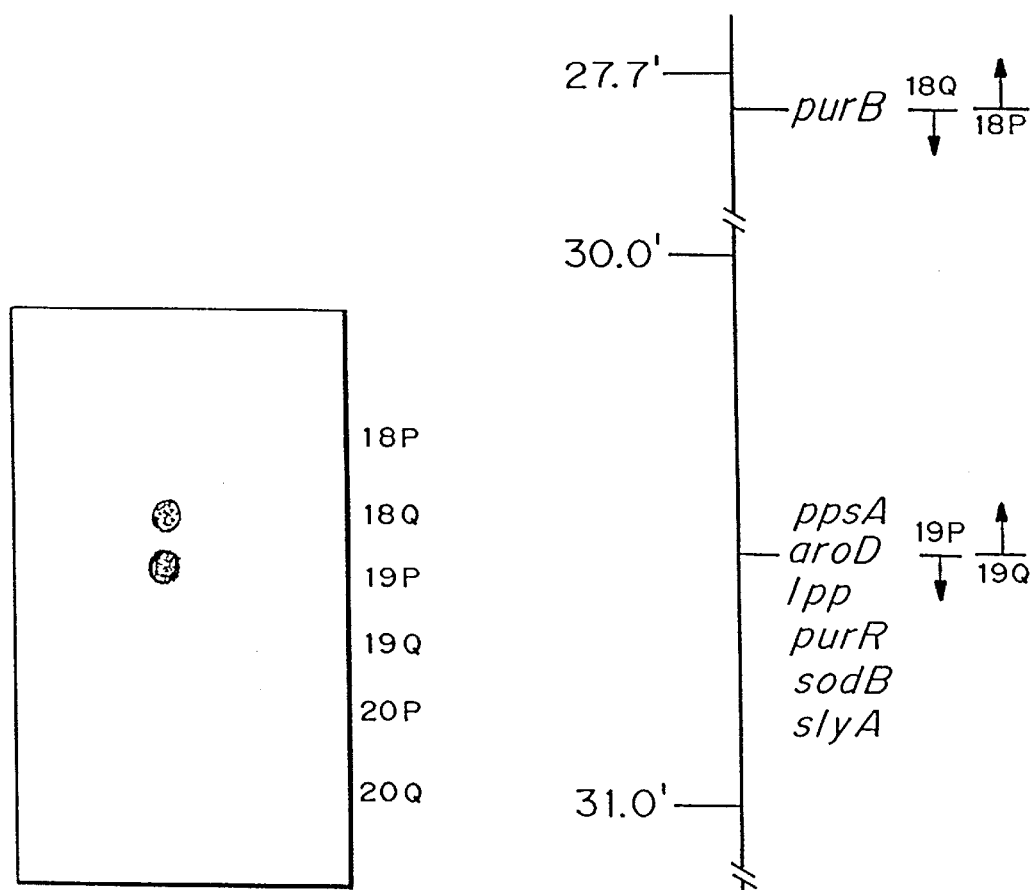
FIGS. 7A and 7B show the mapping of VGC2 on the *S. typhimurium* chromosome. (A) DNA probes from three regions of VGC2 were used in Southern hybridisation analysis of lysates from a set of *S. typhimurium* strains harbouring locked in Mud-P22 prophages. Lysates which hybridised to a 7.5 kb PstI fragment (probe A in FIG. 8) are shown. The other two probes used hybridised to the same lysates. (B) The insertion points and packaging directions of the phage are shown along with the map position in minutes (edition VIII, ref 22 in Example 4). The phage designations correspond to the following strains: 18P, TT15242; 18Q, 15241; 19P, TT15244; 19Q, TT15243; 20P, TT15246 and 20Q, TT15245 (Ref in Example 4). The locations of mapped genes are shown by horizontal bars and the approximate locations of other genes are indicated.

A total of 1152 uniquely tagged insertion mutants (from two microtitre dishes) were tested for virulence in BALB/c mice in twelve pools, each representing a 96-well microtitre dish. Animals received an intraperitoneal injection of approximately $10^3$ cells of each of 96 transposon mutants of a microtitre dish ($10^5$ organisms in total). Three days after injection mice were sacrificed, and bacteria were recovered by plating spleen homogenates onto laboratory medium. Approximately 10,000 colonies recovered from each mouse were pooled and DNA was extracted. The tags present in this DNA sample were amplified and labelled by the PCR, and colony blots probed and compared with the hybridisation pattern obtained using tags amplified from the inoculum (FIG. 3). As a control, an aroA mutant of S. typhimurium was tagged and employed as one of the 96 mutants in the inoculum. This strain would not be expected to be recovered in the spleen because its virulence is severely attenuated (Buchmeier et al, 1993). Forty-one mutants were identified whose DNA hybridized to labelled tags from the inoculum but not from labelled tags from bacteria recovered from the spleen. The experiment was repeated and the same forty-one mutants were again identified. Two of these were the aroA mutant (one per pool), as expected. Another was an auxotrophic mutant (it failed to grow on minimal medium). All of the mutants had normal colony morphology.

EXAMPLE 2

Cloning and Partial Charcterisation of Sequence Flaking the Transposon

DNA was extracted from one of the mutants described in Example 1 (Pool F10), digested with SstI, and subcloned on the basis of kanamycin resistance. The sequence of 450 bp flanking one end of the transposon was determined using primer P7. This sequence shows 80% identity to the E. coli clp (Ion) gene, which encodes a heat-regulated protease (FIG. 5 SEQ ID Nos. 39 and 40). To our knowledge, this gene has not previously been implicated as a virulence determinant.

Partial sequences of thirteen further Salmonella typhimurium virulence genes are shown in FIG. 6 (sequences A2 to A9 and B1 to B5SEQ ID Nos 8–36 ). Deduced amino acid sequences of P2D6, S4C3, P3F4, P7G2 and P9B7 bear similarities to a family of secretion-associated proteins that have been conserved throughout bacterial pathogens of animals and plants, and which are known in Salmonella as the inv family. In S. typhimurium the inv genes are required for bacterial invasion into intestinal tissue. The virulence of inv mutants is attenuated when they are inoculated by the oral route, but not when they are administered intraperitoneally. The discovery of inv-related genes that are required for virulence following intraperitoneal inoculation suggests a new secretion apparatus which might be required for invasion of non-phagocytic cells of the spleen and other organs. The products of these new genes might represent better drug targets than the inv proteins in the treatment of established infections.

Further characterisation of the genes identified in this example is described in Example 4.

EXAMPLE 3

$LD_{50}$ Determination and Mouse Vaccination Study

Mutations identified by the method of the invention attenuate virulence.

Five of the mutations in genes not previously implicated in virulence were transferred by P22-mediated transduction to the nalidixic acid-sensitive parent strain of S. typhimurium 12028. Transductants were checked by restriction mapping then injected by the intraperitoneal route into groups of BALB/c mice to determine their 50% lethal dose ($LD_{50}$). The $LD_{50}$ values for mutants S4C3, P7G2, P3F4 and P9B7 were all several orders of magnitude higher than that of the wild-type strain. No difference in the $LD_{50}$ was detected for mutant P1F10; however, there was a statistically significant decrease in the proportion of P1F10 cells recovered from the spleens of mice injected with an inoculum consisting of an equal proportion of this strain and the wild-type strain. This implies that this mutation does attenuate virulence, but to a degree that is not detectable by $LD_{50}$.

Mutants P3F4 and P9B7 were also administered by the oral route at an inoculum level of $10^7$ cells/mouse. None of the mice became ill, indicating that the oral $LD_{50}$ levels of these mutants are at least an order of magnitude higher than that of the wild-type strain.

In the mouse vaccination study groups of five female BALB/c mice of 20–25 g in mass were initially inoculated orally (p.o.) or intraperitoneally (i.p.) with serial ten fold dilutions of Salmonella typhimurium mutant strains P3F4 and P9B7. After four weeks the mice were then inoculated with 500 c.f.u. of the parental wild type strain. Deaths were then recorded over four weeks.

A group of two mice of the same age and batch as the mice inoculated with the mutant strains were also inoculated i.p. with 500 c.f.u. of the wild type strain as a positive control. Both non-immunised mice died as expected within four weeks.

Results are tabulated below:

1) p.o. initial inoculation with mutant strain P3F4

| initial inoculum in c.f.u. | no. mice surviving first challenge | no. mice surviving wild type challenge |
|---|---|---|
| $5 \times 10^9$ | 5 | 2 (40%) |
| $5 \times 10^8$ | 5 | 2 (40%) |
| $5 \times 10^7$ | 5 | 0 (0%) |

2) i.p. initial inoculum with mutant strain P3F4

| initial inoculum in c.f.u. | no. mice surviving first challenge | no. mice surviving wild type challenge |
|---|---|---|
| $5 \times 10^6$ | 3 | 3 (100%) |
| $5 \times 10^5$ | 5 | 4 (80%) |
| $5 \times 10^4$ | 6 | 5 (83%) |
| $5 \times 10^3$ | 5 | 4 (80%) |

3) p.o. initial inoculum with mutant strain P9B7

| initial inoculum in c.f.u. | no. mice surviving first challenge | no. mice surviving wild type challenge |
|---|---|---|
| $5 \times 10^9$ | 5 | 0 (0%) |

4) i.p. initial inoculum with mutant P9B7

| initial inoculum in c.f.u. | no. mice surviving first challenge | no. mice surviving wild type challenge |
|---|---|---|
| $5 \times 10^6$ | 4 | 2 (50%) |

From these experiments I conclude that mutant P3P4 appears to give some protection against subsequent wild type challenge. This protection appears greater in mice that were immunised i.p.

EXAMPLE 4

Identification of a Virulence Locus Encoding a Second Type III Secrection System in *Salmonella typhimrium*

Abbreviations used in this Example are VGC1, virulence gene cluster 1; VGC2, virulence gene cluster 2.

Background to the Experiments Described

*Salmonella typhimurium* is a principal agent of gastroenteritis in humans and produces a systemic illness in mice which serves as a model for human typhoid fever (1). Following oral inoculation of mice with *S. typhimurium*, the bacteria pass from the lumen of the small intestine through the intestinal mucosa, via enterocytes or M cells of the Peyer's patch follicles (2). The bacteria then invade macrophages and neutrophils, enter the reticuloendothelial system and disseminate to other organs, including the spleen and liver, where further reproduction results in an overwhelming and fatal bacteremia (3). To invade host cells, to survive and replicate in a variety of physiologically stressful intracellular and extracellular environments and to circumvent the specific antibacterial activities of the immune system, *S. typhimurium* employs a sophisticated repertoire of virulence factors (4).

To gain a more comprehensive understanding of virulence mechanisms of *S. typhimurium* and other pathogens the transposon mutagenesis system described in Example 1, which is conveniently called 'signature-tagged mutagenesis' (STM), which combines the strength of mutational analysis with the ability to follow simultaneously the fate of a large number of different mutants within a single animal (5 and Example 1; Reference 5 was published after the priority date for this invention). Using this approach we identified 43 mutants with attenuated virulence from a total of 1152 mutants that were screened. The nucleotide sequences of DNA flanking the insertion points of transposons in 5 of these mutants showed that they were related to genes encoding type III secretion systems of a variety of bacterial pathogens (6, 7). The products of the inv/spa gene cluster of *S. typhimurium* (8, 9) are proteins that form a type III secretion system required for the assembly of surface appendages mediating entry into epithelial cells (10). Hence the virulence of strains carrying mutations in the inv/spa cluster is attenuated only if the inoculum is administered orally and not when given intraperitoneally (8). In contrast the 5 mutants identified by STM are avirulent following intraperitoneal inoculation (5).

In this example we show that the transposon insertion points of these 5 mutants and an additional 11 mutants identified by STM all map to the same region of the *S. typhimurium* chromosome. Further analysis of this region reveals additional genes whose deduced products have sequence similarity to other components of type m-secretion systems. This chromosomal region which we refer to as virulence gene cluster 2 (VGC2) is not present in a number of other enteric bacteria, and represents an important locus for *S. typhimurium* virulence.

Materials and Methods

Bacterial Strains, Transduction and Growth Media. *Salmonella enterica* serotypes 5791 (*aberdeen*), 423180 (*gallinarum*), 7101 (*cubana*) and 12416 (*typhimurium* LT2) were obtained from the National Collections of Type Cultures, Public Health Laboratory Service, UK. *Salmonella typhi* BRD123 genomic DNA was a gift from G. Dougan, enteropathogenic *Escherichia coli* (EPEC), enterohemorrhagic *E. coli* (EHEC), *Vibrio cholera* biotype El Tor, *Shigella flexneri* serotype 2 and *Staphylococcus aureus* were clinical isolates obtained from the Department of Infectious Diseases and Bacteriology, Royal Postgraduate Medical School, UK. Genomic DNA from *Yersinia pestis* was a gift from J. Heesemann. However, genomic DNA can be isolated using standard methods. The bacterial strains and the methods used to generate signature-tagged mini-Tn5 transposon mutants of *S. typhimurium* NCTC strain 12023 have been described previously (5, 11). Routine propagation of plasmids was in *E. coli* DH5α. Bacteria were grown in LB broth (12) supplemented with the appropriate antibiotics. Before virulence levels of individual mutant strains were assessed, the mutations were first transferred by phage P22 mediated transduction (12) to the nalidixic acid sensitive parental strain of *S. typhimurium* 12023. Transductants were analysed by restriction digestion and Southern hybridisation before use as inoculum.

Lambda Library Screening. Lambda (λ) clones with overlapping insert DNAs covering VGC2 were obtained by standard methods (13) from a λ1059 library (14) containing inserts from a partial Sau3A digest of *S. typhimurium* LT2 genomic DNA. The library was obtained via K. Sanderson, from the Salmonella Genetic Stock Centre (SGSC), Calgary, Canada.

Mud-P22 Lysogens. Radiolabelled DNA probes were hybridised to Hybond N (Amersham) filters bearing DNA prepared from lysates of a set of *S. typhimurium* strains harbouring Mud-P22 prophages at known positions in the *S. typhimurium* genome. Preparation of mitomycin-induced Mud-P22 lysates was as described (12, 15). The set of Mud-P2 prophages was originally assembled by Benson and Goldman (16) and was obtained from the SGSC.

Gel Electrophoresis and Southern Hybridisation. Gel electrophoresis was performed in 1% or 0.6% agarose gels run in 0.5× TBE. Gel fractionated DNA was transferred to Hybond N or N+membranes (Amersham) and stringent hybridisation and washing procedures (permitting hybridisation between nucleotide sequences with 10% or less mismatches) were as described by Holden et al, (17). For non-stringent conditions (permitting hybridisation between sequences with 50% mismatches) filters were hybridised overnight at 42° C. in 10% formamide/0.25 M $Na_2HPO_4$/7% SDS and the most stringent step was with 20 mM $Na_2HPO_4$/1% SDS at 42° C. DNA fragments used as probes were labelled with [$^{32}$P]dCTP using the 'Radprime' system (Gibco-BRL) or with [digoxigenin-11]dUTP and detected using the Digoxigenin system (Boehringer Mannheim) according to the manufacturers' instructions, except that hybridisation was performed in the same solution as that used for radioactively labelled probes. Genomic DNA was prepared for Southern hybridisation as described previously (13).

Molecular Cloning and Nucleotide Sequencing. Restriction endonucleases and T4 DNA ligase were obtained from Gibco-BRL. General molecular biology techniques were as described in Sambrook et al, (18). Nucleotide sequencing was performed by the dideoxy chain termination method (19) using a T7 sequencing kit (Pharmacia). Sequences were assembled with the MacVector 3.5 software or AssemblyLIGN packages. Nucleotide and derived amino acid sequences were compared with those in the European Molecular Biology Laboratory (EMBL) and SwissProt databases using the BLAST and FASTA programs of the GCG package from the University of Wisconsin (version 8) (20) on the network service at the Human Genome Mapping Project Resource Centre, Hinxton, UK.

Virulence Tests. Groups of five female BALB/c mice (20–25 g) were inoculated orally (p.o.) or intraperitoneally (i.p.) with 10-fold dilutions of bacteria suspended in physiological saline. For preparation of the inoculum, bacteria were grown overnight at 37° C. in LB broth with shaking (50 rpm) and then used to inoculate fresh medium for various lengths of time until an optical density (OD) at 560 nm of 0.4 to 0.6 had been reached. For cell densities of $5 \times 10^8$ colony forming units (cfu) per ml and above, cultures were concentrated by centrifugation and resuspended in saline. The concentration of cfu/ml was checked by plating a dilution series of the inoculum onto LB agar plates. Mice were inoculated i.p. with 0.2 ml volumes and p.o. by gavage with the same volume of inoculum. The LD50 values were calculated after 28 days by the method of Reed and Meunch (21).

Results

Localisation of Transposon Insertions. The generation of a bank of *Salmonella typhimurium* mini Tn5 transposon mutants and the screen used to identify 43 mutants with attenuated virulence have been described previously (5). Transposons and flanking DNA regions were cloned from exconjugants by selection for kanamycin resistance or by inverse PCR. Nucleotide sequences of 300–600 bp of DNA flanking the transposons were obtained for 33 mutants. Comparison of these sequences with those in the DNA and protein databases indicated that 14 mutants resulted from transposon insertions into previously known virulence genes, 7 arose from insertions into new genes with similarity to known genes of the enterobacteria and 12 resulted from insertions into sequences without similarity to entries in the DNA and protein databases (ref. 5, Example 1 and this Example).

Three lines of evidence suggested that 16 of 19 transposon insertions into new sequences were clustered in three regions of the genome, initially designated A, B and C. First, comparing nucleotide sequences from regions flanking transposon insertion points with each other and with those in the databases showed that some sequences overlapped with one another or had strong similarity to different regions of the same gene. Second, Southern analysis of genomic DNA digested with several restriction enzymes and probed with restriction fragments flanking transposon insertion points indicated that some transposon insertions were located on the same restriction fragments. Third, when the same DNA probes were hybridised to plaques from a *S. typhimurium* λ DNA library, the probes from mutants which the previous two steps had suggested might be linked were found to hybridise to the same λ DNA clones. Thus two mutants (P9B7 and P12F5) were assigned to cluster A, five mutants (P2D6, P9B6, P11C3, P11D10 and P11H10) to cluster B and nine mutants (P3F4, P4F8, P7A3, P7B8, P7G2, P8G12, P9G4, P10E11 and P11B9) to cluster C (FIG. 8).

Hybridisation of DNA probes from these three clusters to lysates from a set of *S. typhimurium* strains harbouring locked-in Mud-P22 prophages (15, 16) showed that the three loci were all located in the minute 30 to 31 region (edition VIII, ref. 22) (FIG. 7), indicating that the three loci were closely linked or constituted one large virulence locus. To determine if any of the λ clones covering clusters A, B and C contained overlapping DNA inserts, DNA fragments from the terminal regions of each clone were used as probes in Southern hybridisation analysis of the other λ clones. Hybridising DNA fragments showed that several λ clones overlap and that clusters A, B and C comprise one contiguous region (FIG. 8). DNA fragments from the ends of this region were then used to probe the λ library to identify further clones containing inserts representing the adjacent regions. No λ clones were identified that covered the extreme right hand terminus of the locus so this region was obtained by cloning a 6.5 kb EcoRI/XbaI from a lysate of the Mud-P22 prophage strain TT15244 (16).

Restriction mapping and Southern hybridisation analysis were then used to construct a physical map of this locus (FIG. 8). To distinguish this locus from the well characterised inv/spa gene cluster at minute 63 (edition VIII, ref. 22) (8, 9, 23, 24, 25, 26), we refer to the latter as virulence gene cluster 1 (VGC1) and have termed the new virulence locus cluster 2 (VGC2). FIG. 2 shows the position of two portions of DNA whose nucleotide sequence has been determined ("Sequence 1" and "Sequence 2"). The nucleotide sequence is shown in FIGS. 11 and 12.

Figure 9:
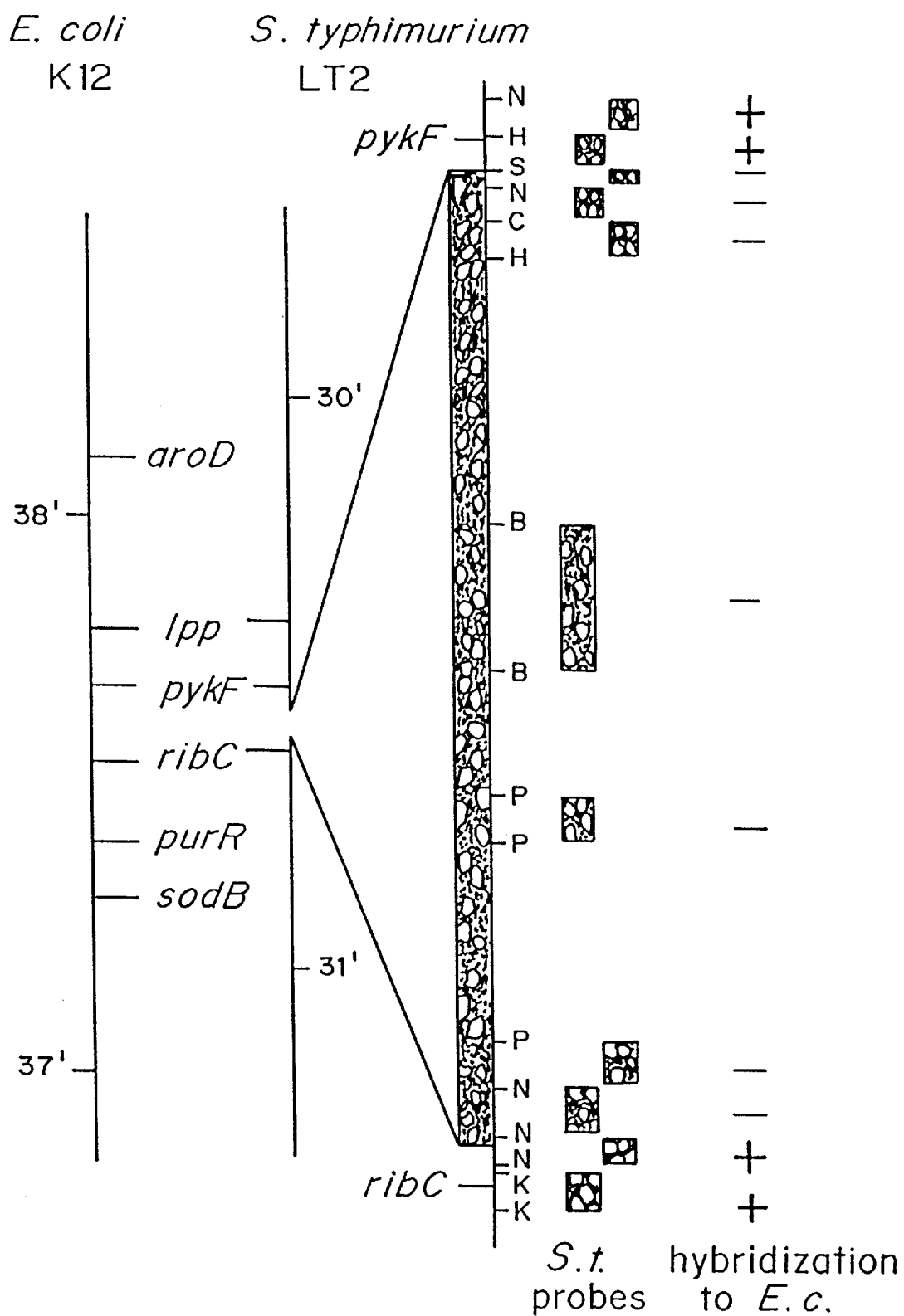
FIG. 9 describes mapping the boundaries of VGC2. (A) The positions of mapped genes at minutes 37 to 38 on the *E. coli* K12 chromosome are aligned with the corresponding region of the *S. typhimurium* LT2 chromosome (minutes 30 to 31). An expanded map of the VGC2 region is shown with 11 *S. typhimurium* (*S. t.*) DNA fragments used as probes (thick bars) and the restriction sites used to generate them: B, BamHI; C, ClaI; H, HindII; K, KpnI; P, PstI; N, NsiI and S, SalI. Probes that hybridised to *E. coli* K12 (*E. c.*) genomic DNA are indicated by +; those which failed to hybridise are indicated by −.

Mapping the boundaries of VGC2 on the *S. typhimurium* chromosome. Nucleotide sequencing of λ clone 7 at the left hand side of VGC2 revealed the presence of an open reading frame (ORF) whose deduced amino acid sequence is over 90% identical to the derived product of a segment of the ydhE$^\ddagger$ gene of *E. coli* and sequencing of the 6.5 kb EcoRI/XbaI cloned fragment on the right hand side of VGC2 revealed the presence of an ORF whose predicted amino acid sequence is over 90% identical to pyruvate kinase I of *E. coli* encoded by the pykF gene (27). On the *E. coli* chromosome ydhE and pykF are located close to one another, at minute 37 to 38 (28). Eleven non-overlapping DNA fragments distributed along the length of VGC2 were used as probes in non-stringent Southern hybridisation analysis of *E.coli* and *S. typhimurium* genomic DNA. Hybridising DNA fragments showed that a region of approximately 40 kb comprising VGC2 was absent from the *E.coli* genome and localised the boundaries of VGC2 to within 1 kb (FIG. 9). Comparison of the location of the XbaI site close to the right hand end of VGC2 (FIG. 8) with a map of known XbaI sites (29) at the minute 30 region of the chromosome (22) enables a map position of 30.7 minutes to be deduced for VGC2.

Structure of VGC2. Nucleotide sequencing of portions of VGC2 has revealed the presence of 19 ORFs (FIG. 8). The G+C content of approximately 26 kb of nucleotide sequence within VGC2 is 44.6%, compared to 47% for VGC1 (9) and 51–53% estimated for the entire Salmonella genome (30).

The complete deduced amino acid sequences of ORFs 1–11 are similar to those of proteins of type III secretion systems (6, 7), which are known to be required for the export of virulence determinants in a variety of bacterial pathogens of plants and animals (7). The predicted proteins of ORFs 1–8 (FIG. 8) are similar in organisation and sequence to the products of the yscN-U genes of *Yersinia pseudotuberculosis* (31), to invC/spaS of the inv/spa cluster in VGC1 of *Salmonella typhimurium* (8, 9) and to spa47/spa40 of the spa/mxi cluster of *Shigella flexneri* (32, 33, 34, 35, ). For example the predicted amino acid sequence of ORF 3 (FIG. 8) is 50% identical to YscS of *Y. pseudotuberculosis* (31), 34% identical to Spa9 from *S. flexneri* (35) and 37% identical to SpaQ of VGC1 of *S. typhimurium* (9). The predicted protein product of ORF9 is closely related to the LcrD family of proteins with 43% identity to LcrD of *Y. enterocolitica* (36), 39% identity to MxiA of *S. flexneri* (32) and 40% identity to InvA of VGC1 (23). Partial nucleotide sequences for the remaining ORFs shown in FIG. 8 indicate that the predicted protein from ORF10 is most similar to *Y. enterocolitica* YscJ (37) a lipoprotein located in the bacterial outer membrane, with ORF11 similar to *S. typhimurium* InvG, a member of the PulD family of translocases (38). ORF12 and ORF13 show significant similarity to the sensor and regulatory subunits respectively, from a variety of proteins comprising two component regulatory systems (39). There is ample coding capacity for further genes between ORFs 9 and 10, ORFs 10 and 11, and between ORF 19 and the right hand end of VGC2.

Figure 10A:
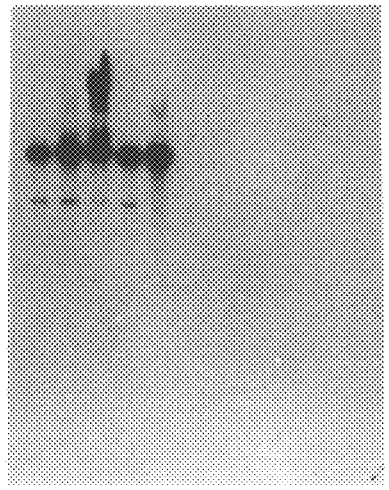
FIG. 10 shows that VGC2 is conserved among and specific to the Salmonellae. Genomic DNA from Salmonella serovars and other pathogenic bacteria was restricted with PstI (A), HindIII or EcoRV (B) and subjected to Southern hybridisation analysis, using a 2.2 kb PstI/HindIII fragment from λ clone 7 as a probe (probe B FIG. 2). The filters were hybridised and washed under stringent (A) or non-stringent (B) conditions.

VGC2 is conserved among and is specific to the Salmonellae. A 2.2 kb PstI/HindIII fragment located at the centre of VGC2 (probe B, FIG. 8) lacking sequence similarity to entries in the DNA and protein databases was used as a probe in Southern hybridisation analysis of genomic DNA from Salmonella serovars and other pathogenic bacteria (FIG. 10A). DNA fragments hybridising under non-stringent conditions showed that VGC2 is present in *S. aberdeen, S. gallinarum, S. cubana, S. typhi* and is absent from EPEC, EHEC, *Y. pestis, S. flexneri, V. cholera* and *S. aureus*. Thus VGC2 is conserved among and is likely to be specific to the Salmonellae.

Figure 10B:
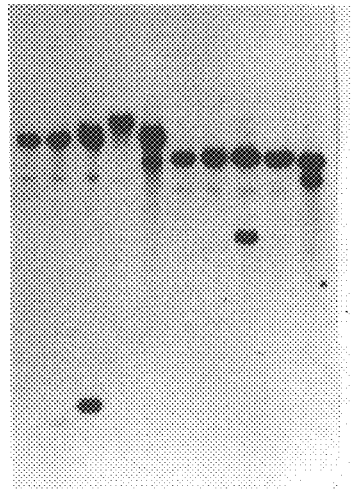

To determine if the organisation of the locus is conserved among the Salmonella serovars tested, stringent Southern hybridisations with genomic DNA digested with two further restriction enzymes were carried out. Hybridising DNA fragments showed that there is some heterogeneity in the arrangement of restriction sites between *S. typhimurium* LT2 and *S. gallinarum, S. cubana* and *S. typhi* (FIG. 10B). Furthermore, *S. gallinarum* and *S. typhi* contain additional hybridising fragments to those present in the other Salmonellae examined, suggesting that regions of VGC2 have been duplicated in these species.

VGC2 is required for virulence in mice. Previous experiments showed that the $LD_{50}$ values for i.p. inoculation of transposon mutants P3F4, P7G2, P9B7 and P11C3 were at least 100-fold greater than the wild type strain (5). In order to clarify the importance of VGC2 in the process of infection, the p.o. and i.p. $LD_{50}$ values for mutants P3F4 and P9B7 were determined (Table 1). Both mutants showed a reduction in virulence of at least five orders of magnitude by either route of inoculation in comparison with the parental strain. This profound attenuation of virulence by both routes of inoculation demonstrates that VGC2 is required for events in the infective process after epithelial cell penetration in BALB/c mice.

TABLE 1

$LD_{50}$ values of *S. typhimurium* strains.

| Strain | $LD_{50}$ (cfu) | |
|---|---|---|
| | i.p. | p.o. |
| 12023 wild type | 4.2 | $6.2 \times 10^4$ |
| P3F4 | $1.5 \times 10^6$ | $>5 \times 10^9$ |
| P9B7 | $>1.5 \times 10^6$ | $>5 \times 10^9$ | cfu, colony forming units

Discussion

A hitherto unknown virulence locus in *S. typhimurium* of approximately 40 kb located at minute 30.7 on the chromosome by mapping the insertion points of a group of signature-tagged transposon mutants with attenuated virulence has been identified (5). This locus is referred to as virulence gene cluster 2 (VGC2) to distinguish it from the inv/spa virulence genes at 63 minutes (edition VIII, ref. 22) which we suggest be renamed VGC1. VGC1 and VGC2 both encode components of type III secretion systems. However, these secretion systems-are functionally distinct.

Of 19 mutants that arose from insertions into new genes (ref. 5 and this example) 16 mapped to the same region of the chromosome. It is possible that mini-Tn5 insertion occurs preferentially in VGC2. Alternatively, as the negative selection used to identify mutants with attenuated virulence (5) was very stringent (reflected by the high $LD_{50}$ values for VGC2 mutants) it is possible that, among the previously unknown genes, only mutations in those of VGC2 result in a degree of attenuation sufficient to be recovered in the screen. The failure of previous searches for *S. typhimurium* virulence determinants to identify VGC2 might stem from reliance on cell culture assays rather than a live animal model of infection. A previous study which identified regions of the *S. typhimurium* LT2 chromosome unique to Salmonellae (40) located one such region (RF333) to minutes 30.5–32. Therefore, RF333 may correspond to VGC2, although it was not known that RF333 was involved in virulence determination.

Comparisons with the type III secretion systems encoded by the virulence plasmids of Yersinia and Shigella as well as with VGC1 of Salmonella indicates that VGC2 encodes the basic structural components of the secretory apparatus. Furthermore, the order of ORFs 1–8 in VGC2 is the same as the gene order in homologues in Yersinia, Shigella and VGC 1 of *S. typhimurium*. The fact that the organisation and structure of the VGC2 secretion system is no more closely related to VGC1 than to the corresponding genes of Yersinia, together with the low G+C content of VGC2 suggests that VGC2, like VGC1 (40, 41, 42) was acquired independently by *S. typhimurium* via horizontal transmission. The proteins encoded by ORFs 12 and 13 show strong similarity to bacterial two component regulators (39) and could regulate either ORFs 1–11 and/or the secreted proteins of this system.

Many genes in VGC1 have been-shown to be important for entry of *S. typhimurium* into epithelial cells. This process requires bacterial contact (2) and results in cytoskeletal rearrangements leading to localised membrane ruffling (43, 44). The role of VGC1 and its restriction to this stage of the infection is reflected in the approximately 50-fold attenuation of virulence in BALB/c mice inoculated p.o. with VGC1 mutants and by the fact that VGC1 mutants show no loss of virulence when administered i.p. (8). The second observation also explains why no VGC1 mutants were obtained in our screen (5). In contrast, mutants in VGC2 are profoundly attenuated following both p.o. and i.p. inoculation. This shows that, unlike VGC1, VGC2 is required for virulence in mice after epithelial cell penetration, but these findings do not exclude a role for VGC1 in this early stage of infection.

Thus in summary mapping the insertion points of 16 signature-tagged transposon mutants on the *Salmonella typhimurium* chromosome led to the identification of a 40 kb virulence gene cluster at minute 30.7. This locus is conserved among all other Salmonella species examined, but not present in a variety of other pathogenic bacteria or in *Escherichia coli* K12. Nucleotide sequencing of a portion of this locus revealed 11 open reading frames whose predicted proteins encode components of a type III secretion system. To distinguish between this and the type III secretion system encoded by the inv/spa invasion locus we refer to the inv/spa locus as virulence gene cluster 1 (VGC1) and the new locus as VGC2. VGC2 has a lower G+C content than that of the Salmonella genome and is flanked by genes whose products share greater than 90% identity with those of the *E. coli* ydhE and pykF genes. Thus VGC2 was probably acquired horizontally by insertion into a region corresponding to that between the ydhE and pykF genes of *E. coil*. Virulence studies of VGC2 mutants have shown them to be attenuated by at least five orders of magnitude compared with the wild type strain following oral or intraperitoneal inoculation.

REFERENCE FOR THIS EXAMPLE

1. Carter, P. B. & Collins, F. M. (1974) *J. Exp. Med.* 139, 1189–1203.
2. Takeuchi, A. (1967) *Am. J. Pathol.* 50, 109–136.
3. Finlay, B. B. (1994) *Curr. Top. Microbiol. Immunol.* 192, 163–185.
4. Groisman, E. A. & Ochman, H. (1994) *Trends Microbiol.* 2, 289–293.
5. Hensel, M., Shea, J. E., Gleeson, C., Jones, M. D., Dalton, E. & Holden, D. W. (1995) *Science* 269, 400–403.
6. Salmond, G. P. C. & Reeves, P. J. (1993) *Trends Biochem. Sci.* 18, 7–12.
7. Van Gijsegem, F., Genin., S. & Boucher, C. (1993) *Trends Microbiol.* 1, 175–180.
8. Galan, J. E. & Curtiss, R. (1989) *Proc. Natl. Acad. Sci. U.S.A.* 86, 6383–6387.
9. Groisman, E. A. & Ochman, H. (1993) *EMBO J.* 12, 3779–3787.
10. Ginocchio, C. C., Olmsted, S. B., Wells, C. L. & Galan, J. E. (1994) *Cell* 76, 717–724.
11. de Lorenzo, V. & Timmis, K. N. (1994) *Methods Enzymol.* 264, 386–405.
12. Davis, R. H., Botstein, D. & Roth, J. R. (1980) *Advanced Bacterial Genetics*, Cold Spring Harbor Laboratory, Cold Spring Harbor, N.Y.
13. Ausubel, F. M., Brent, R., Kingston, R. E., Moore, D. D., Seidman, J. G., Smith, J. A. and Struhl, K. (1987) *Current Protocols in Molecular Biology* Vol 4 John Wiley and Sons, Inc, New York.
14. Maurer, R., Osmond, B. C., Shekhtman, E., Wong, A. & Botstein, D. (1984) *Genetics* 108, 1–23.
15. Youderain, P., Sugiono, P., Brewer, K. L., Higgins, N. P. & Elliott, T. (1988) *Genetics* 118, 581–592.
16. Benson, N. R. & Goldman, B. S. (1992) *J. Bacteriol.* 174, 1673–1681.
17. Holden, D. W., Kronstad, J. W. & Leong, S. (1989) *EMBO J.* 8, 1927–1934.
18. Sambrook, J., Fritsch, E. F. & Maniatis, T. (1989) *Molecular cloning: a laboratory manual* (Cold Spring Harbor Laboratory, Cold Spring Harbor, N.Y.).
19. Sanger, F., Nicklen, S. & Coulson, A. R. (1977) *Proc. Natl. Acad. Sci. U.S.A.* 74, 5463–5467.
20. Devereux, J., Hearberli, P. & Smithies, O. (1984) *Nucl. Acids Res.* 12, 387–399.
21. Reed, L. J. & Muench, H. (1938) *Am. J. Hyg.* 27, 493–497.
22. Sanderson, K. E., Hessel, A. & Rudd, K. E. (1995) *Microbiol. Rev.* 59, 241–303.
23. Galan, J. E., Ginocchio, C. & Costeas, P. (1992) *J. Bacteriol.* 174, 4338–4349.
24. Ginocchio, C., Pace, J. & Galan, J. E. (1992) *Proc. Natl. Acad. Sci. U.S.A.* 89, 5976–5980.
25. Eichelberg, K., Ginocchio, C. C. & Galan, J. E. (1994) *J. Bacteriol.* 176, 4501–4510.
26. Collazo, C. M., Zierler, M. K. & Galan, J. E. (1995) *Mol. Microbiol.* 15, 25–38.
27. Ohara, O., Dorit, R. L. & Gilbert, W. (1989) *Proc. Natl. Acad. Sci. USA* 86, 6883–6887.
28. Bachman, B. (1990) *Micro. Rev.* 54, 130–197.
29. Liu, S. L., Hessel, A. & Sanderson, K. E. (1993) *J. Bacteriol.* 175, 4104–4120.
30. Fasman, G. D. (1976) *CRC HandBook of Biochemistry and Molecular Biology*, CRC Press, Cleveland.
31. Bergman, T., Erickson, K., Galyov, E., Persson, C. & Wolf Watz, H. (1994) *J. Bacteriol.* 176, 2619–2626.
32. Andrews, G. P. & Maurelli, A. T. (1992) *Infect. Immun.* 60, 3287–3295.
33. Allaoui, A., Sansonetti, P. J. & Parsot, C. (1993) *Mol. Microbiol.* 7, 59–68.
34. Venkatesan, M., Buysse, J. M. & Oaks, E. V. (1992) *J. Bacteriol.* 174, 1990–2001.
35. Sasakawa, C., Komatsu, K., Tobe, T., Suzuki, T. & Yoshikawa, M. (1993) *J. Bacteriol.* 175, 2334–2346.
36. Plano, G. V., Barve, S. S. & Straley, S. C. (1991) *J. Bacteriol.* 173, 7293–7303.
37. Michiels, T., Vanooteghem, J. C., Lambert de Rouvroit, C., China, B., Gustin, A., Boudry, P. & Cornelis, G. R. (1991) *J. Bacteriol.* 173, 4994–5009.
38. Kaniga, K., Bossio, J. C. & Galan, J. E. (1994) *Mol. Microbiol.* 13, 555–568.
39. Ronson, C. W., Nixon, B. T. & Ausubel, F. M. (1987) *Cell* 49, 579–581.
40. Groisman, E. A., Sturmoski, M. A., Solomon, F. R., Lin, R. & Ochman, H. (1993) *Proc. Natl. Acad. Sci. U.S.A.* 90, 1033–1037.
41. Altmeyer, R. M., McNern, J. K., Bossio, J. C., Rosenshine, I., Finlay, B. B. & Galan, J. E. (1993) *Mol. Microbiol.* 7, 89–98.
42. Li, J., Ochman, H., Groisman, E. A., Boyd, E. F., Soloman, F., Nelson, K. & Selander, R. K. (1995) *Proc. Natl. Acad. Sci. USA* 92, 7252–7256.
43. Finlay, B. B. & Rauschkowski, S. (1991) *J. Cell Sci.* 99, 283–296.
44. Francis, C. L., Starnbach, M. N. & Falkow, S. (1992) *Mol. Microbiol.* 6, 3077–3087.

EXAMPLE 5

Identification of Virulence Genes in *Streptococcus pneumoniae*

(a) Mutagenesis

In the absence of a convenient transposon system, the most efficient way of creating tagged mutants of *Strepto-* coccus pneumoniae is to use insertion-duplication mutagenesis (Morrison et al (1984) *J. Bacteriol.* 159, 870). Random *S. pneumoniae* DNA fragments of 200–400 bp will be generated by genomic DNA digestion with a restriction enzyme or by physical shearing by sonication followed by gel fractionation and DNA end-repair using T4 DNA polymerase. The fragments are ligated into plasmid pJDC9 (Pearce et al.(1993) *Mol. Microbiol.* 9, 1037 which carries the erm gene for erythromycin selection in *E.coli* and *S. pneumoniae*), previously modified by incorporation of DNA sequence tags into one of the polylinker cloning sites. The size of cloned *S. pneumoniae* DNA is sufficient to ensure homologous recombination, and reduces the possibility of generating an unrepresentative library in *E. coli* (expression of *S. pneumoniae* proteins can be toxic to *E.coli*). Alternative vectors carrying different selectable markers are available and can be used in place of pJDC9. Tagged plasmids carrying DNA fragments are introduced to an appropriate *S. pneumoniae* strain selected on the basis of serotype and virulence in a murine model of pneumococcal pneumonia. Regulation of competence for genetic transformation in *S. pneumoniae* is governed by competence factor, a peptide of 17 amino acids which has been characterized recently by Don Morrison's group at the University of Illinois at Chicago and which is described Havarstein, Coomaraswamy and Morrison (1995) *Proc. Natl. Acad. Sci. USA* 92, 11140–11144. Incorporation of minute quantities of this peptide in transformation experiments leads to very efficient transformation frequencies in some encapsulated clinical isolates of *S. pneumoniae*. This overcomes a major hurdle in pneumococcal molecular genetics and the availability of the peptide greatly facilitates the construction of *S. pneumoniae* mutant banks and allows flexibility in choosing the strain(s) to be mutated. A proportion of transformants are analysed to verify homologous integration of the plasmid sequences, and checked for stability. The very low level of reversion associated with mutants generated by insertion-duplication is minimized by the fact that the duplicated regions will be short (200–400 bp); however if the level of reversion is unacceptably high, antibiotic selection is maintained during growth of the transformants in culture and during growth in the animal.

(b) Animal Model

The *S. pneumoniae* mutant bank is organized into pools for inoculation into Swiss and/or C57B1/6 mice. Preliminary experiments are conducted to determine the optimum complexity of the pools and the optimum inoculum level. One attractive model utilises inocula of $10^5$ cfu, delivered by mouth to the trachea (Veber et al (1993) *J. Antimicrobial Chemotherapy* 32, 473). Swiss mice develop acute pneumonia within 34 days, and C57B1/6 mice develop subacute pneumonia within 8–10 days. These pulmonary models of infection yield $10^8$ cfu/lung (Veber et al (1993) *J. Antimicrobial Chemotherapy* 32, 473) at the time of death. If required, mice are also injected intraperitoneally for the identification of genes required for bloodstream infection (Sullivan et al (1993) *Antimicrobial Agents and Chemotherapy* 37, 234).

(c) Virulence Gene Identification

Once the parameters of the infection model are optimized, a mutant bank consisting of several thousand strains is subjected to virulence tests. Mutants with attenuated virulence are identified by hybridisation analysis, using labelled tags from the 'input' and 'recovered' pools as probes. If *S. pneumoniae* DNA cannot be colony blotted easily, chromosomal DNA is liberated chemically or enzymatically in the wells of microtitre dishes prior to transfer onto nylon membranes using a dot-blot apparatus. DNA flanking the integrated plasmid is cloned by plasmid rescue in *E.coli* (Morrison et al (1984) *J. Bacteriol.* 159, 870), and sequenced. Genomic DNA libraries are constructed in appropriate vectors maintained in either *E. coli* or a Gram-positive host strain, and are probed with restriction fragments flanking the integrated plasmid to isolate cloned virulence genes which is then fully sequenced and subjected to detailed functional analysis.

EXAMPLE 6

Identification of Virulence Genes in *Enterococcus faecalis*

(a) Mutagenesis

Mutagenesis of *E. faecalis* is accomplished using plasmid pAT112 or a derivative, developed for this purpose. pAT112 carries genes for selection in both Gram-negative and Gram-positive bacteria, and the att site of Tn1545. It therefore requires the presence in the host strain of the integrase for transposition, and stable, single copy insertions are obtained if the host does not contain an excisionase gene (Trieu-Cuot et al (1991) *Gene* 106, 21). Recovery of DNA flanking the integrated plasmid is accomplished by restriction digestion of genomic DNA, intramolecular ligation and transformation of *E. coli*. The presence of single sites for restriction enzymes in pAT112 and its derivatives will (Trieu-Cuot et al (1991) *Gene* 106, 21) allows the incorporation of DNA sequence tags prior to transfer to a virulent strain of *E. faecalis* carrying plasmid pAT145 (to provide the integrase function) by either conjugation, electroporation or transformation (Trieu-Cuot et al (1991) *Gene* 106, 21; Wirth et al (1986) *J. Bacteriol.* 165, 831).

(b) Animal Model

A large number of insertion mutants are analysed for random integration of the plasmid by isolating DNA from transcipients, restriction enzyme digestion and Southern hybridisation. Individual mutants are stored in the wells of microtitre dishes, and complexity and size of pooled inocula are optimised prior to screening of the mutant bank. Two different models of infection caused by *E. faecalis* are employed. The first is a well established rat model of endocarditis, involving tail vein injection of up to $10^8$ cfu of *E. faecalis* into animals that have a catheter inserted across the aortic valve (Whitman et al (1993) *Antimicrobial Agents and Chemotherapy* 37, 1069). Animals are sacrificed at various times after inoculation, and bacterial vegetations on the aortic valve are excised, homogenized and plated to culture medium to recover bacterial colonies. Virulent bacteria are also recovered from the blood at various times after inoculation. The second model is of peritonitis in mice, following intraperitoneal injection of up to $10^9$ cfu of *E. faecalis* (Chenoweth et al (1990) *Antimicrobial Agents and Chemotherapy* 34, 1800). As with the *S. pneumoniae* model, preliminary experiments are done to establish the optimum complexity of the pools and the optimum inoculum level, prior to screening the mutant bank.

(c) Virulence Gene Identification

Isolation of DNA flanking the site of integration of pAT112 using its *E.coli* origin of replication is simplified by the lack of sites for most of the commonly used 6 bp recognition restriction enzymes in the vector. Therefore DNA from the strains of interest are digested with one of these enzymes, self-ligated, transformed into *E.coli* and sequenced using primers based on the sequences adjacent to the att sites on the plasmid. A genomic DNA library of *E. faecalis* are probed with sequences of interest to identify intact copies of virulence genes which are then sequenced.

EXAMPLE 7

Identification of Virulence Genes in *Pseudomonas aeruginosa*

(a) Mutagenesis

Since transposon Tn5 has been used by others to mutagenise *Pseudomonas aeruginosa*, and the mini-Tn5 derivative that was used for the identification of *Salmonella typhimurium* virulence genes (Example 1) is reported to have broad utilisation among Gram-negative bacteria, including several pseudomonads (DeLorenzo and Timaris (1994) *Methods Enzymol.* 264, 386), a *P. aeruginosa* mutant bank is constructed using our existing pool of signature tagged mini-Tn5 transposons by conjugal transfer of the suicide vector to one or more virulent (and possibly mucoid) recipient strains. This approach represents a significant time saving. Other derivatives of Tn5 designed specifically for *P. aeruginosa* mutagenesis (Rella et al (1985) *Gene* 33, 293), may alternatively be employed with the mini Tn5 transposon.

(b) Animal Model and Virulence Gene Identification

The bank of *P. aeruginosa* insertion mutants is screened for attenuated virulence in a chronic pulmonary infection model in rats. Suspensions of *P. aeruginosa* cells are introduced into a bronchus following tracheotomy, and disease develops over a 30 day period (Woods et al (1982) *Infect. Immun.* 36, 1223). Bacteria are recovered by plating lung homogenates to laboratory medium and sequence tags from these are used to probe DNA colony blots of bacteria used as the inoculum. It is also possible to subject the mutant bank to virulence tests in a model of endogenous bacteremia (Hirakata et al (1992) *Antimicrobial Agents and Chemotherapy* 36, 1198), and cystic fibrosis (Davidson et al (1995) *Nature Genetics* 9, 351) in mice. Cloning and sequencing of DNA flanking the transposons is done as described in Example 1. Genomic DNA libraries for the isolation and sequencing of intact copies of the genes are constructed in the laboratory by standard methods.

EXAMPLE 8

Identification of Virulence Genes in *Aspergillus fumigatus*

(a) Mutagenesis

The functional equivalent of transposon mutagenesis in fungi is restriction enzyme mediated integration (REMI) of transforming DNA (Schiestl and Petes (1991) *Proc. Natl. Acad. Sci.* 88, 7585). In this process, fungal cells are transformed with DNA fragments carrying a selectable marker in the presence of a restriction enzyme, and single copy integrations occur at different genomic sites, defined by the target sequence of the restriction enzyme. REMI has already been used successfully to isolate virulence genes of Cochliobolus (Lu et al (1994) *Proc. Natl. Acad. Sci. USA* 91, 12649) and Ustilago (Bolker et al (1995) *Mol. Gen. Genet.* 248, 547), and have shown that incorporation of active restriction enzyme with a plasmid encoding hygromycin resistance leads to single and apparently random integration of the linear plasmid into the *A. fumigatus* genome. Sequence tags are introduced into a convenient site in one of two vectors for hygromycin resistance, and used to transform a clinical isolate of *A. fumigatus*.

(b) Animal Model and Virulence Gene Identification

The low-dose model of aspergillosis in neutropenic mice in particular closely matches the course of pulmonary disease in humans (Smith et al (1994) *Infect. Immun.* 62, 5247). Mice are inoculated intranasally with up to 1,000,000 conidiospores/mouse, and virulent fungal mutants are recovered 7–10 days later by using lung homogenates to inoculate liquid medium. Hyphae are collected after a few hours, from which DNA is extracted for amplification and labelling of tags to probe colony blots of DNA from the pool of transformants comprising the inoculum. DNA from the regions flanking the REMI insertion points are cloned by digesting the transformant DNA with a restriction enzyme that cuts outside the REMI vector, self ligation and transformation of *E. coli*. Primers based on the known sequence of the plasmid are used to determine the adjacent *A. fumigatus* DNA sequences. To prove that the insertion of the vector was the cause of the avirulent phenotype, the recovered plasmid is recut with the same restriction enzyme used for cloning, and transformed back into the wild-type *A. fumigatus* parent strain. Transformants that have arisen by homologous recombination are then subjected to virulence tests.

REFERENCES (Other Than for Example 4)

Ausubel, F. M., Brent, R., Kingston, R. E., Moore, D. D., Seidman, J. G., Smith, J. A. and Struhl, K. (1987) *Current Protocols in Molecular Biology*, New York: John Wiley and Sons.

Buchmeier, N. A., Lipps, C. J., So, M. Y. and Heffron, F. (1993) Recombination-deficient mutants of *Salmonella typhimurium* are avirulent and sensitive to the oxidative burst of macrophages. *Mol. Microbiol.* 7, 933–936.

Carter, P. B. and Collins, F. M. (1974) The route of enteric infection in normal mice. *J. Exp. Med.* 139, 1189–1203.

de Lorenzo, V. and Timmis, K. N (1994) Analysis and construction of stable phenotypes in Gram-negative bacteria with Tn5-and Tn10-derived minitransposons. *Methods Enzymol.* 264, 386–405.

de Lorenzo, V., Herrero, M., Jakubzik, U. and Timmis, K. N. (1990) Mini-Tn5 transposon derivatives for insertion mutagenesis, promoter probing, and chromosomal insertion of cloned DNA in gram-negative eubacteria. *J. Bacteriol* 172, 6568–6572.

Fields, P. I., Groisman, E. A. and Heffron, F. (1989) A *Salmonella* locus that controls resistance to microbicidal proteins from phagocytic cells. *Science* 243, 1059–1062.

Finlay, B. B., Starnbach, M. N., Francis, C. L., Stocker, B. A., Chatfield, S., Dougan, G. and Falkow, S. (1988) Identification and characterization of TnphoA mutants of *Salmonella* that are unable to pass through a polarized MDCK epithelial cell monolayer. *Mol. Microbiol.* 2, 757–766.

Groisman, E. A., Chiao, E., Lipps, C. J., Heffron, F. (1989) *Salmonella typhimurium* phoP virulence gene is a transcriptional regulator. *Proc. Natl. Acad. Sci. USA.* 86, 7077–7081.

Groisman, E. A. and Ochman, H. (1994) How to become a pathogen. *Trends Microbiol.* 2, 289–293.

Groisman, E. A. and Saier, M. H., Jr. (1990) Salmonella virulence: new clues to intramacrophage survival. *Trends Biochem. Sci.* 15, 30–33.

Herrero, M., de Lorenzo, V. and Timmis, K. N. (1990) Transposon vectors containing non-antibiotic resistance selection markers for cloning and stable chromosomal insertion of foreign genes in Gram-negative bacteria. *J. Bacteriol.* 172, 6557–6567.

Holden D. W., Kronstad J. W., Leong S. A. (1989) Mutation in a heat-regulated hsp70 gene of *Ustilago maydis. EMBO J.* 8, 1927–1934.

Holland J., Towner K. J., Williams P. (1992) Tn916 insertion mutagenesis in *Escherichia coli* and *Haemophilus influenzae* type b following conjugative transfer. *J. Gen. Microbiol.* 138, 509–515.

Mahan, M. J., Slauch, J. M., Mekalanos, J. J. (1993) Selection of bacterial virulence genes that are specifically induced in host tissues. *Science* 259, 686–688.

Miller, S. I., Kukral, A. M. and Mekalanos, J. J. (1989a) A two-component regulatory system (phoP phoQ) controls *Salmonella typhimurium* virulence. *Proc. Natl. Acad. Sci. USA.* 86, 5054–5058.

Miller, I., Maskell, D., Hormaeche, C., Johnson, K., Pickard, D. and Dougan, G. (1989b) Isolation of orally attenuated *Salmonella typhimurium* following TnphoA mutagenesis. *Infect. Immun.* 57, 2758–2763.

Miller, V. L. and Mekalanos, J. J. (1988) A novel suicide vector and its use in construction of invertion mutations: osmoregulation of outer membrane proteins and virulence determinants in *Vibrio cholerae* requires toxR. *J. Bacteriol.* 170, 2575–2583.

Sambrook, J., Fritsch, E. F. and Maniatis, T. (1989) *Molecular cloning: a laboratory manual*, Cold Spring Harbor, New York: Cold Spring Harbor Laboratory.

Sanger, F., Nicklen, S. and Coulson, A. R. (1977) DNA sequencing with chain terminating inhibitors. *Proc. Natl. Acad. Sci. USA.* 74, 5463–5467.

Schiestl R. H., and Petes T. D. (1991) Integration of DNA fragments by illegitimate recombination in *Saccharomyces cerevisiae*. *Proc. Natl. Acad. Sci USA.* 88, 7585–7589.

```

I claim:

1. A method for identifying a microorganism having a reduced adaptation to a particular environment comprising the steps of:

(a) providing a plurality of mutant microorganisms wherein each mutant has a gene insertionally inactivated with a nucleic acid comprising a unique marker sequence so that each mutant contains a different marker sequence;

(b) providing individually a stored sample of each mutant of step (a) and providing individually stored nucleic acid comprising the unique marker sequence from each individual mutant;

(c) introducing a plurality of the mutants of step (a) into the said particular environment and allowing those microorganisms which are able to do so to grow in the said environment;

(d) retrieving microorganisms from the said environment or a selected part thereof and isolating the nucleic acid from the retrieved microorganisms;

(e) comparing any marker sequences in the nucleic acid isolated in step (d) to the unique marker sequence of each individual mutant stored as in step (b); and (f) selecting an individual mutant which does not contain any of the marker sequences as isolated in step (d), wherein the selected individual mutant has a reduced adaptation to the particular environment.

2. The method of claim 1 wherein the plurality of microorganisms as defined in step (a) is produced from a plurality of microorganisms, each of which comprises a nucleic acid comprising a unique marker sequence, by changing the condition of the microorganisms from a first given condition to a second given condition wherein in the first given condition the nucleic acid comprising a unique marker is maintained episomally and in the second given condition the nucleic acid comprising a unique marker sequence insertionally inactivates a gene.

3. The method of claim 1 further comprising after step (a), removing auxotrophs from the plurality of mutants produced in step (a).

4. The method of claim 1 for identifying a gene which allows a microorganism to adapt to a particular environment, further comprising the step:

(g) isolating the insertionally-inactivated gene from the individual mutant selected in step (f).

5. The method of claim 4 further comprising the step: (h) isolating from a wild-type microorganism the corresponding wild-type gene using the insertionally-inactivated gene isolated in step (g) as a probe.

6. The method of claim 1 wherein the particular environment is a differentiated multicellular organism.

7. The method of claim 6 wherein the multicellular organism is a plant.

8. The method of claim 6 wherein the multicellular organism is a non-human animal.

9. The method claim 8 wherein the animal is selected from the group consisting of a mouse, rat, rabbit, dog and monkey.

10. The method of claim 9 wherein the animal is a mouse.

11. The method of claim 6 wherein in step (d) the microorganisms are retrieved from the said environment at a site remote from the site of introduction in step (c).

12. The method of claim 8 wherein in step (c) the microorganism is introduced orally or intraperitoneally.

13. The method of claim 12 wherein in step (d) the microorganisms are retrieved from the spleen.

14. The method of claim 1 wherein the microorganism is a bacterium.

15. The method of claim 1 wherein the microorganism is a fungus.

16. The method of claim 7 wherein the microorganism is a bacterium pathogenic to plants.

17. The method of claim 7 wherein the microorganism is a fungus pathogenic to plants.

18. The method of claim 8 wherein the microorganism is a bacterium pathogenic to animals.

19. The method of claim 8 wherein the microorganism is a fungus pathogenic to animals.

20. The method of claim 18 wherein the bacterium is selected from the group consisting of *Bordetella pertussis, Campylobacter jejuni, Clostridium botulinum, Escherichia coli, Haemophilus ducreyi, Haemophilus influenzae, Helicobacter pylori, Klebsiella pneumoniae, Legionella pneumophila*, Listeria species, *Neisseria gonorrhoeae, Neisseria meningitidis*, Pseudomonas species, Salmonella species, Shigella species, *Staphylococcus aureus, Streptococcus pyogenes, Streptococcus pneumoniae*, Vibrio species, and *Yersinia pestis.*

21. The method of claim 19 wherein the fungus is selected from the group consisting of Aspergillus species, *Cryptococcus neoformans* and *Histoplasma capsulatum.*

22. The method of claim 1 wherein in step (a) the gene is insertionally inactivated using a transposon or transposon like element or other DNA sequence carrying a unique marker sequence.

23. The method of claim 1 wherein in step (a) each different marker sequence is flanked on either side by sequences common to all of said nucleic acid.

24. The method of claim 23 wherein in step (b) the nucleic acid comprising the unique marker is isolated using DNA amplification techniques and oligonucleotide primers which hybridise to the said common sequences.

25. The method of claim 23 wherein in step (d) the nucleic acid comprising a plurality of said marker sequences is isolated using DNA amplification techniques and oligonucleotide primers which hybridise to the common sequences.

26. The method of claim 1 further comprising after step (f), determining whether the mutant selected in step (f) is an auxotroph.

* * * * *

                         SEQUENCE LISTING (1) GENERAL INFORMATION:

(iii) NUMBER OF SEQUENCES: 501

(2) INFORMATION FOR SEQ ID NO: 1:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Synthetic oligonucleotide (xi) SEQUENCE DESCRIPTION: SEQ ID NO: 1:

CTAGGTACCT ACAACCTCAA GCTTNKNKNK NKNKNKNKNK NKNKNKNKNK NKNKNKNKNK        60

NKNKAAGCTT GGTTAGAATG GGTACCATG                                         89

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Synthetic oligonucleotide (xi) SEQUENCE DESCRIPTION: SEQ ID NO: 2:

TACCTACAAC CTCAAGCT                                                     18

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA
```

(iii) HYPOTHETICAL: NO (iii) ANTI-SENSE: NO (vi) ORIGINAL SOURCE:
            (A) ORGANISM: Synthetic oligonucleotide (xi) SEQUENCE DESCRIPTION: SEQ ID NO: 3:

CATGGTACCC ATTCTAAC                                                  18

(2) INFORMATION FOR SEQ ID NO: 4:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (vi) ORIGINAL SOURCE:
            (A) ORGANISM: Synthetic oligonucleotide (xi) SEQUENCE DESCRIPTION: SEQ ID NO: 4:

TACCCATTCT AACCAAGC                                                  18

(2) INFORMATION FOR SEQ ID NO: 5:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (vi) ORIGINAL SOURCE:
            (A) ORGANISM: Synthetic oligonucleotide (xi) SEQUENCE DESCRIPTION: SEQ ID NO: 5:

CTAGGTACCT ACAACCTC                                                  18

(2) INFORMATION FOR SEQ ID NO: 6:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iii) ANTI-SENSE: NO (vi) ORIGINAL SOURCE:
            (A) ORGANISM: Synthetic oligonucleotide (xi) SEQUENCE DESCRIPTION: SEQ ID NO: 6:

CCTAGGCGGC CAGATCTGAT                                                20

(2) INFORMATION FOR SEQ ID NO: 7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iii) ANTI-SENSE: NO (vi) ORIGINAL SOURCE:
        (A) ORGANISM: Synthetic oligonucleotide (xi) SEQUENCE DESCRIPTION: SEQ ID NO: 7:

GCACTTGTGT ATAAGAGTCA G                                              21

(2) INFORMATION FOR SEQ ID NO: 8:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 8:

GGTCTTAATG TACGGGCATG GTCTGCATCG ATAACTCCGG CACGCAAATC GCCATCGATA     60

CTCATTTGTT TGGCTGGCAT CCCATCAAGC GAGAAACGTG CGCTAACTTC CGCCACCCTC    120

TCGATACCTT TTGTAATGAC AATAAATTGC ACGATAGTAA TGATGGTAAA TACGACCAAC    180

CCAACGGTGA GATTTCCTCC TACGACAAAC TTACCGAAAG CATCCACAAA TATTACCGGC    240

ATTATGTTGT AACAGTACCC AGCCGTGATG TGCTGATTGG GGAGTTAACA ACCGATTTAT    300

(2) INFORMATION FOR SEQ ID NO: 9:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 9:

GCGCGGACGC TAGTGTGGTG GGTGACAGCC AGACGTTACC GAACGGGATG GGGCAGATCT     60

GTTGGCTTAC AAAAGACATG GCCCATAAGG CGCAAGGTTT TGGGACTGGA CGTTTTCGCG    120

GGCAGACAAC GTATCTCTGT CTTATTAAAA TGTGTCCTGC TTCGGCATAT GTATCGAACC    180

CTCGGAGCAA AGTCGTTTGG GCGCAGAATT AGTACGTTTG GGTCGGTTGC TGTTATTCCT    240

```
TGGGCTCGGA AAAAGAGTGC CAGCGTGAAG GAGTGGGATT TGGCAGACTG GCCGCCTAAT    300
```

(2) INFORMATION FOR SEQ ID NO: 10:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 10:

```
CACTATAGGG AAAGCTTGCA TGCCTGCAGG TCGACTCTAG AGGATCTACT AGTCATATGG     60
ATTGCACTTG TGTATAAGAG TCAGGATTAG AGGACATGCG CCGGGAACCA TACTATCTTT    120
TTCCGGTGCT TCGACGCCAT TTGCGGAAAC CACAGACTTT TTGCGGCGAA TGAGGATAAT    180
TGGCAATGCT AACAACGCTG AAAAGAAAGC GAGAGTGATA AAAGGAAAGC CAGGAATTAA    240
AGCGAGGAGC ATTAAAACCA CAGCGGCTAA TATGAGCGAC TGAGGTTGTC TGGCAATTTG    300
```

(2) INFORMATION FOR SEQ ID NO: 11:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 11:

```
TGCAGGCCGA CTCTAGAGGA TCCCCGGGTA CCGGTAATTT CTTTAACCTC GCATCCCGGT     60
GGATGAAAGG ATATTCTGGC TGCGTAAGTA ATGAATGAAC CGCCCAGTAG ATAAAATATT    120
GAAAGTGATA ACCTGATGTT TTAATAACGA TGCAGGATAT ACATATAACA TGCTGGCATC    180
AAACCAGGTA AGCAAATCAT ATTGTGCTGC CAGGTTATTC AAACTATCGA CCGGTGGTCC    240
AGGCGGGAAT TTTTCCACTA AATGTAGGTG GGATCAATGG GCTAATTGGT ATAGGCGGAT    300
```

(2) INFORMATION FOR SEQ ID NO: 12:

(i) SEQUENCE CHARACTERISTICS:
        (A) LENGTH: 324 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:

(A) ORGANISM: Partial sequence of Salmonella typhimurium
    virulence gene (xi) SEQUENCE DESCRIPTION: SEQ ID NO: 12:

| | | | | | |
|---|---|---|---|---|---|
| CCTGTGATTC | CGGATGAAAT | AGCTTTTACG | AAAGCTGTCA | GACNTGCTGA | AGAATACGCT | 60
| GCAAATGGTA | AGCTTGTAAC | TTTTGGGTAT | TGTTCCAACG | CATGCTGAAA | CGGGTTATGG | 120
| ATATATTCGT | CGCGGTGAGT | TGATAGGAAA | TGACGCTTAT | GCAGTGGCTG | AATTTGTGGA | 180
| GAAACCGGAT | ATCGATACCG | CCCGTGACTA | TTTCAAATCA | GGGGAAATAT | TACTGGCCTA | 240
| GCGGCGATGT | TTTTATTTCG | CGCAAAGCCC | TTATTTAAAC | GAATTAAACG | TATCTATCAC | 300
| CCCCAAATTC | ATACAGCTTG | TGAA | | | | 324

(2) INFORMATION FOR SEQ ID NO: 13:

(i) SEQUENCE CHARACTERISTICS:
        (A) LENGTH: 292 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 13:

| | | | | | |
|---|---|---|---|---|---|
| TTACTAAACA | GGGCCCCGGA | CCATGTAAAC | ACCACGCTTG | CCAACACTAA | AAAACGATGC | 60
| TTGCCGTAAA | AAAATTGAAC | GTTATTTACT | TAATACGCCT | ATTTTATTTA | CATTATGCAC | 120
| GGACAGAGGG | TGAGGATTAA | ATGGATAATA | TTGATAATAA | GTATACTCCA | CAGCTATGTA | 180
| AAATTTTGGG | GGCTATATCG | GATTTGGTTG | TTTTTAATTT | AGCCTTATGG | CTTTCACTAG | 240
| GATGTGTCTA | TTTTTTTTGT | GGTCAAGCAC | AGAGATTTAT | TCCCCAACCA | CC | 292

(2) INFORMATION FOR SEQ ID NO: 14:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 14:

| | | | | | |
|---|---|---|---|---|---|
| TTTCCTTGCC | GTGACAGTCC | GGGATGCGAG | GTTAACGAAA | TTACCGGCAC | CAAAGCTGTG | 60
| GAGGTGAGCG | GTGTCCCCAG | CTGCCTGACT | CGTATTAGTC | AATTAGCTTC | AGTGCTGGAT | 120
| AATGCGTTAA | TCAAACGAAA | AGACAGTGCG | GTGAGTGTAA | GTATATACAC | GCTTAAGTAT | 180
| GCCACTGCGA | TGGATACCCA | GTACCATTAT | CGCGATCAGT | CCGTCGTGGT | TCCAGGGGTC | 240
| GCCTAGTGTA | TTGCGTGAGA | TGAGTAACAC | CAGCGTCCCG | ACGTCATCGA | CGAACAATGG | 300

(2) INFORMATION FOR SEQ ID NO: 15:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
           virulence gene (xi) SEQUENCE DESCRIPTION: SEQ ID NO: 15:

```
CATGAGTAAC CTACCCAACT GTAATCTTTA CCAATATGCA TCATAATCTT CTGCTGGTAA      60
ATGATTGGTA ATATCGGAAA GGTAAGTGAC ATAAGCACGC CATTACGTAA AAGTGCGGCC     120
CCTAAACTGC CACTTTTTAA TAAGGGAAGT AATAAAGAAA GGCTCAATGG TCGAATAAAA     180
GCCACAGCCA ATGCAATAAG CCACTCATTT ACCTGTTGTG CCATTCAACC ATGCTCTCCA     240
ATTCGTAACA TTATCTGCCG GGTATAATTC AACAGGATAC CGCTAAGCCA TGGGTAG        297
```

(2) INFORMATION FOR SEQ ID NO: 16:

(i) SEQUENCE CHARACTERISTICS:
        (A) LENGTH: 184 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
           virulence gene (xi) SEQUENCE DESCRIPTION: SEQ ID NO: 16:

```
ATTCCAGCCC CCGGGCCATC TAACCACTAT GAACAATCAT CTTCTGGGTG GACAATCATT      60
GGTACCATCG GCCAGGCTTG TGCAATATGT ATGTCATCAC GTAAAAGCGC GGCCCCTTAA     120
TCTCCCCATT CTTCCTTAAG GGCAGTTATC ACGGCTGGCT CAATGGCCGG CTTAACAGCC     180
ACAG                                                                  184
```

(2) INFORMATION FOR SEQ ID NO: 17:

(i) SEQUENCE CHARACTERISTICS:
        (A) LENGTH: 306 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
           virulence gene (xi) SEQUENCE DESCRIPTION: SEQ ID NO: 17:

```
GAGGCGCGTC TTCGGTTGAG GGTCGCCCTC CAGATCTTTA TGCTCCTGTT TTACGTCATC      60

TTTACTCATT TTAAGATCTT TTCTAATCTT ATAATATTGA AAAGAATAGT CCAGTATGCC     120

AACGACGAAA TAAAGAAACA TCACCCCAAC CCATAACCAT TTTTTCAATG ATGAAAGCAC     180

AAGCACGCCA CAGGCTACAC CACAGCCCGG AGGGGCCGG AAAGTGCTGG GATCTTGATT     240

AATGAAAAAG GCAAAGGGAA GAGATAGGAT GATGCATGCT GGTTGGAGGC AGATTATTCA     300

TCTTCG                                                                306
```

(2) INFORMATION FOR SEQ ID NO: 18:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 18:

```
AGTTGCCGTA TTTATTAAAT ATTCACCTCA GGTCAATATG GAGGTCTTCC CGGCTAAAAA      60

TCATTGCTTT ACTAGAGATA TCACTCCCTG GGTTGCAATA CAGTACGATT AGTTATCTTG     120

ATGCAGCCTG CTGATTTCAG AATGGCAGCT GACGTACCCG CGAGACAAAC ATTCTGGATT     180

ATGGACGTTA TCAACGCCAA TATAGGGAAG GTGGTGAAGT GGTTGATGAA ATACCCCTAT     240

CCCTTGCATG TTATCGCTGA CAGGACTGTT ATCAGGAGCG GGCATCCTCG ATCGGCT        297
```

(2) INFORMATION FOR SEQ ID NO: 19:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 19:

```
CAAGAGACAG ATCCAACTCG GGCCGATCGC CATAACGCCA GCAGTTTGAA AGATGAAAGC      60

CCAGCTTATC CAGCCATTCC GGTACAGCGT AACGAGCAGG TTGCCAGAAA TAACGATAAA     120

GTTGCAACAC CTCGGGATCA GGTCGGCTCA AAAACGGGGT CTCAGGCAAA AATAGCCGAT     180

CAGGATGCCC ACTCCTAATA ACAGTCCTGT CAACGATAAC ATCAACGGAT AAGGGTATTT     240

CATCAACCAC TTCACCACCT TCCCTTTATT GGCGTTGGAT AACGTCCATA ATCCAGA        297
```

(2) INFORMATION FOR SEQ ID NO: 20:

(i) SEQUENCE CHARACTERISTICS:
        (A) LENGTH: 298 base pairs
        (B) TYPE: nucleic acid (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 20:

```
AGGGCTTTAT TGATTCCATT TTTACACTGA TGAATGTTCC GTTGCGCTGC CCGGATTACA      60
GCCGGATCCT CTAGAGTCGA CCTGCAGAAC CGAGCCAGGA GCAAATTAAT TTTTTTGGGC     120
AATTGCTGAA AGATGAAGCA TCCACCAGTA ACGCCAGTGC TTTATTACCG CAGGTTATGT     180
TGACCAGACA AATAGATTAT ATGCAGTTAA CGGTAGGCGT CGATTATCTT GTCAGAATAT     240
CAGGCGCAGC ATCGCAAGCG CTTAATAAGC TGGGTAACAT GGCATGAAGG GGCAACCC       298
```

(2) INFORMATION FOR SEQ ID NO: 21:

(i) SEQUENCE CHARACTERISTICS:
        (A) LENGTH: 298 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 21:

```
CACTATAGGG AAAGCTTGCA TGCCTGCAGG TCGACTCTAG AGGATCTACT AGTCATATGG      60
ATTCCTAGGC GGCCAGATCT GATCAAGAGA CAGATCCAAC TCGGGCCGAT CGCCATAACG     120
CCAGCAGTTT GAAAGATGAA AGCCCAGCTT ATCCAGCCAT TCCGGTACAG CGTAACGAGC     180
AGGTTGCCAG AAATAACGAT AAAGTTGCAA CACCTCGGGA TCAGGTCGGC TCAAAAACGG     240
GGTCTCAGGC AAAAATAGCC GATCAGGATG CCCACTCCTA ATAACAGTCC TGTCAACG       298
```

(2) INFORMATION FOR SEQ ID NO: 22:

(i) SEQUENCE CHARACTERISTICS:
        (A) LENGTH: 301 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 22:

```
CCCCCCCCCT TCTCCTGGCT TACACAGCCC CAGACCGGCG CTGGAAAAGG CCATTCCCGC      60
CATACAGGAG GCCAGCAACA TATTTTCACG CGCCGCCAGA TCGTGGCCGT AACCCACGGC     120
```

```
TTTCGGCAGC GATTTGCCAA TCATCGCTAT CGCGCCAATC GCCAGGCTGT CGGTAAACGG        180

CGTGGCGTTG AGCGCGCTGT AGGCCTCAAT CGCATGCGTC AACGCATCGA TACCGGTCAT        240

CGCCGTCACG TTTGGCGGAA CGCCTTCGGT CACGGAAGCA TCAAGAATCG CCACGTCCGG        300

C                                                                       301
```

(2) INFORMATION FOR SEQ ID NO: 23:

(i) SEQUENCE CHARACTERISTICS:
        (A) LENGTH: 289 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 23:

```
CGCGAACGTG CGCCGCAACT GCTTGTGGAC GGTGAATTGC AGTTTGACGC CGCTTTCGTG         60

CCGGAGGTCG CCGCGCAAAA AGCGCCTGAC AGCCCGCTGC AAGGCCGCGC CAACGTGATG        120

ATTTTCCCGT CGCTGGAGGC GGGCAATATT GGCTACAAAA TCACTCAGCG TCTGGGAGGC        180

TATCGCGCTG TTGGGCCGCT AATTCAGGGG CTTGGCGCGC CGCTTCACGA CCTCTCCCGA        240

GGCTGTAGCG TGCAGGAAAT TATCGAACTG CGGTTGGTGA GAAAACCAA                   289
```

(2) INFORMATION FOR SEQ ID NO: 24:

(i) SEQUENCE CHARACTERISTICS:
        (A) LENGTH: 303 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 24:

```
CGCCCTAGCA TGCCTGGCGT TGTCCGGTTA TTGCTCGTCA AGCGAACAGA TGCAAAAGGT         60

GAGAGCGACT CTCGAATCAT GGGGGGTCAT GTATCGGGAT GGTGTAATCT GTGATGACTT        120

ATTGGTACGA GAAGTGCAGG ATGTTTTGGA TAAAAATGGG TTACCCGCAT GCTGAAGTAT        180

CCAGCGAAGG GCCGGGAGC GTGTTAATTC ATGATGATAT ACAAATGGAT CAGCAATGGC        240

GCAAGGTTCA ACCATTACTT GCAGATATTC CCGGGTTATT GCACTGGCAG ATTAGTCACT        300

CTC                                                                     303
```

(2) INFORMATION FOR SEQ ID NO: 25:

(i) SEQUENCE CHARACTERISTICS:
        (A) LENGTH: 300 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: Partial sequence of Salmonella typhimurium
               virulence gene (xi) SEQUENCE DESCRIPTION: SEQ ID NO: 25:

CCCTTCCCAG GCTCGACAGG TACACAGCCA GCCACTGGTG CAGGCAGTTA CTTGCTTTCA      60

TCATGGGAAG GAGCAATATC CTGATATATT AAAGAAAGAG CGGGATCCCC TTTCTTTACT     120

GCTGCTAACG TTTCTTGCAA AATGCGTTGA TGAGATTCAT CCAGCACACC ACTGATAACA     180

AAAGAGCGCC GCATTGGCGT AACATTGACA AGCCCCACTA AACCGCTCTC TATTATCGCA     240

GAAATAATAT CATCCCCCTG AGACTGATGA GAGTGACTAT TCTGCCAGCG CAAATAACCC     300

(2) INFORMATION FOR SEQ ID NO: 26:

(i) SEQUENCE CHARACTERISTICS:
           (A) LENGTH: 303 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: Partial sequence of Salmonella typhimurium
               virulence gene (xi) SEQUENCE DESCRIPTION: SEQ ID NO: 26:

ATACCGAGTA TTAAGCGGCT GTGTAACATC GTCATCCAAC AACATACGCA GCGAGCCGCC      60

ACGCCGGAAA AACCGCATCG TGTCATGTGC CTGTTGTAGG GTCGGGTCTT TTTTCATGAG     120

TACGTTTTCT GCGCTATCAT ACTGGAAATT TCCCCCCACT TACTGATAAG CCCTGTCAGT     180

TGGGTAAGGA CAGAGTTAAG CTCCTGAGAC ATTTTTTGGA ATGGTTATCT TTCCCCGACT     240

CATAAAATCG GTATTCCCGC TGGGGGCAAT ATCCAAAGAC GCTTTGGTCG CCCGTAGGGC     300

ACC                                                                  303

(2) INFORMATION FOR SEQ ID NO: 27:

(i) SEQUENCE CHARACTERISTICS:
           (A) LENGTH: 300 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iii) ANTI-SENSE: NO (vi) ORIGINAL SOURCE:
           (A) ORGANISM: Partial sequence of Salmonella typhimurium
               virulence gene (xi) SEQUENCE DESCRIPTION: SEQ ID NO: 27:

GCCGTATGCC TGCAGTTGCC CGGTTATTGC TCGTCAAGCG AACCGATGCC AAAGGTGAGA      60

```
GCGACTCTCG AATCATGGGG GGTCATGTAT CGGGATGGTG TAATCTGTGA TGACTTATTG      120

GTACGAGAAG TGCAGGATGT TTTGGTAAAA ATGGGTTACC CCCATGCTGA AGTATCCAGC      180

GAAGGGGCGG GGAGCGTGTT AATTCACGAT GATATTCAAA TGGGTCAGCA ATGGGGCAAG      240

GTTCAACCCC CACTTGCAGA TATTCCCCCC CCTATTGGAC TGGCAGATTA GTCACTCTCA      300

(2) INFORMATION FOR SEQ ID NO: 28:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 28:

GGGCGACCTG CCCGCGGCGC AACTTTCCCC GAAGCGTTTT CCATTTCCTT GTTCTTAAAT       60

GACCTGGAAA GCTTACCTAA GCCTTGTCTT GCCTATGTGA CAATACTGCT TGGAGAACAC      120

CCGGACGTCC ATGATTATGC TATACAGATC ACAGCGGATG GGGGATGGTG AATCGGTTAT      180

TATACCACAA GTCGCAGCTC TGAGCTTATT GCTATTGAGA TAGAAAAACA CCCCGCTTCA      240

ACTTGGATTT TGAATAATGT AATACGCAAT CACCATACAC TATATTCGGG TGGCGTATAA      300

(2) INFORMATION FOR SEQ ID NO: 29:

(i) SEQUENCE CHARACTERISTICS:
        (A) LENGTH: 266 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 29:

TTCGAGCTGG GGCACCGCTA ATATCTTTAA CCTCGCATCC CGGTGATGAA AGGATATTCT       60

GGCTGCGTAA GTAATGAATG AACCGCCCAG CAGATAAAAT ATTGACAGTG ATAACCCGAT      120

GTTTTTTTAA CGATGCAGGC TATACATATA ACATAGCTGG CCACCAACAC AGCTGAAGTA      180

AATCATATTG TTGCTGCCAG GCTACTTCAC ACTATTGTCC GGCGGGCCAG CGGGGATTTT      240

CCCCCTAAAT CTCGCTGGTT CTCAAA                                          266

(2) INFORMATION FOR SEQ ID NO: 30:

(i) SEQUENCE CHARACTERISTICS:
        (A) LENGTH: 300 base pairs
        (B) TYPE: nucleic acid
        (C) STRANDEDNESS: double
        (D) TOPOLOGY: linear (ii) MOLECULE TYPE: DNA (genomic)
```

(iii) HYPOTHETICAL: NO (iii) ANTI-SENSE: NO (vi) ORIGINAL SOURCE:
              (A) ORGANISM: Partial sequence of Salmonella typhimurium
                  virulence gene (xi) SEQUENCE DESCRIPTION: SEQ ID NO: 30:

AGTCTACGAT TTCGCTATAT CTTCTCTTAA TCATGGCCGC CATTTGTGGA TGCGATTTTA     60

AAATATCCGG GCGATCTTTC ATTAAAAAAT AAAGATTCCC CATGACTTCA CAGATAAAGG    120

TATCGGTATT TTGAGTGATA CGTAACAATT CGTTCTCTTC GTGTGGGTCC ATGATGCGAA    180

GAATAATGGT GGCATCATTT TCATGAGGAT TATGAACCCG AAATCTTTCT CTTTGCGATG    240

CGCAGGCTAA CTCTTTCAAC TCAAAAAAAA TCTCTGTAAG CCGCTCTCGT GTGGGGCGC    300

(2) INFORMATION FOR SEQ ID NO: 31:

(i) SEQUENCE CHARACTERISTICS:
              (A) LENGTH: 299 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iii) ANTI-SENSE: NO (vi) ORIGINAL SOURCE:
              (A) ORGANISM: Partial sequence of Salmonella typhimurium
                  virulence gene (xi) SEQUENCE DESCRIPTION: SEQ ID NO: 31:

GCGCCCCTTT AATTGGTTGA GGCGGCTGGT ATTCTTGTAA GGGTAATACT AGCGAGACCC     60

AGGTTCCACC CCCGGGGACA CTTTTTAGTG TCAGATTACC GCCCATCATT TTAGCCAGGC    120

TTGACGCAAT AGTCAGTCCA ATTCCTGTAC CTTGCGAATT TGTGTCTGCT TGATAAAAAG    180

CAGAAAAGAT TTGAGACTGC TGCTGTTTTT CAATCCCCCC ACCGCTATCG CTAACCAGAA    240

ATATTAATTG TTCCTCACCA AGATTGAGCG CCAGACGTAT CCCTCCCCCC TCGGGAAAT    299

(2) INFORMATION FOR SEQ ID NO: 32:

(i) SEQUENCE CHARACTERISTICS:
              (A) LENGTH: 300 base pairs
              (B) TYPE: nucleic acid
              (C) STRANDEDNESS: double
              (D) TOPOLOGY: linear (ii) MOLECULE TYPE: DNA (genomic)

(iii) HYPOTHETICAL: NO (iii) ANTI-SENSE: NO (vi) ORIGINAL SOURCE:
              (A) ORGANISM: Partial sequence of Salmonella typhimurium
                  virulence gene (xi) SEQUENCE DESCRIPTION: SEQ ID NO: 32:

GGATAAGATC CCGGATAAGT ATGTCAGGCT CGTATGCACA ACAGGCATTA TAAACCTCTA     60

GACCATTTTT AACATGCTCT ACTATTTTAA AATGAGGCCA GGGTAATAAG GCATTCATAA    120

TGCCGTTAAT GATGATTTCA TGATCGTCTA CTAATAAGAT CTTATATTCT TTCATTTGGC    180

TGCCCTCGCG AAAATTAAGA TAATATTAAG TAATGGTGTA GGTTGTGGAG ATCATACGTA    240

TTTTCTGGCG TAAGTCGGTT AGTTCCTCCA GCGCGATGAT TTTCCCCATT TTTACGCGAT      300

(2) INFORMATION FOR SEQ ID NO: 33:

(i) SEQUENCE CHARACTERISTICS:
        (A) LENGTH: 278 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 33:

TTCCATATTG CTCGTCCGGG GAGCGTGTTA ATTCTTGATG ATATACCAAT GGATCTGCAA       60

TGGCGCAAGG TTCAACCATT ACTTGGAGAT ATTCCCGGGT TATTGTACTG GGAGATTAGT      120

CACTCTCATC AGTCTCAGGG GGGTGATGTT ATTTCTGGGA TAATAGAGCA ACGGCGTTAG      180

CAGGGGTCGG TCAGTAGTCA CGGCCAACTT CGGTGCACTT TTGCGTATCA CTGGGGTATC      240

ATAACTGAAT CTCATCCCCC CCACTTTGGT AATCACAC                              278

(2) INFORMATION FOR SEQ ID NO: 34:

(i) SEQUENCE CHARACTERISTICS:
        (A) LENGTH: 301 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Partial sequence of Salmonella typhimurium
            virulence gene (xi) SEQUENCE DESCRIPTION: SEQ ID NO: 34:

AATTCTTTTA CCTCCATAAG CTGCGTGGCA TAGCGATACA GAGTATTAAG CGGGTGTGTT       60

ACATCGTCAT CCAACAACAT ACGCAGCGAG CCGCCACGCC GGAAAAACCG CATCGTGTCA      120

TGTGCCTGTT GTAGGGTCGG GTCTTTTTTT CATGAGTACG TGTTCTGCGC TATCATACTG      180

GAAATTTCCC CCCACTTACT GATAAGCCCT GTCAGTTGGG TAAGGACAGC GTTAAGCTCC      240

TGAGACATTT TTTGAGTTGT TATCTGCCCC CCGACTCATA AGATCGGGTA TTCCGCGGTG      300

G                                                                     301

(2) INFORMATION FOR SEQ ID NO: 35:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Partial sequence of Salmonella typhimurium
                virulence gene (xi) SEQUENCE DESCRIPTION: SEQ ID NO: 35:

ATATCCCTAA TGCTTTTCCT TAAAATAAAT ACCACGGAAG GATACTGGCC ACCTAGCCAA      60

ATTTAGAAAG CAATGAACAT CCGGTTTATT CCTGAAAACG ATTACTCCGG CGCACGTTGT     120

TCTGGCGTTA CCTGAGCCAG CAAACGATAT AATGGGGTGG TGACCCGCAT ACCGGTCATT     180

GGCATCCCAT CCACACCGGA GGGAGTAAAA CTCATTAGGC CATAGGTAAT ATCATTAAGA     240

CGCTCTAATA AATGAGGGTG GGGGGCCCAA ACTACCACTC CAGTATGTAT TGAGTCA       297

(2) INFORMATION FOR SEQ ID NO: 36:

(i) SEQUENCE CHARACTERISTICS:
            (A) LENGTH: 291 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: Partial sequence of Salmonella typhimurium
                virulence gene (xi) SEQUENCE DESCRIPTION: SEQ ID NO: 36:

CCCATGGGCG CAATTTGTTG CGCAGCGTTT ACCCGACCAT CGCGTTTATG AGCTGTAATT      60

CATGGGGGGT AAAAACGGGC GTGACGACCC CAACGGAAGA TAAGGCCGGG CTTAAACAGG     120

AGATTATTGC TAATGCGCAG CGCAAAGTGT TGCTGGCGGA CAGCAGTAAG TATGGCGCGC     180

ATTCGCTCTT TAATGTGGTG CCGCTTGAGC GCTTTAATGA CGTGATTACC GACGTCAATC     240

TGCCGCCGTC AGCGCAGGTT GAACTGAAAG GGCGCGCTTT TTGCGCTAAC G             291

(2) INFORMATION FOR SEQ ID NO: 37:

(i) SEQUENCE CHARACTERISTICS:
            (A) LENGTH: 13417 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iii) ANTI-SENSE: NO (vi) ORIGINAL SOURCE:
            (A) ORGANISM: DNA sequence of VGC II from centre to left
                hand end (xi) SEQUENCE DESCRIPTION: SEQ ID NO: 37:

CTGCAGAACC GAGCCAGGAG CAAATTAATT TTTTTGAACA ATTGCTGAAA GATGAAGCAT      60

CCACCAGTAA CGCCAGTGCT TTATTACCGC AGGTTATGTT GACCAGACAA ATGGATTATA    120

TGCAGTTAAC GGTAGGCGTC GATTATCTTG CCAGAATATC ACGGCGCAGC ATGCCAAGCG    180

CTTAATAAGC TGGATAACAT GGCATGAAGG TTCATCGTAT AGTATTTCTT ACTGTCCTTA    240

CGTTCTTTCT TACGGCATGT GATGTGGATC TTTATCGCTC ATTGCCAGAA GATGAAGCGA    300

-continued

| | |
|---|---|
| ATCAAATGCT GGCATTACTT ATGCAGCATC ATATTGATGC GAAAAAAAAC AGGAAGAGGA | 360 |
| TGGTGTAACC TTACGTGTCG AGCAGTCGGC AGTTTATTAA TGCGGTTGAG GCTACTTAGA | 420 |
| CTTAACGGTT ATCCGCATAG GGCAGTTTAC AACGGCGGAT AAGATGTTTC CGGCTAATCA | 480 |
| GTTAGTGGTA TCACCCCAGG AAGAACAGGC AGAAGATTAA TTTTTTAAAA GAACAAAGAA | 540 |
| TTGAAGGAAT GCTGAGTCAG ATGGAGGGGC GTGATTAATG GCAAAAGTGA CCATTGCGCT | 600 |
| ACCGACTTAT GATGAGGGAA GTAACGCTTC TCCGAGCTCA GTTGCCGTAT TTATAAAATA | 660 |
| TTCACCTCAG GTCAATATGG AGGCCTTTCG GGTAAAAATT AAAGATTTAA TAGAGATGTC | 720 |
| AATCCCTGGG TTGCAATACA GTAAGATTAG TATCTTGATG CAGCCTGCTG AATTCAGAAT | 780 |
| GGTAGCTGAC GTACCCGCGA GACAAACATT CTGGATTATG GACGTTATCA ACGCCAATAA | 840 |
| AGGGAAGGTG GTGAAGTGGT TGATGAAATA CCCTTATCCG TTGATGTTAT CGTTGACAGG | 900 |
| ACTGTTATTA GGAGTGGGCA TCCTGATCGG CTATTTTTGC CTGAGACGCC GTTTTTGAGC | 960 |
| CGACCTGATC CCGAGGTGTT GCAACTTTAT CGTTATTTCT GGCAACCTGC TCGTTACGCT | 1020 |
| GTACCGGAAT GGCTGGATAA GCTGGGCTTT CATCTTCAAA CTGCTGGCGT TATGGCGATC | 1080 |
| GGCCCGAGTT GGATCGTCTT CTTGACAGAG CGTTAAATAG ACTAAGAGGA AGCTCTGTTA | 1140 |
| TTCCAGCCTG TTTAAATGAC AGGCAAAAAC GGCAGGTTCG TCTTGCGCCG CGTATATCGG | 1200 |
| CATTTGCCTT TGGGCTGGGA TTATTCAAAC TCAGGTGTAG TGACTATTTT ATGCTACCAG | 1260 |
| AGTATCGGCA ATTGCTTCTA CAGTGGTTTA GCGAGGATGA GATCTGGCAG CTATATGGTT | 1320 |
| GGTTGGGGCA AAGAGATGGC AAATTACTTC CTCCGCAAGT GATGCAACAA ACTGCATTGC | 1380 |
| AGATCGGTAC CGCCATTCTT AATCGGGAAG CGCATGACGA TGCGGGTTTT ACATGCGCTA | 1440 |
| TTAGTATTAT TACCCCCTCC GCAGCGTATA CTTTGGCCGA AGACTTCTCT TACCGAGATT | 1500 |
| ATCTTCATGG AGCATTTGCT ATGAGTTTTA CTTCACTTCC TCTGACGGAA ATTAACCATA | 1560 |
| AGCTACCCGC TCGAAATATT ATTGAGTCAC AGTGGATAAA ATTACAATTA ACTTTATTTG | 1620 |
| CGCAAGAGCA ACAAGCTAAG AGAGTTTCAC ATGCTATTGT GAGCTCCGCT TACCGTAAGG | 1680 |
| CTGAAAAAAT CATCCGAGAC GCCTATCGTT ATCAGCGTGA ACAGAAAGTT GAGCAGCAAC | 1740 |
| AAGAACTAGC GTGCTTGCGT AAAAATACGC TGGAAAAAAT GGAAGTGGAA TGGCTGGAAC | 1800 |
| AGCATGTAAA ACATTTACAA GACGATGAAA ATCAATTTCG TTCATTGGTC GATCACGCAG | 1860 |
| CGCATCATAT TAAAAATAGT ATAGAACAGG TTCTGTTGGC CTGGTTCGAC CAACAGTCGG | 1920 |
| TAGACAGTGT TATGTGCCAT CGTCTGGCAC GCCAGGCCAC GGCTATGCGC GAAGAGGGAG | 1980 |
| CGCTTTATTT GCGTATTCAT CCTGAAAAAG AGGCATTGAT GCGAGAAACT TTTGGCAAGC | 2040 |
| GGTTTACGTT GATTATCGAG CCTGGTTTCT CTCCCGATCA GGCTGAACTT TCCTCAACAC | 2100 |
| GATATGCCGT TGAATTTTCA CTTTCTCGTC ATTTCAACGC GTTACTGAAA TGGTTACGTA | 2160 |
| ATGGTGAAGA TAAAGAGGT AGCGATGAAT ATTAAAATTA ATGAGATAAA AATGACGCCC | 2220 |
| CCTACAGCAT TTACCCCTGG CCAGGTTATA GAGGAACAAG AGGTTATTTC GCCTTCAATG | 2280 |
| TTAGCTCTCC AGGAGTTACA GGAAACGACG GGGGCAGCGC TCTATGAGAC GATGGAAGAA | 2340 |
| ATAGGAATGG CGCTGAGTGG TAAACTGCGC GAAAATTATA AATTCACTGA TGCTGAGAAA | 2400 |
| CTGGAGCGCA GACAGCAGGC TTTGCTGCGT TTGATAAAAC AAATACAGGA GGATAATGGG | 2460 |
| GCAACGTTGC GTCCGCTTAC CGAAGAGAAT AGTGATCCTG ATTACAGAA TGCGTATCAA | 2520 |
| ATTATCGCTC TTGCAATGGC GCTTACTGCC GGCGGGTTGT CAAAAAGAA AAAACGCGAT | 2580 |
| TTGCAATCGC AACTGGATAC GTTACAGCGG AGGAGGGATG GGAACTTGCC GTTTTTAGTT | 2640 |
| TACTGGAACT TGGCGAAGTG GATACCGTAC GCTGTCCTCT CTGAAGCGTT TTATGCAACA | 2700 |

```
GGCGATAGAC AACGATGAAA TGCCCTTATC GCAGTGGTTC AGACGCGTGG CAGACTGGCC    2760

GGATCGCTGT GAACGGGTCC GTATTTTGCT AAGAGCAGTA GCCTTTGAAC TTAGCATATG    2820

CATCGAACCC TCGGAGCAAA GTCGTTTGGC CGCAGCATTA GTACGTTTGC GTCGTTTGCT    2880

GTTATTCCTT GGCCTTGAAA AAGAGTGCCA GCGTGAGGAG TGGATTTGCC AGTTGCCGCC    2940

TAATACATTA CTGCCGCTAC TACTCGATAT TATTTGTGAG CGCTGGCTTT TCAGTGATTG    3000

GTTGCTTGAT AGACTTACCG CTATAGTTTC TTCATCGAAG ATGTTCAATC GGTTACTCCA    3060

ACAACTTGAT GCGCAGTTTA TGCTGATACC CGATAACTGT TTTAACGACG AAGATCAACG    3120

TGAACAAATT CTCGAAACGC TTCGTGAAGT AAAGATAAAT CAGGTTTTAT TCTGATACCT    3180

GGCTTTCAAT ATTTAGGTAA ATTGGCTTTC TGGCTCATCA TGAGGCGTCA GGATGGATTG    3240

GGATCTCATT ACTGAACGTA ATATTCAGCT TTTTATTCAA TTAGCAGGAT TAGCTGAACG    3300

GCCTTTAGCA ACCAATATGT TCTGGCGGCA AGGACAATAT GAAACTATCA TAACGGTCGT    3360

ATTCTCTTAT GTCAGATACT CAAGCAAACC TTCTTAGACG AAGAACTGCT TTTTAAAGCG    3420

TTGGCTAACT GGAAACCCGC AGCGTTCCAG GGTATTCCTC AACGATTATT TTTGTTGCGC    3480

GATGGGCTTG CAATGAGTTG TTCTCCACCT CTTTCCAGCT CCGCCGAGCT CTGGTTACGA    3540

TTACATCATC GACAAATAAA ATTTCNTGGA GTCGCAATGC GTTCATGGTT AGGTGAGGGA    3600

GTCAGGGCGC AACAGTGGCT CAGTGTATGC GCGGGTCGGC AGGATATGGT TCTGGCGACG    3660

GTGTTATTAA TCGCTATTGT GATGATGCTG TTACCCTTGC CGACCTGGAT GGTTGATATC    3720

CTGATTACTA TCAACCTTAT GTTTTCAGTG ATCCTGCTCT TAATTGCTAT TTATCTTAGT    3780

GACCCTCTCG ATTTATCGGT ATTTCCGTCT TTATTACTTA TTACTACATT ATATCGTTTG    3840

TCACTCACAA TCAGCACATC ACGGCTGGTA CTGTTACAAC ATAATGCCGG TAATATTGTG    3900

GATGCTTTCG GTAAGTTTGT CGTAGGAGGA AATCTCACCG TTGGGTTGGT CGTATTTACC    3960

ATCATTACTA TCGTGCAATT TATTGTCATT ACAAAAGGTA TCGAGAGGGT GGCGGAAGTT    4020

AGCGCACGTT TCTCGCTTGA TGGGATGCCA GGCAAACAAA TGAGTATCGA TGGCGATTTG    4080

CGTGCCGGAG TTATCGATGC AGACCATGCC CGTACATTAA GACAGCATGT CCAGCAGGAA    4140

AGCCGCTTTC TCGGTGCGAT GGACGGTGCG ATGAAATTTG TTAAAGGCGA TACGATTGCC    4200

GGTATTATTG TTGTTCTGGT GAACATTATC GGCGGTATCA TTATCGCTAT CGTACAATAT    4260

GATATGTCGA TGAGTGAGGC TGTTCACACT TATAGCGTAC TGTCAATCGG AGATGGTTTA    4320

TGTGGGCAAA TTCCATCGCT GCTGATTTCC CTTAGCGCGG GAATTATTGT CACCCGTGTC    4380

CCGGGTGAGA AACGCCAGAA CCTGGCGACA GAGTTGAGTT CTCAAATTGC CAGACAACCT    4440

CAGTCGCTCA TATTAACCGC TGTGGTTTTA ATGCTCCTCG CTTTAATTCC TGGCTTTCCT    4500

TTTATCACTC TCGCTTTCTT TTCAGCGTTG TTAGCATTGC CAATTATCCT CATTCGCCGC    4560

AAAAAGTCTG TGGTTTCCGC AAATGGCGTC GAAGCACCGG AAAAAGATAG TATGGTTCCC    4620

GGCGCATGTC CTCTAATCTT ACGTCTTAGC CCGACGTTAC ATTCTGCCGA CCTGATTCGT    4680

GATATTGACG CCATGAGATG GTTTTTATTT GAGGATACCG GCGTCCCTCT CCCTGAGGTG    4740

AATATTGAGG TTTTGCCTGA ACCCACCGAA AAATTGACGG TACTGCTATA TCAGGAACCC    4800

GTATTTAGTT TATCTATTCC CGCTCAGGCG GATTATTTAT TGATAGGCGC GGACGCTAGT    4860

GTGGTGGGTG ACAGCCAGAC GTTACCGAAC GGGATGGGGC AGATCTGTTG GCTTACAAAA    4920

GACATGGCCC ATAAGGCGCA AGGTTTTGGA CTGGACGTTT TCGCGGGCAG CCAACGTATC    4980

TCTGCCTTAT TAAAATGTGT CCTGCTTCGG CATATGGGAG AGTTTATTGG TGTTCAGGAA    5040

ACGCGTTATC TAATGAATGC GATGGAAAAA AACTACTCTG AGCTGGTGAA AGAGCTTCAG    5100
```

```
CGCCAGTTAC CCATTAATAA AATCGCTGAA ACTTTGCAAC GGCTTGTATC AGAGCGGGTT    5160

TCTATTAGAG ATTTACGTCT TATTTTCGGC ACCTTAATTG ACTGGGCGCC ACGTGAAAAA    5220

GATGTCCTGA TGTTGACAGA ATATGTCCGT ATCGCGCTTC GTCGTCATAT TCTGCGTCGT    5280

CTTAATCCGG AAGGAAAACC GCTGCCGATT TTGCGGATCG GCGAAGGTAT TGAAAACCTC    5340

GTGCGTGAAT CCATTCGCCA GACGGCAATG GGGACCTATA CTGCGCTGTC GTCTCGTCAT    5400

AAGACGCAGA TCCTGCAACT TATCGAGCAG GCGCTGAAGC AGTCAGCCAA ATTATTCATT    5460

GTCACTTCTG TCGACACCCG ACGTTTCTTG CGAAAAATTA CAGAAGCCAC CTTGTTCGAC    5520

GTACCGATTT TGTCATGGCA GGAATTAGGA GAGGAGAGCC TTATACAAGT GGTAGAAAGT    5580

ATTGACCTTA GCGAAGAGGA GTTGGCGGAC AATGAAGAAT GAATTGATGC AACGTCTGAG    5640

GCTGAAATAT CCGCCCCCCG ATGGTTATTG TCGATGGGGC CGAATTCAGG ATGTCAGCGC    5700

AACGTTGTTA AATGCGTGGT TGCCTGGGGT ATTTATGGGC GAGTTGTGCT GTATAAAGCC    5760

TGGAGAAGAA CTTGCTGAAG TCGTGGGGAT TAATGGCAGC AAAGCTTTGC TATCTCCTTT    5820

TACGAGTACA ATCGGGCTTC ACTGCGGGCA GCAAGTGATG GCCTTAAGCG ACGCCATCAG    5880

GTTCCCGTGG GCGAAGCGTT ATTAGGGCGA GTTATTGATG GCTTTGGTCG TCCCCTTGAT    5940

GGCCGCGAAC TGCCCGACGT CTGCTGGAAA GACTATGATG CAATGCCTCC TCCCGCAATG    6000

GTTCGACAGC CTATCACTCA ACCATTAATG ACGGGGATTC GCGCTATTGA TAGCGTTGCG    6060

ACCTGTGGCG AAGGGCAACG AGTGGGTATT TTTTCTGCTC CTGGCGTGGG GAAAAGCACG    6120

CTTCTGGCGA TGCTGTGTAA TGCGCCAGAC GCAGACAGCA ATGTTCTGGT GTTAATTGGT    6180

GAACGTGGAC GAGAAGTCCG CGAATTCATC GATTTTACAC TGTCTGAAGA GACCCGAAAA    6240

CGTTGTGTCA TTGTTGTCGC AACCTCTGAC AGACCCGCCT TAGAGCGCGT GAGGGCGCTG    6300

TTTGTGGCCA CCACGATAGC AGAATTTTTT CGCGATAATG GAAAGCGAGT CGTCTTGCTT    6360

GCCGACTCAC TGACGCGTTA TGCCAGGGCC GCACGGAAAT CGCTCTGGCG CCGGAGAGAC    6420

CGCGGTTTCT GGAGAATATC GCCAGGCGTA TTTAGTGCAT TGCCACGACT TTTAGAACGT    6480

ACGGAATGG GAGAAAAAGG CAGTATTACC GCATTTTATA CGGTACTGGT GGAAGGCGAT    6540

GATATGAATG AAGCCGTTGG CGGATGAAGT CCGTTCACTG CTTGATGGAC ATATTGTACT    6600

ATCCCGACGG CTTGCAGAGA GGGGGCATTA TCCTGCCATT GACGTGTTGG CAACGCTCAG    6660

CCGCGTTTTT CCAGTCGTTA CCAGCCATGA GCATCGTCAA CTGGCGGCGA TATTGCGACG    6720

GTGCCTGGCG CTTTACCAGG AGGTTGAACT GTTAATACGC ATTGGGGAAT ACCAGCGAGG    6780

AGTTGATACA GATACTGACA AAGCCATTGA TACCTATCCG GATATTTGCA CATTTTTGCG    6840

ACAAAGTAAG GATGAAGTAT GCGGACCCGA GCTACTTATA GAAAAATTAC ACCAAATACT    6900

CACCGAGTGA TCATGGAAAC TTTGCTGGAG ATAATCGCGC GGCTGAAAAG CAATTACGCG    6960

GCAAGCTTAC CGTACTTGAT CAGCAGCAAC AGGCGATTAT TACGGAACAG CAGATTTGCC    7020

AGACGCGCGC TTTAGCAGTG TCTACCAGAC TGAAAGAATT AATGGGCTGG CAAGGTACGT    7080

TATCTTGTCA TTTATTGTTG GATAAGAAAC AACAAATGGC CGGGTTATTC ACTCAGGCGC    7140

AGAGCTTTTT GACGCAACGG CAAGCAGTTA GAGAATCAGT ATCAGCAGCT TGTCTCCCGG    7200

CGAAGCGAAT TACAGAAGAA TTTTAATGCG CTTATGAAAA AGAAAGAAAA AATTACTATG    7260

GTATTAAGCG ATGCGTATTA CCAAAGTTGA GGGAAGTCTT GGGTTGCCAT GCCAGTCTTA    7320

TCAGGATGAT AACGAGGCGG AGGCGGAACG TATGGACTTT GAACAACTCA TGCACCAGGC    7380

ATTACCCATT GGTGAGAATA ATCCTCCTGC AGCATTGAAT AAGAACGTGG TTTTCACGCA    7440

ACGTTATCGT GTTAGTGGCG GTTATCTTGA CGGTGTAGAG TGTGAAGTAT GTGAATCAGG    7500
```

```
GGGGCTAATC CAGTTAAGAA TCAATGTCCC TCATCATGAA ATTTACCGTT CGATGAAAGC    7560

GCTAAAGCAG TGGCTGGAGT CTCAGTTGCT GCATATGGGG TATATAATTT CCCTGGAGAT    7620

ATTCTATGTT AAGAATAGCG AATGAAGAGC GTCCGTGGGT GGAGATACTT CCAACGCAAG    7680

GCGCTACCAT TGGTGAGCTG ACATTGAGTA TGCAACAATA TCCAGTACAG CAAGGGACAT    7740

TATTTACCAT AAATTATCAT AATGAGCTGG GTAGGGTGTG GATTGCAGAA CAATGCTGGC    7800

AGCGCTGGTG TGAAGGGCTA ATTGGCACCG CTAATCGATC GGCTATCGAT CCTGAATTGC    7860

TATATGGAAT AGCTGAATGG GGGCTGGCGC CGTTATTGCA AGCCAGTGAT GCAACCCTCT    7920

GTCAGAACGA GCCGCCAACA TCCTGCAGTA ATCTACCACA TCAGCTAGCG TTGCATATTA    7980

AATGGACAGT TGAAGAGCAT GAGTTCCATA GCATTATTTT TACATGGCCA ACGGGTTTTT    8040

TGCGCAATAT AGTCGGAGAG CTTTCTGCTG AGCGACAACA GATTTATCCT GCCCCTCCTG    8100

TGGTAGTCCC TGTATATTCA GGCTGGTGCC AGCTTACATT AATCGAACTT GAGTCTATCG    8160

AAATCGGCAT GGGCGTTCGG ATTCATTGCT TCGGCGACAT CAGACTCGGT TTTTTTGCTA    8220

TTCAACTACC TGGGGGAATC TACGCAAGGG TGTTGCTGAC AGAGGATAAC ACGATGAAAT    8280

TTGACGAATT AGTCCAGGAT ATCGAAACGC TACTTGCGTC AGGGAGCCCA ATGTCAAAGA    8340

GTGACGGAAC GTCTTCAGTC GAACTTGAGC AGATACCACA ACAGGTGCTC TTTGAGGTCG    8400

GACGTGCGAG TCTGGAAATT GGACAATTAC GACAACTTAA AACGGGGGAC GTTTTGCCTG    8460

TAGGTGGATG TTTTGCGCCA GAGGTGACGA TAAGAGTAAA TGACCGTATT ATTGGGCAAG    8520

GTGAGTTGAT TGCCTGTGGC AATGAATTTA TGGTGCGTAT TACACGTTGG TATCTTTGCA    8580

AAAATACAGC GTAAACCTGA TAAGAAAAAT AATATGCGAA CAATATAATA GCGTTCCAGG    8640

TCGTGTCATG AGAGATACAG TATGTCTTTA CCCGATTCGC CTTTGCAACT GATTGGTATA    8700

TTGTTTCTGC TTTCAATACT GCCTCTCATT ATCGTCATGG GAACTTCTTT CCTTAAACTG    8760

GCGGTGGTAT TTTCGATTTT ACGAAATGCT CTGGGTATTC AACAAGTCCC CCCAAATATC    8820

GCACTGTATG GCCTTGCGCT TGTACTTTCC TTATTCATTA TGGGGCCGAC GCTATTAGCT    8880

GTAAAAGAGC GCTGGCATCC GGTTCAGGTC GCTGGCGCTC CTTTCTGGAC GTCTGAGTGG    8940

GACAGTAAAG CATTAGCGCC TTATCGACAG TTTTTGCAAA AAAACTCTGA AGAGAAGGAA    9000

GCCAATTATT TCGGAATTT GATAAAACGA ACCTGGCCTG AAGACATAAA AAGAAAGATA    9060

AAACCTGATT CTTTGCTCAT ATTAATTCCG GCATTTACGG TGAGTCAGTT AACGCAGGCA    9120

TTTCGGATTG GATTACTTAT TTATCTTCCC TTTCTGGCTA TTGACCTGCT TATTTCAAAT    9180

ATACTGCTGG CTATGGGGAT GATGATGGTG TCGCCGATGA CCATTTCATT ACCGTTTAAG    9240

CTGCTAATAT TTTTACTGGC AGGCGGTTGG GATCTGACAC TGGCGCAATT GGTACAGAGC    9300

TTTTCATGAA TGATTCTGAA TTGACGCAAT TTGTAACGCA ACTTTATGG ATCGTCCTTT    9360

TTACGTCTAT GCCGGTAGTG TTGGTGGCAT CGGTAGTTGG TGTCATCGTA AGCCTTGTTC    9420

AGGCCTTGAC TCAAATACAG GACCAAACGC TACAGTTCAT GATTAAATTA TTGGCAATTG    9480

CAATAACCTT AATGGTCAGC TACCCATGGC TTAGCGGTAT CCTGTTGAAT TATACCCGGC    9540

AGATAATGTT ACGAATTGGA GAGCATGGTT GAATGGCACA ACAGGTAAAT GAGTGGCTTA    9600

TTGCATTGGC TGTGGCTTTT ATTCGACCAT TGAGCCTTTC TTTATTACTT CCCTTATTAA    9660

AAAGTGGCAG TTTAGGGGCC GCACTTTTAC GTAATGGCGT GCTTATGTCA CTTACCTTTC    9720

CGATATTACC AATCATTTAC CAGCAGAAGA TTATGATGCA TATTGGTAAA GATTACAGTT    9780

GGTTAGGGTT AGTCACTGGA GAGGTGATTA TTGGTTTTTC AATTGGGTTT TGTGCGGCGG    9840

TTCCCTTTTG GGCCGTTGAT ATGGCGGGGT TTCTGCTTGA TACTTTACGT GGCGCGACAA    9900
```

```
TGGGTACGAT ATTCAATTCT ACAATAGAAG CTGAAACCTC ACTTTTTGGC TTGCTTTTCA    9960

GCCAGTTCTT GTGTGTTATT TTCTTTATAA GCGGCGGCAT GGAGTTTATA TTAAACATTC   10020

TGTATGAGTC ATATCAATAT TTACCACCAG GGCGTACTTT ATTATTTGAC CAGCAATTTT   10080

TAAAATATAT CCAGGCAGAG TGGAGAACGC TTTATCAATT ATGTATCAGC TTCTCTCTTC   10140

CTGCCATAAT ATGTATGGTA TTAGCCGATC TGGCTTTAGG TCTTTTAAAT CGGTCGGCAC   10200

AACAATTGAA TGTGTTTTTC TTCTCAATGC CGCTCAAAAG TATATTGGTT CTACTGACGY   10260

CCTGATCTCA TTCCCTTATG CTCTTCATCA CTATTTGGTT GAAAGCGATA AATTTTATAT   10320

TTATCTAAAA GACTGGTTTC CATCTGTATG AGCGAGAAAA CAGAACAGCC TACAGAAAAG   10380

AAATTACGTG ATGGCCGTAA GGAAGGGCAG GTTGTCAAAA GTATTGAAAT AACATCATTA   10440

TTTCAGCTGA TTGCGCTTTA TTTGTATTTT CATTTCTTTA CTGAAAAGAT GATTTTGATA   10500

CTGATTGAGT CAATAACTTT CACATTACAA TTAGTAAATA AACCATTTTC TTATGCATTA   10560

ACGCAATTGA GTCATGCTTT AATAGAGTCA CTGACTTCTG CACTGCTGTT TCTGGGCGCT   10620

GGGGTAATAG TTGCTACTGT GGGTAGCGTG TTTCTTCAGG TGGGGGTGGT TATTGCCAGC   10680

AAGGCCATTG GTTTTAAAAG CGAGCATATA AATCCGGTAA GTAATTTTAA GCAGATATTC   10740

TCTTTACATA GCGTAGTAGA ATTATGTAAA TCCAGCCTAA AAGTTATCAT GCTATCTCTT   10800

ATCTTTGCCT TTTTCTTTTA TTATTATGCC AGTACTTTTC GGGCGCTACC GTACTGTGGG   10860

TTAGCCTGTG GCGTGCTTGT GGTTTCTTCT TTAATAAAAT GGTTATGGGT AGGGGTGATG   10920

GTTTTTTATA TCGTCGTTGG CATACTGGAC TATTCTTTTC AATATTATAA GATTAGAAAA   10980

GCTATCTAAA AATGAGTAAA GATGACGTAA AACAGGAGCA TAAAGATCTG GAGGGCGACC   11040

CTCAAATGAA GACGCGGCGT CGGAAATGCA GAGTGAAATA CAAAGTGGGA GTTTAGCTCA   11100

ATCTGTTAAA CAATCTGTTG CGGTAGTGCG TAATCCAACG CATATTGCGG TTTGTCTTGG   11160

CTATCATCCC ACCGATATGC CAATACCACG CGTCCTGGAA AAAGGCAGTG ATGCTCAAGC   11220

TAACTATATT GTTAACATCG CTGAACGCAA CTGCATCCCC GTTGTTGAAA ATGTTGAGCT   11280

GGCCCGCTCA TTATTTTTTG AAGTGGAACG CGGAGATAAA ATTCCTGAAA CGTTATTTGA   11340

ACCCGTTGCA GCCTTGTTAC GTATGGTGAT GAAGATAGAT TATGCGCATT CTACCGAAAC   11400

ACCATAAATG CTTTTGGTAT GCTTCTTCAG GCCACTGCGA AGGTTAAGAG GGTAATAGCG   11460

TATAGAGCAG TGCTTGACGA TAAAGGTGAG AGACTGAAAA TAATCGCTTT TAGCCTGGCA   11520

CAAGCACCAG ATAGCGTATT ATAAAATTAA ACAAGATAAT GGATTGGTGC GTCTGAATGG   11580

ACTCGAACCA CTCGACCCCC ACCATGTCAA GGTGGTGCTC TAACCAACTG AGCTATGAAC   11640

GGCAACGTTG TAGGTGACAA CGGGGACGAA TATTAGCGTC ACAACCGCAA TGAGGCAAGA   11700

GGGAAATCGC AATTTTCTTC CTGAAATCAC CTGATTGCGG TGGAAATATG CAACATGTCG   11760

AGAAAATAGC CGCCATGCGA CGGCTATCGT CGTATTATCG GAGCGCGCTG CAAAATGATG   11820

GCGGACGGCT GACGTTGTAG ATAGCGCATC CGTAGCATCA TTAACACCGC CGCCGAGGTC   11880

AGGCCGATGA TGAACCCCAT CCAGAAGCCT GCCGGTCCCA TACGATCCAC CACCAAATCC   11940

GTTAACGCCA GGATATAACC GCTGGGTAAA CCTAACACCC AGTAGGCGGT AAAGGTGATA   12000

AAAAAGATGG AACGCGTATC TTTATAACCG CGCAGAATAC CGCTGCCGAT AACCTGTATA   12060

GAGTCGGAAA TCTGGTAAAC CGCAGCGAGC AGCATTAATT GCGGCAAGCG CCACGACCTC   12120

AGGGTTGTCA TTGTAGAGCA AAGCAATATG CTTACGCAGA GTAACGGTAA AAATAGCGGT   12180

AACCACAGCC ATACAAATGC CGACGCCTAA ACCGGTACGC GCTGCGTTTG CGCATCCAGC   12240

GTTGAGCCCT GGCCCAGACC GATAACCCAC TCGAATCGTT ACCGCCGCAG CCAGCGACAT   12300
```

```
CGGCAGTACG AACATCAGCG AGCTAAAGTT AAGCGCAATC TGATGACCGG CGACATCCAC    12360

AATACCTAAT GGCGAAACCA GCAGCGCAAC GACCGCAAAT AACGTCACTT CAAAGAACAG    12420

CCAGCGCAAT CGGCAACCCC AGTTGAATCA GGCGCTTCAT GACGACGCTA TCGGGTTTGC    12480

CAAAGCCTTT TTCATTACGA ATATCACGCA TTGAACGCGC GTGTTTAATG TAAGAAAGCA    12540

TGGCGATAAA CATCACCCAA TAGACCGCCG CAGTCGCAAC GCCGCAGCCG ATACCGCCGA    12600

GTTCCGGCAT ACCAAAATGG CCATAGATAA AAATATAGTT CACCGGAATA TTCACCAGCA    12660

GGCCCAAAAA TCCCATCACC ATACCCGGTT TGGTTTTGGC CAGACCTTCG CACTGGTTTC    12720

GCGCTACCTG AAAGAAAAGG TATCCTGCGC CCCACAGCAG CGCGCGAAGA TAACCCACGG    12780

CTTTATCGGC CAGCGCCGGA TCAATATTAT GCATAGAGCG GATAATGTAT CCGGCATTCC    12840

ACAGGACGAT CATCACCAGC ACGGAGACAA AGCCCGCCAG CCAGAACCCT TGTCGAACCT    12900

GATGCGCGAT ACGCTCACGA CGGCCGGAGC CATTGAGTTG CGCAATCACA GGCGTCAAGG    12960

CCAGCAGTAA GCCGTGACCA AACAAAATGG CGGGAAGCAG ATAGAGGTGC CGATAGCGAC    13020

GGCAGCCATG TCCGTAGCGC TATAGCCTCC CGCCATGACG GTATCGACGA ATCCATTGCG    13080

GTCTATACCA CTTGCGCAAG GATCACCGGT ATCTGAACGA TAATAACTGA CGCGCTTCAC    13140

TGGTATACTT CTGCACGTAT TCACCTTTTA TTTTGTTGTT ATATGAAAGA CTAAAAAGCC    13200

GCCGAAGTGG CAGCCAAAAG AAATAGCAGG GGAAATTTCA GTCTATTGTA GCGGGGTATT    13260

ACTATTTCTC CAGTGAAAAA ACAGTTGTTA ACGGCGCATT GCTGGCAAGC TGTTTTTCCA    13320

CCTGCTATTG TGCTGAACAG TTCTGCTTTT ATTTATTTCA GGAGTTGAAG ATATGTTTAC    13380

GGGGATCGTA CAGGGTACCG CGAAACTGGT ATCGATA                            13417
```

(2) INFORMATION FOR SEQ ID NO: 38:

(i) SEQUENCE CHARACTERISTICS:
        (A) LENGTH: 5746 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: DNA sequence of VGC II cluster C (xi) SEQUENCE DESCRIPTION: SEQ ID NO: 38:

```
GGATCCTTTT TCTTTAATGC TGCTAACGTT TCTTGCAAAA TGCGTTGATG AGATTCATCC      60

AGTACACCAC TGATAACAAA AGAGCGNCGC ATTGGCNWAM MWTKRNNMRN NSCNNNACTA     120

AACCGTTCTC TATTATCGCA GAAATAATAT CATCCCCCTG AGACTGATGA GAGTGACTAA     180

TCTGCCAGTG CAATAACCCG GGAATATCTG CAAGTAATGG TTGAACCTTG CGCCATTGCT     240

GATCCATTTG TATATCATCA TGAATTAACA CGCTCCCCGG CCCTTCGCTG GATACTTCAG     300

CATNSSGGTA ACCCATTTTT ATCAAAACAT CCTGCACTTC TCGTACCAAT AAGTCATCAC     360

AGATTACACC ATCCCGATAC ATGACCCCCC ATGATTCGAG AGTCGCTCTC ACCTTTTGCA     420

TCTGTTCGCT TGACGAGCAA TAACCGGACA ACTGCAGGCT GCCATCTTCT TTCCATTGCG     480

CCCGCACATA ATGAATATTG CTTTTGTCTA ATAAAAACTT AACCCGCAAA GGTAAGTCAT     540

TTACCGTTTC AGGCTGACCA CTAATACTTA ACAGGACACC CATTCCACCG ATGAAAATCA     600

AGAATACGCC AGCCAACCAC CAGTACCCTG ATCTGGAAAC GGGTATTTGA TAATCAGCAA     660
```

```
GTTCACAATC CTGTTTACCA AACGCGATAS SCACTCCCGC AACCTGCAAA ACCCCACTGG      720

ATGGTAGCGG CTTATTTGGA TTAAATCTGC GGCCATTAAC TCTAACTCTG GCTTTCCCGG      780

CATCAACAAA TAAACTATCT GCCTGTTCTC TCAGAATAAT TTTTTCATTT ATAGCCAGCG      840

AATACAAATA TCGCATCCCT TCTCCCCCAG TGACAGGTTA CCTTCATTCA GCCATACTTC      900

CCGGCCTTGT AAAACGTGAC CTAAAAAACG TATTTTCCAG GAACTCTTTG GATTAACCAT      960

GAGATATGCC ATTATTTACT ACTGAGGCTT TAATCAAAAA AAGCCTGATT ACACTATGTA     1020

CTTGAGTCGT ATCATTGCGA AACAAATGAC CTACAACAGG AATATCGCCC AATAAAGGGA     1080

TTTTGTTTTG CGAGTGGATT TGTTTACCTT GTTTAAACCC TCCCAGCAAT NAGACTTTGC     1140

CCGGCCAATA ATGTGGCTTG CGAANCRATT TCAGAATTTT GCACTTCGGG CAGCGGGTCT     1200

GTNTYGCYTT KGNSTATCAC TTTGTTGTCC ATCCTGAANT ATTAAGATTA AGCATTATTT     1260

TTTGCGTGCC ATTGTCATTT AACAAGCGAG GTGTAACGCG WNAACAAAGA ACCCGTAGTG     1320

ATGGATTCAA GTTTAGCCAC TTTTTCTCCC TGCAGTTTGG TATAGAAAGT AATATTTTTA     1380

TCCAGCACAG CCTGGATATT ATTTAAAGTC ACCACAGATG GCTGGGAAAG TACATAAGCC     1440

TGAGAGCTTT TTTCCAGGGC ATTCAGACGC ACCATAAAGT TTGAGGTATC GCTGATTACC     1500

GTTGANNAAC CACTAGCACC ACCGTCATTC AAACCTGTAT TGAACGCAAT TTTCTTGCCA     1560

CCCAGCGACA CTGCCGTTCC CCAGTCGATG CCTAACTGGT AATATCTCC AGCATTAACA     1620

TCGATAATTT TCACCGAAAT CTCTATCATC TGCTGGCGTT GATCTAATTC TGTGATGAGT     1680

TTCCGATACN NNGCCATATT GGNNNCATAA TCACGAACGA TCACTGCATT CTGGCGTNGG     1740

GTCGGCAGCA ACATGGCA ATGCCTGTGT AGCGGGTGAA CCATTGTTCN TCGATGACGT     1800

CGGGACGCTG GTTTTACTCA TCTCACGCAA TACACTAACG ACCCCTGGNN AACCACGACG     1860

GACTGATCGC GATATTGGTA CTGGGTATCC ATCGCAGTGG CATACTTAAG CGTGTATATA     1920

CTTACACTCA CCGCACTGTC TTTTCGTTTG ATTAACGCAT TATCCAGCAC TGAAGCTAAT     1980

TGACTAATAC GAGTCAGGCA GCTGGGAACA CCGCTCACCT CCACAGCTTT GGTACCGGTA     2040

ATTTCTTTAA CCTCGCATCC CGGTGATGAA AGGATATTCT GGCTGCGTAA GTAATGAATG     2100

AACCGTCCAG TAGATAAAAT ATTGAAAGTG ATAACCTGAT GTTTTAATAA CGATGCAGGA     2160

TATACATATA ACATGCTGCC ATCAAACCAG GTAAGCAAAT CATATTGTGC TGCCAGGTTA     2220

TTCAAAATAT CGACCGGTGG TCCAGGCGGA ATTTTTCCAC TAAATGTAGC TGTTATCAAT     2280

GGGCTAATAG TAATAGCCGT ATCATAGTTC TCTGAGAGCA GATGTNAAAA CCTCTGCTAA     2340

TGGCATTTGT CTGGCATAAA GGGTGAAGTC ATTACCTTTC CATGATAACT CATCACTCTT     2400

TGCTGTATTG AGTATAAATA GTAAAATTAA GATTAAACGT TTATTTACTA CCATTTTATA     2460

CCCCACCCGA ATAAAGTTTA TGGTGATTGC GTATTACATT TTTTNAAAAT GCAAGTTAAA     2520

GCCAGGTGTT TTTCTATCTC AATAGCAATA AGCTCAGAGC TACTACTTGT GGTATAATAA     2580

CCGTTTAACC ATCCCCCATC CGCTGTGAGC TGTATAGCAT AATCATGGAC GTCCGGGTGT     2640

GCGCAARCRG TAGTGTCAMM TAGGCAAGAC AAGGCTTAGG TAAGCTTTCC AGGTCATTTA     2700

AGAACAAAGA AATAGAAAAT GCTTCTGAGA AAATTTCTYC YBHNNNNNNN NNNNNNNNNN     2760

NNNNNNNCA TCAATAGTCA TTATCCAGGA TSSKMTWWYM NYYKSSSCYS WKATMYYSWR     2820

WWTTAATGGA ATGCCTTTTA AAACTGCCAG CATGAATCCC TCCTCAGACA TAAATGGGAG     2880

TTTCTATCAA ATTCGCTCAC AACCACATCC GTAAAAAGCC TGATTCACAT TTATTTCGAC     2940

TATACTCTTC TTGTACAATA TCAGGATGCT GTCTACATAT ACCTTGTCAC AGGCGATTCT     3000

ATCATTCGGA TTTTCCGATA AATTNMMCAA TTACATTTTC AGCATTGACA TAAAAACTTA     3060
```

```
CAATTTGNAA AATTATTTAT TAAATAAACT GTTACGATGT TTTTACATCG CCATCTTATT     3120

AAAAAGTAAT TGTAGTCATC GACTNGGTTA TATATGAAGA AATTTATCTT CCTAATGATA     3180

ACACCATCGA TTAATCWWCT GATGAAACTA TATGTACTGC GATAGTGATC AAGTGCCAAA     3240

GATTTTGCAA CAGGCAACTG GAGGGAAGCA TTATGAATTT SSTCAATCTC AAGAATACSS     3300

YSYRNNNNNN TCTTTAGTAA TCAGGCTAAC TTTTTTATTT TTATTAACAA CAATAATTWT     3360

TTGGCTGCTA TCTGTGCTTA CCGCAGCTTA TATATCAATG GTTCRGAAAC GGCAGCATAT     3420

AATAGAGGAT TTATCCGTTC TATCCGAGAT GAATATTGTA CTAAGCAATC AACGGTTTGA     3480

AGAAGCTGAA CGTGACGCTA AAAATTTAAT GTATCAATGC TCATTAGCGA CTGAGATTCA     3540

TCATAACGAT ATTTTCCCTG AGGTGAGCCG GCATCTATCT GTCGGTCCTT CAAATTGCAC     3600

MGCCGACGCT NAACGGAGAG AAGCACCGTC TCTTTCTGCA GTCCTCTGAT ATCGATGAAA     3660

ATAGCTTTCG TCGCGATAGT TTTATTCTTA ATCATAAAAA TGAGATTTCG TTATTATCTA     3720

CTGATAACCC TTCAGATTAT TCAACTCTAC AGCCTTTAAC GCGAAAAAGC TTTCCTTTAT     3780

ACCCAACCCA TGCCGGGTTT TACTGGAGTG AACCAGAATA CATAAACGGC AAAGGATGGC     3840

AACGCTTCCG TTGCGGTTGC CGATCAGGCA AGGCGTATTT TTTGAGGTGA CGGTTAAACT     3900

TCCCGATCTC ATTACTAAGA GCCACCTGCC ATTAGATGAT AGTATTCGAG TATGGCTGGA     3960

TCAAAACAAC CACTTATTGC CGTTTTCATA CATCCCGGCA AAAATACGT ACACAGTTAG     4020

AAAATGTAAC GCTGCATGAT GGATGGCAGC AAATTCCCGG ATTTCTGATA TTACGCACAA     4080

CCTTGCATGG CCCCGGATGG AGTCTGGTTA CGCTGTACCC ATACGGTAAT CTACATAATC     4140

GCATCTTAAA AATTATCCTT CAACAAATCC CCTTTACATT AACAGCATTG GTGTTGATGA     4200

CGTCGGCTTT TTGCTGGTTA CTACATCGCT CACTGGCCAA ACCGTTATGG CGTTTTGTCG     4260

ATGTCATTAA TAAAACCGCA ACTGCACCGC TGAGCACACG TTTACCAGCA CAACGACTGG     4320

ATGAATTAGA TAGTATTGCC GGTGCTTTTA ACCAACTGCT TGATACTCTA CAAGTCCAAT     4380

ACGACAATCT GGAAAACAAA GTCGCAGACG CACCCAGGCG CTAAATGAAG CAAAAAAACG     4440

CGCTGAGCNA GCTAACAAAC GTAAAAGCAT TCATCTTACG GTAATAAGTC ATGAGTTACG     4500

TACTCCGATG AATGGCGTAC TCGGTGCAAT TGAATTATTA CAAACCACCC CTTTAAACAT     4560

AGAGCAACAA GGATTAGCTG ATACCGCCAG AAATTGTACA CTGTCTTTGT TAGCTATTAT     4620

TAATAATCTG CTGGATTTTT CACGCATCGA GTCTGGTCAT TTCACATTAC ATATGGAAGA     4680

AACAGCGTTA CTGCCGTTAC TGGACCAGGC AATGCAAACC ATCCAGGGGC CAGCGCNAAA     4740

GCAAAAAACT GTCATTACGT ACTTTTGTCG GTCAACATGT CCCTCTCTAT TTTCATACCG     4800

ACAGTATCCG TTTACNNCAA ATTTTGGTTA ATTTACTCGG GAACGCGGTA AAATTTACCG     4860

AAACCGGAGG ATACGTCTGA CGGTCAAGCG TCATGAGGAA CAATTAATAT TTCTGGTTAG     4920

CGATAGCGGT AAAGGGATTG AAATACAGCA GCAGTCTCAA ATCTTTACTG CTTTTTATCA     4980

AGCAGACACA AATTCGCAAG GTACAGGAAT TGGACTGACT ATTGCGTCAA GCCTGGCTAA     5040

AATGATGGGC GGTAATCTGA CACTAAAAAG TGTCCCCGGG GTTGGAACCT GTGTCTCGCT     5100

AGTATTACCC TTACAAGAAT ACCAGCCGCC TCAACCAATT AAAGGGACGC TGTCAGNNNC     5160

CGTTCTGCCT GCATCGGCAA CTGGCTTGCT GGGGAATACG CGGTGAACCA CCCCACCAGC     5220

AAAATGCGCT TCTCAANNCN AGAGCTTTTG TATTTCTCCG GAAAACTCTA CGACCTGGCG     5280

CAACAGTTAA TATTGTGTAC ACCAAATATG CCAGTAATAA ATAATTTGTT ACCACCCTGG     5340

CAGTTGCAGA TTCTTTTGGT TGATGATGCC GATATTAATC GGGATATCAT CGGCAAAATG     5400

CTTGTCAGCC TGGGCCAACA CGTCACTATT GCCGCCAGTA GTAACGAGGC TCTGACTTTA     5460
```

6,015,669

-continued

```
TCACAACAGC AGCGATTCGA TTTAGTACTG ATTGACATTA GAATGCCAGA AATAGATGGT      5520

ATTGAATGTG TACGATTATG GCATGATGAG CCGAATAATT TAGATCCTGA CTGCATGTTT      5580

GTGGCACTAT CCGCTAGCGT ASCVNMAGAW RWTMWTCRTY GTDDAAAAAA WRDGRKDHWT      5640

CATHAYANNT TACAAAACCA GTGACATTGG CTACCTTAGC TCGCTACATC AGTATTGCCG      5700

CAGAATACCA ACTTTTACGA AATATAGAGC TACAGGAGCA GGATCC                    5746
```

(2) INFORMATION FOR SEQ ID NO: 39:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 39:

```
CCACCAGCCG CTGGGGTACC AGGGCCAGGC GACGGATATT GAAATTCACG CCCGCGAAAT        60

TTTGAAAGTA AAAGGGCGCA TGAATGAACT TATGRMKYKM MATACGGGTC ANTCTCTTGA       120

GCAGATTGAA SGTGATACTG A                                                141
```

(2) INFORMATION FOR SEQ ID NO: 40:

(i) SEQUENCE CHARACTERISTICS:
        (A) LENGTH: 66 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 40:

```
TGAAGCGGTA GAGTACGGTT TGGTTGACTC AATTTTGACC CATCGTAATT GATGCCCTGG        60

ACGCAA                                                                  66
```

(2) INFORMATION FOR SEQ ID NO: 41:

(i) SEQUENCE CHARACTERISTICS:
        (A) LENGTH: 141 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 41:

```
CCAACCGTTG GGCGGCTACC AGGGCCAGGC GACCGATATC GAAATTCATG CCCGTGAAAT        60

TCTGAAAGTT AAAGGGCGCA TGAATGAACT TATGGCGCTT CATACGGGTC AATCATTAGA       120

ACAGATTGAA CGTGATACCG A                                                141
```

(2) INFORMATION FOR SEQ ID NO: 42:

(i) SEQUENCE CHARACTERISTICS:
            (A) LENGTH: 66 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 42:

TGAAGCGGTG GAATACGGTC TGGTCGATTC GATTCTGACC CATCGTAATT GATGCCAGAG        60

GCGCAA                                                                  66

(2) INFORMATION FOR SEQ ID NO: 43:

(i) SEQUENCE CHARACTERISTICS:
            (A) LENGTH: 107 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 43:

GATATCGAAA TTCATGCCCG TGAAATTCTG AAAGTTAAAG GGCGCATGAA TGAACTTATG        60

GCGCTTCATA CGGGTCAATC ATTAGAACAG ATTGAACGTG ATACCGA                    107

(2) INFORMATION FOR SEQ ID NO: 44:

(i) SEQUENCE CHARACTERISTICS:
            (A) LENGTH: 66 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 44:

TGAAGCGGTG GAATACGGTC TGGTCGATTC GATTCTGACC CATCGTAATT GATGCCAGAG        60

GCGCAA                                                                  66

(2) INFORMATION FOR SEQ ID NO:45:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:45:

Leu Gln Asn Arg Ala Arg Ser Lys Leu Ile Phe Leu Asn Asn Cys
  1               5                  10                  15

(2) INFORMATION FOR SEQ ID NO:46:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:46:

Lys Met Lys His Pro Pro Val Thr Pro Val Leu Tyr Tyr Arg Arg Leu
 1               5                  10                  15

Cys (2) INFORMATION FOR SEQ ID NO:47:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:47:

Pro Asp Lys Trp Ile Ile Cys Ser
 1               5

(2) INFORMATION FOR SEQ ID NO:48:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:48:

Ala Ser Ile Ile Leu Pro Glu Tyr His Gly Ala Ala Cys Gln Ala Leu
 1               5                  10                  15

Asn Lys Leu Asp Asn Met Ala
            20

(2) INFORMATION FOR SEQ ID NO:49:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:49:

Arg Phe Ile Val
 1

(2) INFORMATION FOR SEQ ID NO:50:

(i) SEQUENCE CHARACTERISTICS:
        (A) LENGTH: 79 amino acids (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:50:

Tyr Phe Leu Leu Ser Leu Arg Ser Phe Leu Arg His Val Met Trp Ile
1               5                   10                  15

Phe Ile Ala His Cys Gln Lys Met Lys Arg Ile Lys Cys Trp His Tyr
            20                  25                  30

Leu Cys Ser Ile Ile Leu Met Arg Lys Lys Thr Gly Arg Gly Trp Cys
        35                  40                  45

Asn Leu Thr Cys Arg Ala Val Gly Ser Leu Leu Met Arg Leu Arg Leu
    50                  55                  60

Leu Arg Leu Asn Gly Tyr Pro His Arg Ala Val Tyr Asn Gly Gly
65                  70                  75

(2) INFORMATION FOR SEQ ID NO:51:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:51:

Asp Val Ser Gly
1

(2) INFORMATION FOR SEQ ID NO:52:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:52:

Ser Val Ser Gly Ile Thr Pro Gly Arg Thr Gly Arg Arg Leu Ile Phe
1               5                   10                  15

(2) INFORMATION FOR SEQ ID NO:53:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:53:

Lys Asn Lys Glu Leu Lys Glu Cys
1               5

```
(2) INFORMATION FOR SEQ ID NO:54:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:54:

Val Arg Trp Arg Gly Val Ile Asn Gly Lys Ser Asp His Cys Ala Thr
 1               5                  10                  15

Asp Leu (2) INFORMATION FOR SEQ ID NO:55:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:55:

Arg Phe Ser Glu Leu Ser Cys Arg Ile Tyr Lys Ile Phe Thr Ser Gly
 1               5                  10                  15

Gln Tyr Gly Gly Leu Ser Gly Lys Asn
            20                  25

(2) INFORMATION FOR SEQ ID NO:56:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:56:

Arg Phe Asn Arg Asp Val Asn Pro Trp Val Ala Ile Gln
 1               5                  10

(2) INFORMATION FOR SEQ ID NO:57:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:57:

Tyr Leu Asp Ala Ala Cys
 1               5

(2) INFORMATION FOR SEQ ID NO:58:

(i) SEQUENCE CHARACTERISTICS:
```

(A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:58:

Ile Gln Asn Gly Ser
1               5

(2) INFORMATION FOR SEQ ID NO:59:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:59:

Arg Thr Arg Glu Thr Asn Ile Leu Asp Tyr Gly Arg Tyr Gln Arg Gln
1               5                  10                  15

(2) INFORMATION FOR SEQ ID NO:60:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:60:

Arg Glu Gly Gly Glu Val Val Asp Glu Ile Pro Leu Ser Val Asp Val
1               5                  10                  15

Ile Val Asp Arg Thr Val Ile Arg Ser Gly His Pro Asp Arg Leu Phe
            20                  25                  30

Leu Pro Glu Thr Pro Phe Leu Ser Arg Pro Asp Pro Glu Val Leu Gln
        35                  40                  45

Leu Tyr Arg Tyr Phe Trp Gln Pro Ala Arg Tyr Ala Val Pro Glu Trp
    50                  55                  60

Leu Asp Lys Leu Gly Phe His Leu Gln Thr Ala Gly Val Met Ala Ile
65                  70                  75                  80

Gly Pro Ser Trp Ile Val Phe Leu Thr Glu Arg
                85                  90

(2) INFORMATION FOR SEQ ID NO:61:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:61:

Glu Glu Ala Leu Leu Phe Gln Pro Val
1               5

(2) INFORMATION FOR SEQ ID NO:62:

(i) SEQUENCE CHARACTERISTICS:
        (A) LENGTH: 68 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:62:

Met Thr Gly Lys Asn Gly Arg Phe Val Leu Arg Arg Val Tyr Arg His
1               5                   10                  15

Leu Pro Leu Gly Trp Asp Tyr Ser Asn Ser Gly Val Val Thr Ile Leu
                20                  25                  30

Cys Tyr Gln Ser Ile Gly Asn Cys Phe Tyr Ser Gly Leu Ala Arg Met
            35                  40                  45

Arg Ser Gly Ser Tyr Met Val Gly Trp Gly Lys Glu Met Ala Asn Tyr
        50                  55                  60

Phe Leu Arg Lys
65

(2) INFORMATION FOR SEQ ID NO:63:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:63:

Cys Asn Lys Leu His Cys Arg Ser Val Pro Pro Phe Leu Ile Gly Lys
1               5                   10                  15

Arg Met Thr Met Arg Val Leu His Ala Leu Leu Val Leu Leu Pro Pro
                20                  25                  30

Pro Gln Arg Ile Leu Trp Pro Lys Thr Ser Leu Thr Glu Ile Ile Phe
            35                  40                  45

Met Glu His Leu Leu
        50

(2) INFORMATION FOR SEQ ID NO:64:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:64:

Val Leu Leu His Phe Leu
1               5

(2) INFORMATION FOR SEQ ID NO:65:

(i) SEQUENCE CHARACTERISTICS:
    (A) LENGTH: 17 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:65:

Arg Lys Leu Thr Ile Ser Tyr Pro Leu Glu Ile Leu Leu Ser His Ser
 1               5                  10                  15

Gly (2) INFORMATION FOR SEQ ID NO:66:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:66:

Leu Tyr Leu Arg Lys Ser Asn Lys Leu Arg Glu Phe His Met Leu Leu
 1               5                  10                  15

(2) INFORMATION FOR SEQ ID NO:67:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:67:

Ala Pro Leu Thr Val Arg Leu Lys Lys Ser Ser Glu Thr Pro Ile Val
 1               5                  10                  15

Ile Ser Val Asn Arg Lys Leu Ser Ser Asn Lys Asn
                20                  25

(2) INFORMATION FOR SEQ ID NO:68:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:68:

Arg Ala Cys Val Lys Ile Arg Trp Lys Lys Trp Lys Trp Asn Gly Trp
 1               5                  10                  15

Asn Ser Met (2) INFORMATION FOR SEQ ID NO:69:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:69:

Asn Ile Tyr Lys Thr Met Lys Ile Asn Phe Val His Trp Ser Ile Thr
 1               5                  10                  15

Gln Arg Ile Ile Leu Lys Ile Val
            20

(2) INFORMATION FOR SEQ ID NO:70:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:70:

Asn Arg Phe Cys Trp Pro Gly Ser Thr Asn Ser Arg
 1               5                  10

(2) INFORMATION FOR SEQ ID NO:71:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:71:

Thr Val Leu Cys Ala Ile Val Trp His Ala Arg Pro Arg Leu Trp Arg
 1               5                  10                  15

Lys Arg Glu Arg Phe Ile Cys Val Phe Ile Leu Lys Lys Arg His
            20                  25                  30

(2) INFORMATION FOR SEQ ID NO:72:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:72:

Cys Glu Lys Leu Leu Ala Ser Gly Leu Arg
 1               5                  10

(2) INFORMATION FOR SEQ ID NO:73:

(i) SEQUENCE CHARACTERISTICS:
            (A) LENGTH: 31 amino acids (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:73:

Leu Ser Ser Leu Val Ser Leu Pro Ile Arg Leu Asn Phe Pro Gln His
 1               5                  10                  15

Asp Met Pro Leu Asn Phe His Phe Leu Val Ile Ser Thr Arg Tyr
            20                  25                  30

(2) INFORMATION FOR SEQ ID NO:74:

(i) SEQUENCE CHARACTERISTICS:
        (A) LENGTH: 189 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:74:

Asn Gly Tyr Val Met Val Lys Ile Lys Glu Val Ala Met Asn Ile Lys
 1               5                  10                  15

Ile Asn Glu Ile Lys Met Thr Pro Pro Thr Ala Phe Thr Pro Gly Gln
            20                  25                  30

Val Ile Glu Glu Gln Glu Val Ile Ser Pro Ser Met Leu Ala Leu Gln
        35                  40                  45

Glu Leu Gln Glu Thr Thr Gly Ala Ala Leu Tyr Glu Thr Met Glu Glu
    50                  55                  60

Ile Gly Met Ala Leu Ser Gly Lys Leu Arg Glu Asn Tyr Lys Phe Thr
65                  70                  75                  80

Asp Ala Glu Lys Leu Glu Arg Arg Gln Gln Ala Leu Leu Arg Leu Ile
                85                  90                  95

Lys Gln Ile Gln Glu Asp Asn Gly Ala Thr Leu Arg Pro Leu Thr Glu
            100                 105                 110

Glu Asn Ser Asp Pro Asp Leu Gln Asn Ala Tyr Gln Ile Ile Ala Leu
        115                 120                 125

Ala Met Ala Leu Thr Ala Gly Gly Leu Ser Lys Lys Lys Lys Arg Asp
    130                 135                 140

Leu Gln Ser Gln Leu Asp Thr Leu Gln Arg Arg Arg Asp Gly Asn Leu
145                 150                 155                 160

Pro Phe Leu Val Tyr Trp Asn Leu Ala Lys Trp Ile Pro Tyr Ala Val
                165                 170                 175

Leu Ser Glu Ala Phe Tyr Ala Thr Gly Asp Arg Gln Arg
            180                 185

(2) INFORMATION FOR SEQ ID NO:75:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:75:

Asn Ala Leu Ile Ala Val Val Gln Thr Arg Gly Arg Leu Ala Gly Ser
  1               5                  10                  15
Leu (2) INFORMATION FOR SEQ ID NO:76:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:76:

Thr Gly Pro Tyr Phe Ala Lys Ser Ser Ser Leu
  1               5                  10

(2) INFORMATION FOR SEQ ID NO:77:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:77:

His Met His Arg Thr Leu Gly Ala Lys Ser Phe Gly Arg Ser Ile Ser
  1               5                  10                  15
Thr Phe Ala Ser Phe Ala Val Ile Pro Trp Pro
                 20                  25

(2) INFORMATION FOR SEQ ID NO:78:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:78:

Lys Arg Val Pro Ala
  1               5

(2) INFORMATION FOR SEQ ID NO:79:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:79:

Gly Val Asp Leu Pro Val Ala Ala

```
           1               5

(2) INFORMATION FOR SEQ ID NO:80:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:80:

Tyr Ile Thr Ala Ala Thr Thr Arg Tyr Tyr Leu
 1               5                  10

(2) INFORMATION FOR SEQ ID NO:81:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:81:

Ala Leu Ala Phe Gln
 1               5

(2) INFORMATION FOR SEQ ID NO:82:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:82:

Thr Tyr Arg Tyr Ser Phe Phe Ile Glu Asp Val Gln Ser Val Thr Pro
 1               5                  10                  15
Thr Thr (2) INFORMATION FOR SEQ ID NO:83:

(i) SEQUENCE CHARACTERISTICS:
          (A) LENGTH: 8 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:83:

Cys Ala Val Tyr Ala Asp Thr Arg
 1               5

(2) INFORMATION FOR SEQ ID NO:84:

(i) SEQUENCE CHARACTERISTICS:
```

(A) LENGTH: 5 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:84:

Arg Arg Arg Ser Thr
 1               5

(2) INFORMATION FOR SEQ ID NO:85:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:85:

Thr Asn Ser Arg Asn Ala Ser
 1               5

(2) INFORMATION FOR SEQ ID NO:86:

(i) SEQUENCE CHARACTERISTICS:
            (A) LENGTH: 35 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:86:

Ser Lys Asp Lys Ser Gly Phe Ile Leu Ile Pro Gly Phe Gln Tyr Leu
 1               5                  10                  15

Gly Lys Leu Ala Phe Trp Leu Ile Met Arg Arg Gln Asp Gly Leu Gly
                20                  25                  30

Ser His Tyr
         35

(2) INFORMATION FOR SEQ ID NO:87:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:87:

Tyr Ser Ala Phe Tyr Ser Ile Ser Arg Ile Ser
 1               5                  10

(2) INFORMATION FOR SEQ ID NO:88:

(i) SEQUENCE CHARACTERISTICS:
            (A) LENGTH: 14 amino acids
            (B) TYPE: amino acid (C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:88:

Thr Ala Phe Ser Asn Gln Tyr Val Leu Ala Ala Arg Thr Ile
1               5                   10

(2) INFORMATION FOR SEQ ID NO:89:

(i) SEQUENCE CHARACTERISTICS:
(A) LENGTH: 759 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:89:

Asn Tyr His Asn Gly Arg Ile Leu Leu Cys Gln Ile Leu Lys Gln Thr
1               5                   10                  15

Phe Leu Asp Glu Glu Leu Leu Phe Lys Ala Leu Ala Asn Trp Lys Pro
                20                  25                  30

Ala Ala Phe Gln Gly Ile Pro Gln Arg Leu Phe Leu Leu Arg Asp Gly
            35                  40                  45

Leu Ala Met Ser Cys Ser Pro Pro Leu Ser Ser Ser Ala Glu Leu Trp
    50                  55                  60

Leu Arg Leu His His Arg Gln Ile Lys Phe Xaa Gly Val Ala Met Arg
65                  70                  75                  80

Ser Trp Leu Gly Glu Gly Val Arg Ala Gln Gln Trp Leu Ser Val Cys
                85                  90                  95

Ala Gly Arg Gln Asp Met Val Leu Ala Thr Val Leu Leu Ile Ala Ile
            100                 105                 110

Val Met Met Leu Leu Pro Leu Pro Thr Trp Met Val Asp Ile Leu Ile
        115                 120                 125

Thr Ile Asn Leu Met Phe Ser Val Ile Leu Leu Ile Ala Ile Tyr
130                 135                 140

Leu Ser Asp Pro Leu Asp Leu Ser Val Phe Pro Ser Leu Leu Leu Ile
145                 150                 155                 160

Thr Thr Leu Tyr Arg Leu Ser Leu Thr Ile Ser Thr Ser Arg Leu Val
                165                 170                 175

Leu Leu Gln His Asn Ala Gly Asn Ile Val Asp Ala Phe Gly Lys Phe
            180                 185                 190

Val Val Gly Gly Asn Leu Thr Val Gly Leu Val Val Phe Thr Ile Ile
        195                 200                 205

Thr Ile Val Gln Phe Ile Val Ile Thr Lys Gly Ile Glu Arg Val Ala
210                 215                 220

Glu Val Ser Ala Arg Phe Ser Leu Asp Gly Met Pro Gly Lys Gln Met
225                 230                 235                 240

Ser Ile Asp Gly Asp Leu Arg Ala Gly Val Ile Asp Ala Asp His Ala
                245                 250                 255

Arg Thr Leu Arg Gln His Val Gln Gln Glu Ser Arg Phe Leu Gly Ala
            260                 265                 270

Met Asp Gly Ala Met Lys Phe Val Lys Gly Asp Thr Ile Ala Gly Ile
        275                 280                 285

```
Ile Val Val Leu Val Asn Ile Ile Gly Ile Ile Ala Ile Val
    290                 295             300
Gln Tyr Asp Met Ser Met Ser Glu Ala Val His Thr Tyr Ser Val Leu
305             310                 315                 320
Ser Ile Gly Asp Gly Leu Cys Gly Gln Ile Pro Ser Leu Leu Ile Ser
                325                 330              335
Leu Ser Ala Gly Ile Ile Val Thr Arg Val Pro Gly Glu Lys Arg Gln
            340                 345             350
Asn Leu Ala Thr Glu Leu Ser Ser Gln Ile Ala Arg Gln Pro Gln Ser
            355                 360             365
Leu Ile Leu Thr Ala Val Val Leu Met Leu Leu Ala Leu Ile Pro Gly
        370              375             380
Phe Pro Phe Ile Thr Leu Ala Phe Phe Ser Ala Leu Leu Ala Leu Pro
385             390                 395                 400
Ile Ile Leu Ile Arg Arg Lys Ser Val Val Ser Ala Asn Gly Val
                405             410             415
Glu Ala Pro Glu Lys Asp Ser Met Val Pro Gly Ala Cys Pro Leu Ile
            420                 425             430
Leu Arg Leu Ser Pro Thr Leu His Ser Ala Asp Leu Ile Arg Asp Ile
        435             440             445
Asp Ala Met Arg Trp Phe Leu Phe Glu Asp Thr Gly Val Pro Leu Pro
        450             455             460
Glu Val Asn Ile Glu Val Leu Pro Glu Pro Thr Glu Lys Leu Thr Val
465             470             475                 480
Leu Leu Tyr Gln Glu Pro Val Phe Ser Leu Ser Ile Pro Ala Gln Ala
            485             490             495
Asp Tyr Leu Leu Ile Gly Ala Asp Ala Ser Val Val Gly Asp Ser Gln
            500             505             510
Thr Leu Pro Asn Gly Met Gly Gln Ile Cys Trp Leu Thr Lys Asp Met
        515             520             525
Ala His Lys Ala Gln Gly Phe Gly Leu Asp Val Phe Ala Gly Ser Gln
        530             535             540
Arg Ile Ser Ala Leu Leu Lys Cys Val Leu Leu Arg His Met Gly Glu
545             550             555                 560
Phe Ile Gly Val Gln Glu Thr Arg Tyr Leu Met Asn Ala Met Glu Lys
                565             570             575
Asn Tyr Ser Glu Leu Val Lys Glu Leu Gln Arg Gln Leu Pro Ile Asn
            580             585             590
Lys Ile Ala Glu Thr Leu Gln Arg Leu Val Ser Glu Arg Val Ser Ile
            595             600             605
Arg Asp Leu Arg Leu Ile Phe Gly Thr Leu Ile Asp Trp Ala Pro Arg
        610             615             620
Glu Lys Asp Val Leu Met Leu Thr Glu Tyr Val Arg Ile Ala Leu Arg
625             630             635                 640
Arg His Ile Leu Arg Arg Leu Asn Pro Glu Gly Lys Pro Leu Pro Ile
                645             650             655
Leu Arg Ile Gly Glu Gly Ile Glu Asn Leu Val Arg Glu Ser Ile Arg
            660             665             670
Gln Thr Ala Met Gly Thr Tyr Thr Ala Leu Ser Ser Arg His Lys Thr
        675             680             685
Gln Ile Leu Gln Leu Ile Glu Gln Ala Leu Lys Gln Ser Ala Lys Leu
        690             695             700
Phe Ile Val Thr Ser Val Asp Thr Arg Arg Phe Leu Arg Lys Ile Thr
```

```
                     705                 710                 715                 720
Glu Ala Thr Leu Phe Asp Val Pro Ile Leu Ser Trp Gln Glu Leu Gly
                             725                 730                 735

Glu Glu Ser Leu Ile Gln Val Val Gly Ser Ile Asp Leu Ser Glu Glu
                 740                 745                 750

Glu Leu Ala Asp Asn Glu Glu
        755
```

(2) INFORMATION FOR SEQ ID NO:90:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:90:

```
Ile Asp Ala Thr Ser Glu Ala Glu Ile Ser Ala Pro Arg Trp Leu Leu
 1                   5                  10                  15

Ser Met Gly Pro Asn Ser Gly Cys Gln Arg Asn Val Val Lys Cys Val
                 20                  25                  30

Val Ala Trp Gly Ile Tyr Gly Arg Val Val Leu Tyr Lys Ala Trp Arg
             35                  40                  45

Arg Thr Cys
        50
```

(2) INFORMATION FOR SEQ ID NO:91:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:91:

```
Ser Arg Gly Asp
 1
```

(2) INFORMATION FOR SEQ ID NO:92:

(i) SEQUENCE CHARACTERISTICS:
        (A) LENGTH: 257 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:92:

```
Trp Gln Gln Ser Phe Ala Ile Ser Phe Tyr Glu Tyr Asn Arg Ala Ser
 1                   5                  10                  15

Leu Arg Ala Ala Ser Asp Gly Leu Lys Arg Arg His Gln Val Pro Val
                 20                  25                  30

Gly Glu Ala Leu Leu Gly Arg Val Ile Asp Gly Phe Gly Arg Pro Leu
             35                  40                  45
```

```
Asp Gly Arg Glu Leu Pro Asp Val Cys Trp Lys Asp Tyr Asp Ala Met
 50                  55                  60

Pro Pro Pro Ala Met Val Arg Gln Pro Ile Thr Gln Pro Leu Met Thr
 65                  70                  75                  80

Gly Ile Arg Ala Ile Asp Ser Val Ala Thr Cys Gly Glu Gly Gln Arg
                 85                  90                  95

Val Gly Ile Phe Ser Ala Pro Gly Val Gly Lys Ser Thr Leu Leu Ala
                100                 105                 110

Met Leu Cys Asn Ala Pro Asp Ala Asp Ser Asn Val Leu Val Leu Ile
                115                 120                 125

Gly Glu Arg Gly Arg Glu Val Arg Glu Phe Ile Asp Phe Thr Leu Ser
130                 135                 140

Glu Glu Thr Arg Lys Arg Cys Val Ile Val Val Ala Thr Ser Asp Arg
145                 150                 155                 160

Pro Ala Leu Glu Arg Val Arg Ala Leu Phe Val Ala Thr Thr Ile Ala
                165                 170                 175

Glu Phe Phe Arg Asp Asn Gly Lys Arg Val Val Leu Leu Ala Asp Ser
                180                 185                 190

Leu Thr Arg Tyr Ala Arg Ala Ala Arg Lys Ser Leu Trp Arg Arg Arg
                195                 200                 205

Asp Arg Gly Phe Trp Arg Ile Ser Pro Gly Val Phe Ser Ala Leu Pro
210                 215                 220

Arg Leu Leu Glu Arg Thr Gly Met Gly Glu Lys Gly Ser Ile Thr Ala
225                 230                 235                 240

Phe Tyr Thr Val Leu Val Glu Gly Asp Asp Met Asn Glu Ala Val Gly
                245                 250                 255

Gly (2) INFORMATION FOR SEQ ID NO:93:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:93:

Ser Pro Phe Thr Ala
 1               5

(2) INFORMATION FOR SEQ ID NO:94:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:94:

Trp Thr Tyr Cys Thr Ile Pro Thr Ala Cys Arg Glu Gly Ala Leu Ser
 1               5                  10                  15

Cys His
```

(2) INFORMATION FOR SEQ ID NO:95:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:95:

```
Arg Val Gly Asn Ala Gln Pro Arg Phe Ser Ser Arg Tyr Gln Pro
 1               5                  10                  15
```

(2) INFORMATION FOR SEQ ID NO:96:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:96:

```
Ala Ser Ser Thr Gly Gly Asp Ile Ala Thr Val Pro Gly Ala Leu Pro
 1               5                  10                  15
Gly Gly
```

(2) INFORMATION FOR SEQ ID NO:97:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:97:

```
Thr Val Asn Thr His Trp Gly Ile Pro Ala Arg Ser
 1               5                  10
```

(2) INFORMATION FOR SEQ ID NO:98:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:98:

```
Tyr Leu Ser Gly Tyr Leu His Ile Phe Ala Thr Lys
 1               5                  10
```

(2) INFORMATION FOR SEQ ID NO:99:

(i) SEQUENCE CHARACTERISTICS:
        (A) LENGTH: 59 amino acids
        (B) TYPE: amino acid
        (C) STRANDEDNESS: single (D) TOPOLOGY: linear (ii) MOLECULE TYPE: protein (iii) HYPOTHETICAL: NO (xi) SEQUENCE DESCRIPTION: SEQ ID NO:99:

Ser Met Arg Thr Arg Ala Thr Tyr Arg Lys Ile Thr Pro Asn Thr His
 1               5                  10                  15

Arg Val Ile Met Glu Thr Leu Leu Glu Ile Ile Ala Arg Leu Lys Ser
                20                  25                  30

Asn Tyr Ala Ala Ser Leu Pro Tyr Leu Ile Ser Ser Asn Arg Arg Leu
            35                  40                  45

Leu Arg Asn Ser Arg Phe Ala Arg Arg Ala Leu
        50                  55

(2) INFORMATION FOR SEQ ID NO:100:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:100:

Gln Cys Leu Pro Asp
 1               5

(2) INFORMATION FOR SEQ ID NO:101:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:101:

Trp Ala Gly Lys Val Arg Tyr Leu Val Ile Tyr Cys Trp Ile Arg Asn
 1               5                  10                  15

Asn Lys Trp Pro Gly Tyr Ser Leu Arg Arg Arg Ala Phe
                20                  25

(2) INFORMATION FOR SEQ ID NO:102:

(i) SEQUENCE CHARACTERISTICS:
            (A) LENGTH: 45 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:102:

Arg Asn Gly Lys Gln Leu Glu Asn Gln Tyr Gln Gln Leu Val Ser Arg
 1               5                  10                  15

Arg Ser Glu Leu Gln Lys Asn Phe Asn Ala Leu Met Lys Lys Glu
                20                  25                  30

Lys Ile Thr Met Val Leu Ser Asp Ala Tyr Tyr Gln Ser
    35                  40                  45

(2) INFORMATION FOR SEQ ID NO:103:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:103:

Gly Lys Ser Trp Val Ala Met Pro Val Leu Ser Gly
 1               5                  10

(2) INFORMATION FOR SEQ ID NO:104:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:104:

Arg Gly Gly Gly Gly Thr Tyr Gly Leu
 1               5

(2) INFORMATION FOR SEQ ID NO:105:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:105:

Thr Thr His Ala Pro Gly Ile Thr His Trp
 1               5                  10

(2) INFORMATION FOR SEQ ID NO:106:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:106:

Ser Ser Cys Ser Ile Glu
 1               5

(2) INFORMATION FOR SEQ ID NO:107:

(i) SEQUENCE CHARACTERISTICS:
        (A) LENGTH: 10 amino acids

```
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:107:

Glu Arg Gly Phe His Ala Thr Leu Ser Cys
 1               5                  10

(2) INFORMATION FOR SEQ ID NO:108:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:108:

Trp Arg Leu Ser
 1

(2) INFORMATION FOR SEQ ID NO:109:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:109:

Arg Cys Arg Val
 1

(2) INFORMATION FOR SEQ ID NO:110:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:110:

Ile Arg Gly Ala Asn Pro Val Lys Asn Gln Cys Pro Ser Ser
 1               5                  10

(2) INFORMATION FOR SEQ ID NO:111:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: protein (iii) HYPOTHETICAL: NO
```

(xi) SEQUENCE DESCRIPTION: SEQ ID NO:111:

Asn Leu Pro Phe Asp Glu Ser Ala Lys Ala Val Ala Gly Val Ser Val
 1               5                  10                  15

Ala Ala Tyr Gly Val Tyr Asn Phe Pro Gly Asp Ile Leu Cys
            20                  25                  30

(2) INFORMATION FOR SEQ ID NO:112:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:112:

Arg Met Lys Ser Val Arg Gly Trp Arg Tyr Phe Gln Arg Lys Ala Leu
 1               5                  10                  15

Pro Leu Val Ser
            20

(2) INFORMATION FOR SEQ ID NO:113:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:113:

Val Cys Asn Asn Ile Gln Tyr Ser Lys Gly His Tyr Leu Pro
 1               5                  10

(2) INFORMATION FOR SEQ ID NO:114:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:114:

Ile Ile Ile Met Ser Trp Val Gly Cys Gly Leu Gln Asn Asn Ala Gly
 1               5                  10                  15

Ser Ala Gly Val Lys Gly
            20

(2) INFORMATION FOR SEQ ID NO:115:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:115:

Leu Ala Pro Leu Ile Asp Arg Leu Ser Ile Leu Asn Cys Tyr Met Glu
1               5                   10                  15

(2) INFORMATION FOR SEQ ID NO:116:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:116:

Leu Asn Gly Gly Trp Arg Arg Tyr Cys Lys Pro Val Met Gln Pro Ser
1               5                   10                  15

Val Arg Thr Ser Arg Gln His Pro Ala Val Ile Tyr His Ile Ser
            20                  25                  30

(2) INFORMATION FOR SEQ ID NO:117:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:117:

Arg Cys Ile Leu Asn Gly Gln Leu Lys Ser Met Ser Ser Ile Ala Leu
1               5                   10                  15

Phe Leu His Gly Gln Arg Val Phe Cys Ala Ile
            20                  25

(2) INFORMATION FOR SEQ ID NO:118:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:118:

Ser Glu Ser Phe Leu Leu Ser Asp Asn Arg Phe Ile Leu Pro Leu Leu
1               5                   10                  15

Trp (2) INFORMATION FOR SEQ ID NO:119:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:119:

Ser Leu Tyr Ile Gln Ala Gly Ala Ser Leu His
1               5                   10

(2) INFORMATION FOR SEQ ID NO:120:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:120:

Ser Asn Leu Ser Leu Ser Lys Ser Ala Trp Ala Phe Gly Phe Ile Ala
1               5                   10                  15

Ser Ala Thr Ser Asp Ser Val Phe Leu Leu Phe Asn Tyr Leu Gly Glu
            20                  25                  30

Ser Thr Gln Gly Cys Cys
        35

(2) INFORMATION FOR SEQ ID NO:121:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:121:

Gln Arg Ile Thr Arg
1               5

(2) INFORMATION FOR SEQ ID NO:122:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:122:

Asn Leu Thr Asn
1

(2) INFORMATION FOR SEQ ID NO:123:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:123:

Ser Arg Ile Ser Lys Arg Tyr Leu Arg Gln Gly Ala Gln Cys Gln Arg
1               5                   10                  15

Val Thr Glu Arg Leu Gln Ser Asn Leu Ser Arg Tyr His Asn Arg Cys
            20                  25                  30

Ser Leu Arg Ser Asp Val Arg Val Trp Lys Leu Asp Asn Tyr Asp Asn
            35                  40                  45

Leu Lys Arg Gly Thr Phe Cys Leu
        50              55

(2) INFORMATION FOR SEQ ID NO:124:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:124:

Val Asp Val Leu Arg Gln Arg
1               5

(2) INFORMATION FOR SEQ ID NO:125:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:125:

Met Thr Val Leu Leu Gly Lys Val Ser
1               5

(2) INFORMATION FOR SEQ ID NO:126:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:126:

Leu Pro Val Ala Met Asn Leu Trp Cys Val Leu His Val Gly Ile Phe
1               5                   10                  15

Ala Lys Ile Gln Arg Lys Pro Asp Lys Lys Asn Asn Met Arg Thr Ile
            20                  25                  30

(2) INFORMATION FOR SEQ ID NO:127:

(i) SEQUENCE CHARACTERISTICS:
        (A) LENGTH: 225 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:127:

```
Arg Ser Arg Ser Cys His Glu Arg Tyr Ser Met Ser Leu Pro Asp Ser
 1               5                  10                  15

Pro Leu Gln Leu Ile Gly Ile Leu Phe Leu Leu Ser Ile Leu Pro Leu
            20                  25                  30

Ile Ile Val Met Gly Thr Ser Phe Leu Lys Leu Ala Val Val Phe Ser
        35                  40                  45

Ile Leu Arg Asn Ala Leu Gly Ile Gln Gln Val Pro Pro Asn Ile Ala
    50                  55                  60

Leu Tyr Gly Leu Ala Leu Val Leu Ser Leu Phe Ile Met Gly Pro Thr
65                  70                  75                  80

Leu Leu Ala Val Lys Glu Arg Trp His Pro Val Gln Val Ala Gly Ala
                85                  90                  95

Pro Phe Trp Thr Ser Glu Trp Asp Ser Lys Ala Leu Ala Pro Tyr Arg
            100                 105                 110

Gln Phe Leu Gln Lys Asn Ser Glu Gln Lys Glu Ala Asn Tyr Phe Arg
        115                 120                 125

Asn Leu Ile Lys Arg Thr Trp Pro Glu Asp Ile Lys Arg Lys Ile Lys
    130                 135                 140

Pro Asp Ser Leu Leu Ile Leu Ile Pro Ala Phe Thr Val Ser Gln Leu
145                 150                 155                 160

Thr Gln Ala Phe Arg Ile Gly Leu Leu Ile Tyr Leu Pro Phe Leu Ala
                165                 170                 175

Ile Asp Leu Leu Ile Ser Asn Ile Leu Leu Ala Met Gly Met Met Met
            180                 185                 190

Val Ser Pro Met Thr Ile Ser Leu Pro Phe Lys Leu Leu Ile Phe Leu
        195                 200                 205

Leu Ala Gly Gly Trp Asp Leu Thr Leu Ala Gln Leu Val Gln Ser Phe
    210                 215                 220

Ser
225
```

(2) INFORMATION FOR SEQ ID NO:128:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:128:

```
Met Ile Leu Asn
 1
```

(2) INFORMATION FOR SEQ ID NO:129:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:129:

Arg Asn Phe Tyr Gly Ser Ser Phe Leu Arg Leu Cys Arg
 1               5                  10

(2) INFORMATION FOR SEQ ID NO:130:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:130:

Cys Trp Trp His Arg
 1               5

(2) INFORMATION FOR SEQ ID NO:131:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:131:

Leu Val Ser Ser
 1

(2) INFORMATION FOR SEQ ID NO:132:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:132:

Ala Leu Phe Arg Pro
 1               5

(2) INFORMATION FOR SEQ ID NO:133:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:133:

Leu Lys Tyr Arg Thr Lys Arg Tyr Ser Ser
 1               5                  10

(2) INFORMATION FOR SEQ ID NO:134:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:134:

```
Leu Asn Tyr Trp Gln Leu Gln
 1               5
```

(2) INFORMATION FOR SEQ ID NO:135:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:135:

```
Trp Ser Ala Thr His Gly Leu Ala Val Ser Cys
 1               5                  10
```

(2) INFORMATION FOR SEQ ID NO:136:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:136:

```
Ile Ile Pro Gly Arg
 1               5
```

(2) INFORMATION FOR SEQ ID NO:137:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:137:

```
Cys Tyr Glu Leu Glu Ser Met Val Glu Trp His Asn Arg
 1               5                  10
```

(2) INFORMATION FOR SEQ ID NO:138:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:138:

Met Ser Gly Leu Leu His Trp Leu Trp Leu Leu Phe Asp His
 1               5                   10

(2) INFORMATION FOR SEQ ID NO:139:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:139:

Ala Phe Leu Tyr Tyr Phe Pro Tyr
 1               5

(2) INFORMATION FOR SEQ ID NO:140:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:140:

Lys Val Ala Val
 1

(2) INFORMATION FOR SEQ ID NO:141:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:141:

Gly Pro His Phe Tyr Val Met Ala Cys Leu Cys His Leu Pro Phe Arg
 1               5                   10                  15

Tyr Tyr Gln Ser Phe Thr Ser Arg Arg Leu
                20                  25

(2) INFORMATION FOR SEQ ID NO:142:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:142:

```
Cys Ile Leu Val Lys Ile Thr Val Gly
  1               5
```

(2) INFORMATION FOR SEQ ID NO:143:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:143:

```
Ser Leu Glu Arg
  1
```

(2) INFORMATION FOR SEQ ID NO:144:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:144:

```
Leu Leu Val Phe Gln Leu Gly Phe Val Arg Arg Phe Pro Phe Gly Pro
  1               5                  10                  15

Leu Ile Trp Arg Gly Phe Cys Leu Ile Leu Tyr Val Ala Arg Gln Trp
                 20                  25                  30

Val Arg Tyr Ser Ile Leu Gln
                 35
```

(2) INFORMATION FOR SEQ ID NO:145:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:145:

```
Lys Leu Lys Pro His Phe Leu Ala Cys Phe Ser Ala Ser Ser Cys Val
  1               5                  10                  15

Leu Phe Ser Leu
                 20
```

(2) INFORMATION FOR SEQ ID NO:146:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:146:

Ala Ala Ala Trp Ser Leu Tyr
 1               5

(2) INFORMATION FOR SEQ ID NO:147:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:147:

Thr Phe Cys Met Ser His Ile Asn Ile Tyr His Gln Gly Val Leu Tyr
 1               5                  10                  15

Tyr Leu Thr Ser Asn Phe
            20

(2) INFORMATION FOR SEQ ID NO:148:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:148:

Asn Ile Ser Arg Gln Ser Gly Glu Arg Phe Ile Asn Tyr Val Ser Ala
 1               5                  10                  15

Ser Leu Phe Leu Pro
            20

(2) INFORMATION FOR SEQ ID NO:149:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:149:

Tyr Val Trp Tyr
 1

(2) INFORMATION FOR SEQ ID NO:150:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:150:

Pro Ile Trp Leu
1

(2) INFORMATION FOR SEQ ID NO:151:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:151:

Ile Gly Arg His Asn Asn
1               5

(2) INFORMATION FOR SEQ ID NO:152:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:152:

Met Cys Phe Ser Ser Gln Cys Arg Ser Lys Val Tyr Trp Phe Tyr
1               5                   10                  15

(2) INFORMATION FOR SEQ ID NO:153:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:153:

Xaa Pro Asp Leu Ile Pro Leu Cys Ser Ser Ser Leu Phe Gly
1               5                   10

(2) INFORMATION FOR SEQ ID NO:154:

(i) SEQUENCE CHARACTERISTICS:
        (A) LENGTH: 225 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:154:

Ile Leu Tyr Leu Ser Lys Arg Leu Val Ser Ile Cys Met Ser Glu Lys
1               5                   10                  15

Thr Glu Gln Pro Thr Glu Lys Lys Leu Arg Asp Gly Arg Lys Glu Gly
                20                  25                  30

Gln Val Val Lys Ser Ile Glu Ile Thr Ser Leu Phe Gln Leu Ile Ala
        35                  40                  45

```
Leu Tyr Leu Tyr Phe His Phe Thr Glu Lys Met Ile Leu Ile Leu
         50                  55                  60

Ile Glu Ser Ile Thr Phe Thr Leu Gln Leu Val Asn Lys Pro Phe Ser
 65                  70                  75                  80

Tyr Ala Leu Thr Gln Leu Ser His Ala Leu Ile Glu Ser Leu Thr Ser
                 85                  90                  95

Ala Leu Leu Phe Leu Gly Ala Gly Val Ile Val Ala Thr Val Gly Ser
                100                 105                 110

Val Phe Leu Gln Val Gly Val Val Ile Ala Ser Lys Ala Ile Gly Phe
                115                 120                 125

Lys Ser Glu His Ile Asn Pro Val Ser Asn Phe Lys Gln Ile Phe Ser
130                 135                 140

Leu His Ser Val Val Glu Leu Cys Lys Ser Ser Leu Lys Val Ile Met
145                 150                 155                 160

Leu Ser Leu Ile Phe Ala Phe Phe Phe Tyr Tyr Tyr Ala Ser Thr Phe
                165                 170                 175

Arg Ala Leu Pro Tyr Cys Gly Leu Ala Cys Gly Val Leu Val Val Ser
                180                 185                 190

Ser Leu Ile Lys Trp Leu Trp Val Gly Val Met Val Phe Tyr Ile Val
                195                 200                 205

Val Gly Ile Leu Asp Tyr Ser Phe Gln Tyr Tyr Lys Ile Arg Lys Ala
210                 215                 220

Ile
225
```

(2) INFORMATION FOR SEQ ID NO:155:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:155:

```
Val Lys Met Thr
 1
```

(2) INFORMATION FOR SEQ ID NO:156:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:156:

```
Asn Arg Ser Ile Lys Ile Trp Arg Ala Thr Leu Lys
 1               5                  10
```

(2) INFORMATION FOR SEQ ID NO:157:

(i) SEQUENCE CHARACTERISTICS:
        (A) LENGTH: 8 amino acids
        (B) TYPE: amino acid (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:157:

Arg Arg Gly Val Gly Asn Ala Glu
 1               5

(2) INFORMATION FOR SEQ ID NO:158:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:158:

Asn Thr Lys Trp Glu Phe Ser Ser Ile Cys
 1               5                   10

(2) INFORMATION FOR SEQ ID NO:159:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:159:

Thr Ile Cys Cys Gly Ser Ala
 1               5

(2) INFORMATION FOR SEQ ID NO:160:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:160:

Ser Asn Ala Tyr Cys Gly Leu Ser Trp Leu Ser Ser His Arg Tyr Ala
 1               5                   10                  15

Asn Thr Thr Arg Pro Gly Lys Arg Gln
                20                  25

(2) INFORMATION FOR SEQ ID NO:161:

(i) SEQUENCE CHARACTERISTICS:
          (A) LENGTH: 7 amino acids
          (B) TYPE: amino acid
          (C) STRANDEDNESS: single
          (D) TOPOLOGY: linear (ii) MOLECULE TYPE: protein -continued (iii) HYPOTHETICAL: NO (xi) SEQUENCE DESCRIPTION: SEQ ID NO:161:

Thr Gln Leu His Pro Arg Cys
 1               5

(2) INFORMATION FOR SEQ ID NO:162:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:162:

Ala Gly Pro Leu Ile Ile Phe
 1               5

(2) INFORMATION FOR SEQ ID NO:163:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:163:

Ser Gly Thr Arg Arg
 1               5

(2) INFORMATION FOR SEQ ID NO:164:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:164:

Thr Arg Cys Ser Leu Val Thr Tyr Gly Asp Glu Asp Arg Leu Cys Ala
 1               5                  10                  15

Phe Tyr Arg Asn Thr Ile Asn Ala Phe Gly Met Leu Leu Gln Ala Thr
                20                  25                  30

Ala Lys Val Lys Arg Val Ile Ala Tyr Arg Ala Val Leu Asp Asp Lys
            35                  40                  45

Gly Glu Arg Leu Lys Ile Ile Ala Phe Ser Leu Ala Gln Ala Pro Asp
        50                  55                  60

Ser Val Leu
 65

(2) INFORMATION FOR SEQ ID NO:165:

(i) SEQUENCE CHARACTERISTICS:
        (A) LENGTH: 23 amino acids
        (B) TYPE: amino acid
        (C) STRANDEDNESS: single (D) TOPOLOGY: linear (ii) MOLECULE TYPE: protein (iii) HYPOTHETICAL: NO (xi) SEQUENCE DESCRIPTION: SEQ ID NO:165:

Trp Ile Gly Ala Ser Glu Trp Thr Arg Thr Thr Arg Pro Pro Pro Cys
  1               5                  10                  15

Gln Gly Gly Ala Leu Thr Asn
                 20

(2) INFORMATION FOR SEQ ID NO:166:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:166:

Ala Met Asn Gly Asn Val Val Gly Asp Asn Gly Asp Glu Tyr
  1               5                  10

(2) INFORMATION FOR SEQ ID NO:167:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:167:

Arg His Asn Arg Asn Glu Ala Arg Gly Lys Ser Gln Phe Ser Ser
  1               5                  10                  15

(2) INFORMATION FOR SEQ ID NO:168:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:168:

Asn His Leu Ile Ala Val Glu Ile Cys Asn Met Ser Arg Lys
  1               5                  10

(2) INFORMATION FOR SEQ ID NO:169:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:169:

Pro Pro Cys Asp Gly Tyr Arg Arg Ile Ile Gly Ala Arg Cys Lys Met
 1               5                  10                  15

Met Ala Asp Gly
            20

(2) INFORMATION FOR SEQ ID NO:170:

(i) SEQUENCE CHARACTERISTICS:
        (A) LENGTH: 37 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:170:

Arg Ile Arg Ser Ile Ile Asn Thr Ala Ala Glu Val Arg Pro Met Met
 1               5                  10                  15

Asn Pro Ile Gln Lys Pro Ala Gly Pro Ile Arg Ser Thr Thr Lys Ser
            20                  25                  30

Val Asn Ala Arg Ile
            35

(2) INFORMATION FOR SEQ ID NO:171:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:171:

Pro Leu Gly Lys Pro Asn Thr Gln
 1               5

(2) INFORMATION FOR SEQ ID NO:172:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:172:

Ala Val Lys Val Ile Lys Lys Met Glu Arg Val Ser Leu
 1               5                  10

(2) INFORMATION FOR SEQ ID NO:173:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:173:

Pro Arg Arg Ile Pro Leu Pro Ile Thr Cys Ile Glu Ser Glu Ile Trp
  1               5                  10                  15

(2) INFORMATION FOR SEQ ID NO:174:

(i) SEQUENCE CHARACTERISTICS:
        (A) LENGTH: 43 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:174:

Thr Ala Ala Ser Ser Ile Asn Cys Gly Lys Arg His Asp Leu Arg Val
  1               5                  10                  15

Val Ile Val Glu Gln Ser Asn Met Leu Thr Gln Ser Asn Gly Lys Asn
                 20                  25                  30

Ser Gly Asn His Ser His Thr Asn Ala Asp Ala
             35                  40

(2) INFORMATION FOR SEQ ID NO:175:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:175:

Thr Gly Thr Arg Cys Val Cys Ala Ser Ser Val Glu Pro Trp Pro Arg
  1               5                  10                  15

Pro Ile Thr His Ser Asn Arg Tyr Arg Arg Ser Gln Arg His Arg Gln
                 20                  25                  30

Tyr Glu His Gln Arg Ala Lys Val Lys Arg Asn Leu Met Thr Gly Asp
             35                  40                  45

Ile His Asn Thr
             50

(2) INFORMATION FOR SEQ ID NO:176:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:176:

Trp Arg Asn Gln Gln Arg Asn Asp Arg Lys
  1               5                  10

(2) INFORMATION FOR SEQ ID NO:177:

(i) SEQUENCE CHARACTERISTICS:

(A) LENGTH: 19 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:177:

Arg His Phe Lys Glu Gln Pro Ala Gln Ser Ala Thr Pro Val Glu Ser
 1               5                  10                  15
Gly Ala Ser (2) INFORMATION FOR SEQ ID NO:178:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:178:

Arg Arg Tyr Arg Val Cys Gln Ser Leu Phe His Tyr Glu Tyr His Ala
 1               5                  10                  15
Leu Asn Ala Arg Val
            20

(2) INFORMATION FOR SEQ ID NO:179:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:179:

Cys Lys Lys Ala Trp Arg
 1               5

(2) INFORMATION FOR SEQ ID NO:180:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:180:

Thr Ser Pro Asn Arg Pro Pro Gln Ser Gln Arg Arg Ser Arg Tyr Arg
 1               5                  10                  15
Arg Val Pro Ala Tyr Gln Asn Gly His Arg
            20                  25

(2) INFORMATION FOR SEQ ID NO:181:

(i) SEQUENCE CHARACTERISTICS:

(A) LENGTH: 61 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:181:

Lys Tyr Ser Ser Pro Glu Tyr Ser Pro Ala Gly Pro Lys Ile Pro Ser
 1               5                  10                  15

Pro Tyr Pro Val Trp Phe Trp Pro Asp Leu Arg Thr Gly Phe Ala Leu
             20                  25                  30

Pro Glu Arg Lys Gly Ile Leu Arg Pro Thr Ala Ala Arg Glu Asp Asn
         35                  40                  45

Pro Arg Leu Tyr Arg Pro Ala Pro Asp Gln Tyr Tyr Ala
     50                  55                  60

(2) INFORMATION FOR SEQ ID NO:182:

(i) SEQUENCE CHARACTERISTICS:
            (A) LENGTH: 36 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:182:

Cys Ile Arg His Ser Thr Gly Arg Ser Ser Pro Ala Arg Arg Gln Ser
 1               5                  10                  15

Pro Pro Ala Arg Thr Leu Val Glu Pro Asp Ala Arg Tyr Ala His Asp
             20                  25                  30

Gly Arg Ser His
         35

(2) INFORMATION FOR SEQ ID NO:183:

(i) SEQUENCE CHARACTERISTICS:
            (A) LENGTH: 59 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:183:

Val Ala Gln Ser Gln Ala Ser Arg Pro Ala Val Ser Arg Asp Gln Thr
 1               5                  10                  15

Lys Trp Arg Glu Ala Asp Arg Gly Ala Asp Ser Asp Gly Ser His Val
             20                  25                  30

Arg Ser Ala Ile Ala Ser Arg His Asp Gly Ile Asp Glu Ser Ile Ala
         35                  40                  45

Val Tyr Thr Thr Cys Ala Arg Ile Thr Gly Ile
     50                  55

(2) INFORMATION FOR SEQ ID NO:184:

(i) SEQUENCE CHARACTERISTICS:
            (A) LENGTH: 25 amino acids
            (B) TYPE: amino acid (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:184:

Thr Leu Ile Thr Asp Ala Leu His Trp Tyr Thr Ser Ala Arg Ile His
 1               5                  10                  15

Leu Leu Phe Cys Cys Tyr Met Lys Asp
            20                  25

(2) INFORMATION FOR SEQ ID NO:185:

(i) SEQUENCE CHARACTERISTICS:
          (A) LENGTH: 18 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:185:

Lys Ala Ala Glu Val Ala Ala Lys Arg Asn Ser Arg Gly Asn Phe Ser
 1               5                  10                  15

Leu Leu (2) INFORMATION FOR SEQ ID NO:186:

(i) SEQUENCE CHARACTERISTICS:
          (A) LENGTH: 38 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:186:

Arg Gly Ile Thr Ile Ser Pro Val Lys Lys Gln Leu Leu Thr Ala His
 1               5                  10                  15

Cys Trp Gln Ala Val Phe Pro Pro Ala Ile Val Leu Asn Ser Ser Ala
            20                  25                  30

Phe Ile Tyr Phe Arg Ser
            35

(2) INFORMATION FOR SEQ ID NO:187:

(i) SEQUENCE CHARACTERISTICS:
          (A) LENGTH: 16 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:187:

Arg Tyr Val Tyr Gly Asp Arg Thr Gly Tyr Arg Glu Thr Gly Ile Asp
 1               5                  10                  15

(2) INFORMATION FOR SEQ ID NO:188:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:188:

Cys Arg Thr Glu Pro Gly Ala Asn
  1               5

(2) INFORMATION FOR SEQ ID NO:189:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:189:

Thr Ile Ala Glu Arg
  1               5

(2) INFORMATION FOR SEQ ID NO:190:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:190:

Ser Ile His Gln
  1

(2) INFORMATION FOR SEQ ID NO:191:

(i) SEQUENCE CHARACTERISTICS:
            (A) LENGTH: 63 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:191:

Arg Gln Cys Phe Ile Thr Ala Gly Tyr Val Asp Gln Thr Asn Gly Leu
  1               5                  10                  15

Tyr Ala Val Asn Gly Arg Arg Arg Leu Ser Cys Gln Asn Ile Thr Ala
                 20                  25                  30

Gln His Ala Lys Arg Leu Ile Ser Trp Ile Thr Trp His Glu Gly Ser
             35                  40                  45

Ser Tyr Ser Ile Ser Tyr Cys Pro Tyr Val Leu Ser Tyr Gly Met
         50                  55                  60

(2) INFORMATION FOR SEQ ID NO:192:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:192:

Cys Gly Ser Leu Ser Leu Ile Ala Arg Arg
  1               5                  10

(2) INFORMATION FOR SEQ ID NO:193:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:193:

Ser Glu Ser Asn Ala Gly Ile Thr Tyr Ala Ala Ser Tyr
  1               5                  10

(2) INFORMATION FOR SEQ ID NO:194:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:194:

Cys Glu Lys Lys Gln Glu Glu Asp Gly Val Thr Leu Arg Val Glu Gln
  1               5                  10                  15

Ser Ala Val Tyr
           20

(2) INFORMATION FOR SEQ ID NO:195:

(i) SEQUENCE CHARACTERISTICS:
            (A) LENGTH: 36 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:195:

Gly Tyr Leu Asp Leu Thr Val Ile Arg Ile Gly Gln Phe Thr Thr Ala
  1               5                  10                  15

Asp Lys Met Phe Pro Ala Asn Gln Leu Val Val Ser Pro Gln Glu Glu
                 20                  25                  30

Gln Ala Glu Asp
           35

(2) INFORMATION FOR SEQ ID NO:196:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:196:

Phe Phe Lys Arg Thr Lys Asn
1           5

(2) INFORMATION FOR SEQ ID NO:197:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:197:

Arg Asn Ala Glu Ser Asp Gly Gly Ala
1           5

(2) INFORMATION FOR SEQ ID NO:198:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:198:

Leu Met Ala Lys Val Thr Ile Ala Leu Pro Thr Tyr Asp Glu Gly Ser
1          5               10              15

Asn Ala Ser Pro Ser Ser Val Ala Val Phe Ile Lys Tyr Ser Pro Gln
           20              25              30

Val Asn Met Glu Ala Phe Arg Val Lys Ile Lys Asp Leu Ile Glu Met
       35               40              45

Ser Ile Pro Gly Leu Gln Tyr Ser Lys Ile Ser Ile Leu Met Gln Pro
   50               55              60

Ala Glu Phe Arg Met Val Ala Asp Val Pro Ala Arg Gln Thr Phe Trp
65               70              75              80

Ile Met Asp Val Ile Asn Ala Asn Lys Gly Lys Val Val Lys Trp Leu
           85              90              95

Met Lys Tyr Pro Tyr Pro Leu Met Leu Ser Leu Thr Gly Leu Leu Leu
       100              105             110

Gly Val Gly Ile Leu Ile Gly Tyr Phe Cys Leu Arg Arg Arg Phe
         115              120             125

(2) INFORMATION FOR SEQ ID NO:199:

(i) SEQUENCE CHARACTERISTICS:
        (A) LENGTH: 48 amino acids
        (B) TYPE: amino acid -continued

```
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:199:

Ala Asp Leu Ile Pro Arg Cys Cys Asn Phe Ile Val Ile Ser Gly Asn
 1               5                  10                  15

Leu Leu Val Thr Leu Tyr Arg Asn Gly Trp Ile Ser Trp Ala Phe Ile
             20                  25                  30

Phe Lys Leu Leu Ala Leu Trp Arg Ser Ala Arg Val Gly Ser Ser Ser
         35                  40                  45

(2) INFORMATION FOR SEQ ID NO:200:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:200:

Gln Ser Val Lys
 1

(2) INFORMATION FOR SEQ ID NO:201:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:201:

Thr Lys Arg Lys Leu Cys Tyr Ser Ser Leu Phe Lys
 1               5                  10

(2) INFORMATION FOR SEQ ID NO:202:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:202:

Gln Ala Lys Thr Ala Gly Ser Ser Cys Ala Ala Tyr Ile Gly Ile Cys
 1               5                  10                  15

Leu Trp Ala Gly Ile Ile Gln Thr Gln Val
             20                  25

(2) INFORMATION FOR SEQ ID NO:203:

(i) SEQUENCE CHARACTERISTICS:
        (A) LENGTH: 15 amino acids
```

(B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:203:

Leu Phe Tyr Ala Thr Arg Val Ser Ala Ile Ala Ser Thr Val Val
  1               5                  10                  15

(2) INFORMATION FOR SEQ ID NO:204:

(i) SEQUENCE CHARACTERISTICS:
            (A) LENGTH: 33 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:204:

Asp Leu Ala Ala Ile Trp Leu Val Gly Ala Lys Arg Trp Gln Ile Thr
  1               5                  10                  15

Ser Ser Ala Ser Asp Ala Thr Asn Cys Ile Ala Asp Arg Tyr Arg His
            20                  25                  30

Ser (2) INFORMATION FOR SEQ ID NO:205:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:205:

Ser Gly Ser Ala
  1

(2) INFORMATION FOR SEQ ID NO:206:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:206:

Arg Cys Gly Phe Tyr Met Arg Tyr
  1               5

(2) INFORMATION FOR SEQ ID NO:207:

(i) SEQUENCE CHARACTERISTICS:
            (A) LENGTH: 36 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:207:

Tyr Tyr Tyr Pro Leu Arg Ser Val Tyr Phe Gly Arg Arg Leu Leu Leu
  1               5                  10                  15

Pro Arg Leu Ser Ser Trp Ser Ile Cys Tyr Glu Phe Tyr Phe Thr Ser
             20                  25                  30

Ser Asp Gly Asn
         35

(2) INFORMATION FOR SEQ ID NO:208:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:208:

Ala Thr Arg Ser Lys Tyr Tyr
  1               5

(2) INFORMATION FOR SEQ ID NO:209:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:209:

Val Thr Val Asp Asn Ile Thr Ile Asn Phe Ile Cys Ala Arg Ala Thr
  1               5                  10                  15

Ser (2) INFORMATION FOR SEQ ID NO:210:

(i) SEQUENCE CHARACTERISTICS:
         (A) LENGTH: 12 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:210:

Glu Ser Phe Thr Cys Tyr Cys Glu Leu Arg Leu Pro
  1               5                  10

(2) INFORMATION FOR SEQ ID NO:211:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:211:

Lys Asn His Pro Arg Arg Leu Ser Leu Ser Ala
  1               5                  10

(2) INFORMATION FOR SEQ ID NO:212:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:212:

Ala Ala Thr Arg Thr Ser Val Leu Ala
  1               5

(2) INFORMATION FOR SEQ ID NO:213:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:213:

Lys Tyr Ala Gly Lys Asn Gly Ser Gly Met Ala Gly Thr Ala Cys Lys
  1               5                  10                  15

Thr Phe Thr Arg Arg
              20

(2) INFORMATION FOR SEQ ID NO:214:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:214:

Lys Ser Ile Ser Phe Ile Gly Arg Ser Arg Ser Ala Ser Tyr
  1               5                  10

(2) INFORMATION FOR SEQ ID NO:215:

(i) SEQUENCE CHARACTERISTICS:
            (A) LENGTH: 41 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:215:

Tyr Arg Thr Gly Ser Val Gly Leu Val Arg Pro Thr Val Gly Arg Gln
 1               5                  10                  15

Cys Tyr Val Pro Ser Ser Gly Thr Pro Gly His Gly Tyr Gly Gly Arg
                20                  25                  30

Gly Ser Ala Leu Phe Ala Tyr Ser Ser
            35                  40

(2) INFORMATION FOR SEQ ID NO:216:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:216:

Lys Arg Gly Ile Asp Ala Arg Asn Phe Trp Gln Ala Val Tyr Val Asp
 1               5                  10                  15

Tyr Arg Ala Trp Phe Leu Ser Arg Ser Gly
                20                  25

(2) INFORMATION FOR SEQ ID NO:217:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:217:

Thr Phe Leu Asn Thr Ile Cys Arg
 1               5

(2) INFORMATION FOR SEQ ID NO:218:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:218:

Ile Phe Thr Phe Ser Ser Phe Gln Arg Val Thr Glu Met Val Thr
 1               5                  10                  15

(2) INFORMATION FOR SEQ ID NO:219:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:219:

Ile Leu Lys Leu Met Arg
 1               5

(2) INFORMATION FOR SEQ ID NO:220:

(i) SEQUENCE CHARACTERISTICS:
          (A) LENGTH: 11 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:220:

Arg Pro Leu Gln His Leu Pro Leu Ala Arg Leu
 1               5                  10

(2) INFORMATION FOR SEQ ID NO:221:

(i) SEQUENCE CHARACTERISTICS:
          (A) LENGTH: 10 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:221:

Arg Asn Lys Arg Leu Phe Arg Leu Gln Cys
 1               5                  10

(2) INFORMATION FOR SEQ ID NO:222:

(i) SEQUENCE CHARACTERISTICS:
          (A) LENGTH: 19 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:222:

Leu Ser Arg Ser Tyr Arg Lys Arg Arg Gly Gln Arg Ser Met Arg Arg
 1               5                  10                  15
Trp Lys Lys (2) INFORMATION FOR SEQ ID NO:223:

(i) SEQUENCE CHARACTERISTICS:
          (A) LENGTH: 25 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:223:

Val Val Asn Cys Ala Lys Ile Ile Asn Ser Leu Met Leu Arg Asn Trp
 1               5                  10                  15

```
Ser Ala Asp Ser Arg Leu Cys Cys Val
            20              25
```

(2) INFORMATION FOR SEQ ID NO:224:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:224:

```
Asn Lys Tyr Arg Arg Ile Met Gly Gln Arg Cys Val Arg Leu Pro Lys
 1               5                  10                  15

Arg Ile Val Ile Leu Ile Tyr Arg Met Arg Ile Lys Leu Ser Leu Leu
                20                  25                  30

Gln Trp Arg Leu Leu Pro Ala Gly Cys Gln Lys Arg Lys Asn Ala Ile
            35                  40                  45

Cys Asn Arg Asn Trp Ile Arg Tyr Ser Gly Gly Met Gly Thr Cys
            50                  55                  60

Arg Phe
 65
```

(2) INFORMATION FOR SEQ ID NO:225:

(i) SEQUENCE CHARACTERISTICS:
        (A) LENGTH: 178 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:225:

```
Phe Thr Gly Thr Trp Arg Ser Gly Tyr Arg Thr Leu Ser Ser Leu Lys
 1               5                  10                  15

Arg Phe Met Gln Gln Ala Ile Asp Asn Asp Glu Met Pro Leu Ser Gln
                20                  25                  30

Trp Phe Arg Arg Val Ala Asp Trp Pro Asp Arg Cys Glu Arg Val Arg
            35                  40                  45

Ile Leu Leu Arg Ala Val Ala Phe Glu Leu Ser Ile Cys Ile Glu Pro
            50                  55                  60

Ser Glu Gln Ser Arg Leu Ala Ala Ala Leu Val Arg Leu Arg Arg Leu
 65                  70                  75                  80

Leu Leu Phe Leu Gly Leu Glu Lys Glu Cys Gln Arg Glu Glu Trp Ile
                85                  90                  95

Cys Gln Leu Pro Pro Asn Thr Leu Leu Pro Leu Leu Leu Asp Ile Ile
                100                 105                 110

Cys Glu Arg Trp Leu Phe Ser Asp Trp Leu Leu Asp Arg Leu Thr Ala
            115                 120                 125

Ile Val Ser Ser Ser Lys Met Phe Asn Arg Leu Leu Gln Gln Leu Asp
            130                 135                 140

Ala Gln Phe Met Leu Ile Pro Asp Asn Cys Phe Asn Asp Glu Asp Gln
145                 150                 155                 160

Arg Glu Gln Ile Leu Glu Thr Leu Arg Glu Val Lys Ile Asn Gln Val
                165                 170                 175
```

Leu Phe (2) INFORMATION FOR SEQ ID NO:226:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:226:

Tyr Leu Ala Phe Asn Ile
 1           5

(2) INFORMATION FOR SEQ ID NO:227:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:227:

Val Asn Trp Leu Ser Gly Ser Ser
 1           5

(2) INFORMATION FOR SEQ ID NO:228:

(i) SEQUENCE CHARACTERISTICS:
        (A) LENGTH: 57 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:228:

Gly Val Arg Met Asp Trp Asp Leu Ile Thr Glu Arg Asn Ile Gln Leu
 1         5            10           15

Phe Ile Gln Leu Ala Gly Leu Ala Glu Arg Pro Leu Ala Thr Asn Met
         20            25           30

Phe Trp Arg Gln Gly Gln Tyr Glu Thr Ile Ile Thr Val Val Phe Ser
       35           40           45

Tyr Val Arg Tyr Ser Ser Lys Pro Ser
    50           55

(2) INFORMATION FOR SEQ ID NO:229:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:229:

Thr Lys Asn Cys Phe Leu Lys Arg Trp Leu Thr Gly Asn Pro Gln Arg
  1               5                  10                  15

Ser Arg Val Phe Leu Asn Asp Tyr Phe Cys Cys Ala Met Gly Leu Gln
              20                  25                  30

(2) INFORMATION FOR SEQ ID NO:230:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:230:

Val Val Leu His Leu Phe Pro Ala Pro Pro Ser Ser Gly Tyr Asp Tyr
  1               5                  10                  15

Ile Ile Asp Lys
            20

(2) INFORMATION FOR SEQ ID NO:231:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:231:

Asn Phe Xaa Glu Ser Gln Cys Val His Gly
  1               5                  10

(2) INFORMATION FOR SEQ ID NO:232:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:232:

Val Arg Glu Ser Gly Arg Asn Ser Gly Ser Val Tyr Ala Arg Val Gly
  1               5                  10                  15

Arg Ile Trp Phe Trp Arg Arg Cys Tyr
              20                  25

(2) INFORMATION FOR SEQ ID NO:233:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:233:

Cys Cys Tyr Pro Cys Arg Pro Gly Trp Leu Ile Ser
  1               5                  10

(2) INFORMATION FOR SEQ ID NO:234:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:234:

Leu Leu Ser Thr Leu Cys Phe Gln
  1               5

(2) INFORMATION FOR SEQ ID NO:235:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:235:

Leu Leu Phe Ile Leu Val Thr Leu Ser Ile Tyr Arg Tyr Phe Arg Leu
  1               5                  10                  15

Tyr Tyr Leu Leu Leu His Tyr Ile Val Cys His Ser Gln Ser Ala His
              20                  25                  30

His Gly Trp Tyr Cys Tyr Asn Ile Met Pro Val Ile Leu Trp Met Leu
              35                  40                  45

Ser Val Ser Leu Ser
              50

(2) INFORMATION FOR SEQ ID NO:236:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:236:

Glu Glu Ile Ser Pro Leu Gly Trp Ser Tyr Leu Pro Ser Leu Leu Ser
  1               5                  10                  15

Cys Asn Leu Leu Ser Leu Gln Lys Val Ser Arg Gly Trp Arg Lys Leu
              20                  25                  30

Ala His Val Ser Arg Leu Met Gly Cys Gln Ala Asn Lys
              35                  40                  45

(2) INFORMATION FOR SEQ ID NO:237:

(i) SEQUENCE CHARACTERISTICS:
        (A) LENGTH: 18 amino acids
        (B) TYPE: amino acid (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:237:

Val Ser Met Ala Ile Cys Val Pro Glu Leu Ser Met Gln Thr Met Pro
 1               5                  10                  15

Val His (2) INFORMATION FOR SEQ ID NO:238:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:238:

Asp Ser Met Ser Ser Arg Lys Ala Ala Phe Ser Val Arg Trp Thr Val
 1               5                  10                  15

Arg (2) INFORMATION FOR SEQ ID NO:239:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:239:

Asn Leu Leu Lys Ala Ile Arg Leu Pro Val Leu Leu Leu Phe Trp
 1               5                  10                  15

(2) INFORMATION FOR SEQ ID NO:240:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:240:

Thr Leu Ser Ala Val Ser Leu Ser Leu Ser Tyr Asn Met Ile Cys Arg
 1               5                  10                  15

(2) INFORMATION FOR SEQ ID NO:241:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:241:

Val Arg Leu Phe Thr Leu Ile Ala Tyr Cys Gln Ser Glu Met Val Tyr
  1               5                  10                  15

Val Gly Lys Phe His Arg Cys
             20

(2) INFORMATION FOR SEQ ID NO:242:

(i) SEQUENCE CHARACTERISTICS:
            (A) LENGTH: 23 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:242:

Phe Pro Leu Ala Arg Glu Leu Leu Ser Pro Val Ser Arg Val Arg Asn
  1               5                  10                  15

Ala Arg Thr Trp Arg Gln Ser
             20

(2) INFORMATION FOR SEQ ID NO:243:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:243:

Val Leu Lys Leu Pro Asp Asn Leu Ser Arg Ser Tyr
  1               5                  10

(2) INFORMATION FOR SEQ ID NO:244:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:244:

Pro Leu Trp Phe
  1

(2) INFORMATION FOR SEQ ID NO:245:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:245:

Cys Ser Ser Leu
1

(2) INFORMATION FOR SEQ ID NO:246:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:246:

Phe Leu Ala Phe Leu Leu Ser Leu Ser Leu Ser Phe Gln Arg Cys
1               5                   10                  15

(2) INFORMATION FOR SEQ ID NO:247:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:247:

His Cys Gln Leu Ser Ser Phe Ala Ala Lys Ser Leu Trp Phe Pro Gln
1               5                   10                  15

Met Ala Ser Lys His Arg Lys Lys Ile Val Trp Phe Pro Ala His Val
            20                  25                  30

Leu (2) INFORMATION FOR SEQ ID NO:248:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:248:

Ser Tyr Val Leu Ala Arg Arg Tyr Ile Leu Pro Thr
1               5                   10

(2) INFORMATION FOR SEQ ID NO:249:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:249:

```
Phe Val Ile Leu Thr Pro
 1               5
```

(2) INFORMATION FOR SEQ ID NO:250:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:250:

```
Asp Gly Phe Tyr Leu Arg Ile Pro Ala Ser Leu Ser Leu Arg
 1               5                  10
```

(2) INFORMATION FOR SEQ ID NO:251:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:251:

```
Ile Leu Arg Phe Cys Leu Asn Pro Pro Lys Asn
 1               5                  10
```

(2) INFORMATION FOR SEQ ID NO:252:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:252:

```
Arg Tyr Cys Tyr Ile Arg Asn Pro Tyr Leu Val Tyr Leu Phe Pro Leu
 1               5                  10                  15
Arg Arg Ile Ile Tyr
           20
```

(2) INFORMATION FOR SEQ ID NO:253:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:253:

```
Ala Arg Thr Leu Val Trp Trp Val Thr Ala Arg Arg Tyr Arg Thr Gly
 1               5                  10                  15
Trp Gly Arg Ser Val Gly Leu Gln Lys Thr Trp Pro Ile Arg Arg Lys
            20                  25                  30
```

Val Leu Asp Trp Thr Phe Ser Arg Ala Ala Asn Val Ser Leu Pro Tyr
         35                  40                  45

(2) INFORMATION FOR SEQ ID NO:254:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:254:

Asn Val Ser Cys Phe Gly Ile Trp Glu Ser Leu Leu Val Phe Arg Lys
1               5                   10                  15

Arg Val Ile (2) INFORMATION FOR SEQ ID NO:255:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:255:

Met Arg Trp Lys Lys Thr Thr Leu Ser Trp
1               5                   10

(2) INFORMATION FOR SEQ ID NO:256:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:256:

Lys Ser Phe Ser Ala Ser Tyr Pro Leu Ile Lys Ser Leu Lys Leu Cys
1               5                   10                  15

Asn Gly Leu Tyr Gln Ser Gly Phe Leu Leu Glu Ile Tyr Val Leu Phe
                20                  25                  30

Ser Ala Pro
         35

(2) INFORMATION FOR SEQ ID NO:257:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:257:

Leu Thr Gly Arg His Val Lys Lys Met Ser
 1               5                  10

(2) INFORMATION FOR SEQ ID NO:258:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:258:

Gln Asn Met Ser Val Ser Arg Phe Val Val Ile Phe Cys Val Val Leu
 1               5                  10                  15

Ile Arg Lys Glu Asn Arg Cys Arg Phe Cys Gly Ser Ala Lys Val Leu
                20                  25                  30

Lys Thr Ser Cys Val Asn Pro Phe Ala Arg Arg Gln Trp Gly Pro Ile
            35                  40                  45

Leu Arg Cys Arg Leu Val Ile Arg Arg Ser Cys Asn Leu Ser Ser
 50                  55                  60

Arg Arg
 65

(2) INFORMATION FOR SEQ ID NO:259:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:259:

Ser Ser Gln Pro Asn Tyr Ser Leu Ser Leu Leu Ser Thr Pro Asp Val
 1               5                  10                  15

Ser Cys Glu Lys Leu Gln Lys Pro Pro Cys Ser Thr Tyr Arg Phe Cys
                20                  25                  30

His Gly Arg Asn
            35

(2) INFORMATION FOR SEQ ID NO:260:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:260:

Glu Arg Arg Ala Leu Tyr Lys Trp
 1               5

(2) INFORMATION FOR SEQ ID NO:261:

(i) SEQUENCE CHARACTERISTICS:

```
      (A) LENGTH: 109 amino acids
      (B) TYPE: amino acid
      (C) STRANDEDNESS: single
      (D) TOPOLOGY: linear (ii) MOLECULE TYPE: protein (iii) HYPOTHETICAL: NO (xi) SEQUENCE DESCRIPTION: SEQ ID NO:261:

Lys Val Leu Thr Leu Ala Lys Arg Ser Trp Arg Thr Met Lys Asn Glu
 1               5                  10                  15

Leu Met Gln Arg Leu Arg Leu Lys Tyr Pro Pro Pro Asp Gly Tyr Cys
            20                  25                  30

Arg Trp Gly Arg Ile Gln Asp Val Ser Ala Thr Leu Leu Asn Ala Trp
        35                  40                  45

Leu Pro Gly Val Phe Met Gly Glu Leu Cys Cys Ile Lys Pro Gly Glu
    50                  55                  60

Glu Leu Ala Glu Val Val Gly Ile Asn Gly Ser Lys Ala Leu Leu Ser
65                  70                  75                  80

Pro Phe Thr Ser Thr Ile Gly Leu His Cys Gly Gln Gln Val Met Ala
                85                  90                  95

Leu Ser Asp Ala Ile Arg Phe Pro Trp Ala Lys Arg Tyr
                100                 105

(2) INFORMATION FOR SEQ ID NO:262:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:262:

Gly Glu Leu Leu Met Ala Leu Val Val Pro Leu Met Ala Ala Asn Cys
 1               5                  10                  15

Pro Thr Ser Ala Gly Lys Thr Met Met Gln Cys Leu Leu Pro Gln Trp
            20                  25                  30

Phe Asp Ser Leu Ser Leu Asn His
            35                  40

(2) INFORMATION FOR SEQ ID NO:263:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:263:

Arg Gly Phe Ala Leu Leu Ile Ala Leu Arg Pro Val Ala Lys Gly Asn
 1               5                  10                  15

Glu Trp Val Phe Phe Leu Leu Leu Ala Trp Gly Lys Ala Arg Phe Trp
            20                  25                  30

Arg Cys Cys Val Met Arg Gln Thr Gln Thr Ala Met Phe Trp Cys
            35                  40                  45
```

(2) INFORMATION FOR SEQ ID NO:264:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:264:

```
Leu Val Asn Val Asp Glu Lys Ser Ala Asn Ser Ser Ile Leu His Cys
 1               5                  10                  15

Leu Lys Arg Pro Glu Asn Val Val Ser Leu Leu Ser Gln Pro Leu Thr
            20                  25                  30

Asp Pro Pro
        35
```

(2) INFORMATION FOR SEQ ID NO:265:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:265:

```
Gly Arg Cys Leu Trp Pro Pro Arg
 1               5
```

(2) INFORMATION FOR SEQ ID NO:266:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:266:

```
Gln Asn Phe Phe Ala Ile Met Glu Ser Glu Ser Ser Cys Leu Pro Thr
 1               5                  10                  15

His
```

(2) INFORMATION FOR SEQ ID NO:267:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:267:

```
Arg Val Met Pro Gly Pro His Gly Asn Arg Ser Gly Ala Gly Glu Thr
 1               5                  10                  15
```

Ala Val Ser Gly Glu Tyr Arg Gln Ala Tyr Leu Val His Cys His Asp
            20                  25                  30

Phe (2) INFORMATION FOR SEQ ID NO:268:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:268:

Asn Val Arg Glu Trp Glu Lys Lys Ala Val Leu Pro His Phe Ile Arg
 1               5                  10                  15

Tyr Trp Trp Lys Ala Met Ile
            20

(2) INFORMATION FOR SEQ ID NO:269:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:269:

Met Lys Pro Leu Ala Asp Glu Val Arg Ser Leu Leu Asp Gly His Ile
 1               5                  10                  15

Val Leu Ser Arg Arg Leu Ala Glu Arg Gly His Tyr Pro Ala Ile Asp
            20                  25                  30

Val Leu Ala Thr Leu Ser Arg Val Phe Pro Val Val Thr Ser His Glu
            35                  40                  45

His Arg Gln Leu Ala Ala Ile Leu Arg Arg Cys Leu Ala Leu Tyr Gln
        50                  55                  60

Glu Val Glu Leu Leu Ile Arg Ile Gly Glu Tyr Gln Arg Gly Val Asp
65                  70                  75                  80

Thr Asp Thr Asp Lys Ala Ile Asp Thr Tyr Pro Asp Ile Cys Thr Phe
            85                  90                  95

Leu Arg Gln Ser Lys Asp Glu Val Cys Gly Pro Glu Leu Leu Ile Glu
            100                 105                 110

Lys Leu His Gln Ile Leu Thr Glu
        115                 120

(2) INFORMATION FOR SEQ ID NO:270:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:270:

```
Ser Trp Lys Leu Cys Trp Arg
1               5
```

(2) INFORMATION FOR SEQ ID NO:271:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:271:

```
Lys Ala Ile Thr Arg Gln Ala Tyr Arg Thr
1               5                   10
```

(2) INFORMATION FOR SEQ ID NO:272:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:272:

```
Ser Ala Ala Thr Gly Asp Tyr Tyr Gly Thr Ala Asp Leu Pro Asp Ala
1               5                   10                  15
Arg Phe Ser Ser Val Tyr Gln Thr Glu Arg Ile Asn Gly Leu Ala Arg
            20                  25                  30
Tyr Val Ile Leu Ser Phe Ile Val Gly
            35                  40
```

(2) INFORMATION FOR SEQ ID NO:273:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:273:

```
Glu Thr Thr Asn Gly Arg Val Ile His Ser Gly Ala Glu Leu Phe Asp
1               5                   10                  15
Ala Thr Ala Ser Ser
            20
```

(2) INFORMATION FOR SEQ ID NO:274:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:274:

```
Arg Ile Ser Ile Ser Ser Leu Ser Pro Gly Glu Ala Asn Tyr Arg Arg
 1               5                  10                  15

Ile Leu Met Arg Leu
            20
```

(2) INFORMATION FOR SEQ ID NO:275:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:275:

```
Lys Arg Lys Lys Lys Leu Leu Trp Tyr
 1               5
```

(2) INFORMATION FOR SEQ ID NO:276:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:276:

```
Ala Met Arg Ile Thr Lys Val Glu Gly Ser Leu Gly Leu Pro Cys Gln
 1               5                  10                  15

Ser Tyr Gln Asp Asp Asn Glu Ala Glu Ala Glu Arg Met Asp Phe Glu
            20                  25                  30

Gln Leu Met His Gln Ala Leu Pro Ile Gly Glu Asn Asn Pro Pro Ala
            35                  40                  45

Ala Leu Asn Lys Asn Val Val Phe Thr Gln Arg Tyr Arg Val Ser Gly
        50                  55                  60

Gly Tyr Leu Asp Gly Val Glu Cys Glu Val Cys Glu Ser Gly Gly Leu
 65                  70                  75                  80

Ile Gln Leu Arg Ile Asn Val Pro His His Glu Ile Tyr Arg Ser Met
                85                  90                  95

Lys Ala Leu Lys Gln Trp Leu Glu Ser Gln Leu Leu His Met Gly Tyr
            100                 105                 110

Ile Ile Ser Leu Glu Ile Phe Tyr Val Lys Asn Ser Glu
            115                 120                 125
```

(2) INFORMATION FOR SEQ ID NO:277:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:277:

```
Arg Ala Ser Val Gly Gly Asp Thr Ser Asn Ala Arg Arg Tyr His Trp
```

1               5              10              15

(2) INFORMATION FOR SEQ ID NO:278:

(i) SEQUENCE CHARACTERISTICS:
          (A) LENGTH: 21 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:278:

Ala Asp Ile Glu Tyr Ala Thr Ile Ser Ser Thr Ala Arg Asp Ile Ile
  1               5                  10                  15

Tyr His Lys Leu Ser
              20

(2) INFORMATION FOR SEQ ID NO:279:

(i) SEQUENCE CHARACTERISTICS:
          (A) LENGTH: 12 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:279:

Gly Val Asp Cys Arg Thr Met Leu Ala Ala Leu Val
  1               5                  10

(2) INFORMATION FOR SEQ ID NO:280:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:280:

Arg Ala Asn Trp His Arg
  1               5

(2) INFORMATION FOR SEQ ID NO:281:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:281:

Ser Ile Gly Tyr Arg Ser
  1               5

(2) INFORMATION FOR SEQ ID NO:282:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:282:

Ile Ala Ile Trp Asn Ser
  1               5

(2) INFORMATION FOR SEQ ID NO:283:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:283:

Met Gly Ala Gly Ala Val Ile Ala Ser Gln
  1               5                  10

(2) INFORMATION FOR SEQ ID NO:284:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:284:

Cys Asn Pro Leu Ser Glu Arg Ala Ala Asn Ile Leu Gln
  1               5                  10

(2) INFORMATION FOR SEQ ID NO:285:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:285:

Ser Thr Thr Ser Ala Ser Val Ala Tyr
  1               5

(2) INFORMATION FOR SEQ ID NO:286:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:286:

His Tyr Phe Tyr Met Ala Asn Gly Phe Phe Ala Gln Tyr Ser Arg Arg
  1               5                  10                  15

Ala Phe Cys (2) INFORMATION FOR SEQ ID NO:287:

(i) SEQUENCE CHARACTERISTICS:
           (A) LENGTH: 26 amino acids
           (B) TYPE: amino acid
           (C) STRANDEDNESS: single
           (D) TOPOLOGY: linear (ii) MOLECULE TYPE: protein (iii) HYPOTHETICAL: NO (xi) SEQUENCE DESCRIPTION: SEQ ID NO:287:

Ala Thr Thr Asp Leu Ser Cys Pro Ser Cys Gly Ser Pro Cys Ile Phe
  1               5                  10                  15

Arg Leu Val Pro Ala Tyr Ile Asn Arg Thr
             20                  25

(2) INFORMATION FOR SEQ ID NO:288:

(i) SEQUENCE CHARACTERISTICS:
           (A) LENGTH: 38 amino acids
           (B) TYPE: amino acid
           (C) STRANDEDNESS: single
           (D) TOPOLOGY: linear (ii) MOLECULE TYPE: protein (iii) HYPOTHETICAL: NO (xi) SEQUENCE DESCRIPTION: SEQ ID NO:288:

Val Tyr Arg Asn Arg His Gly Arg Ser Asp Ser Leu Leu Arg Arg His
  1               5                  10                  15

Gln Thr Arg Phe Phe Cys Tyr Ser Thr Thr Trp Gly Asn Leu Arg Lys
             20                  25                  30

Gly Val Ala Asp Arg Gly
             35

(2) INFORMATION FOR SEQ ID NO:289:

(i) SEQUENCE CHARACTERISTICS:
           (A) LENGTH: 4 amino acids
           (B) TYPE: amino acid
           (C) STRANDEDNESS: single
           (D) TOPOLOGY: linear (ii) MOLECULE TYPE: protein (iii) HYPOTHETICAL: NO (xi) SEQUENCE DESCRIPTION: SEQ ID NO:289:

His Asp Glu Ile
  1

(2) INFORMATION FOR SEQ ID NO:290:

(i) SEQUENCE CHARACTERISTICS:
           (A) LENGTH: 19 amino acids
           (B) TYPE: amino acid
           (C) STRANDEDNESS: single
           (D) TOPOLOGY: linear (ii) MOLECULE TYPE: protein (iii) HYPOTHETICAL: NO (xi) SEQUENCE DESCRIPTION: SEQ ID NO:290:

Arg Ile Ser Pro Gly Tyr Arg Asn Ala Thr Cys Val Arg Glu Pro Asn
1               5                   10                  15
Val Lys Glu (2) INFORMATION FOR SEQ ID NO:291:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:291:

Arg Asn Val Phe Ser Arg Thr
1               5

(2) INFORMATION FOR SEQ ID NO:292:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:292:

Ala Asp Thr Thr Thr Gly Ala Leu
1               5

(2) INFORMATION FOR SEQ ID NO:293:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:293:

Gly Arg Thr Cys Glu Ser Gly Asn Trp Thr Ile Thr Thr Thr
1               5                   10

(2) INFORMATION FOR SEQ ID NO:294:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:294:

Asn Gly Gly Arg Phe Ala Cys Arg Trp Met Phe Cys Ala Arg Gly Asp
1               5                   10                  15

Asp Lys Ser Lys
            20

(2) INFORMATION FOR SEQ ID NO:295:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:295:

Pro Tyr Tyr Trp Ala Arg
1               5

(2) INFORMATION FOR SEQ ID NO:296:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:296:

Val Asp Cys Leu Trp Gln
1               5

(2) INFORMATION FOR SEQ ID NO:297:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:297:

Ile Tyr Gly Ala Tyr Tyr Thr Leu Val Ser Leu Gln Lys Tyr Ser Val
1               5                   10                  15

Asn Leu Ile Arg Lys Ile Ile Cys Glu Gln Tyr Asn Ser Val Pro Gly
            20                  25                  30

Arg Val Met Arg Asp Thr Val Cys Leu Tyr Pro Ile Arg Leu Cys Asn
        35                  40                  45

(2) INFORMATION FOR SEQ ID NO:298:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:298:

Leu Val Tyr Cys Phe Cys Phe Gln Tyr Cys Leu Ser Leu Ser Ser Trp
1               5                   10                  15

Glu Leu Leu Ser Leu Asn Trp Arg Trp Tyr Phe Arg Phe Tyr Glu Met
            20                  25                  30

Leu Trp Val Phe Asn Lys Ser Pro Gln Ile Ser His Cys Met Ala Leu
        35                  40                  45

Arg Leu Tyr Phe Pro Tyr Ser Leu Trp Gly Arg Tyr
    50                  55                  60

(2) INFORMATION FOR SEQ ID NO:299:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:299:

Lys Ser Ala Gly Ile Arg Phe Arg Ser Leu Ala Leu Leu Ser Gly Arg
1               5                   10                  15

Leu Ser Gly Thr Val Lys His
            20

(2) INFORMATION FOR SEQ ID NO:300:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:300:

Arg Leu Ile Asp Ser Phe Cys Lys Lys Thr Leu Lys Arg Arg Lys Pro
1               5                   10                  15

Ile Ile Phe Gly Ile
            20

(2) INFORMATION FOR SEQ ID NO:301:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:301:

Asn Glu Pro Gly Leu Lys Thr
1               5

(2) INFORMATION FOR SEQ ID NO:302:

(i) SEQUENCE CHARACTERISTICS:
        (A) LENGTH: 7 amino acids
        (B) TYPE: amino acid

```
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:302:

Asn Leu Ile Leu Cys Ser Tyr
 1               5

(2) INFORMATION FOR SEQ ID NO:303:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:303:

Phe Arg His Leu Arg
 1               5

(2) INFORMATION FOR SEQ ID NO:304:

(i) SEQUENCE CHARACTERISTICS:
            (A) LENGTH: 29 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:304:

Arg Arg His Phe Gly Leu Asp Tyr Leu Phe Ile Phe Pro Phe Trp Leu
 1               5                  10                  15

Leu Thr Cys Leu Phe Gln Ile Tyr Cys Trp Leu Trp Gly
             20                  25

(2) INFORMATION FOR SEQ ID NO:305:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:305:

Trp Cys Arg Arg
 1

(2) INFORMATION FOR SEQ ID NO:306:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein
```

(iii) HYPOTHETICAL: NO (xi) SEQUENCE DESCRIPTION: SEQ ID NO:306:

Pro Phe His Tyr Arg Leu Ser Cys
 1               5

(2) INFORMATION FOR SEQ ID NO:307:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:307:

Tyr Phe Tyr Trp Gln Ala Val Gly Ile
 1               5

(2) INFORMATION FOR SEQ ID NO:308:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:308:

His Trp Arg Asn Trp Tyr Arg Ala Phe His Glu
 1               5                  10

(2) INFORMATION FOR SEQ ID NO:309:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:309:

Ile Asp Ala Ile Cys Asn Ala Thr Phe Met Asp Arg Pro Phe Tyr Val
 1               5                  10                  15

Tyr Ala Gly Ser Val Gly Gly Ile Gly Ser Trp Cys His Arg Lys Pro
            20                  25                  30

Cys Ser Gly Leu Asp Ser Asn Thr Gly Pro Asn Ala Thr Val His Asp
            35                  40                  45

(2) INFORMATION FOR SEQ ID NO:310:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:310:

Ile Ile Gly Asn Cys Asn Asn Leu Asn Gly Gln Leu Pro Met Ala
1               5                   10                  15

(2) INFORMATION FOR SEQ ID NO:311:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:311:

Arg Tyr Pro Val Glu Leu Tyr Pro Ala Asp Asn Val Thr Asn Trp Arg
1               5                   10                  15

Ala Trp Leu Asn Gly Thr Thr Gly Lys
            20                  25

(2) INFORMATION FOR SEQ ID NO:312:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:312:

Val Ala Tyr Cys Ile Gly Cys Gly Phe Tyr Ser Thr Ile Glu Pro Phe
1               5                   10                  15

Phe Ile Thr Ser Leu Ile Lys Lys Trp Gln Phe Arg Gly Arg Thr Phe
                20                  25                  30

Thr (2) INFORMATION FOR SEQ ID NO:313:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:313:

Trp Arg Ala Tyr Val Thr Tyr Leu Ser Asp Ile Thr Asn His Leu Pro
1               5                   10                  15

Ala Glu Asp Tyr Asp Ala Tyr Trp
            20

(2) INFORMATION FOR SEQ ID NO:314:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:314:

Arg Leu Gln Leu Val Arg Val Ser His Trp Arg Gly Asp Tyr Trp Phe
 1               5                  10                  15

Phe Asn Trp Val Leu Cys Gly Gly Ser Leu Leu Gly Arg
            20                  25

(2) INFORMATION FOR SEQ ID NO:315:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:315:

Tyr Gly Gly Val Ser Ala
 1               5

(2) INFORMATION FOR SEQ ID NO:316:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:316:

Tyr Phe Thr Trp Arg Asp Asn Gly Tyr Asp Ile Gln Phe Tyr Asn Arg
 1               5                  10                  15

Ser (2) INFORMATION FOR SEQ ID NO:317:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:317:

Asn Leu Thr Phe Trp Leu Ala Phe Gln Pro Val Leu Val Cys Tyr Phe
 1               5                  10                  15

Leu Tyr Lys Arg Arg His Gly Val Tyr Ile Lys His Ser Val
            20                  25                  30

(2) INFORMATION FOR SEQ ID NO:318:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:318:

Val Ile Ser Ile Phe Thr Thr Arg Ala Tyr Phe Ile Ile
1               5                  10

(2) INFORMATION FOR SEQ ID NO:319:

(i) SEQUENCE CHARACTERISTICS:
        (A) LENGTH: 93 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:319:

Pro Ala Ile Phe Lys Ile Tyr Pro Gly Arg Val Glu Asn Ala Leu Ser
1               5                   10                  15

Ile Met Tyr Gln Leu Leu Ser Ser Cys His Asn Met Tyr Gly Ile Ser
                20                  25                  30

Arg Ser Gly Phe Arg Ser Phe Lys Ser Val Gly Thr Thr Ile Glu Cys
            35                  40                  45

Val Phe Leu Leu Asn Ala Ala Gln Lys Tyr Ile Gly Ser Thr Asp Xaa
        50                  55                  60

Leu Ile Ser Phe Pro Tyr Ala Leu His His Tyr Leu Val Glu Ser Asp
65                  70                  75                  80

Lys Phe Tyr Ile Tyr Leu Lys Asp Trp Phe Pro Ser Val
                85                  90

(2) INFORMATION FOR SEQ ID NO:320:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:320:

Ala Arg Lys Gln Asn Ser Leu Gln Lys Arg Asn Tyr Val Met Ala Val
1               5                   10                  15

Arg Lys Gly Arg Leu Ser Lys Val Leu Lys
                20                  25

(2) INFORMATION FOR SEQ ID NO:321:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:321:

His His Tyr Phe Ser
1               5

(2) INFORMATION FOR SEQ ID NO:322:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:322:

```
Leu Arg Phe Ile Cys Ile Phe Ile Ser Leu Leu Lys Arg
 1               5                  10
```

(2) INFORMATION FOR SEQ ID NO:323:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:323:

```
Leu Ser His Tyr Asn
 1               5
```

(2) INFORMATION FOR SEQ ID NO:324:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:324:

```
Ile Asn His Phe Leu Met His
 1               5
```

(2) INFORMATION FOR SEQ ID NO:325:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:325:

```
Leu Leu His Cys Cys Phe Trp Ala Leu Gly
 1               5                  10
```

(2) INFORMATION FOR SEQ ID NO:326:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:326:

Leu Leu Leu Trp Val Ala Cys Phe Phe Arg Trp Gly Trp Leu Leu Pro
1               5                   10                  15

Ala Arg Pro Leu Val Leu Lys Ala Ser Ile
            20                  25

(2) INFORMATION FOR SEQ ID NO:327:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:327:

Val Ile Leu Ser Arg Tyr Ser Leu Tyr Ile Ala
1               5                   10

(2) INFORMATION FOR SEQ ID NO:328:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:328:

Asn Tyr Val Asn Pro Ala
1               5

(2) INFORMATION FOR SEQ ID NO:329:

(i) SEQUENCE CHARACTERISTICS:
            (A) LENGTH: 27 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:329:

Lys Leu Ser Cys Tyr Leu Leu Ser Leu Pro Phe Ser Phe Ile Ile Met
1               5                   10                  15

Pro Val Leu Phe Gly Arg Tyr Arg Thr Val Gly
            20                  25

(2) INFORMATION FOR SEQ ID NO:330:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:330:

Pro Val Ala Cys Leu Trp Phe Leu Leu
  1               5

(2) INFORMATION FOR SEQ ID NO:331:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:331:

Asn Gly Tyr Gly
  1

(2) INFORMATION FOR SEQ ID NO:332:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:332:

Trp Phe Phe Ile Ser Ser Leu Ala Tyr Trp Thr Ile Leu Phe Asn Ile
  1               5                  10                  15

Ile Arg Leu Glu Lys Leu Ser Lys Asn Glu
                 20                  25

(2) INFORMATION FOR SEQ ID NO:333:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:333:

Arg Lys Thr Gly Ala
  1               5

(2) INFORMATION FOR SEQ ID NO:334:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:334:

```
Arg Ser Gly Gly Arg Pro Ser Asn Glu Asp Ala Ala Ser Glu Met Gln
 1               5                  10                  15

Ser Glu Ile Gln Ser Gly Ser Leu Ala Gln Ser Val Lys Gln Ser Val
            20                  25                  30

Ala Val Val Arg Asn Pro Thr His Ile Ala Val Cys Leu Gly Tyr His
            35                  40                  45

Pro Thr Asp Met Pro Ile Pro Arg Val Leu Glu Lys Gly Ser Asp Ala
        50                  55                  60

Gln Ala Asn Tyr Ile Val Asn Ile Ala Glu Arg Asn Cys Ile Pro Val
 65              70                  75                  80

Val Glu Asn Val Glu Leu Ala Arg Ser Leu Phe Phe Glu Val Glu Arg
                    85                  90                  95

Gly Asp Lys Ile Pro Glu Thr Leu Phe Glu Pro Val Ala Ala Leu Leu
                100                 105                 110

Arg Met Val Met Lys Ile Asp Tyr Ala His Ser Thr Glu Thr Pro
        115                 120                 125
```

(2) INFORMATION FOR SEQ ID NO:335:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:335:

```
Met Leu Leu Val Cys Phe Phe Arg Pro Leu Arg Arg Leu Arg Gly
 1               5                  10                  15
```

(2) INFORMATION FOR SEQ ID NO:336:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:336:

```
Arg Ile Glu Gln Cys Leu Thr Ile Lys Val Arg Asp
 1               5                  10
```

(2) INFORMATION FOR SEQ ID NO:337:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:337:

```
Ser Leu Leu Ala Trp His Lys His Gln Ile Ala Tyr Tyr Lys Ile Lys
 1               5                  10                  15

Gln Asp Asn Gly Leu Val Arg Leu Asn Gly Leu Glu Pro Leu Asp Pro
            20                  25                  30
```

His His Val Lys Val Val Leu
          35

(2) INFORMATION FOR SEQ ID NO:338:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:338:

Pro Thr Glu Leu
1

(2) INFORMATION FOR SEQ ID NO:339:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:339:

Thr Ala Thr Leu
1

(2) INFORMATION FOR SEQ ID NO:340:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:340:

Val Thr Thr Gly Thr Asn Ile Ser Val Thr Thr Ala Met Arg Gln Glu
1               5                  10                  15

Gly Asn Arg Asn Phe Leu Pro Glu Ile Thr
            20                  25

(2) INFORMATION FOR SEQ ID NO:341:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:341:

Leu Arg Trp Lys Tyr Ala Thr Cys Arg Glu Asn Ser Arg His Ala Thr
1               5                  10                  15

Ala Ile Val Val Leu Ser Glu Arg Ala Ala Lys

```
            20                  25

(2) INFORMATION FOR SEQ ID NO:342:

(i) SEQUENCE CHARACTERISTICS:
         (A) LENGTH: 23 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:342:

Trp Arg Thr Ala Asp Val Val Asp Ser Ala Ser Val Ala Ser Leu Thr
 1               5                  10                  15

Pro Pro Pro Arg Ser Gly Arg
            20

(2) INFORMATION FOR SEQ ID NO:343:

(i) SEQUENCE CHARACTERISTICS:
         (A) LENGTH: 32 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:343:

Thr Pro Ser Arg Ser Leu Pro Val Pro Tyr Asp Pro Pro Asn Pro
 1               5                  10                  15

Leu Thr Pro Gly Tyr Asn Arg Trp Val Asn Leu Thr Pro Ser Arg Arg
            20                  25                  30

(2) INFORMATION FOR SEQ ID NO:344:

(i) SEQUENCE CHARACTERISTICS:
         (A) LENGTH: 16 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:344:

Lys Arg Trp Asn Ala Tyr Leu Tyr Asn Arg Ala Glu Tyr Arg Cys Arg
 1               5                  10                  15

(2) INFORMATION FOR SEQ ID NO:345:

(i) SEQUENCE CHARACTERISTICS:
         (A) LENGTH: 24 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:345:

Ser Arg Lys Ser Gly Lys Pro Gln Arg Ala Ala Leu Ile Ala Ala Ser
 1               5                  10                  15
```

```
Ala Thr Thr Ser Gly Leu Ser Leu
            20
```

(2) INFORMATION FOR SEQ ID NO:346:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:346:

```
Ser Lys Ala Ile Cys Leu Arg Arg Val Thr Val Lys Ile Ala Val Thr
 1               5                  10                  15

Thr Ala Ile Gln Met Pro Thr Pro Lys Pro Val Arg Ala Ala Phe Ala
            20                  25                  30

His Pro Ala Leu Ser Pro Gly Pro Asp Arg
            35                  40
```

(2) INFORMATION FOR SEQ ID NO:347:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:347:

```
Pro Thr Arg Ile Val Thr Ala Ala Ala Ser Asp Ile Gly Ser Thr Asn
 1               5                  10                  15

Ile Ser Glu Leu Lys Leu Ser Ala Ile
            20                  25
```

(2) INFORMATION FOR SEQ ID NO:348:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:348:

```
Pro Ala Thr Ser Thr Ile Pro Asn Gly Glu Thr Ser Ser Ala Thr Thr
 1               5                  10                  15

Ala Asn Asn Val Thr Ser Lys Asn Ser Gln Arg Asn Arg Gln Pro Gln
            20                  25                  30

Leu Asn Gln Ala Leu His Asp Asp Ala Ile Gly Phe Ala Lys Ala Phe
            35                  40                  45

Phe Ile Thr Asn Ile Thr His
            50                  55
```

(2) INFORMATION FOR SEQ ID NO:349:

(i) SEQUENCE CHARACTERISTICS:
        (A) LENGTH: 151 amino acids (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:349:

Thr Arg Val Phe Asn Val Arg Lys His Gly Asp Lys His His Pro Ile
 1               5                  10                  15

Asp Arg Arg Ser Arg Asn Ala Ala Asp Thr Ala Glu Phe Arg His
             20                  25                  30

Thr Lys Met Ala Ile Asp Lys Asn Ile Val His Arg Asn Ile His Gln
         35                  40                  45

Gln Ala Gln Lys Ser His His His Thr Arg Phe Gly Phe Gly Gln Thr
     50                  55                  60

Phe Ala Leu Val Ser Arg Tyr Leu Lys Glu Lys Val Ser Cys Ala Pro
 65                  70                  75                  80

Gln Gln Arg Ala Lys Ile Thr His Gly Phe Ile Gly Gln Arg Arg Ile
                 85                  90                  95

Asn Ile Met His Arg Ala Asp Asn Val Ser Gly Ile Pro Gln Asp Asp
                100                 105                 110

His His Gln His Gly Asp Lys Ala Arg Gln Pro Glu Pro Leu Ser Asn
            115                 120                 125

Leu Met Arg Asp Thr Leu Thr Thr Ala Gly Ala Ile Glu Leu Arg Asn
        130                 135                 140

His Arg Arg Gln Gly Gln Gln
145                 150

(2) INFORMATION FOR SEQ ID NO:350:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:350:

Ala Val Thr Lys Gln Asn Gly Gly Lys Gln Ile Glu Val Pro Ile Ala
 1               5                  10                  15

Thr Ala Ala Met Ser Val Ala Leu
             20

(2) INFORMATION FOR SEQ ID NO:351:

(i) SEQUENCE CHARACTERISTICS:
            (A) LENGTH: 25 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:351:

Pro Pro Ala Met Thr Val Ser Thr Asn Pro Leu Arg Ser Ile Pro Leu
 1               5                  10                  15

Ala Gln Gly Ser Pro Val Ser Glu Arg

```
                       20                  25

(2) INFORMATION FOR SEQ ID NO:352:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:352:

Leu Thr Arg Phe Thr Gly Ile Leu Leu His Val Phe Thr Phe Tyr Phe
 1               5                  10                  15

Val Val Ile (2) INFORMATION FOR SEQ ID NO:353:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:353:

Lys Thr Lys Lys Pro Pro Lys Trp Gln Pro Lys Glu Ile Ala Gly Glu
 1               5                  10                  15

Ile Ser Val Tyr Cys Ser Gly Val Leu Leu Phe Leu Gln
                20                  25

(2) INFORMATION FOR SEQ ID NO:354:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:354:

Lys Asn Ser Cys
 1

(2) INFORMATION FOR SEQ ID NO:355:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:355:

Arg Arg Ile Ala Gly Lys Leu Phe Phe His Leu Leu Leu Cys
 1               5                  10
```

(2) INFORMATION FOR SEQ ID NO:356:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:356:

```
Thr Val Leu Leu Leu Phe Ile Ser Gly Val Glu Asp Met Phe Thr Gly
 1               5                  10                  15

Ile Val Gln Gly Thr Ala Lys Leu Val Ser Ile
                20                  25
```

(2) INFORMATION FOR SEQ ID NO:357:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:357:

```
Ala Glu Pro Ser Gln Glu Gln Ile Asn Phe Phe Glu Gln Leu Leu Lys
 1               5                  10                  15

Asp Glu Ala Ser Thr Ser Asn Ala Ser Ala Leu Leu Pro Gln Val Met
                20                  25                  30

Leu Thr Arg Gln Met Asp Tyr Met Gln Leu Thr Val Gly Val Asp Tyr
                35                  40                  45

Leu Ala Arg Ile Ser Arg Arg Ser Met Pro Ser Ala
                50                  55                  60
```

(2) INFORMATION FOR SEQ ID NO:358:

(i) SEQUENCE CHARACTERISTICS:
        (A) LENGTH: 56 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:358:

```
His Gly Met Lys Val His Arg Ile Val Phe Leu Thr Val Leu Thr Phe
 1               5                  10                  15

Phe Leu Thr Ala Cys Asp Val Asp Leu Tyr Arg Ser Leu Pro Glu Asp
                20                  25                  30

Glu Ala Asn Gln Met Leu Ala Leu Leu Met Gln His His Ile Asp Ala
                35                  40                  45

Lys Lys Asn Arg Lys Arg Met Val
                50                  55
```

(2) INFORMATION FOR SEQ ID NO:359:

(i) SEQUENCE CHARACTERISTICS:
        (A) LENGTH: 16 amino acids
        (B) TYPE: amino acid (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:359:

Pro Tyr Val Ser Ser Ser Arg Gln Phe Ile Asn Ala Val Glu Ala Thr
 1               5                  10                  15

(2) INFORMATION FOR SEQ ID NO:360:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:360:

Arg Leu Ser Ala
 1

(2) INFORMATION FOR SEQ ID NO:361:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:361:

Gly Ser Leu Gln Arg Arg Ile Arg Cys Phe Arg Leu Ile Ser
 1               5                  10

(2) INFORMATION FOR SEQ ID NO:362:

(i) SEQUENCE CHARACTERISTICS:
            (A) LENGTH: 30 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:362:

Trp Tyr His Pro Arg Lys Asn Arg Gln Lys Ile Asn Phe Leu Lys Glu
 1               5                  10                  15

Gln Arg Ile Glu Gly Met Leu Ser Gln Met Glu Gly Arg Asp
                20                  25                  30

(2) INFORMATION FOR SEQ ID NO:363:

(i) SEQUENCE CHARACTERISTICS:
            (A) LENGTH: 21 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:363:

Pro Leu Arg Tyr Arg Leu Met Met Arg Glu Val Thr Leu Leu Arg Ala
  1               5                  10                  15

Gln Leu Pro Tyr Leu
            20

(2) INFORMATION FOR SEQ ID NO:364:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:364:

Asn Ile His Leu Arg Ser Ile Trp Arg Pro Phe Gly
  1               5                  10

(2) INFORMATION FOR SEQ ID NO:365:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:365:

Lys Leu Lys Ile
  1

(2) INFORMATION FOR SEQ ID NO:366:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:366:

Arg Cys Gln Ser Leu Gly Cys Asn Thr Val Arg Leu Val Ser
  1               5                  10

(2) INFORMATION FOR SEQ ID NO:367:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:367:

Cys Ser Leu Leu Asn Ser Glu Trp

```
(2) INFORMATION FOR SEQ ID NO:368:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:368:

Leu Thr Tyr Pro Arg Asp Lys His Ser Gly Leu Trp Thr Leu Ser Thr
1               5                  10                  15

Pro Ile Lys Gly Arg Trp
            20

(2) INFORMATION FOR SEQ ID NO:369:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:369:

Asn Thr Leu Ile Arg
1               5

(2) INFORMATION FOR SEQ ID NO:370:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:370:

Gln Asp Cys Tyr
1

(2) INFORMATION FOR SEQ ID NO:371:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:371:

Glu Trp Ala Ser
1

(2) INFORMATION FOR SEQ ID NO:372:
```

```
    (i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:372:

Ser Ala Ile Phe Ala
 1               5

(2) INFORMATION FOR SEQ ID NO:373:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:373:

Asp Ala Val Phe Glu Pro Thr
 1               5

(2) INFORMATION FOR SEQ ID NO:374:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:374:

Ser Arg Gly Val Ala Thr Leu Ser Leu Phe Leu Ala Thr Cys Ser Leu
 1               5                  10                  15

Arg Cys Thr Gly Met Ala Gly
                 20

(2) INFORMATION FOR SEQ ID NO:375:

(i) SEQUENCE CHARACTERISTICS:
        (A) LENGTH: 384 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:375:

Ala Gly Leu Ser Ser Ser Asn Cys Trp Arg Tyr Gly Asp Arg Pro Glu
 1               5                  10                  15

Leu Asp Arg Leu Leu Asp Arg Ala Leu Asn Arg Leu Arg Gly Ser Ser
                20                  25                  30

Val Ile Pro Ala Cys Leu Asn Asp Arg Gln Lys Arg Gln Val Arg Leu
            35                  40                  45

Ala Pro Arg Ile Ser Ala Phe Ala Phe Gly Leu Gly Leu Phe Lys Leu
        50                  55                  60
```

```
Arg Cys Ser Asp Tyr Phe Met Leu Pro Glu Tyr Arg Gln Leu Leu Leu
 65                  70                  75                  80

Gln Trp Phe Ser Glu Asp Glu Ile Trp Gln Leu Tyr Gly Trp Leu Gly
                 85                  90                  95

Gln Arg Asp Gly Lys Leu Leu Pro Pro Gln Val Met Gln Gln Thr Ala
            100                 105                 110

Leu Gln Ile Gly Thr Ala Ile Leu Asn Arg Glu Ala His Asp Asp Ala
        115                 120                 125

Gly Phe Thr Cys Ala Ile Ser Ile Ile Thr Pro Ser Ala Ala Tyr Thr
    130                 135                 140

Leu Ala Glu Asp Phe Ser Tyr Arg Asp Tyr Leu His Gly Ala Phe Ala
145                 150                 155                 160

Met Ser Phe Thr Ser Leu Pro Leu Thr Glu Ile Asn His Lys Leu Pro
                165                 170                 175

Ala Arg Asn Ile Ile Glu Ser Gln Trp Ile Thr Leu Gln Leu Thr Leu
            180                 185                 190

Phe Ala Gln Glu Gln Gln Ala Lys Arg Val Ser His Ala Ile Val Ser
        195                 200                 205

Ser Ala Tyr Arg Lys Ala Glu Lys Ile Ile Arg Asp Ala Tyr Arg Tyr
    210                 215                 220

Gln Arg Glu Gln Lys Val Glu Gln Gln Gln Glu Leu Ala Cys Leu Arg
225                 230                 235                 240

Lys Asn Thr Leu Glu Lys Met Glu Val Glu Trp Leu Glu Gln His Val
                245                 250                 255

Lys His Leu Gln Asp Asp Glu Asn Gln Phe Arg Ser Leu Val Asp His
            260                 265                 270

Ala Ala His His Ile Lys Asn Ser Ile Glu Gln Val Leu Leu Ala Trp
        275                 280                 285

Phe Asp Gln Gln Ser Val Asp Ser Val Met Cys His Arg Leu Ala Arg
        290                 295                 300

Gln Ala Thr Ala Met Ala Glu Glu Gly Ala Leu Tyr Leu Arg Ile His
305                 310                 315                 320

Pro Glu Lys Glu Ala Leu Met Arg Glu Thr Phe Gly Lys Arg Phe Thr
                325                 330                 335

Leu Ile Ile Glu Pro Gly Phe Ser Pro Asp Gln Ala Glu Leu Ser Ser
            340                 345                 350

Thr Arg Tyr Ala Val Glu Phe Ser Leu Ser Arg His Phe Asn Ala Leu
        355                 360                 365

Leu Lys Trp Leu Arg Asn Gly Glu Asp Lys Arg Gly Ser Asp Glu Tyr
370                 375                 380

(2) INFORMATION FOR SEQ ID NO:376:

(i) SEQUENCE CHARACTERISTICS:
        (A) LENGTH: 40 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:376:

Asp Lys Asn Asp Ala Pro Tyr Ser Ile Tyr Pro Trp Pro Gly Tyr Arg
 1               5                  10                  15

Gly Thr Arg Gly Tyr Phe Ala Phe Asn Val Ser Ser Pro Gly Val Thr
```

```
            20                  25                  30

Gly Asn Asp Gly Gly Ser Ala Leu
            35                  40

(2) INFORMATION FOR SEQ ID NO:377:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:377:

Asp Asp Gly Arg Asn Arg Asn Gly Ala Glu Trp
1               5                   10

(2) INFORMATION FOR SEQ ID NO:378:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:378:

Thr Ala Arg Lys Leu
1               5

(2) INFORMATION FOR SEQ ID NO:379:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:379:

Glu Thr Gly Ala Gln Thr Ala Gly Phe Ala Ala Phe Asp Lys Thr Asn
1               5                   10                  15

Thr Gly Gly (2) INFORMATION FOR SEQ ID NO:380:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:380:

Trp Gly Asn Val Ala Ser Ala Tyr Arg Arg Glu
1               5                   10
```

(2) INFORMATION FOR SEQ ID NO:381:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:381:

```
Phe Thr Glu Cys Val Ser Asn Tyr Arg Ser Cys Asn Gly Ala Tyr Cys
 1               5                  10                  15

Arg Arg Val Val Lys Lys Glu Lys Thr Arg Phe Ala Ile Ala Thr Gly
             20                  25                  30

Tyr Val Thr Ala Glu Glu Gly Trp Glu Leu Ala Val Phe Ser Leu Leu
         35                  40                  45

Glu Leu Gly Glu Val Asp Thr Val Arg Cys Pro Leu
     50                  55                  60
```

(2) INFORMATION FOR SEQ ID NO:382:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:382:

```
Ser Val Leu Cys Asn Arg Arg
 1               5
```

(2) INFORMATION FOR SEQ ID NO:383:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:383:

```
Thr Thr Met Lys Cys Pro Tyr Arg Ser Gly Ser Asp Ala Trp Gln Thr
 1               5                  10                  15

Gly Arg Ile Ala Val Asn Gly Ser Val Phe Cys
             20                  25
```

(2) INFORMATION FOR SEQ ID NO:384:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:384:

```
Pro Leu Asn Leu Ala Tyr Ala Ser Asn Pro Arg Ser Lys Val Val Trp
  1               5                  10                  15
Pro Gln His
```

(2) INFORMATION FOR SEQ ID NO:385:

(i) SEQUENCE CHARACTERISTICS:
        (A) LENGTH: 54 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:385:

```
Tyr Val Cys Val Val Cys Cys Tyr Ser Leu Ala Leu Lys Lys Ser Ala
  1               5                  10                  15

Ser Val Arg Ser Gly Phe Ala Ser Cys Arg Leu Ile His Tyr Cys Arg
             20                  25                  30

Tyr Tyr Ser Ile Leu Phe Val Ser Ala Gly Phe Ser Val Ile Gly Cys
                 35                  40                  45

Leu Ile Asp Leu Pro Leu
             50
```

(2) INFORMATION FOR SEQ ID NO:386:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:386:

```
Phe Leu His Arg Arg Cys Ser Ile Gly Tyr Ser Asn Asn Leu Met Arg
  1               5                  10                  15
Ser Leu Cys
```

(2) INFORMATION FOR SEQ ID NO:387:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:387:

```
Tyr Pro Ile Thr Val Leu Thr Thr Lys Ile Asn Val Asn Lys Phe Ser
  1               5                  10                  15
Lys Arg Phe Val Lys
             20
```

(2) INFORMATION FOR SEQ ID NO:388:

(i) SEQUENCE CHARACTERISTICS:
        (A) LENGTH: 13 amino acids
        (B) TYPE: amino acid
        (C) STRANDEDNESS: single (D) TOPOLOGY: linear (ii) MOLECULE TYPE: protein (iii) HYPOTHETICAL: NO (xi) SEQUENCE DESCRIPTION: SEQ ID NO:388:

Ile Arg Phe Tyr Ser Asp Thr Trp Leu Ser Ile Phe Arg
 1               5                  10

(2) INFORMATION FOR SEQ ID NO:389:

(i) SEQUENCE CHARACTERISTICS:
        (A) LENGTH: 27 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:389:

Ile Gly Phe Leu Ala His His Glu Ala Ser Gly Trp Ile Gly Ile Ser
 1               5                  10                  15

Leu Leu Asn Val Ile Phe Ser Phe Leu Phe Asn
             20                  25

(2) INFORMATION FOR SEQ ID NO:390:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:390:

Leu Asn Gly Leu
 1

(2) INFORMATION FOR SEQ ID NO:391:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:391:

Gln Pro Ile Cys Ser Gly Gly Lys Asp Asn Met Lys Leu Ser
 1               5                  10

(2) INFORMATION FOR SEQ ID NO:392:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:392:

Arg Ser Tyr Ser Leu Met Ser Asp Thr Gln Ala Asn Leu Leu Arg Arg
 1               5                  10                  15

Arg Thr Ala Phe
            20

(2) INFORMATION FOR SEQ ID NO:393:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:393:

Leu Glu Thr Arg Ser Val Pro Gly Tyr Ser Ser Thr Ile Ile Phe Val
 1               5                  10                  15

Ala Arg Trp Ala Cys Asn Glu Leu Phe Ser Thr Ser Phe Gln Leu Arg
                20                  25                  30

Arg Ala Leu Val Thr Ile Thr Ser Ser Thr Asn Lys Ile Xaa Trp Ser
            35                  40                  45

Arg Asn Ala Phe Met Val Arg
        50                  55

(2) INFORMATION FOR SEQ ID NO:394:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:394:

Gly Ser Gln Gly Ala Thr Val Ala Gln Cys Met Arg Gly Ser Ala Gly
 1               5                  10                  15

Tyr Gly Ser Gly Asp Gly Val Ile Asn Arg Tyr Cys Asp Asp Ala Val
                20                  25                  30

Thr Leu Ala Asp Leu Asp Gly
            35

(2) INFORMATION FOR SEQ ID NO:395:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:395:

Tyr Pro Asp Tyr Tyr Gln Pro Tyr Val Phe Ser Asp Pro Ala Leu Asn
 1               5                  10                  15

Cys Tyr Leu Ser
            20

(2) INFORMATION FOR SEQ ID NO:396:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:396:

```
Pro Ser Arg Phe Ile Gly Ile Ser Val Phe Ile Thr Tyr Tyr Ile
 1               5                  10                  15

Ile Ser Phe Val Thr His Asn Gln His Ile Thr Ala Gly Thr Val Thr
             20                  25                  30

Thr
```

(2) INFORMATION FOR SEQ ID NO:397:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:397:

```
Tyr Cys Gly Cys Phe Arg
 1               5
```

(2) INFORMATION FOR SEQ ID NO:398:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:398:

```
Val Cys Arg Arg Arg Lys Ser His Arg Trp Val Gly Arg Ile Tyr His
 1               5                  10                  15

His Tyr Tyr Arg Ala Ile Tyr Cys His Tyr Lys Arg Tyr Arg Glu Gly
             20                  25                  30

Gly Gly Ser
         35
```

(2) INFORMATION FOR SEQ ID NO:399:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:399:

```
Arg Thr Phe Leu Ala
 1               5
```

(2) INFORMATION FOR SEQ ID NO:400:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:400:

```
Trp Asp Ala Arg Gln Thr Asn Glu Tyr Arg Trp Arg Phe Ala Cys Arg
 1               5                  10                  15

Ser Tyr Arg Cys Arg Pro Cys Pro Tyr Ile Lys Thr Ala Cys Pro Ala
            20                  25                  30

Gly Lys Pro Leu Ser Arg Cys Asp Gly Arg Cys Asp Glu Ile Cys
        35                  40                  45
```

(2) INFORMATION FOR SEQ ID NO:401:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:401:

```
Arg Arg Tyr Asp Cys Arg Tyr Tyr Cys Cys Ser Gly Glu His Tyr Arg
 1               5                  10                  15

Arg Tyr His Tyr Arg Tyr Arg Thr Ile
            20                  25
```

(2) INFORMATION FOR SEQ ID NO:402:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:402:

```
Tyr Val Asp Glu
 1
```

(2) INFORMATION FOR SEQ ID NO:403:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:403:

Gly Cys Ser His Leu
1               5

(2) INFORMATION FOR SEQ ID NO:404:

(i) SEQUENCE CHARACTERISTICS:
            (A) LENGTH: 19 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:404:

Arg Thr Val Asn Arg Arg Trp Phe Met Trp Ala Asn Ser Ile Ala Ala
1               5                   10                  15

Asp Phe Pro (2) INFORMATION FOR SEQ ID NO:405:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:405:

Arg Gly Asn Tyr Cys His Pro Cys Pro Gly
1               5                   10

(2) INFORMATION FOR SEQ ID NO:406:

(i) SEQUENCE CHARACTERISTICS:
            (A) LENGTH: 73 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:406:

Glu Thr Pro Glu Pro Gly Asp Arg Val Glu Phe Ser Asn Cys Gln Thr
1               5                   10                  15

Thr Ser Val Ala His Ile Asn Arg Cys Gly Phe Asn Ala Pro Arg Phe
                20                  25                  30

Asn Ser Trp Leu Ser Phe Tyr His Ser Arg Phe Leu Phe Ser Val Val
            35                  40                  45

Ser Ile Ala Asn Tyr Pro His Ser Pro Gln Lys Val Cys Gly Phe Arg
        50                  55                  60

Lys Trp Arg Arg Ser Thr Gly Lys Arg
65                  70

(2) INFORMATION FOR SEQ ID NO:407:

(i) SEQUENCE CHARACTERISTICS:
            (A) LENGTH: 12 amino acids
            (B) TYPE: amino acid
            (C) STRANDEDNESS: single (D) TOPOLOGY: linear (ii) MOLECULE TYPE: protein (iii) HYPOTHETICAL: NO (xi) SEQUENCE DESCRIPTION: SEQ ID NO:407:

Tyr Gly Ser Arg Arg Met Ser Ser Asn Leu Thr Ser
  1               5                  10

(2) INFORMATION FOR SEQ ID NO:408:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:408:

Pro Asp Val Thr Phe Cys Arg Pro Asp Ser
  1               5                  10

(2) INFORMATION FOR SEQ ID NO:409:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:409:

Arg His Glu Met Val Phe Ile
  1               5

(2) INFORMATION FOR SEQ ID NO:410:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:410:

Gly Tyr Arg Arg Pro Ser Pro
  1               5

(2) INFORMATION FOR SEQ ID NO:411:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:411:

```
Thr His Arg Lys Ile Asp Gly Thr Ala Ile Ser Gly Thr Arg Ile
1               5                   10                  15
```

(2) INFORMATION FOR SEQ ID NO:412:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:412:

```
Phe Ile Tyr Ser Arg Ser Gly Gly Leu Phe Ile Asp Arg Arg Gly Arg
1               5                   10                  15
```

(2) INFORMATION FOR SEQ ID NO:413:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:413:

```
Gln Pro Asp Val Thr Glu Arg Asp Gly Ala Asp Leu Leu Ala Tyr Lys
1               5                   10                  15
Arg His Gly Pro
            20
```

(2) INFORMATION FOR SEQ ID NO:414:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:414:

```
Gly Ala Arg Phe Trp Thr Gly Arg Phe Arg Gly Gln Pro Thr Tyr Leu
1               5                   10                  15
Cys Leu Ile Lys Met Cys Pro Ala Ser Ala Tyr Gly Arg Val Tyr Trp
                20                  25                  30
Cys Ser Gly Asn Ala Leu Ser Asn Glu Cys Asp Gly Lys Lys Leu Leu
            35                  40                  45
```

(2) INFORMATION FOR SEQ ID NO:415:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:415:

```
Ala Gly Glu Arg Ala Ser Ala Pro Val Thr His
  1               5                  10
```

(2) INFORMATION FOR SEQ ID NO:416:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:416:

```
Asn Phe Ala Thr Ala Cys Ile Arg Ala Gly Phe Tyr
  1               5                  10
```

(2) INFORMATION FOR SEQ ID NO:417:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:417:

```
Arg Phe Thr Ser Tyr Phe Arg His Leu Asn
  1               5                  10
```

(2) INFORMATION FOR SEQ ID NO:418:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:418:

```
Leu Gly Ala Thr
  1
```

(2) INFORMATION FOR SEQ ID NO:419:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:419:

```
Lys Arg Cys Pro Asp Val Asp Arg Ile Cys Pro Tyr Arg Ala Ser Ser
  1               5                  10                  15
Ser Tyr Ser Ala Ser Ser
             20
```

(2) INFORMATION FOR SEQ ID NO:420:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:420:

```
Ser Gly Arg Lys Thr Ala Ala Asp Phe Ala Asp Arg Arg Arg Tyr
 1               5                  10                  15
```

(2) INFORMATION FOR SEQ ID NO:421:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:421:

```
Lys Pro Arg Ala
 1
```

(2) INFORMATION FOR SEQ ID NO:422:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:422:

```
Ile His Ser Pro Asp Gly Asn Gly Asp Leu Tyr Cys Ala Val Val Ser
 1               5                  10                  15
Ser
```

(2) INFORMATION FOR SEQ ID NO:423:

(i) SEQUENCE CHARACTERISTICS:
        (A) LENGTH: 60 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:423:

```
Asp Ala Asp Pro Ala Thr Tyr Arg Ala Gly Ala Glu Ala Val Ser Gln
 1               5                  10                  15
Ile Ile His Cys His Phe Cys Arg His Pro Thr Phe Leu Ala Lys Asn
                20                  25                  30
Tyr Arg Ser His Leu Val Arg Arg Thr Asp Phe Val Met Ala Gly Ile
                35                  40                  45
Arg Arg Gly Glu Pro Tyr Thr Ser Gly Arg Lys Tyr
```

```
         50                  55                  60

(2) INFORMATION FOR SEQ ID NO:424:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:424:

Arg Arg Gly Val Gly Gly Gln
  1               5

(2) INFORMATION FOR SEQ ID NO:425:

(i) SEQUENCE CHARACTERISTICS:
         (A) LENGTH: 21 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:425:

Asn Ile Arg Pro Pro Met Val Ile Val Asp Gly Ala Glu Phe Arg Met
  1               5                  10                  15

Ser Ala Gln Arg Cys
             20

(2) INFORMATION FOR SEQ ID NO:426:

(i) SEQUENCE CHARACTERISTICS:
         (A) LENGTH: 14 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:426:

Met Arg Gly Cys Leu Gly Tyr Leu Trp Ala Ser Cys Ala Val
  1               5                  10

(2) INFORMATION FOR SEQ ID NO:427:

(i) SEQUENCE CHARACTERISTICS:
         (A) LENGTH: 33 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:427:

Ser Leu Glu Lys Asn Leu Leu Lys Ser Trp Gly Leu Met Ala Ala Lys
  1               5                  10                  15

Leu Cys Tyr Leu Leu Leu Arg Val Gln Ser Gly Phe Thr Ala Gly Ser
                 20                  25                  30
```

Lys (2) INFORMATION FOR SEQ ID NO:428:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:428:

Ala Thr Pro Ser Gly Ser Arg Gly Arg Ser Val Ile Arg Ala Ser Tyr
 1               5                  10                  15

(2) INFORMATION FOR SEQ ID NO:429:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:429:

Trp Leu Trp Ser Ser Pro
 1               5

(2) INFORMATION FOR SEQ ID NO:430:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:430:

Trp Pro Arg Thr Ala Arg Arg Leu Leu Glu Arg Leu
 1               5                  10

(2) INFORMATION FOR SEQ ID NO:431:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:431:

Cys Asn Ala Ser Ser Arg Asn Gly Ser Thr Ala Tyr His Ser Thr Ile
 1               5                  10                  15

Asn Asp Gly Asp Ser Arg Tyr
                20

(2) INFORMATION FOR SEQ ID NO:432:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:432:

Arg Cys Asp Leu Trp Arg Arg Ala Thr Ser Gly Tyr Phe Phe Cys Ser
 1               5                  10                  15

Trp Arg Gly Glu Lys His Ala Ser Gly Asp Ala Val
            20                  25

(2) INFORMATION FOR SEQ ID NO:433:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:433:

Cys Ala Arg Arg Gln Gln Cys Ser Gly Val Asn Trp
 1               5                  10

(2) INFORMATION FOR SEQ ID NO:434:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:434:

Thr Trp Thr Arg Ser Pro Arg Ile His Arg Phe Tyr Thr Val
 1               5                  10

(2) INFORMATION FOR SEQ ID NO:435:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:435:

Arg Asp Pro Lys Thr Leu Cys His Cys Cys Arg Asn Leu
 1               5                  10

(2) INFORMATION FOR SEQ ID NO:436:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:436:

Gln Thr Arg Leu Arg Ala Arg Glu Gly Ala Val Cys Gly His His Asp
1               5                   10                  15

Ser Arg Ile Phe Ser Arg
            20

(2) INFORMATION FOR SEQ ID NO:437:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:437:

Trp Lys Ala Ser Arg Leu Ala Cys Arg Leu Thr Asp Ala Leu Cys Gln
1               5                   10                  15

Gly Arg Thr Glu Ile Ala Leu Ala Pro Glu Arg Pro Arg Phe Leu Glu
            20                  25                  30

Asn Ile Ala Arg Arg Ile
        35

(2) INFORMATION FOR SEQ ID NO:438:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:438:

Cys Ile Ala Thr Thr Phe Arg Thr Tyr Gly Asn Gly Arg Lys Arg Gln
1               5                   10                  15

Tyr Tyr Arg Ile Leu Tyr Gly Thr Gly Gly Arg Arg
            20                  25

(2) INFORMATION FOR SEQ ID NO:439:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:439:

Ser Arg Trp Arg Met Lys Ser Val His Cys Leu Met Asp Ile Leu Tyr
1               5                   10                  15

Tyr Pro Asp Gly Leu Gln Arg Gly Gly Ile Ile Leu Pro Leu Thr Cys
            20                  25                  30

Trp Gln Arg Ser Ala Ala Phe Phe Gln Ser Leu Pro Ala Met Ser Ile

```
             35                  40                  45
Val Asn Trp Arg Arg Tyr Cys Asp Gly Ala Trp Arg Phe Thr Arg Arg
         50                  55                  60
Leu Asn Cys
 65
```

(2) INFORMATION FOR SEQ ID NO:440:

(i) SEQUENCE CHARACTERISTICS:
        (A) LENGTH: 41 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:440:

```
Tyr Ala Leu Gly Asn Thr Ser Glu Glu Leu Ile Gln Ile Leu Thr Lys
 1               5                  10                  15
Pro Leu Ile Pro Ile Arg Ile Phe Ala His Phe Cys Asp Lys Val Arg
             20                  25                  30
Met Lys Tyr Ala Asp Pro Ser Tyr Leu
         35                  40
```

(2) INFORMATION FOR SEQ ID NO:441:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:441:

```
Lys Asn Tyr Thr Lys Tyr Ser Pro Ser Asp His Gly Asn Phe Ala Gly
 1               5                  10                  15
Asp Asn Arg Ala Ala Glu Lys Gln Leu Arg Gly Lys Leu Thr Val Leu
             20                  25                  30
Asp Gln Gln Gln Ala Ile Ile Thr Glu Gln Gln Ile Cys Gln Thr
         35                  40                  45
Arg Ala Leu Ala Val Ser Thr Arg Leu Lys Glu Leu Met Gly Trp Gln
         50                  55                  60
Gly Thr Leu Ser Cys His Leu Leu Asp Lys Lys Gln Gln Met Ala
 65                  70                  75              80
Gly Leu Phe Thr Gln Ala Gln Ser Phe Leu Thr Gln Arg Gln Ala Val
                 85                  90                  95
Arg Glu Ser Val Ser Ala Ala Cys Leu Pro Ala Lys Arg Ile Thr Glu
                100                 105                 110
Glu Phe
```

(2) INFORMATION FOR SEQ ID NO:442:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:442:

Cys Ala Tyr Glu Lys Glu Arg Lys Asn Tyr Tyr Gly Ile Lys Arg Cys
  1               5                  10                  15

Val Leu Pro Lys Leu Arg Glu Val Leu Gly Cys His Ala Ser Leu Ile
             20                  25                  30

Arg Met Ile Thr Arg Arg Arg Arg Asn Val Trp Thr Leu Asn Asn Ser
         35                  40                  45

Cys Thr Arg His Tyr Pro Leu Val Arg Ile Ile Leu Leu Gln His
         50                  55                  60

(2) INFORMATION FOR SEQ ID NO:443:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:443:

Ile Arg Thr Trp Phe Ser Arg Asn Val Ile Val Leu Val Ala Val Ile
  1               5                  10                  15

Leu Thr Val (2) INFORMATION FOR SEQ ID NO:444:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:444:

Ser Val Lys Tyr Val Asn Gln Gly Gly
  1               5

(2) INFORMATION FOR SEQ ID NO:445:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:445:

Glu Ser Met Ser Leu Ile Met Lys Phe Thr Val Arg
  1               5                  10

(2) INFORMATION FOR SEQ ID NO:446:

(i) SEQUENCE CHARACTERISTICS:
        (A) LENGTH: 13 amino acids
        (B) TYPE: amino acid
        (C) STRANDEDNESS: single (D) TOPOLOGY: linear (ii) MOLECULE TYPE: protein (iii) HYPOTHETICAL: NO (xi) SEQUENCE DESCRIPTION: SEQ ID NO:446:

Ser Ser Gly Trp Ser Leu Ser Cys Cys Ile Trp Gly Ile
 1               5                  10

(2) INFORMATION FOR SEQ ID NO:447:

(i) SEQUENCE CHARACTERISTICS:
        (A) LENGTH: 328 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:447:

Phe Pro Trp Arg Tyr Ser Met Leu Arg Ile Ala Asn Glu Glu Arg Pro
 1               5                  10                  15

Trp Val Glu Ile Leu Pro Thr Gln Gly Ala Thr Ile Gly Glu Leu Thr
                20                  25                  30

Leu Ser Met Gln Gln Tyr Pro Val Gln Gln Gly Thr Leu Phe Thr Ile
            35                  40                  45

Asn Tyr His Asn Glu Leu Gly Arg Val Trp Ile Ala Glu Gln Cys Trp
        50                  55                  60

Gln Arg Trp Cys Glu Gly Leu Ile Gly Thr Ala Asn Arg Ser Ala Ile
65                  70                  75                  80

Asp Pro Glu Leu Leu Tyr Gly Ile Ala Glu Trp Gly Leu Ala Pro Leu
                85                  90                  95

Leu Gln Ala Ser Asp Ala Thr Leu Cys Gln Asn Glu Pro Pro Thr Ser
            100                 105                 110

Cys Ser Asn Leu Pro His Gln Leu Ala Leu His Ile Lys Trp Thr Val
        115                 120                 125

Glu Glu His Glu Phe His Ser Ile Ile Phe Thr Trp Pro Thr Gly Phe
130                 135                 140

Leu Arg Asn Ile Val Gly Glu Leu Ser Ala Glu Arg Gln Gln Ile Tyr
145                 150                 155                 160

Pro Ala Pro Pro Val Val Val Pro Val Tyr Ser Gly Trp Cys Gln Leu
                165                 170                 175

Thr Leu Ile Glu Leu Glu Ser Ile Glu Ile Gly Met Gly Val Arg Ile
            180                 185                 190

His Cys Phe Gly Asp Ile Arg Leu Gly Phe Phe Ala Ile Gln Leu Pro
        195                 200                 205

Gly Gly Ile Tyr Ala Arg Val Leu Leu Thr Glu Asp Asn Thr Met Lys
210                 215                 220

Phe Asp Glu Leu Val Gln Asp Ile Glu Thr Leu Leu Ala Ser Gly Ser
225                 230                 235                 240

Pro Met Ser Lys Ser Asp Gly Thr Ser Ser Val Glu Leu Glu Gln Ile
                245                 250                 255

Pro Gln Gln Val Leu Phe Glu Val Gly Arg Ala Ser Leu Glu Ile Gly
            260                 265                 270

Gln Leu Arg Gln Leu Lys Thr Gly Asp Val Leu Pro Val Gly Gly Cys
        275                 280                 285

-continued

```
Phe Ala Pro Glu Val Thr Ile Arg Val Asn Asp Arg Ile Ile Gly Gln
    290                 295                 300
Gly Glu Leu Ile Ala Cys Gly Asn Glu Phe Met Val Arg Ile Thr Arg
305                 310                 315                 320
Trp Tyr Leu Cys Lys Asn Thr Ala
                325
```

(2) INFORMATION FOR SEQ ID NO:448:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:448:

```
Tyr Ala Asn Asn Ile Ile Ala Phe Gln Val Val Ser
  1               5                  10
```

(2) INFORMATION FOR SEQ ID NO:449:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:449:

```
Glu Ile Gln Tyr Val Phe Thr Arg Phe Ala Phe Ala Thr Asp Trp Tyr
  1               5                  10                  15
Ile Val Ser Ala Phe Asn Thr Ala Ser His Tyr Arg His Gly Asn Phe
                 20                  25                  30
Phe Pro
```

(2) INFORMATION FOR SEQ ID NO:450:

(i) SEQUENCE CHARACTERISTICS:
        (A) LENGTH: 59 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:450:

```
Thr Gly Gly Gly Ile Phe Asp Phe Thr Lys Cys Ser Gly Tyr Ser Thr
  1               5                  10                  15
Ser Pro Pro Lys Tyr Arg Thr Val Trp Pro Cys Ala Cys Thr Phe Leu
                 20                  25                  30
Ile His Tyr Gly Ala Asp Ala Ile Ser Cys Lys Arg Ala Leu Ala Ser
            35                  40                  45
Gly Ser Gly Arg Trp Arg Ser Phe Leu Asp Val
       50                  55
```

(2) INFORMATION FOR SEQ ID NO:451:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:451:

Ser Ile Ser Ala Leu Ser Thr Val Phe Ala Lys Lys Leu
 1               5                  10

(2) INFORMATION FOR SEQ ID NO:452:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:452:

Arg Glu Gly Ser Gln Leu Phe Ser Glu Phe Asp Lys Thr Asn Leu Ala
 1               5                  10                  15

(2) INFORMATION FOR SEQ ID NO:453:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:453:

Arg His Lys Lys Lys Asp Lys Thr
 1               5

(2) INFORMATION FOR SEQ ID NO:454:

(i) SEQUENCE CHARACTERISTICS:
            (A) LENGTH: 31 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:454:

Phe Phe Ala His Ile Asn Ser Gly Ile Tyr Gly Glu Ser Val Asn Ala
 1               5                  10                  15

Gly Ile Ser Asp Trp Ile Thr Tyr Leu Ser Ser Leu Ser Gly Tyr
                20                  25                  30

(2) INFORMATION FOR SEQ ID NO:455:

(i) SEQUENCE CHARACTERISTICS:
            (A) LENGTH: 24 amino acids
            (B) TYPE: amino acid
            (C) STRANDEDNESS: single
            (D) TOPOLOGY: linear (ii) MOLECULE TYPE: protein (iii) HYPOTHETICAL: NO (xi) SEQUENCE DESCRIPTION: SEQ ID NO:455:

```
Pro Ala Tyr Phe Lys Tyr Thr Ala Gly Tyr Gly Asp Asp Gly Val
 1               5                  10                  15

Ala Asp Asp His Phe Ile Thr Val
                20
```

(2) INFORMATION FOR SEQ ID NO:456:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:456:

```
Ala Ala Asn Ile Phe Thr Gly Arg Arg Leu Gly Ser Asp Thr Gly Ala
 1               5                  10                  15

Ile Gly Thr Glu Leu Phe Met Asn Asp Ser Glu Leu Thr Gln Phe Val
                20                  25                  30

Thr Gln Leu Leu Trp Ile Val Leu Phe Thr Ser Met Pro Val Val Leu
                35                  40                  45

Val Ala Ser Val Val Gly Val Ile Val Ser Leu Val Gln Ala Leu Thr
                50                  55                  60

Gln Ile Gln Asp Gln Thr Leu Gln Phe Met Ile Lys Leu Leu Ala Ile
65                  70                  75                  80

Ala Ile Thr Leu Met Val Ser Tyr Pro Trp Leu Ser Gly Ile Leu Leu
                85                  90                  95

Asn Tyr Thr Arg Gln Ile Met Leu Arg Ile Gly Glu His Gly
                100                 105                 110
```

(2) INFORMATION FOR SEQ ID NO:457:

(i) SEQUENCE CHARACTERISTICS:
        (A) LENGTH: 230 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:457:

```
Met Ala Gln Gln Val Asn Glu Trp Leu Ile Ala Leu Ala Val Ala Phe
 1               5                  10                  15

Ile Arg Pro Leu Ser Leu Ser Leu Leu Leu Pro Leu Leu Lys Ser Gly
                20                  25                  30

Ser Leu Gly Ala Ala Leu Leu Arg Asn Gly Val Leu Met Ser Leu Thr
                35                  40                  45

Phe Pro Ile Leu Pro Ile Ile Tyr Gln Gln Lys Ile Met Met His Ile
                50                  55                  60

Gly Lys Asp Tyr Ser Trp Leu Gly Leu Val Thr Gly Glu Val Ile Ile
65                  70                  75                  80

Gly Phe Ser Ile Gly Phe Cys Ala Ala Val Pro Phe Trp Ala Val Asp
```

```
                    85                  90                   95
Met Ala Gly Phe Leu Leu Asp Thr Leu Arg Gly Ala Thr Met Gly Thr
                100                 105                 110

Ile Phe Asn Ser Thr Ile Glu Ala Glu Thr Ser Leu Phe Gly Leu Leu
                115                 120                 125

Phe Ser Gln Phe Leu Cys Val Ile Phe Phe Ile Ser Gly Gly Met Glu
                130                 135                 140

Phe Ile Leu Asn Ile Leu Tyr Glu Ser Tyr Gln Tyr Leu Pro Pro Gly
145                 150                 155                 160

Arg Thr Leu Leu Phe Asp Gln Gln Phe Leu Lys Tyr Ile Gln Ala Glu
                165                 170                 175

Trp Arg Thr Leu Tyr Gln Leu Cys Ile Ser Phe Ser Leu Pro Ala Ile
                180                 185                 190

Ile Cys Met Val Leu Ala Asp Leu Ala Leu Gly Leu Leu Asn Arg Ser
                195                 200                 205

Ala Gln Gln Leu Asn Val Phe Phe Ser Met Pro Leu Lys Ser Ile
                210                 215                 220

Leu Val Leu Leu Thr Xaa
225                 230

(2) INFORMATION FOR SEQ ID NO:458:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:458:

Ser His Ser Leu Met Leu Phe Ile Thr Ile Trp Leu Lys Ala Ile Asn
  1               5                  10                  15

Phe Ile Phe Ile
            20

(2) INFORMATION FOR SEQ ID NO:459:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:459:

Lys Thr Gly Phe His Leu Tyr Glu Arg Glu Asn Arg Thr Ala Tyr Arg
  1               5                  10                  15

Lys Glu Ile Thr
            20

(2) INFORMATION FOR SEQ ID NO:460:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

(ii) MOLECULE TYPE: protein (iii) HYPOTHETICAL: NO (xi) SEQUENCE DESCRIPTION: SEQ ID NO:460:

```
Gly Arg Ala Gly Cys Gln Lys Tyr
  1               5
```

(2) INFORMATION FOR SEQ ID NO:461:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:461:

```
Asn Asn Ile Ile Ile Ser Ala Asp Cys Ala Leu Phe Val Phe Ser Phe
  1               5                  10                  15
Leu Tyr
```

(2) INFORMATION FOR SEQ ID NO:462:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:462:

```
Lys Asp Asp Phe Asp Thr Asp
  1               5
```

(2) INFORMATION FOR SEQ ID NO:463:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:463:

```
Val Asn Asn Phe His Ile Thr Ile Ser Lys
  1               5                  10
```

(2) INFORMATION FOR SEQ ID NO:464:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:464:

```
Thr Ile Phe Leu Cys Ile Asn Ala Ile Glu Ser Cys Phe Asn Arg Val
 1               5                  10                  15

Thr Asp Phe Cys Thr Ala Val Ser Gly Arg Trp Gly Asn Ser Cys Tyr
                20                  25                  30

Cys Gly
```

(2) INFORMATION FOR SEQ ID NO:465:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:465:

```
Arg Val Ser Ser Gly Gly Gly Tyr Cys Gln Gln Gly His Trp Phe
 1               5                  10                  15
```

(2) INFORMATION FOR SEQ ID NO:466:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:466:

```
Lys Arg Ala Tyr Lys Ser Gly Lys
 1               5
```

(2) INFORMATION FOR SEQ ID NO:467:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:467:

```
Ala Asp Ile Leu Phe Thr
 1               5
```

(2) INFORMATION FOR SEQ ID NO:468:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:468:

```
Arg Ser Arg Ile Met
 1               5
```

(2) INFORMATION FOR SEQ ID NO:469:

(i) SEQUENCE CHARACTERISTICS:
        (A) LENGTH: 66 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:469:

```
Ile Gln Pro Lys Ser Tyr His Ala Ile Ser Tyr Leu Cys Leu Phe Leu
 1               5                  10                  15
Leu Leu Leu Cys Gln Tyr Phe Ser Gly Ala Thr Val Leu Trp Val Ser
             20                  25                  30
Leu Trp Arg Ala Cys Gly Phe Phe Asn Lys Met Val Met Gly Arg
         35                  40                  45
Gly Asp Gly Phe Leu Tyr Arg Arg Trp His Thr Gly Leu Phe Phe Ser
     50                  55                  60
Ile Leu
 65
```

(2) INFORMATION FOR SEQ ID NO:470:

(i) SEQUENCE CHARACTERISTICS:
        (A) LENGTH: 39 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:470:

```
Lys Ser Tyr Leu Lys Met Ser Lys Asp Asp Val Lys Gln Glu His Lys
 1               5                  10                  15
Asp Leu Glu Gly Asp Pro Gln Met Lys Thr Arg Arg Arg Lys Cys Arg
             20                  25                  30
Val Lys Tyr Lys Val Gly Val
         35
```

(2) INFORMATION FOR SEQ ID NO:471:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:471:

```
Leu Asn Leu Leu Asn Asn Leu Leu Arg
 1               5
```

(2) INFORMATION FOR SEQ ID NO:472:

(i) SEQUENCE CHARACTERISTICS:
        (A) LENGTH: 80 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:472:

Cys Val Ile Gln Arg Ile Leu Arg Phe Val Leu Ala Ile Ile Pro Pro
  1               5                  10                  15

Ile Cys Gln Tyr His Ala Ser Trp Lys Lys Ala Val Met Leu Lys Leu
             20                  25                  30

Thr Ile Leu Leu Thr Ser Leu Asn Ala Thr Ala Ser Pro Leu Leu Lys
         35                  40                  45

Met Leu Ser Trp Pro Ala His Tyr Phe Leu Lys Trp Asn Ala Glu Ile
     50                  55                  60

Lys Phe Leu Lys Arg Tyr Leu Asn Pro Leu Gln Pro Cys Tyr Val Trp
 65                  70                  75                  80

(2) INFORMATION FOR SEQ ID NO:473:

(i) SEQUENCE CHARACTERISTICS:
         (A) LENGTH: 22 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:473:

Ile Met Arg Ile Leu Pro Lys His His Lys Cys Phe Trp Tyr Ala Ser
  1               5                  10                  15

Ser Gly His Cys Glu Gly
             20

(2) INFORMATION FOR SEQ ID NO:474:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:474:

Glu Gly Asn Ser Val
  1               5

(2) INFORMATION FOR SEQ ID NO:475:

(i) SEQUENCE CHARACTERISTICS:
         (A) LENGTH: 7 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:475:

Glu Thr Glu Asn Asn Arg Phe
  1               5

```
(2) INFORMATION FOR SEQ ID NO:476:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:476:

Pro Gly Thr Ser Thr Arg
 1               5

(2) INFORMATION FOR SEQ ID NO:477:

(i) SEQUENCE CHARACTERISTICS:
         (A) LENGTH: 13 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:477:

Arg Ile Ile Lys Leu Asn Lys Ile Met Asp Trp Cys Val
 1               5                  10

(2) INFORMATION FOR SEQ ID NO:478:

(i) SEQUENCE CHARACTERISTICS:
         (A) LENGTH: 26 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:478:

Met Asp Ser Asn His Ser Thr Pro Thr Met Ser Arg Trp Cys Ser Asn
 1               5                  10                  15

Gln Leu Ser Tyr Glu Arg Gln Arg Cys Arg
                20                  25

(2) INFORMATION FOR SEQ ID NO:479:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: protein (iii) HYPOTHETICAL: NO (xi) SEQUENCE DESCRIPTION: SEQ ID NO:479:

Gln Arg Gly Arg Ile Leu Ala Ser Gln Pro Gln
 1               5                  10

(2) INFORMATION FOR SEQ ID NO:480:

(i) SEQUENCE CHARACTERISTICS:
         (A) LENGTH: 48 amino acids
         (B) TYPE: amino acid
```

(C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:480:

Gly Lys Arg Glu Ile Ala Ile Phe Phe Leu Lys Ser Pro Asp Cys Gly
 1               5                  10                  15

Gly Asn Met Gln His Val Glu Lys Ile Ala Ala Met Arg Arg Leu Ser
            20                  25                  30

Ser Tyr Tyr Arg Ser Ala Leu Gln Asn Asp Gly Gly Arg Leu Thr Leu
        35                  40                  45

(2) INFORMATION FOR SEQ ID NO:481:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:481:

Ile Ala His Pro
 1

(2) INFORMATION FOR SEQ ID NO:482:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:482:

His Arg Arg Arg Gly Gln Ala Asp Asp Glu Pro His Pro Glu Ala Cys
 1               5                  10                  15

Arg Ser His Thr Ile His His Gln Ile Arg
            20                  25

(2) INFORMATION FOR SEQ ID NO:483:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:483:

Arg Gln Asp Ile Thr Ala Gly
 1               5

(2) INFORMATION FOR SEQ ID NO:484:

(i) SEQUENCE CHARACTERISTICS:
        (A) LENGTH: 40 amino acids

```
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:484:

His Pro Val Gly Gly Lys Gly Asp Lys Lys Asp Gly Thr Arg Ile Phe
  1               5                  10                  15

Ile Thr Ala Gln Asn Thr Ala Ala Asp Asn Leu Tyr Arg Val Gly Asn
                 20                  25                  30

Leu Val Asn Arg Ser Glu Gln His
             35                  40

(2) INFORMATION FOR SEQ ID NO:485:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:485:

Leu Arg Gln Ala Pro Arg Pro Gln Gly Cys His Cys Arg Ala Lys Gln
  1               5                  10                  15

Tyr Ala Tyr Ala Glu
             20

(2) INFORMATION FOR SEQ ID NO:486:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:486:

Pro Gln Pro Tyr Lys Cys Arg Arg Leu Asn Arg Tyr Ala Leu Arg Leu
  1               5                  10                  15

Arg Ile Gln Arg
             20

(2) INFORMATION FOR SEQ ID NO:487:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:487:

Ala Leu Ala Gln Thr Asp Asn Pro Leu Glu Ser Leu Pro Pro Gln Pro
  1               5                  10                  15

Ala Thr Ser Ala Val Arg Thr Ser Ala Ser
```

20                  25

(2) INFORMATION FOR SEQ ID NO:488:

(i) SEQUENCE CHARACTERISTICS:
          (A) LENGTH: 37 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:488:

Ala Gln Ser Asp Asp Arg Arg His Pro Gln Tyr Leu Met Ala Lys Pro
 1               5                  10                  15

Ala Ala Gln Arg Pro Gln Ile Thr Ser Leu Gln Arg Thr Ala Ser Ala
            20                  25                  30

Ile Gly Asn Pro Ser
            35

(2) INFORMATION FOR SEQ ID NO:489:

(i) SEQUENCE CHARACTERISTICS:
          (A) LENGTH: 28 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:489:

Ile Arg Arg Phe Met Thr Thr Leu Ser Gly Leu Pro Lys Pro Phe Ser
 1               5                  10                  15

Leu Arg Ile Ser Arg Ile Glu Arg Ala Cys Leu Met
            20                  25

(2) INFORMATION FOR SEQ ID NO:490:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:490:

Glu Ser Met Ala Ile Asn Ile Thr Gln
 1               5

(2) INFORMATION FOR SEQ ID NO:491:

(i) SEQUENCE CHARACTERISTICS:
          (A) LENGTH: 20 amino acids
          (B) TYPE: amino acid
          (C) STRANDEDNESS: single
          (D) TOPOLOGY: linear (ii) MOLECULE TYPE: protein (iii) HYPOTHETICAL: NO (xi) SEQUENCE DESCRIPTION: SEQ ID NO:491:

```
Thr Ala Ala Val Ala Thr Pro Gln Pro Ile Pro Pro Ser Ser Gly Ile
  1               5                  10                  15

Pro Lys Trp Pro
            20
```

(2) INFORMATION FOR SEQ ID NO:492:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:492:

```
Phe Thr Gly Ile Phe Thr Ser Arg Pro Lys Asn Pro Ile Thr Ile Pro
  1               5                  10                  15

Gly Leu Val Leu Ala Arg Pro Ser His Trp Phe Arg Ala Thr
            20                  25                  30
```

(2) INFORMATION FOR SEQ ID NO:493:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:493:

```
Lys Lys Arg Tyr Pro Ala Pro His Ser Ser Ala Arg Arg
  1               5                  10
```

(2) INFORMATION FOR SEQ ID NO:494:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:494:

```
Pro Thr Ala Leu Ser Ala Ser Ala Gly Ser Ile Leu Cys Ile Glu Arg
  1               5                  10                  15

Ile Met Tyr Pro Ala Phe His Arg Thr Ile Ile Thr Ser Thr Glu Thr
            20                  25                  30

Lys Pro Ala Ser Gln Asn Pro Cys Arg Thr
            35                  40
```

(2) INFORMATION FOR SEQ ID NO:495:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:495:

Cys Ala Ile Arg Ser Arg Arg Pro Glu Pro Leu Ser Cys Ala Ile Thr
  1               5                  10                  15

Gly Val Lys Ala Ser Ser Lys Pro
             20

(2) INFORMATION FOR SEQ ID NO:496:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:496:

Pro Asn Lys Met Ala Gly Ser Arg
  1               5

(2) INFORMATION FOR SEQ ID NO:497:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:497:

Arg Arg Gln Pro Cys Pro
  1               5

(2) INFORMATION FOR SEQ ID NO:498:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:498:

Arg Tyr Ser Leu Pro Pro
  1               5

(2) INFORMATION FOR SEQ ID NO:499:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:499:

Arg Tyr Arg Arg Ile His Cys Gly Leu Tyr His Leu Arg Lys Asp His

```
                1               5              10              15
Arg Tyr Leu Asn Ala Asn Asn
                               20

(2) INFORMATION FOR SEQ ID NO:500:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:500:

Arg Ala Ser Leu Val Tyr Phe Cys Thr Tyr Ser Pro Phe Ile Leu Leu
  1               5                  10                  15

Leu Tyr Glu Arg Leu Lys Ser Arg Arg Ser Gly Ser Gln Lys Lys
                 20                  25                  30

(2) INFORMATION FOR SEQ ID NO:501:

(i) SEQUENCE CHARACTERISTICS:
        (A) LENGTH: 63 amino acids
        (B) TYPE: amino acid
        (C) STRANDEDNESS: single
        (D) TOPOLOGY: linear (ii) MOLECULE TYPE: protein (iii) HYPOTHETICAL: NO (xi) SEQUENCE DESCRIPTION: SEQ ID NO:501:

Gln Gly Lys Phe Gln Ser Ile Val Ala Gly Tyr Tyr Tyr Phe Ser Ser
  1               5                  10                  15

Glu Lys Thr Val Val Asn Gly Ala Leu Leu Ala Ser Cys Phe Ser Thr
                 20                  25                  30

Cys Tyr Cys Ala Glu Gln Phe Cys Phe Tyr Leu Phe Gln Glu Leu Lys
                 35                  40                  45

Ile Cys Leu Arg Gly Ser Tyr Arg Val Pro Arg Asn Trp Tyr Arg
                 50                  55                  60
```